(12) United States Patent
Rau et al.

(10) Patent No.: US 11,311,604 B2
(45) Date of Patent: *Apr. 26, 2022

(54) CONTROLLED-RELEASE CNP AGONISTS WITH LOW NPR-C BINDING

(71) Applicant: ASCENDIS PHARMA GROWTH DISORDERS A/S, Hellerup (DK)

(72) Inventors: Harald Rau, Dossenheim (DE); Ulrich Hersel, Heidelberg (DE); Kennett Sprogøe, Holte (DK); Frank Faltinger, Heidelberg (DE); Thomas Wegge, Heidelberg (DE); Felix Cleemann, Mainz (DE)

(73) Assignee: ASCENDIS PHARMA GROWTH DISORDERS A/S, Hellerup (DK)

( * ) Notice: Subject to any disclaimer, the term of this patent is extended or adjusted under 35 U.S.C. 154(b) by 654 days.

This patent is subject to a terminal disclaimer.

(21) Appl. No.: 16/066,980

(22) PCT Filed: Jan. 5, 2017

(86) PCT No.: PCT/EP2017/050220
§ 371 (c)(1),
(2) Date: Jun. 28, 2018

(87) PCT Pub. No.: WO2017/118704
PCT Pub. Date: Jul. 13, 2017

(65) Prior Publication Data
US 2019/0000926 A1    Jan. 3, 2019

(30) Foreign Application Priority Data

Jan. 8, 2016    (EP) .................................. 16150633
Jul. 13, 2016    (EP) .................................. 16179292
Sep. 29, 2016    (EP) .................................. 16191480

(51) Int. Cl.
*A61K 38/22*    (2006.01)
*A61K 47/60*    (2017.01)

(52) U.S. Cl.
CPC .............. *A61K 38/22* (2013.01); *A61K 47/60* (2017.08)

(58) Field of Classification Search
CPC ......... A61K 38/22; A61K 47/60; A61P 19/00; A61P 19/02
See application file for complete search history.

(56) References Cited

U.S. PATENT DOCUMENTS

| | | |
|---|---|---|
| 6,833,358 B1 | 12/2004 | Nakata et al. |
| 7,585,837 B2 | 9/2009 | Shechter et al. |
| 8,198,242 B2 | 6/2012 | Wendt et al. |
| 8,377,884 B2 | 2/2013 | Wendt et al. |
| 8,618,124 B2 | 12/2013 | Greenwald et al. |
| 8,703,893 B2 | 4/2014 | Hernandez et al. |
| 8,754,190 B2 | 6/2014 | Ashley et al. |
| 8,946,405 B2 | 2/2015 | Ashley et al. |
| 10,052,366 B2 | 8/2018 | Crine et al. |
| 10,835,578 B2 | 11/2020 | Rau et al. |
| 11,154,593 B2 | 10/2021 | Rau et al. |
| 2003/0068313 A1 | 4/2003 | Nakao |
| 2004/0137557 A1 | 7/2004 | DeFrees et al. |
| 2008/0113027 A1 | 5/2008 | Asgharian et al. |
| 2012/0035101 A1 | 2/2012 | Fares et al. |
| 2012/0276190 A1 | 11/2012 | Fitzgerald et al. |
| 2012/0316114 A1 | 12/2012 | Wendt et al. |
| 2017/0080049 A1 | 3/2017 | Morozumi |
| 2017/0368189 A1 | 12/2017 | Sprogoe et al. |
| 2019/0008977 A1 | 1/2019 | Rau et al. |
| 2019/0015481 A1 | 1/2019 | Rau et al. |
| 2019/0022237 A1 | 1/2019 | Sprogøe et al. |
| 2019/0255183 A1 | 8/2019 | Sprogøe et al. |
| 2019/0328840 A1 | 10/2019 | Sprogøe et al. |
| 2019/0328841 A1 | 10/2019 | Sprogøe et al. |
| 2020/0276270 A1 | 9/2020 | Holton-Anderson et al. |
| 2021/0069339 A1 | 3/2021 | Sprogøe et al. |
| 2021/0077584 A1 | 3/2021 | Rau et al. |
| 2021/0177952 A1 | 6/2021 | Rau et al. |

FOREIGN PATENT DOCUMENTS

| | | |
|---|---|---|
| EP | 1534334 B1 | 6/2014 |
| EP | 2853273 A1 | 4/2015 |
| EP | 3078387 A1 | 10/2016 |
| EP | 3135296 A1 | 3/2017 |
| WO | WO 02/089789 A1 | 11/2002 |
| WO | WO 2004/047871 A2 | 6/2004 |
| WO | WO 2005/099768 A2 | 10/2005 |
| WO | WO 2006/136586 A2 | 12/2006 |
| WO | WO 2008/031045 A2 | 3/2008 |
| WO | WO 2008/034122 A2 | 3/2008 |
| WO | WO 2008/136611 A1 | 11/2008 |
| WO | WO 2008/155134 A1 | 12/2008 |
| WO | WO 2009/009712 A1 | 1/2009 |
| WO | WO 2009/067639 A2 | 5/2009 |
| WO | WO 2009/095479 A2 | 8/2009 |

(Continued)

OTHER PUBLICATIONS

WIPO Application No. PCT/EP2016/050298, PCT International Preliminary Report on Patentability dated Jul. 11, 2017.
Delgado et al., "The Uses and Properties of PEG-Linked Proteins," Critical Re-views in Therapeutic Drug Carrier Systems, , 9(3,4):249-304, (1992).
Furuya et al., "Structural requirements of C-type natriuretic peptide for elevation of cyclic GMP in cultured vascular smooth muscle cells," Biochemical and Biophysical Research Communications, 183(3):964-969, (1992).
U.S. Appl. No. 15/538,641, Non-Final Office Action dated Sep. 6, 2018.

(Continued)

*Primary Examiner* — Marcela M Cordero Garcia
(74) *Attorney, Agent, or Firm* — Alston & Bird LLP

(57) ABSTRACT

The present invention relates to a controlled-release CNP agonist having low NPR-C affinity; to pharmaceutical compositions comprising said controlled-release CNP agonist; their use; and to methods of treatment.

10 Claims, 1 Drawing Sheet
Specification includes a Sequence Listing.

(56) References Cited

FOREIGN PATENT DOCUMENTS

| | | |
|---|---|---|
| WO | WO 2009/143412 A2 | 11/2009 |
| WO | WO 2009/156481 A1 | 12/2009 |
| WO | WO 2010/033217 A1 | 3/2010 |
| WO | WO 2010/091122 A1 | 8/2010 |
| WO | WO 2010/135541 A2 | 11/2010 |
| WO | WO 2011/012722 A1 | 2/2011 |
| WO | WO 2011/075471 A2 | 6/2011 |
| WO | WO 2011/082368 A2 | 7/2011 |
| WO | WO 2011/089214 A1 | 7/2011 |
| WO | WO 2011/089215 A1 | 7/2011 |
| WO | WO 2011/089216 A1 | 7/2011 |
| WO | WO 2011/123813 A2 | 10/2011 |
| WO | WO 2011/144756 A1 | 11/2011 |
| WO | WO 2013/024047 A1 | 2/2013 |
| WO | WO 2013/024048 A1 | 2/2013 |
| WO | WO 2013/024049 A1 | 2/2013 |
| WO | WO 2013/024052 A1 | 2/2013 |
| WO | WO 2013/024053 A1 | 2/2013 |
| WO | WO 2013/036857 A1 | 3/2013 |
| WO | WO 2013/160340 A1 | 10/2013 |
| WO | WO 2015/083582 A1 | 6/2015 |
| WO | WO 2015/129812 A1 | 9/2015 |
| WO | WO 2016/020373 A1 | 2/2016 |
| WO | WO 2016/110577 A1 | 7/2016 |
| WO | WO 2017/100400 A2 | 6/2017 |
| WO | WO 2017/118693 A1 | 7/2017 |
| WO | WO 2017/118698 A1 | 7/2017 |
| WO | WO 2017/118700 A1 | 7/2017 |
| WO | WO 2017/118703 A1 | 7/2017 |
| WO | WO 2017/118704 A1 | 7/2017 |
| WO | WO 2017/118707 A1 | 7/2017 |
| WO | WO 2018/060314 A1 | 4/2018 |
| WO | WO 2020/165081 A1 | 8/2020 |

OTHER PUBLICATIONS

U.S. Appl. No. 16/066,058, Non-Final Office Action dated Dec. 31, 2019.
U.S. Appl. No. 16/067,057, Requirement for Restriction/Election dated Oct. 4, 2019.
U.S. Appl. No. 16/067,057, Final Office Action dated Dec. 2, 2019.
U.S. Appl. No. 16/067,057, Non-Final Office Action dated Jun. 25, 2019.
U.S. Appl. No. 16/067,057, Notice of Allowance dated Apr. 9, 2020.
U.S. Appl. No. 16/067,070, Non-Final Office Action dated Dec. 30, 2019.
U.S. Appl. No. 16/067,095, Requirement for Restriction/Election dated Aug. 21, 2019.
U.S. Appl. No. 16/067,095, Non-Final Office Action dated Mar. 20, 2020.
U.S. Appl. No. 16/067,095, Requirement for Restriction/Election dated Oct. 10, 2019.
U.S. Appl. No. 16/067,111, Non-Final Office Action dated Feb. 5, 2020.
U.S. Appl. No. 16/067,111, Requirement for Restriction/Election dated Aug. 30, 2019.
U.S. Appl. No. 16/269,097, Non-Final Office Action mailed Feb. 5, 2020.
De Plater, et al., "A C-type natriuretic peptide from the venom of the platypus (*Ornithorhynchus anatinus*): Structure and pharmacology," Comparative Biochemistry and Physiology Part C, 120, 99-110, (1998).
Jiang, et al., "Effect of Sialylated O-Glycans in Pro-Brain Natriuretic Peptide Stability," Clin Chem, 56(6): 959-966, (Jun. 2010).
Oefner, et al., "Structure of Human Neutral Endopeptidase (Neprilysin) Complexed with Phosphoramindon," J. Mol. Biol., 296, 341-349, (2000).
Sakaguchi, et al., "Characterisation of C-type natriuretic peptide receptors in the gill of dogfish *Triakis scyllia*," Journal of Endocrinology, 156, 127-124, (1998).
STNext search notes for U.S. Pat. No. 10,052,366, Accession No. 2013:644347, Dated Feb. 11, 2021.
Takano, et al., "Molecular evolution of shark C-type natriuretic peptides," Zoolog Sci, 11 (3):441-454, (1994).
Yampolsky, et al., "The Exchangeability of Amino Acids in Proteins," Genetics, 170: 1459-1472, (Aug. 2005).
U.S. Appl. No. 16/066,058, Non-Final Office Action dated Feb. 23, 2021.
U.S. Appl. No. 16/067,057, Corrected Notice of Allowance mailed Sep. 18, 2020.
U.S. Appl. No. 16/067,057, Notice of Allowance dated Jul. 29, 2020.
U.S. Appl. No. 16/067,070, Final Office Action dated Aug. 28, 2020.
U.S. Appl. No. 16/067,070, Non-Final Office Action dated Jan. 26, 2021.
U.S. Appl. No. 16/067,095, Final Office Action dated Nov. 10, 2020.
U.S. Appl. No. 16/067,111, Final Office Action dated Sep. 17, 2020.
U.S. Appl. No. 16/066,058, Final Office Action dated Aug. 20, 2020.
U.S. Appl. No. 16/067,111, Notice of Allowance dated Feb. 5, 2021.
"BioMarin Announces Decision to Start Phase 3 Program for PEG-PAL in 2Q 2013," BioMarin, Press Release, 3 pages, (2012). [Author Unknown].
"PEG Products," JenKem Technology USA, 7 pages, (2015). [Retrieved from the Internet: <URL: http://www.jenkemusa.com/products>]. [Author Unknown].
Bowie et al., "Deciphering the Message in Protein Sequences: Tolerance to Amino Acid Substitutions," Science, 247:1306-1310, (1990). [Retrieved from the Internet May 18, 2011: <URL: http://www.sciencemag.org >].
Farnum et al., "In vivo Delivery of Fluoresceinated Dextrans to the Murine Growth Plate: Imaging of Three Vascular Routes by Multiphoton Microscopy," Anat Rec A Discov Mol Cell Evol Biol, 288(1):91-103, doi:10.1002/ar.a.20272, (2006).
Igaki et ai., "Effects of Intravenously Administered C-type Natriuretic Peptide in Humans: Comparison with Atrial Natriuretic Peptide," Hypertens Res, 21:7-13, (1998).
Lorget et al., "Evaluation of the Therapeutic Potential of a CNP Analog in a Fgfr3 Mouse Model Recapitulating Achondroplasia," AJHG, 91(6):1108-1114, (2012).
Martz et al., "sFGFR for achondroplasia," SciBX, 6(40), 2 pages, doi:10.1038/scibx.2013.1120,(2013).
Martz et al., "sFGFR for achondroplasia," SciBX, Nature Publishing Group, 2 pages, (2013).
Merrifield, "Solid Phase Peptide Synthesis, I. The Synthesis of a Tetrapeptide," J. Am. Chem. Soc., 85(14):2149-2154, doi: 10.1021/ja00897a025, (1963).
Potter et al., "Natriuretic peptide metabolism, clearance and degradation," FEBS J, 278(11):1808-1817, doi: 10.1111/j.1742-4658.2011.08082.x, (2011).
Samson et al., "C-type natriuretic peptide mediates the hypothalamic actions of the natriuretic peptides to inhibit luteinizing hormone secretion," Endocrinology, 132(2):504-509, doi: 10.1210/END0.132.2.8425472, (1993).
Wang et al., "Effect of liposome-encapsulated C-type natriuretic peptide on vascular response," Database Chemabs, 1 page, Accession No. 1999:790321, (1999).
Wendt et al., "Neutral Endopeptidase-Resistant C-Type Natriuretic Peptide Variant Represents a New Therapeutic Approach for Treatment of Fibroblast Growth Factor Receptor 3-Related Dwarfism," J Pharmacol Exp Ther, 353(1):132-149, (2015).
U.S. Appl. No. 15/538,641, Requirement for Restriction/Election dated Jun. 14, 2018.
WIPO Application No. PCT/EP2016/050298, PCT International Search Report dated Apr. 8, 2017.
WIPO Application No. PCT7EP2016/050298, PCT Written Opinion of the International Searching Authority dated Apr. 8, 2017.
WIPO Application No. PCT/EP2017/050201, PCT International Preliminary Report on Patentability dated Jul. 10, 2018.
WIPO Application No. PCT/EP2017/050201, PCT International Search Report dated Apr. 12, 2017.
WIPO Application No. PCT/EP2017/050201, PCT Written Opinion of the International Searching Authority dated Apr. 12, 2017.

(56) References Cited

OTHER PUBLICATIONS

WIPO Application No. PCT/EP2017/0502091, PCT International Preliminary Reporton Patentability dated Jul. 10, 2018.
WIPO Application No. PCT/EP2017/0502091, PCT Written Opinion of the international Searching Authority dated Apr. 11, 2017.
WIPO Application No. PCT/EP2017/050213, PCT International Preliminary Report on Patentability dated Jul. 10, 2018.
WIPO Application No. PCT/EP2017/050213, PCT International Search Report dated May 11, 2017.
WIPO Application No. PCT/EP2017/050213, PCT Written Opinion of the International Searching Authority dated May 11, 2017.
WIPO Application No. PCT/EP2017/050217, PCT International Preliminary Report on Patentability dated Jul. 10, 2018.
WIPO Application No. PCT/EP2017/050217, PCT International Search Report dated Apr. 4, 2017.
WIPO Application No. PCT/EP2017/050217, PCT Written Opinion of the International Searching Authority dated Apr. 4, 2017.
WIPO Application No. PCT/EP2017/050220, PCT International Preliminary Report on Patentability dated Jul. 10, 2018.
WIPO Application No. PCT/EP2017/050220, PCT International Search Report dated Apr. 10, 2017.
WIPO Application No. PCT/EP2017/050220, PCT Written Opinion of the International Searching Authority dated Apr. 10, 2017.
WIPO Application No. PCT/EP2017/050224, PCT International Preliminary Report on Patentability dated Jul. 10, 2018.
WIPO Application No. PCT/EP2017/050224, PCT International Search Report dated Mar. 23, 2017.
WIPO Application No. PCT/EP2017/050224, PCT Written Opinion of the International Searching Authority dated Mar. 23, 2017.
WIPO Application No. PCT/EP2017/6562691, PCT International Search Report dated Apr. 11, 2017.
NOF America Corporation, Sunbright® CS, GS, AS, HS, TS and PS Series (NHS active esters/Carbonate), retreived from the internet at: www.nofamerica.com/store/index.php?dispatch=categories.view&category_id=7 on Mar. 19, 2021.
U.S. Appl. No. 16/067,095, Non-Final Office Action dated Apr. 5, 2021.
U.S. Appl. No. 16/067,095, Notice of Allowance dated Jul. 28, 2021.
U.S. Appl. No. 16/067,111, Notice of Allowance dated Sep. 1, 2021.
U.S. Appl. No. 16/993,127, Requirement for Restriction/Election dated Jul. 28, 2021.
U.S. Appl. No. 17/005,272, Non-Final Office Action dated Aug. 16, 2021.
U.S. Appl. No. 17/184,561, Non-Final Office Action dated May 3, 2021.
U.S. Appl. No. 17/184,561, Notice of Allowance dated Aug. 18, 2021.
U.S. Appl. No. 16/067,070, Notice of Allowance dated Jun. 3, 2021.
U.S. Appl. No. 16/067,111, Notice of Allowance dated May 12, 2021.
WIPO Application No. PCT/EP2020/053304, PCT International Search Report and Written Opinion of the International Searching Authority dated Aug. 4, 2020.
Ansel, et al., "Drug Dosage and Terminology," Pharmaceutical Dosage Forms and Drug Delivery, Seventh Edition, pp. 48-53, (1999).
Einav, et al., "The hepatitis C virus (HCV) NS4B RNA binding inhibitor clemizole is highly synergistic with HCV protease inhibitors," Journal of Infectious Diseases, 202(1):65-74, (2010).
Molina Clinical Policy, Subject: Recombinant Human Growth Hormone: Pediatric Conditions Without GHD, Policy No. MCP-004-C, 24 pages, (2010).
Ramaswami, et al., "Treatment of Achondroplasia with Growth hormones: Six Year of Experience," Pediatric Research, 22 pages, (1999).
Tallarida, "Quantitative Methods for Assessing Drug Synergism," Genes & Cancer, 2(11) pp. 1003-1008, (2011).
Yamashita, et al., "Statin treatment rescues FGFR3 skeletal dysplasia phenotypes," Nature, 513, 507-511, (2014).
U.S. Appl. No. 16/338,185, Final Office Action dated Apr. 7, 2021.
U.S. Appl. No. 16/338,185, Non-Final Office Action dated Oct. 25, 2021.
U.S. Appl. No. 16/338,185, Non-Final Office Action dated Nov. 18, 2020.
U.S. Appl. No. 16/338,185, Requirement for Restriction/Election dated Jul. 6, 2020.
WIPO Application No. PCT/EP2017/074596, PCT International Preliminary Report on Patentability dated Apr. 2, 2019.
U.S. Appl. No. 16/667,676, Notice of Allowance dated Oct. 18, 2021.
U.S. Appl. No. 16/067,095, Non-Final Office Action dated Nov. 19, 2021.
U.S. Appl. No. 17/184,561, Corrected Notice of Allowance dated Sep. 23, 2021.

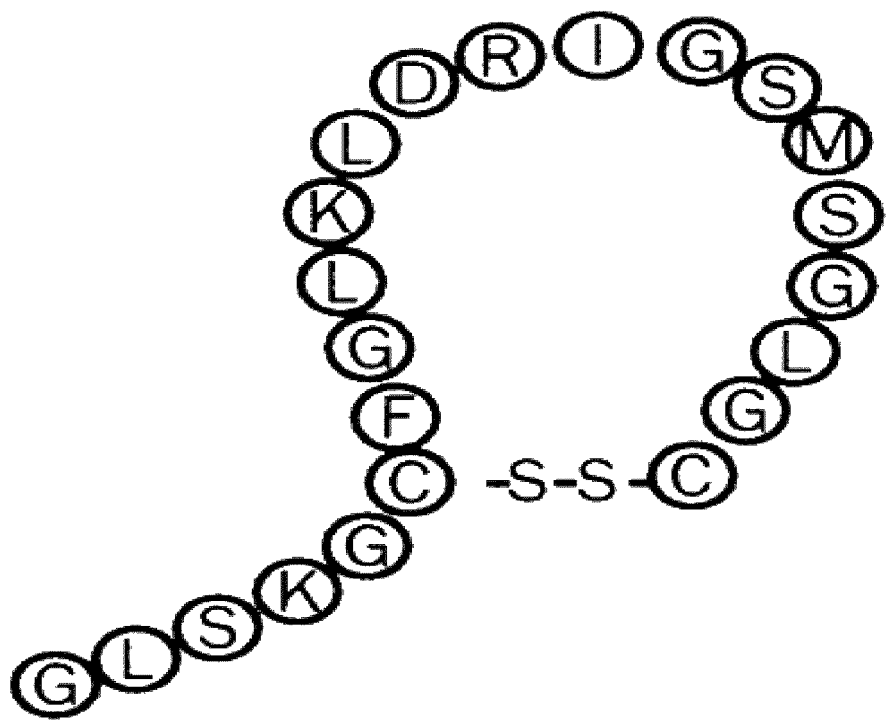

CONTROLLED-RELEASE CNP AGONISTS WITH LOW NPR-C BINDING

CROSS REFERENCE TO RELATED APPLICATIONS

This application is a continuation of U.S. Ser. No. 15/538,641 filed Jun. 21, 2017, which is the US national phase of PCT/EP2016/050298 filed Jan. 8, 2016, incorporated by reference in its entirety for all purposes, which claims priority to EP 15150584.9 filed Jan. 9, 2015 and EP15160457.6 filed Mar. 24, 2015.

REFERENCE TO A SEQUENCE LISTING

This application includes a sequence listing submitted herewith as a text filed named "526321_SEQLIST.txt" created on Feb. 6, 2019, and containing 47,637 bytes. The material contained in this text file is incorporated by reference.

The present invention relates to a controlled-release CNP agonist having low NPR-C affinity; to pharmaceutical compositions comprising said controlled-release CNP agonist; their use; and to methods of treatment.

Achondroplasia (ACH) is caused by a gain-of-function mutation in FGFR3. Binding of CNP to its receptor, natriuretic-peptide receptor B (NPR-B), inhibits FGFR3 downstream signaling and thus triggers endochondral growth and skeletal overgrowth, as observed in both mice and humans overexpressing CNP. Overproduction of CNP in the cartilage or continuous delivery of CNP through intravenous (iv) infusion normalizes the dwarfism of achondroplastic mice, suggesting that administration of CNP at supraphysiological levels is a strategy for treating ACH.

However, given its short half-life (2 min after iv administration) CNP as a therapeutic agent is challenging in a pediatric population because it would require continuous infusion. Furthermore, as CNP is extensively inactivated in the subcutaneous tissue iv infusion is required.

Potter (FEBS Journal 278 (2011) 1808-1817) describes the clearance of CNP to occur by two degradation routes: receptor-mediated degradation and degradation by extracellular proteases. CNP is degraded by the action of neutral endopeptidase 24.11 (NEP) and is removed from systemic circulation by natriuretic peptide clearance receptor, NPR-C, that binds to and deposits CNP into lysosomes, where CNP is degraded.

The NPR-C receptor binds all three natriuretic peptides, ANP, BNP and CNP. NPR-C is a disulfide linked homodimer that is homologous to the extracellular domains of NPR-B and NPR-A, but contains only 37 intracellular amino acids. The majority of physiological data indicate that the primary role of NPR-C is to clear natriuretic peptides from the extracellular environment via a receptor-mediated internalization and degradation process (FEBS Journal 278 (2011) 1808-1817).

It is worth noting that the evolution of a separate receptor to clear peptide signaling molecules from the cardiovascular system is relatively unique to the natriuretic peptide system, because most other peptide signaling molecules, such as angiotensin II, endothelin, and vasopressin, are primarily degraded by extracellular proteases, and the vast majority of insulin is internalized by its cognate tyrosine kinase signaling receptor, not a separate non-tyrosine kinase receptor (FEBS Journal 278 (2011) 1808-1817).

Reduction of binding to the NPR-C receptor represents a unique challenge to develop a controlled-release CNP agonist, and a reduction in receptor-mediated internalization and degradation process would serve to prolong the half-life of CNP.

Increasing exposure to efficacious levels of the natriuretic peptide CNP is challenging. As natriuretic peptides are a family of hormones that may affect blood volume and blood pressure, an increase in dose may be associated with cardiovascular adverse effects. A study in healthy volunteers demonstrated that CNP injection caused a transient but significant decrease in both systolic and diastolic blood pressure with a significant increase in heart rate (Igaki, et al. Hypertens Res 1998; 21: 7-13). Similarly, a CNP variant with increased NEP resistance (BMN-111) in development for the treatment of achondroplasia, has demonstrated mild hypotension in a Phase 1 study in healthy volunteers (BioMarin press release Sep. 26, 2012). Studies of BMN-111 in animals and man have demonstrated that as the dose increases, arterial blood pressure (BP) drops and heart rate (HR) increases.

CNP produces hemodynamic effects in mice, nonhuman primates, rats, dogs, and humans. In order to evaluate the cardiovascular effects of various CNP variants, anesthetized wild-type FVB/nJ male mice were fitted with a pressure monitoring catheter connected to a telemetry transmitter. All variants showed similar BP-reducing and HR-increasing activity. In most animals, effects were observed within 5 minutes of subcutaneous administration, with maximal drop in MAP occurring between 5 and 20 minutes postdose. This timing correlated well with the maximum concentration of the CNP variants, and demonstrated a clear PK/PD relationship for this physiologic response. Because the hemodynamic responses were similar between the doses and variants tested, cardiovascular activity was determined not to be a differentiating property (Wendt et. al. J Pharmacol Exp Ther 353:132-149, April 2015).

In addition to investigating various variants of CNP, different CNP conjugates were obtained by conjugating the CNP moiety to either PEG or proteinaceous compounds. These PEGylated and chimeric CNP exhibited a similar hemodynamic response as observed for the non-PEGylated CNP variants (Wendt, J Pharmacol Exp Ther 353:132-149, April 2015)

As these compounds all result in CNP compounds with significant residual activity, these compounds are subject to receptor-mediated internalization and degradation process by the NPR-C receptor, which limits the achievable half-life extension.

In summary, there is a need for a more efficacious and safer CNP treatment.

It is therefore an object of the present invention to at least partially overcome the shortcomings described above.

This object is achieved with a controlled-release CNP agonist from which CNP agonist is released with a release half-life of at least 6 hours under physiological conditions and which controlled-release CNP agonist has an affinity, as defined by the $IC_{50}$, to the NPR-C receptor that is at least 5-fold higher than the affinity of the corresponding free CNP agonist.

It was surprisingly found that such reversible inactivation of CNP's affinity towards NPR-C allows for extended half-life of the controlled-release CNP agonist providing continuous release of the corresponding free CNP agonist.

It was furthermore surprisingly found that a continuous release of CNP is more efficacious than a once-daily bolus injection, so the continuous release from the controlled-release CNP agonist even further increases efficacy.

Within the present invention the terms are used having the meaning as follows.

As used herein the term "CNP agonist" refers to any compound that activates natriuretic peptide receptor B (NPR-B) and has an $EC_{50}$ with regard to NPR-B that is at most 50-fold higher than the NPR-B activity of CNP-22 (SEQ ID NO:1).

As used herein "$EC_{50}$" with regard to NPR-B refers to the concentration with which a half-maximum cGMP production is elicited. NPR-B activity in the form of its $EC_{50}$ of the controlled-release CNP agonist, of the released CNP agonist and of CNP-22 is measured by cultivating NIH-3T3 (Murine Embryo Fibroblast cell line) cells which express NPR-B on their cell surface, incubating the cells with the controlled-release CNP agonist, the corresponding released CNP agonist or CNP-22, respectively, and determining the intracellular production of the second messenger cGMP with a standard cGMP assay. In particular the assay is performed as follows:
(1) murine NIH-3T3 cells expressing endogenous NPR-B are cultivated in DMEM F-12 medium with 5% FBS and 5 mM glutamine at 37° C. and 5% $CO_2$;
(2) for each assay 50,000 cells are resuspended in Dulbecco's PBS with IBMX and incubated with either the controlled-release CNP agonist, the corresponding released CNP agonist or CNP-22; each in different concentrations;
(3) after incubating for 30 min at 37° C. and 5% $CO_2$, the cells are lysed and cGMP levels are determined; and
(4) generating an $EC_{50}$ value from the determined cGMP levels.

Preferably, the IBMX concentration in step (2) is 0.5 mM.

Step (3) can be performed using any assay for measuring cGMP which is a standard procedure well known to the person skilled in the art. Preferably step (3) is done with a cGMP TR-FRET assay, more preferably with the cGMP TR-FRET assay from Cisbio, Cat. No. 62GM2PEB.

As during such experiments the controlled-release CNP agonist releases a certain amount of CNP agonist which released CNP agonist would distort the results, measurements for the NPR-B activity of the controlled-release CNP agonist are preferably made in the form of a stable analog which does not release CNP agonist.

As used herein "$IC_{50}$" with regard to NPR-C is determined by using a ligand binding competition assay, in which assay the compound for which the $IC_{50}$ with regard to NPR-C binding is to be determined is allowed to bind to NPR-C expressed by cells in tissue culture, which binding is competed away by using a fluorescently-labelled version of said compound and measuring the fluorescence associated with the cells. The $IC_{50}$ with regard to NPR-C is the concentration of the labelled version of the compound for which the $IC_{50}$ with regard to NPR-C binding is to be determined gives a half-maximum fluorescence signal. In particular, the assay is performed as follows:
(1) Growing cells of a Hek293 cell line expressing NPR-C are trypsinized from the cell flask bottom, counted, seeded in a 96-well plate ($1.5 \times 10^5$/well), centrifuged and the supernatants are discarded;
(2) Controlled-release CNP agonist and released CNP agonist are serially diluted in dilution buffer and transferred to the micro plate and mixed with cells.
(3) After incubation at room temperature, fluorescence-labelled version of said compound is added to each well with a constant concentration and cells are incubated for additional 45 min at room temperature.
(4) Cells are analyzed by flow cytometry using mean fluorescence intensity of the FITC channel (FL1, Beckman Coulter FC500MPL) as read out.
(5) Standard curve and sample curve are generated in an analysis software (PLA 2.0) using a 4PL fit for potency and/or $IC_{50}$ calculation.

Preferably, the dilution buffer is PBS containing 0.2% BSA

The NPR-C expressing Hek293 cell line can be developed as follows: The coding region of the NPR-C reference sequence (BC131540) is cloned into a lentiviral vector under a CMV promoter for constitutive receptor expression. A bicistronic element located on the vector for puromycin resistance is used as eukaryotic selection marker. After transduction, stably growing cell pools are subjected to qRT-PCR for confirmation of receptor mRNA-expression compared to parental Hek293 cells.

As used herein the term "controlled-release CNP agonist" refers to any compound, conjugate, crystal or admixture that comprises at least one CNP agonist and from which the at least one CNP agonist is released with a release half-life of at least 6 hours.

As used herein the term "CNP agonist equivalent" refers to molar content of CNP agonist comprised in a controlled-release CNP agonist.

As used herein the term "release half-life" refers to the time needed until half of all CNP agonist molecules are released from the controlled-release CNP agonist under physiological conditions.

As used herein the term "CNP" refers to all CNP polypeptides, preferably from mammalian species, more preferably from human and mammalian species, more preferably from human and murine species, as well as their variants, analogs, orthologs, homologs, and derivatives and fragments thereof, that are characterized by regulating the growth, proliferation and differentiation of cartilaginous growth plate chondrocytes. Preferably, the term "CNP" refers to the CNP polypeptide of SEQ ID NO:24 as well as its variants, homologs and derivatives exhibiting essentially the same biological activity, i.e. regulating the growth, proliferation and differentiation of cartilaginous growth plate chondrocytes. More preferably, the term "CNP" refers to the polypeptide of SEQ ID NO:24. In another preferred embodiment the term "CNP" refers to the polypeptide of SEQ ID NO:20. In another preferred embodiment the term "CNP" refers to the polypeptide of SEQ ID NO:21. In another preferred embodiment the term "CNP" refers to the polypeptide of SEQ ID NO:22. In another preferred embodiment the term "CNP" refers to the polypeptide of SEQ ID NO:23. In another preferred embodiment the term "CNP" refers to the polypeptide of SEQ ID NO:30.

Naturally occurring CNP-22 (SEQ ID NO:1) has the following sequence:

GLSKGCFGLKLDRIGSMSGLGC, wherein the cysteines at position 6 and 22 are connected through a disulfide-bridge, as illustrated in FIG. 1.

SEQ ID NO:24 has the following sequence:

LQEHPNARKYKGANKKGLSKGCFGLKLDRIGSMSGLGC, wherein the cysteines at position 22 and 38 are connected through a disulfide-bride.

The term "CNP" also includes all CNP variants, analogs, orthologs, homologs and derivatives and fragments thereof as disclosed in WO 2009/067639 A2 and WO 2010/135541 A2, which are herewith incorporated by reference.

Accordingly, the term "CNP" also refers preferably to the following peptide sequences:

SEQ ID NO: 2 (CNP-53):
DLRVDTKSRAAWARLLQEHPNARKYKGANKKGLSKGCFGLKLDRIGSMSGLGC;

SEQ ID NO: 3 (G-CNP-53):
GDLRVDTKSRAAWARLLQEHPNARKYKGANKKGLSKGCFGLKLDRIGSMSGLGC;

SEQ ID NO: 4 (M-CNP-53):
MDLRVDTKSRAAWARLLQEHPNARKYKGANKKGLSKGCFGLKLDRIGSMSGLGC;

SEQ ID NO: 5 (P-CNP-53):
PDLRVDTKSRAAWARLLQEHPNARKYKGANKKGLSKGCFGLKLDRIGSMSGLGC;

SEQ ID NO: 6 (CNP-53 M48N):
DLRVDTKSRAAWARLLQEHPNARKYKGANKKGLSKGCFGLKLDRIGSNSGLGC;

SEQ ID NO: 7 (CNP-53 Δ15-31):
DLRVDTKSRAAWARGLSKGCFGLKLDRIGSMSGLGC;

SEQ ID NO: 8 (CNP-52):
LRVDTKSRAAWARLLQEHPNARKYKGANKKGLSKGCFGLKLDRIGSMSGLGC;

SEQ ID NO: 9 (CNP-51):
RVDTKSRAAWARLLQEHPNARKYKGANKKGLSKGCFGLKLDRIGSMSGLGC;

SEQ ID NO: 10 (CNP-50):
VDTKSRAAWARLLQEHPNARKYKGANKKGLSKGCFGLKLDRIGSMSGLGC;

SEQ ID NO: 11 (CNP-49):
DTKSRAAWARLLQEHPNARKYKGANKKGLSKGCFGLKLDRIGSMSGLGC;

SEQ ID NO: 12 (CNP-48):
TKSRAAWARLLQEHPNARKYKGANKKGLSKGCFGLKLDRIGSMSGLGC;

SEQ ID NO: 13 (CNP-47):
KSRAAWARLLQEHPNARKYKGANKKGLSKGCFGLKLDRIGSMSGLGC;

SEQ ID NO: 14 (CNP-46):
SRAAWARLLQEHPNARKYKGANKKGLSKGCFGLKLDRIGSMSGLGC;

SEQ ID NO: 15 (CNP-45):
RAAWARLLQEHPNARKYKGANKKGLSKGCFGLKLDRIGSMSGLGC;

SEQ ID NO: 16 (CNP-44):
AAWARLLQEHPNARKYKGANKKGLSKGCFGLKLDRIGSMSGLGC;

SEQ ID NO: 17 (CNP-44 Δ14-22):
AAWARLLQEHPNAGLSKGCFGLKLDRIGSMSGLGC;

SEQ ID NO: 18 (CNP-44 Δ15-22):
AAWARLLQEHPNARGLSKGCFGLKLDRIGSMSGLGC;

SEQ ID NO: 19 (CNP-43):
AWARLLQEHPNARKYKGANKKGLSKGCFGLKLDRIGSMSGLGC;

SEQ ID NO: 20 (CNP-42):
WARLLQEHPNARKYKGANKKGLSKGCFGLKLDRIGSMSGLGC;

SEQ ID NO: 21 (CNP-41):
ARLLQEHPNARKYKGANKKGLSKGCFGLKLDRIGSMSGLGC;

SEQ ID NO: 22 (CNP-40):
RLLQEHPNARKYKGANKKGLSKGCFGLKLDRIGSMSGLGC;

SEQ ID NO: 23 (CNP-39):
LLQEHPNARKYKGANKKGLSKGCFGLKLDRIGSMSGLGC;

SEQ ID NO: 24 (CNP-38):
LQEHPNARKYKGANKKGLSKGCFGLKLDRIGSMSGLGC;

SEQ ID NO: 25 (CNP-37):
QEHPNARKYKGANKKGLSKGCFGLKLDRIGSMSGLGC;

SEQ ID NO: 26 (CNP-37 Q1pQ, wherein pQ = pyroglutamate):
pQEHPNARKYKGANKKGLSKGCFGLKLDRIGSMSGLGC;

SEQ ID NO: 27 (G-CNP-37):
GQEHPNARKYKGANKKGLSKGCFGLKLDRIGSMSGLGC;

SEQ ID NO: 28 (P-CNP-37):
PQEHPNARKYKGANKKGLSKGCFGLKLDRIGSMSGLGC;

SEQ ID NO: 29 (M-CNP-37):
MQEHPNARKYKGANKKGLSKGCFGLKLDRIGSMSGLGC;

SEQ ID NO: 30 (PG-CNP-37):
PGQEHPNARKYKGANKKGLSKGCFGLKLDRIGSMSGLGC;

SEQ ID NO: 31 (MG-CNP-37):
MGQEHPNARKYKGANKKGLSKGCFGLKLDRIGSMSGLGC;

SEQ ID NO: 32 (CNP-37 M32N):
QEHPNARKYKGANKKGLSKGCFGLKLDRIGSNSGLGC;

SEQ ID NO: 33 (G-CNP-37 M32N):
GQEHPNARKYKGANKKGLSKGCFGLKLDRIGSNSGLGC;

SEQ ID NO: 34 (G-CNP-37 K14Q):
GQEHPNARKYKGANQKGLSKGCFGLKLDRIGSMSGLGC;

SEQ ID NO: 35 (G-CNP-37 K14P):
GQEHPNARKYKGANPKGLSKGCFGLKLDRIGSMSGLGC;

SEQ ID NO: 36 (G-CNP-37 K14Q, Δ15):
GQEHPNARKYKGANQGLSKGCFGLKLDRIGSMSGLGC;

SEQ ID NO: 37 (G-CNP-37 K14Q, K15Q):
GQEHPNARKYKGANQQGLSKGCFGLKLDRIGSMSGLGC;

SEQ ID NO: 38 (CNP-36):
EHPNARKYKGANKKGLSKGCFGLKLDRIGSMSGLGC;

SEQ ID NO: 39 (CNP-35):
HPNARKYKGANKKGLSKGCFGLKLDRIGSMSGLGC;

SEQ ID NO: 40 (CNP-34):
PNARKYKGANKKGLSKGCFGLKLDRIGSMSGLGC;

SEQ ID NO: 41 (CNP-33):
NARKYKGANKKGLSKGCFGLKLDRIGSMSGLGC;

SEQ ID NO: 42 (CNP-32):
ARKYKGANKKGLSKGCFGLKLDRIGSMSGLGC;

SEQ ID NO: 43 (CNP-31):
RKYKGANKKGLSKGCFGLKLDRIGSMSGLGC;

SEQ ID NO: 44 (CNP-30):
KYKGANKKGLSKGCFGLKLDRIGSMSGLGC;

SEQ ID NO: 45 (CNP-29):
YKGANKKGLSKGCFGLKLDRIGSMSGLGC;

SEQ ID NO: 46 (CNP-28):
KGANKKGLSKGCFGLKLDRIGSMSGLGC;

SEQ ID NO: 47 (GHKSEVAHRF-CNP-28):
GHKSEVAHRFKGANKKGLSKGCFGLKLDRIGSMSGLGC;

SEQ ID NO: 48 (CNP-27):
GANKKGLSKGCFGLKLDRIGSMSGLGC;

SEQ ID NO: 49 (CNP-27 K4Q, K5Q):
GANQQGLSKGCFGLKLDRIGSMSGLGC;

SEQ ID NO: 50 (CNP-27 K4R, K5R):
GANRRGLSKGCFGLKLDRIGSMSGLGC;

SEQ ID NO: 51 (CNP-27 K4P, K5R):
GANPRGLSKGCFGLKLDRIGSMSGLGC;

SEQ ID NO: 52 (CNP-27 K4S, K5S):
GANSSGLSKGCFGLKLDRIGSMSGLGC;

SEQ ID NO: 53 (CNP-27 K4P, K5R):
GANGANPRGLSRGCFGLKLDRIGSMSGLGC;

SEQ ID NO: 54 (CNP-27 K4R, K5R, K9R):
GANRRGLSRGCFGLKLDRIGSMSGLGC;

SEQ ID NO: 55 (CNP-27 K4R, K5R, K9R, M22N):
GANRRGLSRGCFGLKLDRIGSNSGLGC;

SEQ ID NO: 56 (P-CNP-27 K4R, K5R, K9R):
PGANRRGLSRGCFGLKLDRIGSMSGLGC;

SEQ ID NO: 57 (M-CNP-27 K4R, K5R, K9R):
MGANRRGLSRGCFGLKLDRIGSMSGLGC;

SEQ ID NO: 58 (HSA fragment-CNP-27):
GHKSEVAHRFKGANKKGLSKGCFGLKLDRIGSMSGLG;

SEQ ID NO: 59 (HSA fragment-CNP-27 M22N):
GHKSEVAHRFKGANKKGLSKGCFGLKLDRIGSNSGLGC;

SEQ ID NO: 60 (M-HSA fragment-CNP-27):
MGHKSEVAHRFKGANKKGLSKGCFGLKLDRIGSMSGLGC;

SEQ ID NO: 61 (P-HSA fragment-CNP-27):
PGHKSEVAHRFKGANKKGLSKGCFGLKLDRIGSMSGLGC;

SEQ ID NO: 62 (CNP-26):
ANKKGLSKGCFGLKLDRIGSMSGLGC;

SEQ ID NO: 63 (CNP-25):
NKKGLSKGCFGLKLDRIGSMSGLGC;

SEQ ID NO: 64 (CNP-24):
KKGLSKGCFGLKLDRIGSMSGLGC;

SEQ ID NO: 65 (CNP-23):
KGLSKGCFGLKLDRIGSMSGLGC;

SEQ ID NO: 66 (R-CNP-22):
RGLSKGCFGLKLDRIGSMSGLGC;

SEQ ID NO: 67 (ER-CNP-22):
ERGLSKGCFGLKLDRIGSMSGLGC;

SEQ ID NO: 68 (R-CNP-22 K4R):
RGLSRGCFGLKLDRIGSMSGLGC;

SEQ ID NO: 69 (ER-CNP-22 4KR):
ERGLSRGCFGLKLDRIGSMSGLGC;

SEQ ID NO: 70 (RR-CNP-22):
RRGLSRGCFGLKLDRIGSMSGLGC;

SEQ ID NO: 71 (HRGP fragment-CNP-22):
GHHSHEQHPHGANQQGLSKGCFGLKLDRIGSMSGLGC;

SEQ ID NO: 72 (HRGP fragment-CNP-22):
GAHHPHEHDTHGANQQGLSKGCFGLKLDRIGSMSGLGC;

SEQ ID NO: 73 (HRGP fragment-CNP-22):
GHHSHEQHPHGANPRGLSKGCFGLKLDRIGSMSGLGC;

SEQ ID NO: 74 (IgG$_1$(F$_c$) fragment-CNP-22):
GQPREPQVYTLPPSGLSKGCFGLKLDRIGSMSGLGC;

SEQ ID NO: 75 (HSA fragment-CNP-22):
GQHKDDNPNLPRGANPRGLSKGCFGLKLDRIGSMSGLGC;

SEQ ID NO: 76 (HSA fragment-CNP-22):
GERAFKAWAVARLSQGLSKGCFGLKLDRIGSMSGLGC;

SEQ ID NO: 77 (osteocrin NPR C inhibitor
fragment-CNP22):
FGIPMDRIGRNPRGLSKGCFGLKLDRIGSMSGLGC;

SEQ ID NO: 78 (FGF2 heparin-binding domain
fragment-CNP22):
GKRTGQYKLGSKTGPGPKGLSKGCFGLKLDRIGSMSGLGC;

SEQ ID NO: 79 (IgG$_1$(F$_c$) fragment-CNP-22 K4R):
GQPREPQVYTGANQQGLSRGCFGLKLDRIGSMSGLGC;

SEQ ID NO: 80 (HSA fragment-CNP-22 K4R):
GVPQVSTSTGANQQGLSRGCFGLKLDRIGSMSGLGC;

SEQ ID NO: 81 (fibronectin fragment-CNP-22 K4R):
GQPSSSQSTGANQQGLSRGCFGLKLDRIGSMSGLGC;

SEQ ID NO: 82 (fibronectin fragment-CNP-22 K4R):
GQTHSSGTQSGANQQGLSRGCFGLKLDRIGSMSGLGC;

SEQ ID NO: 83 (fibronectin fragment-CNP-22 K4R):
GSTGQWHSESGANQQGLSRGCFGLKLDRIGSMSGLGC;

SEQ ID NO: 84 (zinc finger fragment-CNP-22 K4R):
GSSSSSSSSSGANQQGLSRGCFGLKLDRIGSMSGLGC;

SEQ ID NO: 85 (CNP-21):
LSKGCFGLKLDRIGSMSGLGC;

SEQ ID NO: 86 (CNP-20):
SKGCFGLKLDRIGSMSGLGC;

SEQ ID NO: 87 (CNP-19):
KGCFGLKLDRIGSMSGLGC;

SEQ ID NO: 88 (CNP-18):
GCFGLKLDRIGSMSGLGC;

SEQ ID NO: 89 (CNP-17):
CFGLKLDRIGSMSGLGC;

SEQ ID NO: 90 (BNP fragment-CNP-17-BNP fragment):
SPKMVQGSGCFGLKLDRIGSMSGLGCKVLRRH;

SEQ ID NO: 91 (CNP-38 L1G):
GQEHPNARKYKGANKKGLSKGCFGLKLDRIGSMSGLGC;

SEQ ID NO: 92 (Ac-CNP-37; wherein Ac = acetyl):
Ac-QEHPNARKYKGANKKGLSKGCFGLKLDRIGSMSGLGC.

It is understood that the equivalents of the cysteines in positions 22 and 38 of SEQ ID NO:24 are also connected through a disulfide-bridge in SEQ ID NOs: 2 to 92.

More preferably, the term "CNP" refers to the sequence of SEQ ID NOs 2, 19, 20, 21, 22, 23, 24, 25, 26, 30, 32, 38, 39, 40, 41, 42, 43, 91, 92. Even more preferably, the term "CNP" refers to the sequence of SEQ ID NOs 23, 24, 25, 26, 38, 39, 91 and 92. In a particularly preferred embodiment the term "CNP" refers to the sequence of SEQ ID NO:24.

In another preferred embodiment the term "CNP" refers to a sequence of SEQ ID NO:93 QEHPNARX$_1$YX$_2$GANX$_3$X$_4$GLSX$_5$GCFGLX$_6$LDR IGSMSGLGC,
wherein $X_1$, $X_2$, $X_3$, $X_4$, $X_5$ and $X_6$ are independently of each other selected from the group consisting of K, R, P, S and Q, with the provision that at least one of $X_1$, $X_2$, $X_3$, $X_4$, $X_5$ and $X_6$ is selected from the group consisting of R, P, S and Q; preferably $X_1$, $X_2$, $X_3$, $X_4$, $X_5$ and $X_6$ are selected from the group consisting of K and R, with the provision that at least one of $X_1$, $X_2$, $X_3$, $X_4$, $X_5$ and $X_6$ is R;
even more preferably to a sequence of SEQ ID NO:94 QEHPNARKYKGANX$_1$X$_2$GLSX$_3$GCFGLX$_4$LDR IGSMSGLGC,
wherein $X_1$, $X_2$, $X_3$ and $X_4$ are independently of each other selected from the group consisting of K, R, P, S and Q, with the provision that at least one of $X_1$, $X_2$, $X_3$ and $X_4$ is selected from the group consisting of R, P, S and Q; preferably $X_1$, $X_2$, $X_3$ and $X_4$ are selected from K and R, with the provision that at least one of $X_1$, $X_2$, $X_3$ and $X_4$ is R;

and most preferably to a sequence of SEQ ID NO:95 QEHPNARKYKGANX$_1$X$_2$GLSKGCFGLKLDRIGSMSGLGC, wherein $X_1X_2$ are selected from the group consisting of KR, RK, KP, PK, SS, RS, SR, QK, QR, KQ, RQ, RR and QQ.

It is understood that in all CNP sequences given in this specification the equivalents of the cysteines in positions 22 and 38 of SEQ ID NO:24 are also connected through a disulfide-bridge in SEQ ID NOs: 93 to 95.

It is understood that the present invention also encompasses CNP variants in which any one or more, up to all, residues susceptible to deamidation or a deamidation-like reaction (e.g., isomerization) may be converted to other residue(s) via deamidation or a deamidation-like reaction to any extent, up to 100% conversion per converted residue. In certain embodiments, the disclosure encompasses CNP variants in which:

(1) any one or more, up to all, asparagine (Asn/N) residues may be converted to aspartic acid or aspartate, and/or to isoaspartic acid or isoaspartate, via deamidation up to about 5%, 10%, 20%, 30%, 40%, 50%, 60%, 70%, 80%, 90% or 100% conversion per converted residue; or (2) any one or more, up to all, glutamine (Gln/Q) residues may be converted to glutamic acid or glutamate, and/or to isoglutamic acid or isoglutamate, via deamidation up to about 5%, 10%, 20%, 30%, 40%, 50%, 60%, 70%, 80%, 90% or 100% conversion per converted residue; or (3) any one or more, up to all, aspartic acid or aspartate (Asp/D) residues may be converted to isoaspartic acid or isoaspartate via a deamidation-like reaction (also called isomerization) up to about 5%, 10%, 20%, 30%, 40%, 50%, 60%, 70%, 80%, 90% or 100% conversion per converted residue; or (4) any one or more, up to all, glutamic acid or glutamate (Glu/E) residues may be converted to isoglutamic acid or isoglutamate via a deamidation-like reaction (also called isomerization) up to about 5%, 10%, 20%, 30%, 40%, 50%, 60%, 70%, 80%, 90% or 100% conversion per converted residue; or (5) the N-terminal glutamine (if present) may be converted into pyroglutamate up to about 5%, 10%, 20%, 30%, 40%, 50%, 60%, 70%, 80%, 90% or 100% conversion; or (6) a combination of the above.

FIG. 1 shows CNP-22 (SEQ ID NO:1) with cysteines connected by a disulfide bridge.

As used herein, the term "CNP polypeptide variant" refers to a polypeptide from the same species that differs from a reference CNP polypeptide. Preferably, such reference CNP polypeptide sequence is the sequence of SEQ ID NO:24. Generally, differences are limited so that the amino acid sequence of the reference and the variant are closely similar overall and, in many regions, identical. Preferably, CNP polypeptide variants are at least 70%, 80%, 90%, or 95% identical to a reference CNP polypeptide, preferably the CNP polypeptide of SEQ ID NO:24. By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. These alterations of the reference sequence may occur at the amino (N-terminal) or carboxy terminal (C-terminal) positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein. Preferably, the query sequence is the sequence of SEQ ID NO:24.

Such CNP polypeptide variants may be naturally occurring variants, such as naturally occurring allelic variants encoded by one of several alternate forms of a CNP occupying a given locus on a chromosome or an organism, or isoforms encoded by naturally occurring splice variants originating from a single primary transcript. Alternatively, a CNP polypeptide variant may be a variant that is not known to occur naturally and that can be made by mutagenesis techniques known in the art.

It is known in the art that one or more amino acids may be deleted from the N-terminus or C-terminus of a bioactive peptide or protein without substantial loss of biological function. Such N- and/or C-terminal deletions are also encompassed by the term CNP polypeptide variant.

It is also recognized by one of ordinary skill in the art that some amino acid sequences of CNP polypeptides can be varied without significant effect of the structure or function of the peptide. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, which is hereby incorporated by reference in its entirety, wherein the authors indicate that there are two main approaches for studying the tolerance of the amino acid sequence to change.

The term CNP polypeptide also encompasses all CNP polypeptides encoded by CNP analogs, orthologs, and/or species homologs. As used herein, the term "CNP analog" refers to CNP of different and unrelated organisms which perform the same functions in each organism, but which did not originate from an ancestral structure that the organisms' ancestors had in common. Instead, analogous CNPs arose separately and then later evolved to perform the same or similar functions. In other words, analogous CNP polypeptides are polypeptides with quite different amino acid sequences but that perform the same biological activity, namely regulating the growth, proliferation and differentiation of cartilaginous growth plate chondrocytes.

As used herein the term "CNP ortholog" refers to CNP within two different species which sequences are related to each other via a common homologous CNP in an ancestral species, but which have evolved to become different from each other.

As used herein, the term "CNP homolog" refers to CNP of different organisms which perform the same functions in each organism and which originate from an ancestral structure that the organisms' ancestors had in common. In other words, homologous CNP polypeptides are polypeptides with quite similar amino acid sequences that perform the same biological activity, namely regulating the growth, proliferation and differentiation of cartilaginous growth plate chondrocytes. Preferably, CNP polypeptide homologs may be defined as polypeptides exhibiting at least 40%, 50%, 60%, 70%, 80%, 90% or 95% identity to a reference CNP polypeptide, preferably the CNP polypeptide of SEQ ID NO:24.

Thus, a CNP polypeptide according to the invention may be, for example: (i) one in which at least one of the amino acid residues is substituted with a conserved or non-conserved amino acid residue, preferably a conserved amino acid residue, and such substituted amino acid residue may or may not be one encoded by the genetic code; and/or (ii) one in which at least one of the amino acid residues includes a substituent group; and/or (iii) one in which the CNP polypeptide is fused with another compound, such as a compound to increase the half-life of the polypeptide (for example, polyethylene glycol); and/or (iv) one in which additional amino acids are fused to the CNP polypeptide, such as an IgG Fc fusion region peptide or leader or secretory sequence or a sequence which is employed for purification of the above form of the polypeptide or a pre-protein sequence.

As used herein, the term "CNP polypeptide fragment" refers to any peptide comprising a contiguous span of a part of the amino acid sequence of a CNP polypeptide, preferably the polypeptide of SEQ ID NO:24.

More specifically, a CNP polypeptide fragment comprises at least 6, such as at least 8, at least 10 or at least 17 consecutive amino acids of a CNP polypeptide, more preferably of the polypeptide of SEQ ID NO:24. A CNP polypeptide fragment may additionally be described as subgenuses of CNP polypeptides comprising at least 6 amino acids, wherein "at least 6" is defined as any integer between 6 and the integer representing the C-terminal amino acid of a CNP polypeptide, preferably of the polypeptide of SEQ ID No:24. Further included are species of CNP polypeptide fragments at least 6 amino acids in length, as described above, that are further specified in terms of their N-terminal and C-terminal positions. Also encompassed by the term "CNP polypeptide fragment" as individual species are all CNP polypeptide fragments, at least 6 amino acids in length, as described above, that may be particularly specified by a N-terminal and C-terminal position. That is, every combination of a N-terminal and C-terminal position that a fragment at least 6 contiguous amino acid residues in length could occupy, on any given amino acid sequence of a CNP polypeptide, preferably the CNP polypeptide of SEQ ID:NO24 is included in the present invention.

The term "CNP" also includes poly(amino acid) conjugates which have a sequence as described above, but having a backbone that comprises both amide and non-amide linkages, such as ester linkages, like for example depsipeptides. Depsipeptides are chains of amino acid residues in which the backbone comprises both amide (peptide) and ester bonds. Accordingly, the term "side chain" as used herein refers either to the moiety attached to the alpha-carbon of an amino acid moiety, if the amino acid moiety is connected through amine bonds such as in polypeptides, or to any carbon atom-comprising moiety attached to the backbone of a poly(amino acid) conjugate, such as for example in the case of depsipeptides. Preferably, the term "CNP" refers to polypeptides having a backbone formed through amide (peptide) bonds.

As the term CNP includes the above-described variants, analogs, orthologs, homologs, derivatives and fragments of CNP, all references to specific positions within a reference sequence also include the equivalent positions in the variants, analogs, orthologs, homologs, derivatives and fragments of a CNP moiety, even if not specifically mentioned.

As used herein, the term "ring moiety" refers to the stretch of consecutive amino acid residues of the CNP drug or moiety that is located between two cysteine residues that form an intramolecular disulfide bridge or between homologous amino acid residues which are connected through a chemical linker. Preferably, the ring moiety is located between two cysteine residues that form an intramolecular disulfide bridge. These two cysteines correspond to the cysteines at position 22 and position 38 in the sequence of CNP-38 (SEQ ID NO:24). Accordingly, amino acids 23 to 37 are located in said ring moiety, if the CNP drug or moiety has the sequence of CNP-38.

Independently of the length of the CNP moiety, the sequence of the ring moiety of wild-type CNP is FGLKLDRIGSMSGLG (SEQ ID NO:96).

As described above, the term "CNP" relates to CNP drugs or moieties having different numbers of amino acids. The person skilled in the art understands that in CNP drugs or moieties of different lengths the positions of equivalent amino acids vary and the skilled artisan will have no difficulty identifying the two cysteines forming the disulfide bridge or their two homologous amino acid residues connected to each other through a chemical linker in longer, shorter and/or otherwise modified CNP versions.

As the term CNP includes the above-described variants, analogs, orthologs, homologs, derivatives and fragments of CNP, the term "ring moiety" also includes the corresponding variants, analogs, orthologs, homologs, derivatives and fragments of the sequence of SEQ ID NO:96. Accordingly, all references to specific positions within a reference sequence also include the equivalent positions in variants, analogs, orthologs, homologs, derivatives and fragments of a CNP moiety, even if not explicitly mentioned.

As used herein, the term "random coil" refers to a peptide or protein adopting/having/forming, preferably having, a conformation which substantially lacks a defined secondary and tertiary structure as determined by circular dichroism spectroscopy performed in aqueous buffer at ambient temperature, and pH 7.4. Preferably, ambient temperature is about 20° C., i.e. between 18° C. and 22° C., most preferably ambient temperature is 20° C.

As used herein the term "micelle" means an aggregate of amphiphilic molecules dispersed in a liquid colloid. In aqueous solution a typical micelle forms an aggregate with the hydrophilic moiety of the surfactant molecules facing the surrounding solvent and the hydrophobic moiety of the surfactant molecule facing inwards, also called "normal-phase micelle". "Invers micelles" have the hydrophilic moiety facing inwards and the hydrophobic moiety facing the surrounding solvent.

As used herein the term "liposome" refers to a vesicle, preferably a spherical vesicle, having at least one lipid bilayer. Preferably, liposomes comprise phospholipids, even more preferably phosphatidylcholine. The term "liposome" refers to various structures and sizes, such as, for example, to multilamellar liposome vesicles (MLV) having more than one concentric lipid bilayer with an average diameter of 100 to 1000 nm, small unilamellar liposome vesicles (SUV) having one lipid bilayer and an average diameter of 25 to 100 nm, large unilamellar liposome vesicles (LUV) having one lipid bilayer and an average diameter of about 1000 μm and giant unilamellar vesicles (GUV) having one lipid bilayer and an average diameter of 1 to 100 μm. The term "liposome" also includes elastic vesicles such as transferosomes and ethosomes, for example.

As used herein the term "aquasome" refers to spherical nanoparticles having a diameter of 60 to 300 nm that comprise at least three layers of self-assembled structure, namely a solid phase nanocrystalline core coated with an oligomeric film to which drug molecules are adsorbed with or without modification of the drug.

As used herein the term "ethosome" refers to lipid vesicles comprising phospholipids and ethanol and/or isopropanol in relatively high concentration and water, having a size ranging from tens of nanometers to micrometers.

As used herein the term "LeciPlex" refers to positively charged phospholipid-based vesicular system which comprises soy PC, a cationic agent, and a bio-compatible solvent like PEG 300, PEG 400, diethylene glycol monoethyl ether, tetrahydrofurfuryl alcohol polyethylene glycol ether or 2-pyrrolidone or N-methyl-2-pyrrolidone.

As used herein the term "niosome" refers to unilamellar or multilamellar vesicles comprising non-ionic surfactants.

As used herein the term "pharmacosome" refers to ultrafine vesicular, micellar or hexagonal aggregates from lipids covalently bound to biologically active moieties.

As used herein the term "proniosome" refers to dry formulations of surfactant-coated carrier which on rehydration and mild agitation gives niosomes.

As used herein the term "polymersome" refers to an artificial spherical vesicle comprising a membrane formed from amphiphilic synthetic block copolymers and may optionally comprise an aqueous solution in its core. A polymersome has a diameter ranging from 50 nm to 5 µm and larger. The term also includes syntosomes, which are polymersomes engineered to comprise channels that allow certain chemicals to pass through the membrane into or out of the vesicle.

As used herein the term "sphingosome" refers to a concentric, bilayered vesicle in which an aqueous volume is entirely enclosed by a membranous lipid bilayer mainly composed of natural or synthetic sphingolipid.

As used herein the term "transferosome" refers to ultraflexible lipid vesicles comprising an aqueous core that are formed from a mixture of common polar and suitable edge-activated lipids which facilitate the formation of highly curved bilayers which render the transferosome highly deformable.

As used herein the term "ufasome" refers to a vesicle comprising unsaturated fatty acids.

As used herein the term "aptamer" refers to an oligonucleotide or peptide molecule that binds a specific molecule. The term "aptamer" includes DNA, RNA, XNA and peptide aptamers.

As used herein, the term "oligonucleotide" refers to a short nucleic acid polymer of up to 100 bases.

As used herein the term "polypeptide" refers to a peptide comprising up to and including 50 amino acid monomers. Only for CNP drugs and CNP moieties also sequences having more than 50 amino acids will be referred to as "polypeptide" for simplification.

As used herein the term "protein" refers to a peptide of more than 50 amino acid residues. Preferably a protein comprises at most 20000 amino acid residues, such as at most 15000 amino acid residues, such as at most 10000 amino acid residues, such as at most 5000 amino acid residues, such as at most 4000 amino acid residues, such as at most 3000 amino acid residues, such as at most 2000 amino acid residues, such as at most 1000 amino acid residues.

As used herein the terms "small molecule drug" and "small molecule biologically active moiety" refer to drugs and biologically active moieties that are organic compounds having a molecular weight of no more than 1 kDa, such as up to 900 kDa.

As used herein the term "natural product" refers to purified organic compounds isolated from natural sources that are produced by the pathways of primary or secondary metabolism.

As used herein the term "physiological conditions" refers to an aqueous buffer at pH 7.4, 37° C.

As used herein the term "pharmaceutical composition" refers to a composition containing one or more active ingredients, such as for example the controlled-release CNP agonists of the present invention, and one or more excipients, as well as any product which results, directly or indirectly, from combination, complexation or aggregation of any two or more of the ingredients of the composition, or from dissociation of one or more of the ingredients, or from other types of reactions or interactions of one or more of the ingredients. Accordingly, the pharmaceutical compositions of the present invention encompass any composition made by admixing one or more controlled-release CNP agonists of the present invention and a pharmaceutically acceptable excipient.

As used herein the term "liquid composition" refers to a mixture comprising water-soluble controlled-release CNP agonist and one or more solvents, such as water.

The term "suspension composition" relates to a mixture comprising water-insoluble controlled-release CNP agonist and one or more solvents, such as water.

As used herein, the term "dry composition" means that a pharmaceutical composition is provided in a dry form. Suitable methods for drying are spray-drying and lyophilization, i.e. freeze-drying. Such dry composition of controlled-release CNP agonist of the present invention has a residual water content of a maximum of 10%, preferably less than 5% and more preferably less than 2%, determined according to Karl Fischer. Preferably, the pharmaceutical composition of the present invention is dried by lyophilization.

The term "drug" as used herein refers to a substance used in the treatment, cure, prevention, or diagnosis of a disease or used to otherwise enhance physical or mental well-being. If a drug is conjugated to another moiety, the moiety of the resulting product that originated from the drug is referred to as "biologically active moiety".

As used herein the term "prodrug" refers to a biologically active moiety reversibly and covalently connected to a specialized protective group through a reversible prodrug linker moiety which is a linker moiety comprising a reversible linkage with the biologically active moiety and wherein the specialized protective group alters or eliminates undesirable properties in the parent molecule. This also includes the enhancement of desirable properties in the drug and the suppression of undesirable properties. The specialized non-toxic protective group is referred to as "carrier". A prodrug releases the reversibly and covalently bound biologically active moiety in the form of its corresponding drug. In other words, a prodrug is a conjugate comprising a biologically active moiety which is covalently and reversibly conjugated to a carrier moiety via a reversible prodrug linker moiety, which covalent and reversible conjugation of the carrier to the reversible prodrug linker moiety is either directly or through a spacer. Such conjugate releases the formerly conjugated biologically active moiety in the form of a free drug.

A "biodegradable linkage" or a "reversible linkage" is a linkage that is hydrolytically degradable, i.e. cleavable, in the absence of enzymes under physiological conditions (aqueous buffer at pH 7.4, 37° C.) with a half-life ranging from one hour to six months, preferably from one hour to four months, even more preferably from one hour to three months, even more preferably from one hour to two months, even more preferably from one hour to one month. Accordingly, a stable linkage is a linkage having a half-life under physiological conditions (aqueous buffer at pH 7.4, 37° C.) of more than six months.

Accordingly, a "reversible prodrug linker moiety" is a moiety which is covalently conjugated to a biologically active moiety, such as a CNP agonist moiety, through a reversible linkage and is also covalently conjugated to a carrier moiety, such as —Z or —Z', wherein the covalent conjugation to said carrier moiety is either directly or through a spacer moiety, such as -L²-. Preferably the linkage between —Z or —Z' and -L²- is a stable linkage.

As used herein, the term "traceless prodrug linker" means a reversible prodrug linker which upon cleavage releases the drug in its free form. As used herein, the term "free form" of a drug means the drug in its unmodified, pharmacologically active form.

As used herein, the term "excipient" refers to a diluent, adjuvant, or vehicle with which the therapeutic, such as a drug or prodrug, is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such compositions will contain a therapeutically effective amount of the drug or biologically active moiety, together with a suitable amount of excipient so as to provide the form for proper administration to the patient. The formulation should suit the mode of administration.

As used herein, the term "reagent" means a chemical compound which comprises at least one functional group for reaction with the functional group of another chemical compound or drug. It is understood that a drug comprising a functional group (such as a primary or secondary amine or hydroxyl functional group) is also a reagent.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X-", whereas each "-" indicates attachment to another moiety. Accordingly, a biologically active moiety is released from a prodrug as a drug.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N(R¹)—" can be attached to two moieties or interrupting a moiety either as "—C(O)N(R¹)—" or as "—N(R¹)C(O)—". Similarly, a moiety

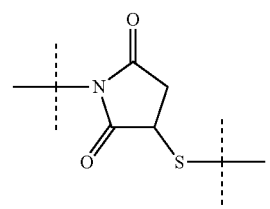

can be attached to two moieties or can interrupt a moiety either as

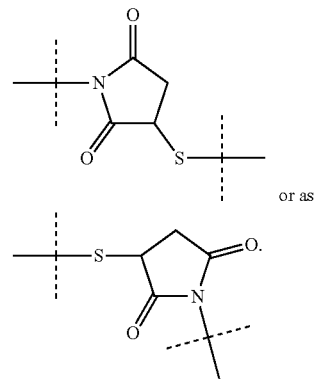

or as

As used herein, the term "functional group" means a group of atoms which can react with other groups of atoms. Functional groups include but are not limited to the following groups: carboxylic acid (—(C=O)OH), primary or secondary amine (—NH₂, —NH—), maleimide, thiol (—SH), sulfonic acid (—(O=S=O)OH), carbonate, carbamate (—O(C=O)N<), hydroxyl (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, sulfonamides, sulfuric acid, vinyl sulfone, vinyl ketone, diazoalkane, oxirane, and aziridine.

In case the controlled-release CNP agonists of the present invention comprise one or more acidic or basic groups, the invention also comprises their corresponding pharmaceutically or toxicologically acceptable salts, in particular their pharmaceutically utilizable salts. Thus, the controlled-release CNP agonists of the present invention comprising acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Controlled-release CNP agonists of the present invention comprising one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the controlled-release CNP agonists of the present invention simultaneously comprise acidic and basic groups, the invention also includes, in addition to the salt forms mentioned, inner salts or betaines (zwitterions). The respective salts can be obtained by customary methods which are known to the person skilled in the art like, for example by contacting these prodrugs with an organic or inorganic acid or base in a solvent or dispersant, or by anion exchange or cation exchange with other salts. The present invention also includes all salts of the prodrugs of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means a substance that does cause harm when administered to a patient and preferably means approved by a regulatory agency, such as the EMA (Europe) and/or the FDA (US) and/or any other national regulatory agency for use in animals, preferably for use in humans.

As used herein the term "about" in combination with a numerical value is used to indicate a range ranging from and including the numerical value plus and minus no more than 10% of said numerical value, more preferably no more than 8% of said numerical value, even more preferably no more than 5% of said numerical value and most preferably no more than 2% of said numerical value. For example, the phrase "about 200" is used to mean a range ranging from and including 200+/−10%, i.e. ranging from and including 180 to 220; preferably 200+/−8%, i.e. ranging from and including 184 to 216; even more preferably ranging from and including 200+/−5%, i.e. ranging from and including 190 to 210; and most preferably 200+/−2%, i.e. ranging from and including 196 to 204. It is understood that a percentage given as "about 20%" does not mean "20%+/−10%", i.e. ranging from and including 10 to 30%, but "about 20%" means ranging from and including 18 to 22%, i.e. plus and minus 10% of the numerical value which is 20.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical groups and/or moieties, such as, for example, one or more functional groups. Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferable has a molecular weight of at most 1000 kDa, such as at most 750 kDa, such as at most 500 kDa, such as at most 300 kDa, such as at most 200 kDa, such as at most 100 kDa. It is understood that for insoluble polymers, such as hydrogels, no meaningful molecular weight ranges can be provided. It is understood that also a protein is a polymer in which the amino acids are the repeating structural units, even though the side chains of each amino acid may be different.

As used herein, the term "polymeric" means a reagent or a moiety comprising one or more polymers or polymer moieties. A polymeric reagent or moiety may optionally also comprise one or more other moiety/moieties, which are preferably selected from the group consisting of:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

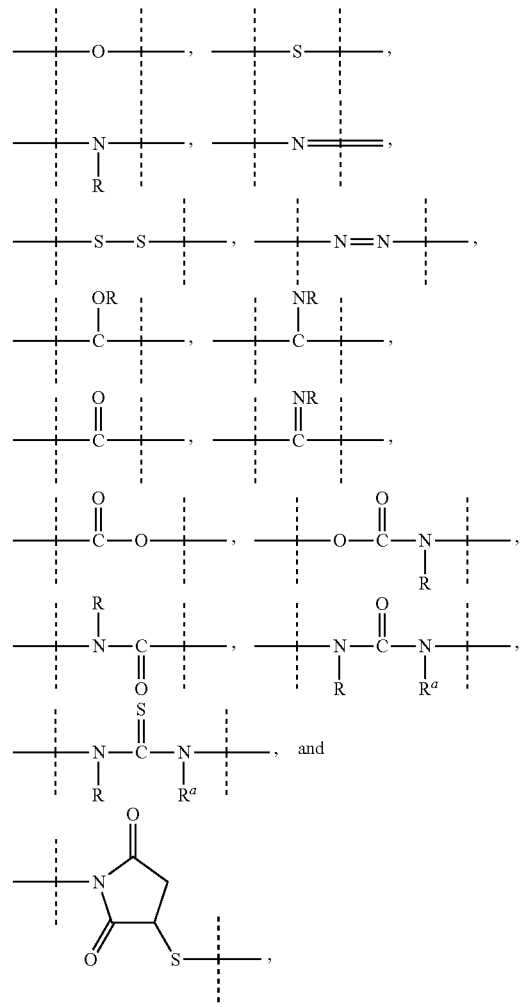

wherein
dashed lines indicate attachment to the remainder of the moiety or reagent, and —R and —R$^a$ are independently of each other selected from the group consisting of —H, methyl, ethyl, propyl, butyl, pentyl and hexyl.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising "x" monomer units any integer given for "x" therefore corresponds to the arithmetic mean number of monomers. Any range of integers given for "x" provides the range of integers in which the arithmetic mean numbers of monomers lies. An integer for "x" given as "about x" means that the arithmetic mean numbers of monomers lies in a range of integers of x+/−10%, preferably x+/−8%, more preferably x+/−5% and most preferably x+/−2%.

As used herein, the term "number average molecular weight" means the ordinary arithmetic mean of the molecular weights of the individual polymers.

As used herein the term "water-soluble" with reference to a carrier means that when such carrier is part of the controlled-release CNP agonists of the present invention at least 1 g of the controlled-release CNP agonists comprising such water-soluble carrier can be dissolved in one liter of water at 20° C. to form a homogeneous solution. Accordingly, the term "water-insoluble" with reference to a carrier means that when such carrier is part of a controlled-release CNP agonists of the present invention less than 1 g of the controlled-release CNP agonists comprising such water-insoluble carrier can be dissolved in one liter of water at 20° C. to form a homogeneous solution.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity.

As used herein the term "thermogelling" means a compound that is a liquid or a low viscosity solution having a viscosity of less than 500 cps at 25° C. at a shear rate of about 0.1/second at a low temperature, which low temperature ranges between about 0° C. to about 10° C., but which is a higher viscosity compound of less than 10000 cps at 25° C. at a shear rate of about 0.1/second at a higher temperature, which higher temperature ranges between about 30° C. to about 40° C., such as at about 37° C.

As used herein, the term "PEG-based" in relation to a moiety or reagent means that said moiety or reagent comprises PEG. Preferably, a PEG-based moiety or reagent comprises at least 10% (w/w) PEG, such as at least 20% (w/w) PEG, such as at least 30% (w/w) PEG, such as at least 40% (w/w) PEG, such as at least 50% (w/w), such as at least 60 (w/w) PEG, such as at least 70% (w/w) PEG, such as at least 80% (w/w) PEG, such as at least 90% (w/w) PEG, such as at least 95% (w/w) PEG. The remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

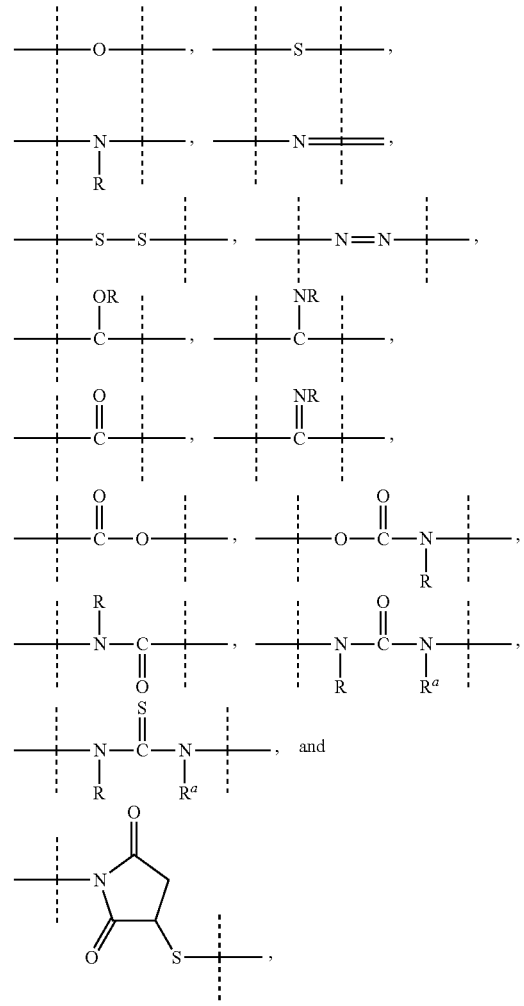

wherein
dashed lines indicate attachment to the remainder of the moiety or reagent, and
—R and —R$^a$ are independently of each other selected from the group consisting of —H, methyl, ethyl, propyl, butyl, pentyl and hexyl.

As used herein, the term "PEG-based comprising at least X % PEG" in relation to a moiety or reagent means that said moiety or reagent comprises at least X % (w/w) ethylene glycol units (—CH$_2$CH$_2$O—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

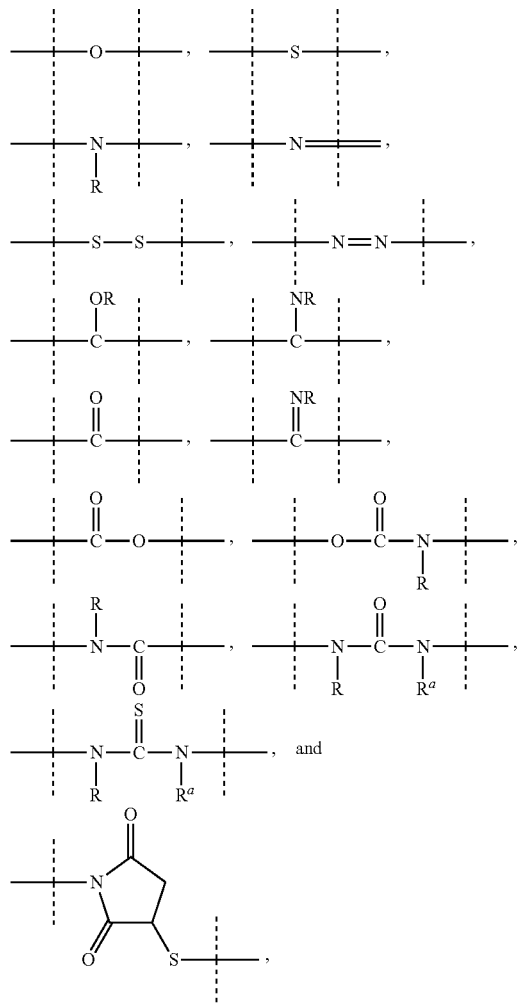

wherein
dashed lines indicate attachment to the remainder of the moiety or reagent, and
—R and —$R^a$ are independently of each other selected from the group consisting of —H, methyl, ethyl, propyl, butyl, pentyl and hexyl.

The term "hyaluronic acid-based comprising at least X % hyaluronic acid" is used accordingly.

The term "substituted" as used herein means that one or more —H atom(s) of a molecule or moiety are replaced by a different atom or a group of atoms, which are referred to as "substituent".

Preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more —R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

—R$^{x1}$, —R$^{x1a}$, —R$^{x1b}$ are independently of each other selected from the group consisting of —H, -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more —R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different;

each —R$^{x3}$, —R$^{x3a}$, —R$^{x4}$, —R$^{x4a}$, —R$^{x4b}$ is independently selected from the group consisting of —H and $C_{1-6}$ alkyl; wherein $C_{1-6}$ alkyl is optionally substituted with one or more halogen, which are the same or different.

More preferably, the one or more further optional substituents are independently of each other selected from the group consisting of halogen, —CN, —COOR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-10}$ alkyl, $C_{2-10}$ alkenyl, and $C_{2-10}$ alkynyl; wherein -T$^0$, $C_{1-10}$ alkyl, $C_{2-10}$ alkenyl, and $C_{2-10}$ alkynyl are optionally substituted with one or more —R$^{x2}$, which are the same or different and wherein $C_{1-10}$ alkyl, $C_{2-10}$ alkenyl, and $C_{2-10}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —R$^{x1}$, —R$^{x1a}$, —R$^{x1b}$, —R$^{x3}$, —R$^{x3a}$ is independently selected from the group consisting of —H, halogen, $C_{1-6}$ alkyl, $C_{2-6}$ alkenyl, and $C_{2-6}$ alkynyl;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —$R^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different;

each —$R^{x4}$, —$R^{x4a}$, —$R^{x4b}$ is independently selected from the group consisting of —H, halogen, $C_{1-6}$ alkyl, $C_{2-6}$ alkenyl, and $C_{2-6}$ alkynyl;

Even more preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-6}$ alkyl, $C_{2-6}$ alkenyl, and $C_{2-6}$ alkynyl; wherein —R$^0$, $C_{1-6}$ alkyl, $C_{2-6}$ alkenyl, and $C_{2-6}$ alkynyl are optionally substituted with one or more —$R^{x2}$, which are the same or different and wherein $C_{1-6}$ alkyl, $C_{2-6}$ alkenyl, and $C_{2-6}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —$R^{x1}$, —$R^{x1a}$, —$R^{x1b}$, —$R^{x2}$, —$R^{x3}$, —$R^{x3a}$ is independently selected from the group consisting of —H, halogen, $C_{1-6}$ alkyl, $C_{2-6}$ alkenyl, and $C_{2-6}$ alkynyl;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more —$R^{x2}$, which are the same or different.

Preferably, a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

The term "interrupted" means that a moiety is inserted between two carbon atoms or—if the insertion is at one of the moiety's ends—between a carbon or heteroatom and a hydrogen atom, preferably between a carbon and a hydrogen atom.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —CH$_2$—, —CH$_2$—CH$_2$—, —CH(CH$_3$)—, —CH$_2$—CH$_2$—CH$_2$—, —CH(C$_2$H$_5$)— and —C(CH$_3$)$_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the $C_{2-6}$ alkenyl group, then an example for such $C_{2-6}$ alkenyl is —CH=CH—. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means a straight-chain or branched hydrocarbon moiety comprising at least one carbon-carbon triple bond having 2 to 6 carbon atoms. If present at the end of a molecule, examples are —C≡CH, —CH$_2$—C≡CH, CH$_2$—CH$_2$—C≡CH and CH$_2$—C≡C—CH$_3$. When two moieties of a molecule are linked by the alkynyl group, then an example is —C≡C—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkynyl or $C_{2-50}$ alkynyl may optionally be interrupted by one or more moieties which are preferably selected from the group consisting of

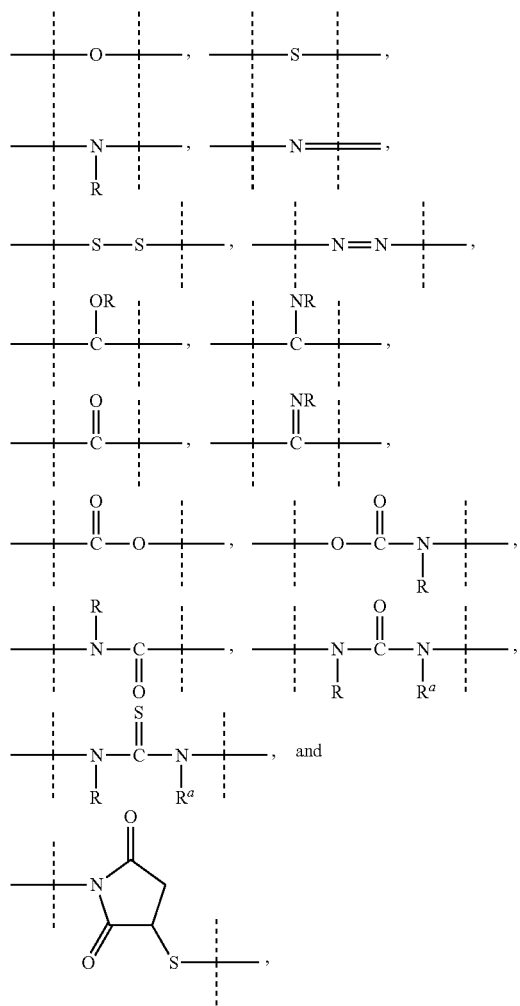

wherein
dashed lines indicate attachment to the remainder of the moiety or reagent; and
—R and —$R^a$ are independently of each other selected from the group consisting of —H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

It is understood that the phrase "the pair $R^x/R^y$ is joined together with the atom to which they are attached to form a $C_{3-10}$ cycloalkyl or a 3- to 10-membered heterocyclyl" in relation with a moiety of the structure

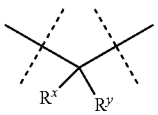

means that $R^x$ and $R^y$ form the following structure:

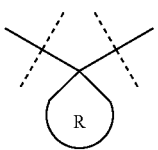

wherein R is $C_{3-10}$ cycloalkyl or 3- to 10-membered heterocyclyl.

It is also understood that the phrase "the pair $R^x/R^y$ is joint together with the atoms to which they are attached to form a ring A" in relation with a moiety of the structure

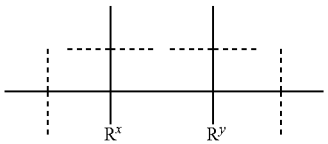

means that $R^x$ and $R^y$ form the following structure:

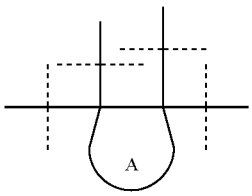

As used herein, "halogen" means fluoro, chloro, bromo or iodo. It is generally preferred that halogen is fluoro or chloro.

In general, the term "comprise" or "comprising" also encompasses "consist of" or "consisting of".

Preferably the $IC_{50}$ with regard to NPR-C of the released CNP agonist is measured after the release of 50% of the CNP agonist comprised in the controlled-release CNP agonist.

The controlled-release CNP agonist of the present invention releases at least one CNP agonist under physiological conditions with a release half-life of at least 6 hours. Preferably the controlled-release CNP agonist of the present invention releases at least one CNP agonist under physiological conditions with a release half-life of at least 12 hours. Even more preferably the controlled-release CNP agonist of the present invention releases at least one CNP agonist under physiological conditions with a release half-life of at least 24 hours. Even more preferably the controlled-release CNP agonist of the present invention releases at least one CNP agonist under physiological conditions with a release half-life of at least 48 hours. Even more preferably the controlled-release CNP agonist of the present invention releases at least one CNP agonist under physiological conditions with a release half-life of at least 72 hours. Even more preferably the controlled-release CNP agonist of the present invention releases at least one CNP agonist under physiological conditions with a release half-life of at least 96 hours. Even more preferably the controlled-release CNP agonist of the present invention releases at least one CNP agonist under physiological conditions with a release half-life of at least 120 hours. Even more preferably the controlled-release CNP agonist of the present invention releases at least one CNP agonist under physiological conditions with a release half-life of at least 144 hours. Even more preferably the controlled-release CNP agonist of the present invention releases at least one CNP agonist under physiological conditions with a release half-life of at least 168 hours. Even more preferably the controlled-release CNP agonist of the present invention releases at least one CNP agonist under physiological conditions with a release half-life of at least 192 hours.

The controlled-release CNP agonist has an affinity, as defined by the $IC_{50}$, to the NPR-C receptor that is at least 5-fold higher than the affinity of the corresponding free CNP agonist. Preferably, the controlled-release CNP agonist has an affinity, as defined by the $IC_{50}$, to the NPR-C receptor that is at least 10-fold higher than the affinity of the corresponding free CNP agonist. Even more preferably the controlled-release CNP agonist has an affinity, as defined by the $IC_{50}$, to the NPR-C receptor that is at least 20-fold higher than the affinity of the corresponding free CNP agonist. Even more preferably the controlled-release CNP agonist has an affinity, as defined by the $IC_{50}$, to the NPR-C receptor that is at least 50-fold higher than the affinity of the corresponding free CNP agonist. Even more preferably the controlled-release CNP agonist has an affinity, as defined by the $IC_{50}$, to the NPR-C receptor that is at least 100-fold higher than the affinity of the corresponding free CNP agonist. Even more preferably the controlled-release CNP agonist has an affinity, as defined by the $IC_{50}$, to the NPR-C receptor that is at least 250-fold higher than the affinity of the corresponding free CNP agonist. Even more preferably the controlled-release CNP agonist has an affinity, as defined by the $IC_{50}$, to the NPR-C receptor that is at least 500-fold higher than the affinity of the corresponding free CNP agonist. Even more preferably the controlled-release CNP agonist has an affinity, as defined by the $IC_{50}$, to the NPR-C receptor that is at least 1000-fold higher than the affinity of the corresponding free CNP agonist.

The controlled-release CNP agonist preferably comprises a CNP agonist selected from the group consisting of small molecules, natural products, oligonucleotides, polypeptides and proteins.

In one embodiment the CNP agonist comprises a small molecule. Preferably, the CNP agonist is a small molecule.

In another embodiment the CNP agonist comprises a natural product. Preferably, the CNP agonist is a natural product.

In another embodiment the CNP agonist comprises an oligonucleotide. Preferably, such oligonucleotide is selected from the group consisting of antisense oligonucleotides, aptamers, RNAi and siRNA. Preferably, the CNP agonist is an oligonucleotide, more preferably selected from the group consisting of antisense oligonucleotides, aptamers, RNAi and siRNA.

In another embodiment the CNP agonist comprises a protein. Preferably, the CNP agonist is a protein.

In a preferred embodiment the CNP agonist comprises a polypeptide. More preferably the CNP agonist is a polypeptide. Preferably the CNP agonist comprises a CNP molecule or moiety. More preferably the CNP agonist is CNP. Even more preferably the CNP agonist comprises a CNP molecule or moiety having the sequence of SEQ ID NO:24, SEQ ID NO:25 or SEQ ID NO:30. Even more preferably the CNP agonist is CNP having the sequence of SEQ ID NO:24, SEQ ID NO:25 or SEQ ID NO:30. Even more preferably the CNP agonist comprises a CNP molecule or moiety CNP having the sequence of SEQ ID NO:24. Most preferably the CNP agonist is a CNP having the sequence of SEQ ID NO:24. Most preferably the CNP agonist is a CNP having the sequence of SEQ ID NO:24. It is also preferred that the CNP agonist is a CNP having the sequence of SEQ ID NO:20. It is also preferred that the CNP agonist is a CNP having the sequence of SEQ ID NO:21. It is also preferred that the CNP agonist is a CNP having the sequence of SEQ ID NO:22. It is also preferred that the CNP agonist is a CNP having the sequence of SEQ ID NO:22. It is also preferred that the CNP agonist is a CNP having the sequence of SEQ ID NO:30.

In one embodiment the controlled-release CNP agonist is water-insoluble.

Preferably, the controlled-release CNP agonist is selected from the group consisting of crystals, nanoparticles, microparticles, nanospheres and microspheres.

In one embodiment the controlled-release CNP agonist is a crystal comprising at least one CNP agonist.

In another embodiment the controlled-release CNP agonist is a nanoparticle comprising at least one CNP agonist.

In another embodiment the controlled-release CNP agonist is a microparticle comprising at least one CNP agonist.

In another embodiment the controlled-release CNP agonist is a nanosphere comprising at least one CNP agonist.

In another embodiment the controlled-release CNP agonist is a microsphere comprising at least one CNP agonist.

In one embodiment the controlled-release CNP agonist is a vesicle comprising at least one CNP agonist. Preferably, such vesicle comprising at least one CNP agonist is a micelle, liposome or polymersome.

In one embodiment the controlled-release CNP agonist is a micelle comprising at least one CNP agonist.

In another embodiment the controlled-release CNP agonist is a liposome comprising at least one CNP agonist. Preferably, such liposome is selected from the group consisting of aquasomes; non-ionic surfactant vesicles, such as niosomes and proniosomes; cationic liposomes, such as LeciPlex; transfersomes; ethosomes; ufasomes; sphingosomes; and pharmacosomes.

In another embodiment the controlled-release CNP agonist is a polymersome comprising at least one CNP agonist.

In another embodiment the controlled-release CNP agonist comprises at least one CNP agonist non-covalently embedded in a water-insoluble polymer. Preferably, such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In a preferred embodiment the controlled-release CNP comprises at least one CNP agonist non-covalently embedded in poly(lactic-co-glycolic acid) (PLGA).

In another embodiment the controlled-release CNP agonist comprises at least one CNP agonist covalently and reversibly conjugated to a water-insoluble polymer. Preferably such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

Preferably such controlled-release CNP agonist comprising at least one CNP agonist covalently and reversibly conjugated to a water-insoluble polymer is a CNP agonist prodrug comprising a conjugate D-L, wherein -D is a CNP agonist moiety; and
-L comprises a reversible prodrug linker moiety $-L^1-$;
  wherein $-L^1-$ is substituted with $-L^2-Z'$ and is optionally further substituted; wherein
-$L^2-$ is a single chemical bond or a spacer moiety; and
—Z' is a water-insoluble carrier moiety.

It is understood that a multitude of moieties $-L^2-L^1-D$ is connected to a water-insoluble carrier —Z'.

The water-insoluble carrier —Z' is preferably a hydrogel. Preferably, such hydrogel comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

If the carrier —Z' is a hydrogel, it is preferably a hydrogel comprising PEG or hyaluronic acid. Most preferably such hydrogel comprises PEG. In an equally preferred embodiment such hydrogel comprises hyaluronic acid.

Even more preferably, the carrier —Z' is a hydrogel as described in WO 2006/003014 A2, WO 2011/012715 A1 or WO 2014/056926 A1, which are herewith incorporated by reference in their entirety.

In another embodiment —Z' is a polymer network formed through the physical aggregation of polymer chains, which physical aggregation is preferably caused by hydrogen bonds, crystallization, helix formation or complexation. In one embodiment such polymer network is a thermogelling polymer.

In another embodiment the controlled-release CNP agonist is water soluble.

In one embodiment the CNP agonist is a polypeptide or protein and the controlled-release CNP agonist is a fusion protein comprising such polypeptide or protein CNP agonist moiety fused to one or more further polypeptide or protein moiety. Preferably, the CNP agonist is released from the fusion protein through enzymatic cleavage. Preferably, such at least one or more further polypeptide or protein moieties are selected from the group consisting of carboxyl-terminal peptide of the chorionic gonadotropin as described in US 2012/0035101 A1 which are herewith incorporated by reference; albumin; XTEN sequences as described in WO 2011123813 A2 which are herewith incorporated by reference; proline/alanine random coil sequences as described in WO 2011/144756 A1 which are herewith incorporated by reference; proline/alanine/serine random coil sequences as described in WO 2008/155134 A1 and WO 2013/024049 A1 which are herewith incorporated by reference; and Fc fusion proteins.

In a preferred embodiment the controlled-release CNP agonist is a CNP agonist prodrug of formula (Ia) or (Ib)

wherein
-D is a CNP agonist moiety;
-$L^1$- is a reversible prodrug linker moiety;
-$L^2$- is a single chemical bond or a spacer moiety;
—Z is a water-soluble carrier moiety;

x is an integer selected from the group consisting of 1, 2, 3, 4, 5, 6, 7, 8, 9, 10, 11, 12, 13, 14, 15 or 16; and
y is an integer selected from the group consisting of 1, 2, 3, 4 and 5.

Preferably, x of formula (Ia) is an integer selected from the group consisting of 1, 2, 3, 4, 6 and 8. More preferably x of formula (Ia) is an integer selected from the group consisting of 1, 2, 4, and 6. Even more preferably x of formula (Ia) is an integer selected from the group consisting of 1, 4 and 6 and most preferably x of formula (Ia) is 1.

Preferably, y of formula (Ib) is an integer selected from the group consisting of 2, 3, 4 and 5, even more preferably an integer selected from the group consisting of 2, 3 or 4 and most preferably an integer selected from the group consisting of 2 or 3.

In another preferred embodiment y of formula (Ib) is an integer selected from the group consisting of 1, 2 or 3. In one preferred embodiment y of formula (Ib) is 1. In an equally preferred embodiment y of formula (Ib) is 2.

Preferably the controlled-release CNP agonist is a CNP agonist prodrug of formula (Ia) with x=1.

The moiety -$L^1$- is a reversible prodrug linker from which the drug, i.e. the CNP agonist, is released in its free form, i.e. -$L^1$- is a traceless prodrug linker. Suitable prodrug linkers are known in the art, such as for example the reversible prodrug linker moieties disclosed in WO 2005/099768 A2, WO 2006/136586 A2, WO 2011/089216 A1 and WO 2013/024053 A1, which are incorporated by reference herewith.

In another embodiment is a reversible prodrug linker as described in WO 2011/012722 A1, WO 2011/089214 A1, WO 2011/089215 A1, WO 2013/024052 A1 and WO 2013/160340 A1 which are incorporated by reference herewith.

The moiety -$L^1$- can be connected to -D through any type of linkage, provided that it is reversible. Preferably, -$L^1$- is connected to -D through a linkage selected from the group consisting of amide, ester, carbamate, acetal, aminal, imine, oxime, hydrazone, disulfide and acylguanidine. Even more preferably -$L^1$- is connected to -D through a linkage selected from the group consisting of amide, ester, carbamate and acylguanidine. It is understood that these linkages may not per se be reversible, but that neighboring groups comprised in -$L^1$- may render the linkage reversible.

In a preferred embodiment, the moiety -$L^1$- is connected to -D through an amide linkage.

A particularly preferred moiety -$L^1$- is disclosed in WO 2009/095479 A2. Accordingly, in one preferred embodiment the moiety -$L^1$- is of formula (II):

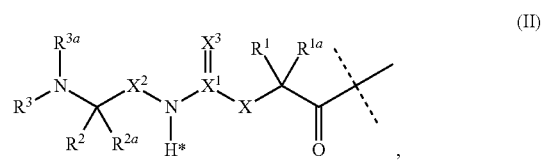

wherein the dashed line indicates the attachment to a nitrogen of -D which is a CNP agonist moiety by forming an amide bond;
—X— is —$C(R^4R^{4a})$—; —$N(R^4)$—; —O—; —$C(R^4R^{4a})$—$C(R^5R^{5a})$—; —$C(R^5R^{5a})$—$C(R^4R^{4a})$—; —$C(R^4R^{4a})$—$N(R^6)$—; —$N(R^6)$—$C(R^4R^{4a})$—; —$C(R^4R^{4a})$—O—; —O—$C(R^4R^{4a})$—; or —$C(R^7R^{7a})$—;
$X^1$ is C; or S(O);
—$X^2$— is —$C(R^8R^{8a})$—; or —$C(R^8R^{8a})$—$C(R^9R^{9a})$—;

=$X^3$ is =O; =S; or =N—CN;
—$R^1$, —$R^{1a}$, —$R^2$, —$R^{2a}$, —$R^4$, —$R^{4a}$, —$R^5$, —$R^{5a}$, —$R^6$, —$R^8$, —$R^{8a}$, —$R^9$, —$R^{9a}$ are independently selected from the group consisting of —H; and $C_{1-6}$ alkyl;
—$R^3$, —$R^{3a}$ are independently selected from the group consisting of —H; and $C_{1-6}$ alkyl, provided that in case one of —$R^3$, —$R^{3a}$ or both are other than —H they are connected to N to which they are attached through an $SP^3$-hybridized carbon atom;
—$R^7$ is —$N(R^{10}R^{10a})$; or —$NR^{10}$—(C=O)—$R^{11}$;
—$R^{7a}$, —$R^{10}$, —$R^{10a}$, —$R^{11}$ are independently of each other —H; or $C_{1-6}$ alkyl;
optionally, one or more of the pairs-$R^{1a}$/—$R^{4a}$, $R^{1a}$/—$R^{5a}$, —$R^{1a}$/—$R^{7a}$, —$R^{4a}$/—$R^{5a}$, —$R^{8a}$/—$R^{9a}$ form a chemical bond;
optionally, one or more of the pairs —$R^1$/—$R^{1a}$, —$R^2$/—$R^{2a}$, —$R^4$/—$R^{4a}$, —$R^5$/—$R^{5a}$, —$R^8$/—$R^{8a}$, —$R^9$/—$R^{9a}$ are joined together with the atom to which they are attached to form a $C_{3-10}$ cycloalkyl; or 3- to 10-membered heterocyclyl;
optionally, one or more of the pairs —$R^1$/—$R^4$, —$R^1$/—$R^5$, —$R^1$/—$R^6$, —$R^1$/—$R^{7a}$, —$R^4$/—$R^5$, —$R^4$/—$R^6$, —$R^8$/—$R^9$, —$R^2$/—$R^3$ are joined together with the atoms to which they are attached to form a ring A;
optionally, $R^3/R^{3a}$ are joined together with the nitrogen atom to which they are attached to form a 3- to 10-membered heterocycle;
A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and
wherein is substituted with -$L^2$-Z or -$L^2$-Z' and wherein -$L^1$- is optionally further substituted, provided that the hydrogen marked with the asterisk in formula (II) is not replaced by -$L^2$-Z or -$L^2$-Z' or a substituent;
wherein
-$L^2$- is a single chemical bond or a spacer;
—Z is a water-soluble carrier; and
—Z' is a water-insoluble carrier.
Preferably -$L^1$- of formula (II) is substituted with one moiety -$L^2$-Z or -$L^2$-Z'.
In one embodiment -$L^1$- of formula (II) is not further substituted.
It is understood that if —$R^3$/—$R^{3a}$ of formula (II) are joined together with the nitrogen atom to which they are attached to form a 3- to 10-membered heterocycle, only such 3- to 10-membered heterocycles may be formed in which the atoms directly attached to the nitrogen are $SP^3$-hybridized carbon atoms. In other words, such 3- to 10-membered heterocycle formed by —$R^3$/—$R^{3a}$ together with the nitrogen atom to which they are attached has the following structure:

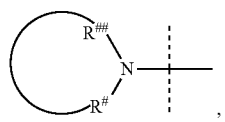

wherein
the dashed line indicates attachment to the rest of -$L^1$-;
the ring comprises 3 to 10 atoms comprising at least one nitrogen; and
$R^\#$ and $R^{\#\#}$ represent an $SP^3$-hybridized carbon atom.

It is also understood that the 3- to 10-membered heterocycle may be further substituted.
Exemplary embodiments of suitable 3- to 10-membered heterocycles formed by —$R^3$/—$R^{3a}$ of formula (II) together with the nitrogen atom to which they are attached are the following:

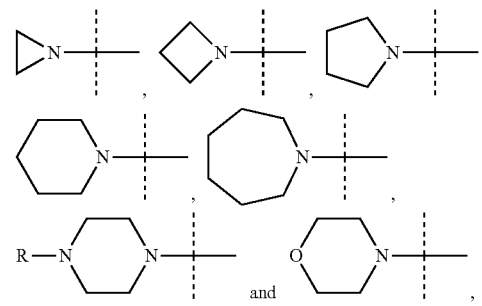

wherein
dashed lines indicate attachment to the rest of the molecule; and
—R is selected from the group consisting of —H and $C_{1-6}$ alkyl.
-$L^1$- of formula (II) may optionally be further substituted. In general, any substituent may be used as far as the cleavage principle is not affected, i.e. the hydrogen marked with the asterisk in formula (II) is not replaced and the nitrogen of the moiety

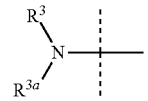

of formula (II) remains part of a primary, secondary or tertiary amine, i.e. —$R^3$ and —$R^{3a}$ are independently of each other —H or are connected to —N< through an $SP^3$-hybridized carbon atom.
In one embodiment —$R^1$ or —$R^{1a}$ of formula (II) is substituted with -$L^2$-Z or -$L^2$-Z'. In another embodiment —$R^2$ or —$R^{2a}$ of formula (II) is substituted with -$L^2$-Z or -$L^2$-Z'. In another embodiment —$R^3$ or —$R^{3a}$ of formula (II) is substituted with -$L^2$-Z or -$L^2$-Z'. In another embodiment —$R^4$ of formula (II) is substituted with -$L^2$-Z or -$L^2$-Z'. In another embodiment —$R^5$ or —$R^{5a}$ of formula (II) is substituted with -$L^2$-Z or -$L^2$-Z'. In another embodiment —$R^6$ of formula (II) is substituted with -$L^2$-Z or -$L^2$-Z'. In another embodiment —$R^7$ or —$R^{7a}$ of formula (II) is substituted with -$L^2$-Z or -$L^2$-Z'. In another embodiment —$R^8$ or —$R^{8a}$ of formula (II) is substituted with -$L^2$-Z or -$L^2$-Z'. In another embodiment —$R^9$ or —$R^{9a}$ of formula (II) is substituted with -$L^2$-Z or -$L^2$-Z'.
Most preferably —$R^4$ of formula (II) is substituted with -$L^2$-Z or -$L^2$-Z'.
Preferably, —X— of formula (II) is —$C(R^4R^{4a})$— or —$N(R^4)$—. Most preferably, —X— of formula (II) is —$C(R^4R^{4a})$—.
Preferably, $X^1$ of formula (II) is C.
Preferably, =$X^3$ of formula (II) is =O.
Preferably, —$X^2$— of formula (II) is —$C(R^8R^{8a})$—.
Preferably —$R^8$ and —$R^{8a}$ of formula (II) are independently selected from the group consisting of —H, methyl and ethyl. More preferably at least one of —$R^8$ and —$R^{8a}$ of formula (II) is —H. Even more preferably both —R$^8$ and —R$^{8a}$ of formula (II) are —H.

Preferably, —R$^1$ and —R$^{1a}$ of formula (II) are independently selected from the group consisting of —H, methyl and ethyl. More preferably, at least one of —R$^1$ and —R$^{1a}$ of formula (II) is —H. Even more preferably both —R$^1$ and —R$^{1a}$ of formula (II) are —H.

Preferably, —R$^2$ and —R$^{2a}$ of formula (II) are independently selected from the group consisting of —H, methyl and ethyl. More preferably, at least one of —R$^2$ and —R$^{2a}$ of formula (II) is —H. Even more preferably both —R$^2$ and —R$^{2a}$ of formula (II) are H.

Preferably, —R$^3$ and —R$^{3a}$ of formula (II) are independently selected from the group consisting of —H, methyl, ethyl, propyl and butyl. Even more preferably at least one of —R$^3$ and —R$^{3a}$ of formula (II) is methyl. In an equally preferred embodiment —R$^3$ and —R$^{3a}$ of formula (II) are both —H. In another equally preferred embodiment —R$^3$ and —R$^{3a}$ of formula (II) are both methyl.

Preferably, —R$^3$ of formula (II) is —H and —R$^{3a}$ of formula (II) is methyl.

Preferably, —R$^4$ and —R$^{4a}$ of formula (II) are independently selected from the group consisting of —H, methyl and ethyl. More preferably, at least one of —R$^4$ and —R$^{4a}$ of formula (II) is —H. Even more preferably both —R$^4$ and —R$^{4a}$ of formula (II) are —H.

Preferably the moiety is of formula (IIa):

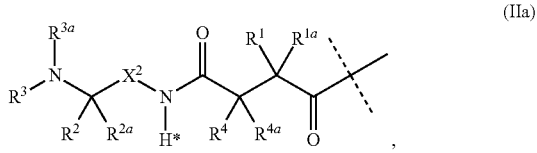

(IIa)

wherein the dashed line indicates the attachment to a nitrogen of -D which is a CNP agonist moiety by forming an amide bond;
—R$^1$, —R$^{1a}$, —R$^2$, —R$^{2a}$, —R$^3$, —R$^{3a}$, —R$^4$, —R$^{4a}$ and —X$^2$— are used as defined in formula (II); and
wherein -L$^1$- is substituted with -L$^2$-Z or -L$^2$-Z' and wherein -L$^1$- is optionally further substituted, provided that the hydrogen marked with the asterisk in formula (IIa) is not replaced by -L$^2$-Z or -L$^2$-Z' or a substituent.

Preferably of formula (IIa) is substituted with one moiety -L$^2$-Z or -L$^2$-Z'.

Preferably the moiety of formula (IIa) is not further substituted.

Preferably, —R$^1$ and —R$^{1a}$ of formula (IIa) are independently selected from the group consisting of —H, methyl and ethyl. More preferably, at least one of —R$^1$ and —R$^{1a}$ of formula (IIa) is —H. Even more preferably both —R$^1$ and —R$^{1a}$ of formula (IIa) are —H.

Preferably, —R$^4$ and —R$^{4a}$ of formula (IIa) are independently selected from the group consisting of —H, methyl and ethyl. More preferably, at least one of —R$^4$ and —R$^{4a}$ of formula (IIa) is —H. Even more preferably both —R$^4$ and —R$^{4a}$ of formula (IIa) are —H.

Preferably, —X$^2$— of formula (IIa) is —C(R$^8$R$^{8a}$)—.

Preferably —R$^8$ and —R$^{8a}$ of formula (IIa) are independently selected from the group consisting of —H, methyl and ethyl. More preferably at least one of —R$^8$ and —R$^{8a}$ of formula (IIa) is —H. Even more preferably both —R$^8$ and —R$^{8a}$ of formula (IIa) are —H.

Preferably, —R$^2$ and —R$^{2a}$ of formula (IIa) are independently selected from the group consisting of —H, methyl and ethyl. More preferably, at least one of —R$^2$ and —R$^{2a}$ of formula (IIa) is —H. Even more preferably both —R$^2$ and —R$^{2a}$ of formula (IIa) are H.

Preferably, —R$^3$ and —R$^{3a}$ of formula (IIa) are independently selected from the group consisting of —H, methyl, ethyl, propyl and butyl. Even more preferably at least one of —R$^3$ and —R$^{3a}$ of formula (IIa) is methyl. In an equally preferred embodiment —R$^3$ and —R$^{3a}$ of formula (IIa) are both —H. In another equally preferred embodiment —R$^3$ and —R$^{3a}$ of formula (IIa) are both methyl.

Preferably, —R$^3$ of formula (IIa) is —H and —R$^{3a}$ of formula (IIa) is methyl.

Preferably the moiety -L$^1$- is of formula (IIb):

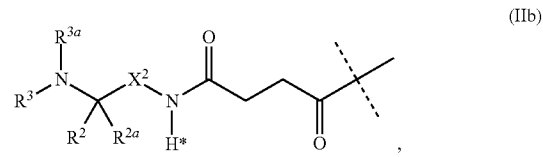

(IIb)

wherein the dashed line indicates the attachment to a nitrogen of -D which is a CNP agonist moiety by forming an amide bond;
—R$^2$, —R$^{2a}$, —R$^3$, —R$^{3a}$ and —X$^2$— are used as defined in formula (II); and
wherein -L$^1$- is substituted with -L$^2$-Z or -L$^2$-Z' and wherein -L$^1$- is optionally further substituted, provided that the hydrogen marked with the asterisk in formula (IIb) is not replaced by -L$^2$-Z or -L$^2$-Z' or a substituent.

Preferably -L$^1$- of formula (IIb) is substituted with one moiety -L$^2$-Z or -L$^2$-Z'.

Preferably the moiety -L$^1$- of formula (IIb) is not further substituted.

Preferably, —X$^2$— of formula (IIb) is —C(R$^8$R$^{8a}$)—.

Preferably —R$^8$ and —R$^{8a}$ of formula (IIb) are independently selected from the group consisting of —H, methyl and ethyl. More preferably at least one of —R$^8$ and —R$^{8a}$ of formula (IIb) is —H. Even more preferably both —R$^8$ and —R$^{8a}$ of formula (IIb) are —H.

Preferably, —R$^2$ and —R$^{2a}$ of formula (IIb) are independently selected from the group consisting of —H, methyl and ethyl. More preferably, at least one of —R$^2$ and —R$^{2a}$ of formula (IIb) is —H. Even more preferably both —R$^2$ and —R$^{2a}$ of formula (IIb) are H.

Preferably, —R$^3$ and —R$^{3a}$ of formula (IIb) are independently selected from the group consisting of —H, methyl, ethyl, propyl and butyl. Even more preferably at least one of —R$^3$ and —R$^{3a}$ of formula (IIb) is methyl. In an equally preferred embodiment —R$^3$ and —R$^{3a}$ of formula (IIb) are both —H. In another equally preferred embodiment —R$^3$ and —R$^{3a}$ of formula (IIb) are both methyl.

Most preferably, —R$^3$ of formula (IIb) is —H and —R$^{3a}$ of formula (IIb) is methyl.

Even more preferably the moiety -L$^1$- is of formula (IIb'):

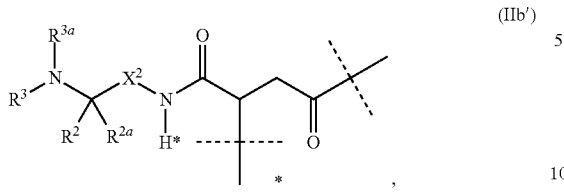
(IIb')

wherein
wherein the dashed line indicates the attachment to a nitrogen of D which is a CNP agonist moiety by forming an amide bond;
the dashed line marked with the asterisk indicates attachment to -L$^2$-;
—R$^2$, —R$^{2a}$, —R$^3$, —R$^{3a}$ and —X$^2$— are used as defined in formula (II); and
wherein -L$^1$- is optionally further substituted, provided that the hydrogen marked with the asterisk in formula (IIb') is not replaced by a substituent.

Preferably the moiety -L$^1$- of formula (IIb') is not further substituted.

Preferably, —X$^2$— of formula (IIb') is —C(R$^8$R$^{8a}$)—.

Preferably —R$^8$ and —R$^{8a}$ of formula (IIb') are independently selected from the group consisting of —H, methyl and ethyl. More preferably at least one of —R$^8$ and —R$^{8a}$ of formula (IIb') is —H. Even more preferably both —R$^8$ and —R$^{8a}$ of formula (IIb') are —H.

Preferably, —R$^2$ and —R$^{2a}$ of formula (IIb') are independently selected from the group consisting of —H, methyl and ethyl. More preferably, at least one of —R$^2$ and —R$^{2a}$ of formula (IIb') is —H. Even more preferably both —R$^2$ and —R$^{2a}$ of formula (IIb') are H.

Preferably, —R$^3$ and —R$^{3a}$ of formula (IIb') are independently selected from the group consisting of —H, methyl, ethyl, propyl and butyl. Even more preferably at least one of —R$^3$ and —R$^{3a}$ of formula (IIb') is methyl. In an equally preferred embodiment —R$^3$ and —R$^{3a}$ of formula (IIb') are both —H. In another equally preferred embodiment —R$^3$ and —R$^{3a}$ of formula (IIb') are both methyl.

Most preferably, —R$^3$ of formula (IIb') is —H and —R$^{3a}$ of formula (IIb') is methyl.

Preferably the moiety is of formula (IIc):

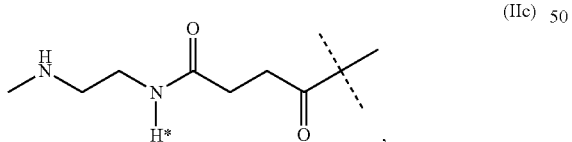
(IIc)

wherein the dashed line indicates the attachment to a nitrogen of -D which is a CNP agonist moiety by forming an amide bond; and
wherein -L$^1$- is substituted with -L$^2$-Z or -L$^2$-Z' and wherein is optionally further substituted, provided that the hydrogen marked with the asterisk in formula (IIc) is not replaced by -L$^2$-Z or -L$^2$-Z' or a substituent.

Preferably -L$^1$- of formula (IIc) is substituted with one moiety -L$^2$-Z or -L$^2$-Z'.

Preferably the moiety -L$^1$- of formula (IIc) is not further substituted.

In another preferred embodiment the moiety -L$^1$- is of formula (IIc-a):

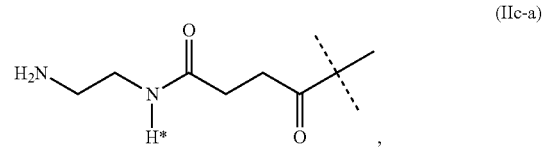
(IIc-a)

wherein the dashed line indicates the attachment to a nitrogen of -D which is a CNP agonist moiety by forming an amide bond; and
wherein -L$^1$- is substituted with -L$^2$-Z or -L$^2$-Z' and wherein -L$^1$- is optionally further substituted, provided that the hydrogen marked with the asterisk in formula (IIc-a) is not replaced by -L$^2$-Z or -L$^2$-Z' or a substituent.

Preferably -L$^1$- of formula (IIc-a) is substituted with one moiety -L$^2$-Z or -L$^2$-Z'.

Preferably the moiety -L$^1$- of formula (IIc-a) is not further substituted.

In another preferred embodiment the moiety is of formula (IIc-b):

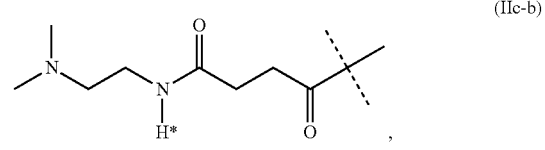
(IIc-b)

wherein the dashed line indicates the attachment to a nitrogen of -D which is a CNP agonist moiety by forming an amide bond; and
wherein -L$^1$- is substituted with -L$^2$-Z or -L$^2$-Z' and wherein -L$^1$- is optionally further substituted, provided that the hydrogen marked with the asterisk in formula (IIc-b) is not replaced by -L$^2$-Z or -L$^2$-Z' or a substituent.

Preferably -L$^1$- of formula (IIc-b) is substituted with one moiety -L$^2$-Z or -L$^2$-Z'.

Preferably the moiety -L$^1$- of formula (IIc-b) is not further substituted.

Even more preferably the moiety -L$^1$- is selected from the group consisting of formula (IIc-i), (IIc-ii), (IIc-iii), (IIc-iv) and (IIc-v):

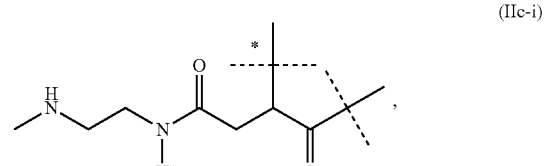
(IIc-i)

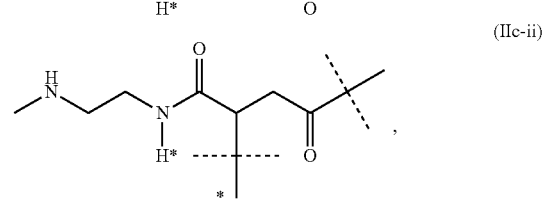
(IIc-ii)

-continued (IIc-iii)
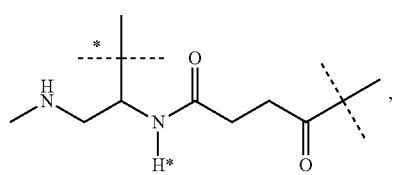

(IIc-iv)
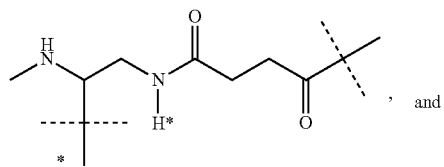
, and (IIc-v)
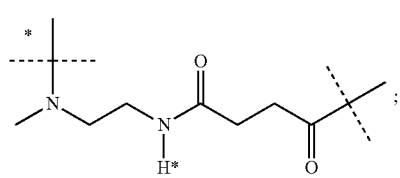
;

wherein
the unmarked dashed line indicates the attachment to a nitrogen of -D which is a CNP agonist moiety by forming an amide bond;

the dashed line marked with the asterisk indicates attachment to -$L^2$-Z or -$L^2$-Z'; and -$L^1$- is optionally further substituted, provided that the hydrogen marked with the asterisk in formula (IIc-i), (IIc-ii), (IIc-iii), (IIc-iv) and (IIc-v) is not replaced by a substituent.

Preferably, the moiety -$L^1$- of formula (IIc-i), (IIc-ii), (IIc-iii), (IIc-iv) and (IIc-v) is not further substituted.

In a particularly preferred embodiment the moiety -$L^1$- is of formula (IIc-ii)

(IIc-ii)
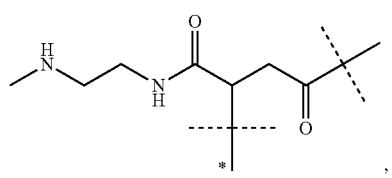
, wherein
the unmarked dashed line indicates the attachment to a nitrogen of -D which is a CNP agonist moiety by forming an amide bond; and the dashed line marked with the asterisk indicates attachment to -$L^2$-Z or -$L^2$-Z'.

Preferably -$L^1$- of formula (IIc-ii) is substituted with one moiety -$L^2$-Z or -$L^2$-Z'.

In an equally preferred embodiment the moiety -$L^1$- is selected from the group consisting of formula (IIc-i'), (IIc-ii'), (IIc-iii'), (IIc-iv') and (IIc-v'):

(IIc-i')
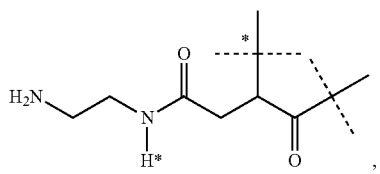
, (IIc-ii')
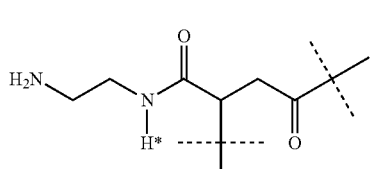
, (IIc-iii')
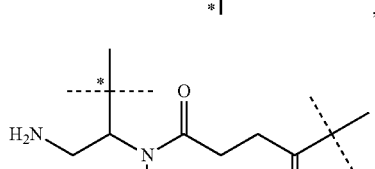
, (IIc-iv')
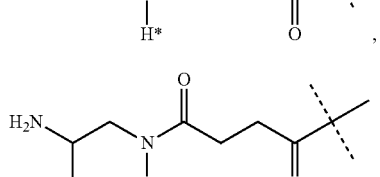
, and (IIc-v')
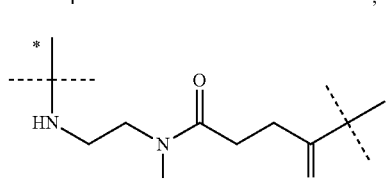
;

wherein
the unmarked dashed line indicates the attachment to a nitrogen of -D which is a CNP agonist moiety by forming an amide bond;

the dashed line marked with the asterisk indicates attachment to -$L^2$-Z or -$L^2$-Z'; and -$L^1$- is optionally further substituted, provided that the hydrogen marked with the asterisk in formula (IIc-i'), (IIc-ii'), (IIc-iii'), (IIc-iv') and (IIc-v') is not replaced by a substituent.

Preferably, the moiety -$L^1$- of formula (IIc-i'), (IIc-ii'), (IIc-iii'), (IIc-iv') and (IIc-v') is not further substituted.

In another particularly preferred embodiment the moiety -$L^1$- is of formula (IIc-ii')

(IIc-ii')
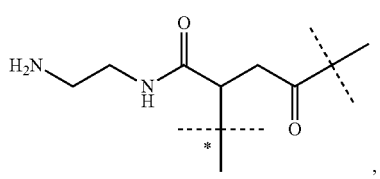
, wherein
the unmarked dashed line indicates the attachment to a nitrogen of -D which is a CNP agonist moiety by forming an amide bond; and the dashed line marked with the asterisk indicates attachment to -L²-Z or -L²-Z'.

Preferably -L¹- of formula (IIc-ii') is substituted with one moiety -L²-Z or -L²-Z'.

In an equally preferred embodiment the moiety -L¹- is selected from the group consisting of formula (IIc-i"), (IIc-ii"), (IIc-iii") and (IIc-iv"):

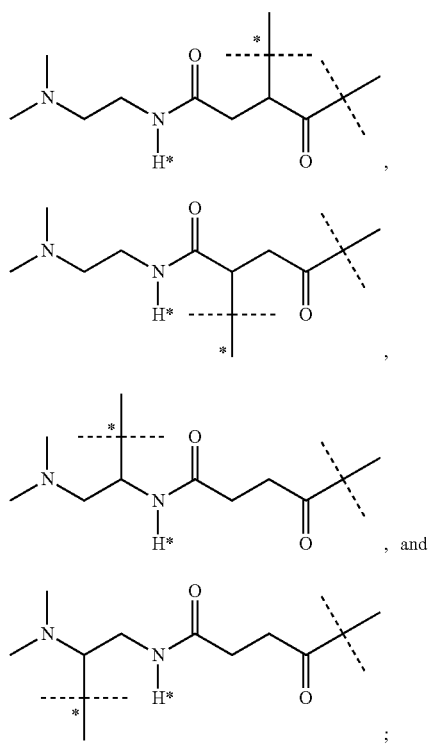

wherein
the unmarked dashed line indicates the attachment to a nitrogen of -D which is a CNP agonist moiety by forming an amide bond;
the dashed line marked with the asterisk indicates attachment to -L²-Z or -L²-Z'; and
-L¹- is optionally further substituted, provided that the hydrogen marked with the asterisk in formula (IIc-i"), (IIc-ii"), (IIc-iii") and (IIc-iv") is not replaced by a substituent.

Preferably, the moiety -L¹- of formula (IIc-i"), (IIc-ii"), (IIc-iii") and (IIc-iv") is not further substituted.

In another particularly preferred embodiment the moiety -L¹- is of formula (IIc-ii")

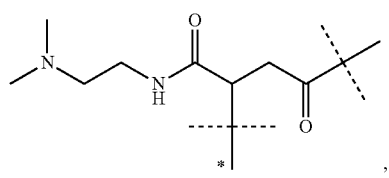

wherein
the unmarked dashed line indicates the attachment to a nitrogen of -D which is a CNP agonist moiety by forming an amide bond; and the dashed line marked with the asterisk indicates attachment to -L²-Z or -L²-Z'.

Preferably -L¹- of formula (IIc-ii") is substituted with one moiety -L²-Z or -L²-Z'.

The optional further substituents of -L¹- of formula (II), (IIa), (IIb), (IIb'), (IIc), (IIc-a), (IIc-b), (IIc-i), (IIc-ii), (IIc-iii), (IIc-iv), (IIc-v), (IIc-i'), (IIc-ii'), (IIc-iii'), (IIc-iv'), (IIc-v'), (IIc-i"), (IIc-ii"), (IIc-iii"), (IIc-iv") are preferably as described above.

Another preferred moiety -L¹- is disclosed in WO2016/020373A1. Accordingly, in another preferred embodiment the moiety -L¹- is of formula (III):

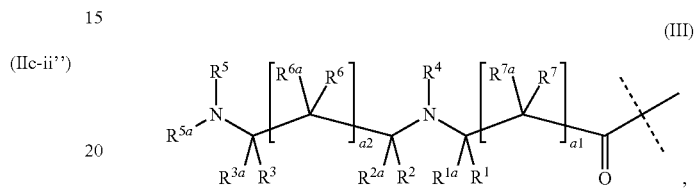

wherein
the dashed line indicates attachment to a primary or secondary amine or hydroxyl of -D which is a CNP moiety by forming an amide or ester linkage, respectively;
—$R^1$, —$R^{1a}$, —$R^2$, —$R^{2a}$, —$R^3$ and —$R^{3a}$ are independently of each other selected from the group consisting of —H, —$C(R^8R^{8a}R^{8b})$—$C(=O)R^8$, —C≡N, —$C(=NR^8)R^{8a}$, —$CR^8(=CR^{8a}R^{8b})$, —C≡$CR^8$ and -T;
—$R^4$, —$R^5$ and —$R^{5a}$ are independently of each other selected from the group consisting of —H, —$C(R^9R^{9a}R^{9b})$ and -T;
a1 and a2 are independently of each other 0 or 1;
each —$R^6$, —$R^{6a}$, —$R^7$, —$R^{7a}$, —$R^8$, —$R^{8a}$, —$R^{8b}$, —$R^9$, —$R^{9a}$, —$R^{9b}$ are independently of each other selected from the group consisting of —H, halogen, —CN, —$COOR^{10}$, —$OR^{10}$, —$C(O)R^{10}$, —$C(O)N(R^{10}R^{10a})$, —$S(O)_2N(R^{10}R^{10a})$, —$S(O)N(R^{10}R^{10a})$, —$S(O)_2R^{10}$, —$S(O)R^{10}$, —$N(R^{10})S(O)_2N(R^{10a}R^{10b})$, —$SR^{10}$, —$N(R^{10}R^{10a})$, —$NO_2$, —$OC(O)R^{10}$, —$N(R^{10})C(O)R^{10a}$, —$N(R^{10})S(O)_2R^{10a}$, —$N(R^{10})S(O)R^{10a}$, —$N(R^{10})C(O)OR^{10a}$, —$N(R^{10})C(O)N(R^{10a}R^{10b})$, —$OC(O)N(R^{10}R^{10a})$, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —$C(O)N(R^{12})$—, —$S(O)_2N(R^{12})$—, —$S(O)N(R^{12})$—, —$S(O)_2$—, —S(O)—, —$N(R^{12})S(O)_2N(R^{12a})$—, —S—, —$N(R^{12})$—, —$OC(OR^{12})(R^{12a})$—, —$N(R^{12})C(O)N(R^{12a})$—, and —$OC(O)N(R^{12})$—;
each —$R^{10}$, —$R^{10a}$, —$R^{10b}$ is independently selected from the group consisting of —H, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —$C(O)N(R^{12})$—, —$S(O)_2N(R^{12})$—, —$S(O)N(R^{12})$—, —$S(O)_2$—, —S(O)—, —$N(R^{12})S(O)_2N(R^{12a})$—, —S—, —N(R$^{12}$)—, —OC(OR$^{12}$)(R$^{12a}$)—, —N(R$^{12}$)C(O)N(R$^{12a}$)—, and —OC(O)N(R$^{12}$)—;

each T is independently of each other selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T is independently optionally substituted with one or more —R$^{11}$, which are the same or different;

each —R$^{11}$ is independently of each other selected from halogen, —CN, oxo (=O), —COOR$^{13}$, —OR$^{13}$, —C(O)R$^{13}$, —C(O)N(R$^{13}$R$^{13a}$), —S(O)$_2$N(R$^{13}$R$^{13a}$), —S(O)N(R$^{13}$R$^{13a}$), —S(O)$_2$R$^{13}$, —S(O)R$^{13}$, —N(R$^{13}$)S(O)$_2$N(R$^{13a}$R$^{13b}$), —SR$^{13}$, —N(R$^{13}$R$^{13a}$), —NO$_2$, —OC(O)R$^{13}$, —N(R$^{13}$)C(O)R$^{13a}$, —N(R$^{13}$)S(O)$_2$R$^{13a}$, —N(R$^{13}$)S(O)R$^{13a}$, —N(R$^{13}$)C(O)OR$^{13a}$, —N(R$^{13}$)C(O)N(R$^{13a}$R$^{13b}$), —OC(O)N(R$^{13}$R$^{13a}$), and C$_{1-6}$ alkyl; wherein C$_{1-6}$ alkyl is optionally substituted with one or more halogen, which are the same or different;

each —R$^{12}$, —R$^{12a}$, —R$^{13}$, —R$^{13a}$, —R$^{13b}$ is independently selected from the group consisting of —H, and C$_{1-6}$ alkyl; wherein C$_{1-6}$ alkyl is optionally substituted with one or more halogen, which are the same or different;

optionally, one or more of the pairs —R$^1$/—R$^{1a}$, —R$^2$/—R$^{2a}$, —R$^3$/R$^{3a}$, —R$^6$/—R$^{6a}$, —R$^7$/—R$^{7a}$ are joined together with the atom to which they are attached to form a C$_{3-10}$ cycloalkyl or a 3- to 10-membered heterocyclyl;

optionally, one or more of the pairs —R$^1$/—R$^2$, —R$^1$/—R$^3$, —R$^1$/—R$^4$, —R$^1$/—R$^5$, —R$^1$/—R$^6$, —R$^1$/—R$^7$, —R$^2$/—R$^3$, —R$^2$/—R$^4$, —R$^2$/—R$^5$, —R$^2$/—R$^6$, —R$^2$/—R$^7$, —R$^3$/—R$^4$, —R$^3$/—R$^5$, —R$^3$/—R$^6$, —R$^3$/—R$^7$, —R$^4$/—R$^5$, —R$^4$/—R$^6$, —R$^4$/—R$^7$, —R$^5$/—R$^6$, —R$^5$/—R$^7$, —R$^6$/—R$^7$ are joint together with the atoms to which they are attached to form a ring A;

A is selected from the group consisting of phenyl; naphthyl; indenyl; indanyl; tetralinyl; C$_{3-10}$ cycloalkyl; 3- to 10-membered heterocyclyl; and 8- to 11-membered heterobicyclyl;

wherein -L$^1$- is substituted with -L$^2$-Z or -L$^2$-Z' and wherein -L$^1$- is optionally further substituted;
wherein
-L$^2$- is a single chemical bond or a spacer;
—Z is a water-soluble carrier; and
Z' is a water-insoluble carrier.

The optional further substituents of -L$^1$- of formula (III) are preferably as described above.

Preferably -L$^1$- of formula (III) is substituted with one moiety -L$^2$-Z or -L$^2$-Z'.

In one embodiment -L$^1$- of formula (III) is not further substituted.

Additional preferred embodiments for -L$^1$- are disclosed in EP1536334B1, WO2009/009712A1, WO2008/034122A1, WO2009/143412A2, WO2011/082368A2, and U.S. Pat. No. 8,618,124B2, which are herewith incorporated by reference in their entirety.

Additional preferred embodiments for -L$^1$- are disclosed in U.S. Pat. No. 8,946,405B2 and U.S. Pat. No. 8,754,190B2, which are herewith incorporated by reference in their entirety. Accordingly, a preferred moiety -L$^1$- is of formula (IV):

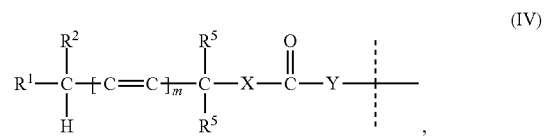

(IV)

wherein
the dashed line indicates attachment to -D which is a CNP agonist moiety and wherein attachment is through a functional group of -D selected from the group consisting of —OH, —SH and —NH$_2$;

m is 0 or 1;

at least one or both of —R$^1$ and —R$^2$ is/are independently of each other selected from the group consisting of —CN, —NO$_2$, optionally substituted aryl, optionally substituted heteroaryl, optionally substituted alkenyl, optionally substituted alkynyl, —C(O)R$^3$, —S(O)R$^3$, —S(O)$_2$R$^3$, and —SR$^4$, one and only one of —R$^1$ and —R$^2$ is selected from the group consisting of —H, optionally substituted alkyl, optionally substituted arylalkyl, and optionally substituted heteroarylalkyl;

—R$^3$ is selected from the group consisting of —H, optionally substituted alkyl, optionally substituted aryl, optionally substituted arylalkyl, optionally substituted heteroaryl, optionally substituted heteroarylalkyl, —OR$^9$ and —N(R$^9$)$_2$;

—R$^4$ is selected from the group consisting of optionally substituted alkyl, optionally substituted aryl, optionally substituted arylalkyl, optionally substituted heteroaryl, and optionally substituted heteroarylalkyl;

each —R$^5$ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;

—R$^9$ is selected from the group consisting of —H and optionally substituted alkyl;

—Y— is absent and —X— is —O— or —S—; or
—Y— is —N(Q)CH$_2$— and —X— is —O—;

Q is selected from the group consisting of optionally substituted alkyl, optionally substituted aryl, optionally substituted arylalkyl, optionally substituted heteroaryl and optionally substituted heteroarylalkyl;

optionally, —R$^1$ and —R$^2$ may be joined to form a 3 to 8-membered ring; and optionally, both —R$^9$ together with the nitrogen to which they are attached form a heterocyclic ring;

wherein -L$^1$- is substituted with -L$^2$-Z or -L$^2$-Z' and wherein is optionally further substituted;
wherein
-L$^2$- is a single chemical bond or a spacer;
—Z is a water-soluble carrier; and
—Z' is a water-insoluble carrier.

The optional further substituents of -L$^1$- of formula (IV) are preferably as described above.

Preferably -L$^1$- of formula (IV) is substituted with one moiety -L$^2$-Z or -L$^2$-Z'.

In one embodiment -L$^1$- of formula (IV) is not further substituted.

Only in the context of formula (IV) the terms used have the following meaning:

The term "alkyl" as used herein includes linear, branched or cyclic saturated hydrocarbon groups of 1 to 8 carbons, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds.

The term "alkynyl" includes non-aromatic unsaturated hydrocarbons with carbon-carbon triple bonds.

The term "aryl" includes aromatic hydrocarbon groups of 6 to 18 carbons, preferably 6 to 10 carbons, including groups such as phenyl, naphthyl, and anthracenyl. The term "heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instance, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4 to 8 membered aromatic or non-aromatic ring comprising 3 to 7 carbon atoms and at least one N, O, or S atom. Examples are piperidinyl, piperazinyl, tetrahydropyranyl, pyrrolidine, and tetrahydrofuranyl, as well as the exemplary groups provided for the term "heteroaryl" above.

When a ring system is optionally substituted, suitable substituents are selected from the group consisting of alkyl, alkenyl, alkynyl, or an additional ring, each optionally further substituted. Optional substituents on any group, including the above, include halo, nitro, cyano, —OR, —SR, —NR$_2$, —OCOR, —NRCOR, —COOR, —CONR$_2$, —SOR, —SO$_2$R, —SONR$_2$, —SO$_2$NR$_2$, wherein each R is independently alkyl, alkenyl, alkynyl, aryl or heteroaryl, or two R groups taken together with the atoms to which they are attached form a ring.

An additional preferred embodiment for -L$^1$- is disclosed in WO2013/036857A1, which is herewith incorporated by reference in its entirety. Accordingly, a preferred moiety is of formula (V):

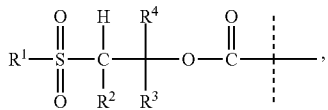

(V)

wherein
the dashed line indicates attachment to -D which is a CNP agonist moiety and wherein attachment is through an amine functional group of -D;
—R$^1$ is selected from the group consisting of optionally substituted C$_1$-C$_6$ linear, branched, or cyclic alkyl; optionally substituted aryl; optionally substituted heteroaryl; alkoxy; and —NR$^5{}_2$;
—R$^2$ is selected from the group consisting of —H; optionally substituted C$_1$-C$_6$ alkyl; optionally substituted aryl; and optionally substituted heteroaryl;
—R$^3$ is selected from the group consisting of —H; optionally substituted C$_1$-C$_6$ alkyl; optionally substituted aryl; and optionally substituted heteroaryl;
—R$^4$ is selected from the group consisting of —H; optionally substituted C$_1$-C$_6$ alkyl; optionally substituted aryl; and optionally substituted heteroaryl;
each —R$^5$ is independently of each other selected from the group consisting of —H; optionally substituted C$_1$-C$_6$ alkyl; optionally substituted aryl; and optionally substituted heteroaryl; or when taken together two —R$^5$ can be cycloalkyl or cycloheteroalkyl;
wherein is substituted with -L$^2$-Z or -L$^2$-Z' and wherein is optionally further substituted;
wherein
-L$^2$- is a single chemical bond or a spacer;
—Z is a water-soluble carrier; and
—Z' is a water-insoluble carrier.

The optional further substituents of -L$^1$- of formula (V) are preferably as described above.

Preferably -L$^1$- of formula (V) is substituted with one moiety -L$^2$-Z or -L$^2$-Z'.

In one embodiment -L$^1$- of formula (V) is not further substituted.

Only in the context of formula (V) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 C.

"Aryl" includes aromatic hydrocarbon groups of 6-18 carbons, preferably 6-10 carbons, including groups such as phenyl, naphthyl, and anthracene "Heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms. Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketene; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

A further preferred embodiment for is disclosed in U.S. Pat. No. 7,585,837B2, which is herewith incorporated by reference in its entirety. Accordingly, a preferred moiety is of formula (VI):

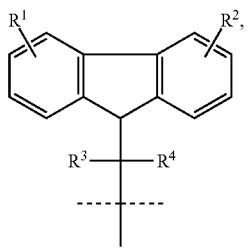

(VI)

wherein
the dashed line indicates attachment to -D which is a CNP agonist moiety and wherein attachment is through an amine functional group of -D;

$R^1$ and $R^2$ are independently selected from the group consisting of hydrogen, alkyl, alkoxy, alkoxyalkyl, aryl, alkaryl, aralkyl, halogen, nitro, —$SO_3H$, —$SO_2NHR^5$, amino, ammonium, carboxyl, $PO_3H_2$, and $OPO_3H_2$;

$R^3$, $R^4$, and $R^5$ are independently selected from the group consisting of hydrogen, alkyl, and aryl;

wherein -$L^1$- is substituted with -$L^2$-Z or -$L^2$-Z' and wherein -$L^1$- is optionally further substituted;

wherein
-$L^2$- is a single chemical bond or a spacer;
—Z is a water-soluble carrier; and
—Z' is a water-insoluble carrier.

Suitable substituents for formulas (VI) are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

Preferably -$L^1$- of formula (VI) is substituted with one moiety -$L^2$-Z or -$L^2$-Z'.

In one embodiment -$L^1$- of formula (VI) is not further substituted.

Only in the context of formula (VI) the terms used have the following meaning:

The terms "alkyl", "alkoxy", "alkoxyalkyl", "aryl", "alkaryl" and "aralkyl" mean alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

A further preferred embodiment for -$L^1$- is disclosed in WO2002/089789A1, which is herewith incorporated by reference in its entirety. Accordingly, a preferred moiety is of formula (VII):

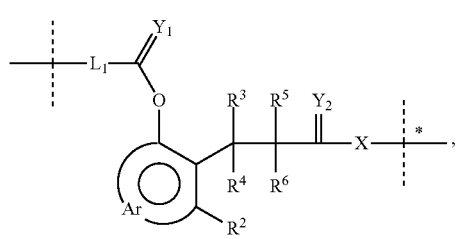

(VII)

wherein
the dashed line indicates attachment to -D which is a CNP agonist moiety and wherein attachment is through an amine functional group of -D;

$L_1$ is a bifunctional linking group, $Y_1$ and $Y_2$ are independently O, S or $NR^7$;

$R^2$, $R^3$, $R^4$, $R^5$, $R^6$ and $R^7$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

Ar is a moiety which when included in formula (VII) forms a multisubstituted aromatic hydrocarbon or a multi-substituted heterocyclic group;

X is a chemical bond or a moiety that is actively transported into a target cell, a hydrophobic moiety, or a combination thereof, y is 0 or 1;

wherein -$L^1$- is substituted with -$L^2$-Z or -$L^2$-Z' and wherein -$L^1$- is optionally further substituted;

wherein
-$L^2$- is a single chemical bond or a spacer;
—Z is a water-soluble carrier; and
—Z' is a water-insoluble carrier.

The optional further substituents of -$L^1$- of formula (VII) are preferably as described above.

Preferably -$L^1$- of formula (VII) is substituted with one moiety -$L^2$-Z or -$L^2$-Z'.

In one embodiment -$L^1$- of formula (VII) is not further substituted.

Only in the context of formula (VII) the terms used have the following meaning:

The term "alkyl" shall be understood to include, e.g. straight, branched, substituted $C_{1-12}$ alkyls, including alkoxy, $C_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophone; alkoxy includes moeities such as methoxy; and phenoxy includes moieties such as 3-nitrophenoxy. Halo-shall be understood to include fluoro, chloro, iodo and bromo.

In another preferred embodiment -$L^1$- comprises a substructure of formula (VIII)

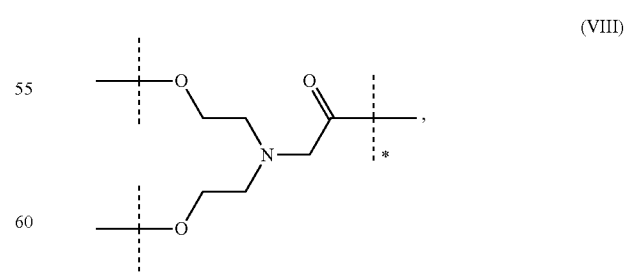

(VIII)

wherein
the dashed line marked with the asterisk indicates attachment to a nitrogen of -D which is a CNP agonist moiety by forming an amide bond;

the unmarked dashed lines indicate attachment to the remainder of -L$^1$-; and wherein -L$^1$- is substituted with -L$^2$-Z or -L$^2$-Z' and wherein -L$^1$- is optionally further substituted;

wherein

-L$^2$- is a single chemical bond or a spacer;

—Z is a water-soluble carrier; and

Z' is a water-insoluble carrier.

The optional further substituents of -L$^1$- of formula (VIII) are preferably as described above.

Preferably -L$^1$- of formula (VIII) is substituted with one moiety -L$^2$-Z or -L$^2$-Z'.

In one embodiment -L$^1$- of formula (VIII) is not further substituted.

In another preferred embodiment -L$^1$- comprises a substructure of formula (IX)

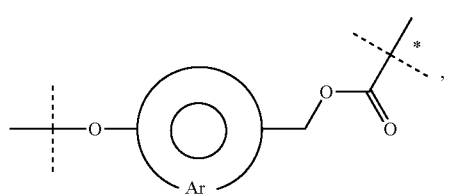

(IX)

wherein the dashed line marked with the asterisk indicates attachment to a nitrogen of -D which is a CNP agonist moiety by forming a carbamate bond;

the unmarked dashed lines indicate attachment to the remainder of -L$^1$-; and wherein -L$^1$- is substituted with -L$^2$-Z or -L$^2$-Z' and wherein -L$^1$- is optionally further substituted;

wherein

-L$^2$- is a single chemical bond or a spacer;

—Z is a water-soluble carrier; and

—Z' is a water-insoluble carrier.

The optional further substituents of -L$^1$- of formula (IX) are preferably as described above.

Preferably -L$^1$- of formula (IX) is substituted with one moiety -L$^2$-Z or -L$^2$-Z'.

In one embodiment -L$^1$- of formula (IX) is not further substituted.

Preferably -D of formula (Ia), (Ib), (II), (IIa), (IIb), (IIb'), (IIc), (IIc-a), (IIc-b), (IIc-i), (IIc-ii), (IIc-iii), (IIc-iv), (IIc-v), (IIc-i'), (IIc-ii'), (IIc-iii'), (IIc-iv'), (IIc-v'), (IIc-i''), (IIc-ii''), (IIc-iii''), (IIc-iv''), (III), (IV), (V), (VI), (VII), (VIII) and (IX) is a CNP moiety. The moiety -D may be connected to -L$^1$- through any functional group of D-H and is preferably connected to -L$^1$- through an amine functional group of D-H. This may be the N-terminal amine functional group or an amine functional group provided by a lysine side chain, i.e. by the lysines at position 9, 11, 15, 16, 20 and 26, if the CNP has the sequence of SEQ ID NO:24.

It was surprisingly found that attachment of -L$^1$- to the ring of a CNP moiety significantly reduces the CNP prodrug's affinity to NPR-B compared to attachment at the N-terminus or to the non-ring part of CNP, which reduced affinity to NPR-B in turn reduces the risk of cardiovascular side effects, such as hypotension.

Accordingly, -L$^1$- is preferably conjugated to the side chain of an amino acid residue of said ring moiety of -D or to the backbone of said ring moiety of -D. Even more preferably, -L$^1$- is covalently and reversibly conjugated to the side chain of an amino acid residue of said ring moiety of -D. If -D is a CNP moiety with the sequence of SEQ ID NO:24, -L$^1$- is preferably conjugated to the amine functional group provided by the lysine at position 26 of the corresponding drug D-H.

The moiety -L$^2$- is a chemical bond or a spacer moiety.

In one embodiment -L$^2$- is a chemical bond.

In another embodiment -L$^2$- is a spacer moiety.

When -L$^2$- is other than a single chemical bond, -L$^2$- is preferably selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently of each other selected from the group consisting of —H, -T, C$_{1-50}$ alkyl, C$_{2-50}$ alkenyl, and C$_{2-50}$ alkynyl; wherein -T, C$_{1-50}$ alkyl, C$_{2-50}$ alkenyl, and C$_{2-50}$ alkynyl are optionally substituted with one or more —R$^{y2}$, which are the same or different, and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —R$^{y2}$, which are the same or different;

each —R$^{y2}$ is independently selected from the group consisting of halogen, —CN, oxo (=O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{y3a}$, —R$^{y4}$, —R$^{y4a}$, —R$^{y5}$, —R$^{y5a}$ and —R$^{y5b}$ is independently selected from the group consisting of —H, and C$_{1-6}$ alkyl, wherein C$_{1-6}$ alkyl is optionally substituted with one or more halogen, which are the same or different.

When -L$^2$- is other than a single chemical bond, -L$^2$- is even more preferably selected from -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC (OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-20}$ alkyl, C$_{2-20}$ alkenyl, and C$_{2-20}$ alkynyl are optionally substituted with one or more —R$^{y2}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and R$^{y1a}$ are independently of each other selected from the group consisting of —H, -T, C$_{1-10}$ alkyl, C$_{2-10}$ alkenyl, and C$_{2-10}$ alkynyl; wherein -T, C$_{1-10}$ alkyl, C$_{2-10}$ alkenyl, and C$_{2-10}$ alkynyl are optionally substituted with one or more —R$^{y2}$, which are the same or different, and wherein C$_{1-10}$ alkyl, C$_{2-10}$ alkenyl, and C$_{2-10}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —R$^{y2}$, which are the same or different;

—R$^{y2}$ is selected from the group consisting of halogen, —CN, oxo (=O), —COOR$^5$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{Y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

When -L$^2$- is other than a single chemical bond, -L$^2$- is even more preferably selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently selected from the group consisting of —H, -T, C$_{1-10}$ alkyl, C$_{2-10}$ alkenyl, and C$_{2-10}$ alkynyl;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —R$^{y2}$ is independently selected from the group consisting of halogen, and C$_{1-6}$ alkyl; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

Even more preferably, -L$^2$- is a C$_{1-20}$ alkyl chain, which is optionally interrupted by one or more groups independently selected from —O—, -T- and —C(O)N(R$^{y1}$)—; and which C$_{1-20}$ alkyl chain is optionally substituted with one or more groups independently selected from —OH, -T and —C(O)N(R$^{y6}$R$^{y6a}$); wherein —R$^{y1}$, —R$^{y6}$, —R$^{y6a}$ are independently selected from the group consisting of H and C$_{1-4}$ alkyl and wherein T is selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

Preferably, -L$^2$- has a molecular weight in the range of from 14 g/mol to 750 g/mol.

Preferably, -L$^2$- comprises a moiety selected from

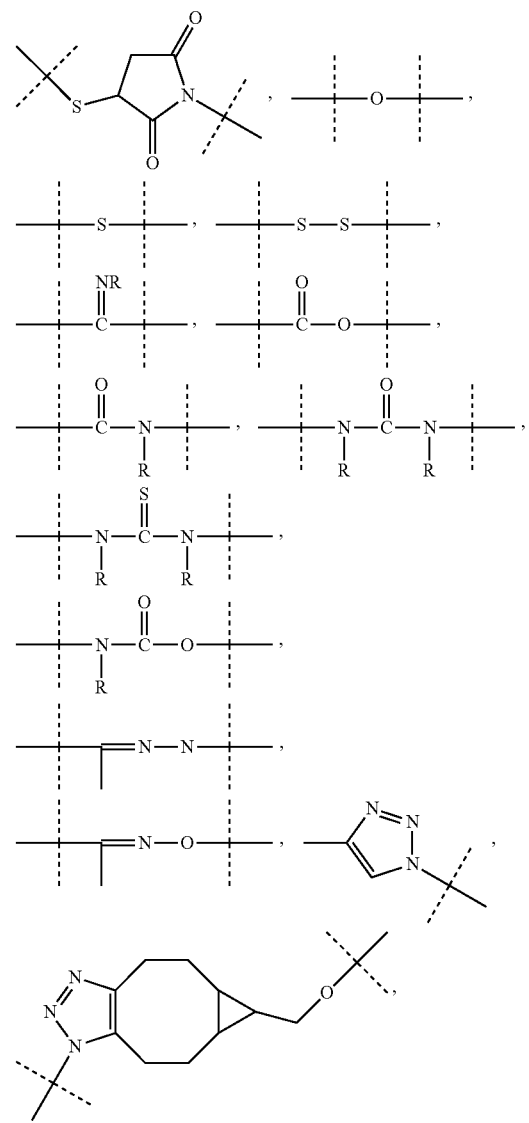

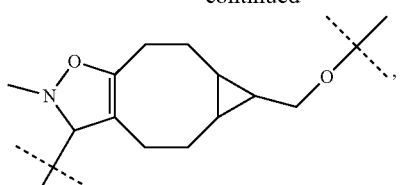

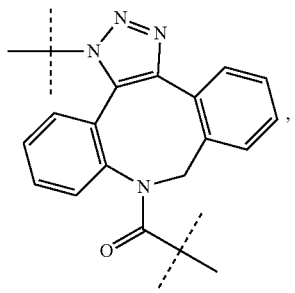

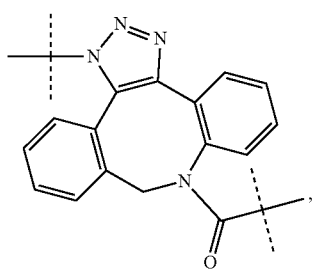

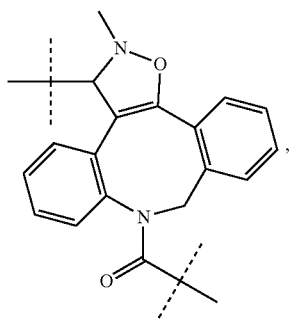

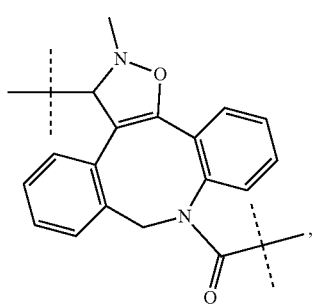

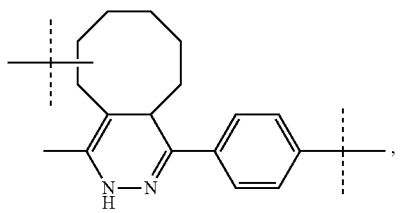

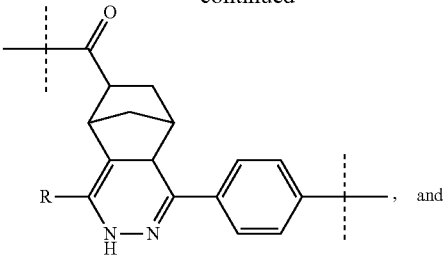

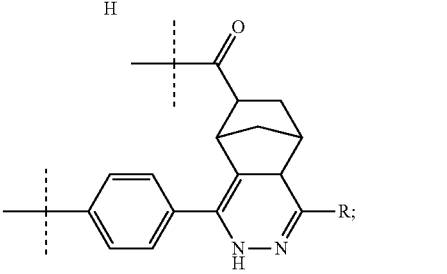

, and wherein
dashed lines indicate attachment to the rest of -L$^2$-, -L$^1$-, —Z and/or —Z', respectively; and
—R and —R$^a$ are independently of each other selected from the group consisting of —H, methyl, ethyl, propyl, butyl, pentyl and hexyl.

In one preferred embodiment -L$^2$- has a chain lengths of 1 to 20 atoms.

As used herein the term "chain length" with regard to the moiety -L$^2$- refers to the number of atoms of -L$^2$- present in the shortest connection between and —Z.

Preferably, -L$^2$- is of formula (i)

(i)

wherein
the dashed line marked with the asterisk indicates attachment to -L$^1$-;
the unmarked dashed line indicates attachment to —Z or —Z';
—R$^1$ is selected from the group consisting of —H, C$_{1-6}$ alkyl, C$_{2-6}$ alkenyl and C$_{2-6}$ alkynyl;
n is selected from the group consisting of 0, 1, 2, 3, 4, 5, 6, 7, 8, 9, 10, 11, 12, 13, 14, 15, 16, 17 and 18; and
wherein the moiety of formula (i) is optionally further substituted.

Preferably —R$^1$ of formula (i) is selected from the group consisting of —H, methyl, ethyl, propyl, and butyl. Even more preferably —R$^1$ of formula (i) is selected from the group consisting of —H, methyl, ethyl and propyl. Even more preferably —R$^1$ of formula (i) is selected from the group consisting of —H and methyl. Most preferably —R$^1$ of formula (i) is methyl.

Preferably n of formula (i) is selected from the group consisting of 0, 1, 2, 3, 4, 5, 6, 7, 8, 9 and 10. Even more preferably n of formula (i) is selected from the group consisting of 0, 1, 2, 3, 4 and 5. Even more preferably n of formula (i) is selected from the group consisting of 0, 1, 2 and 3. Even more preferably n of formula (i) is selected from the group consisting of 0 and 1. Most preferably n of formula (i) is 0.

In one preferred embodiment -L²- is a moiety selected from the group consisting of

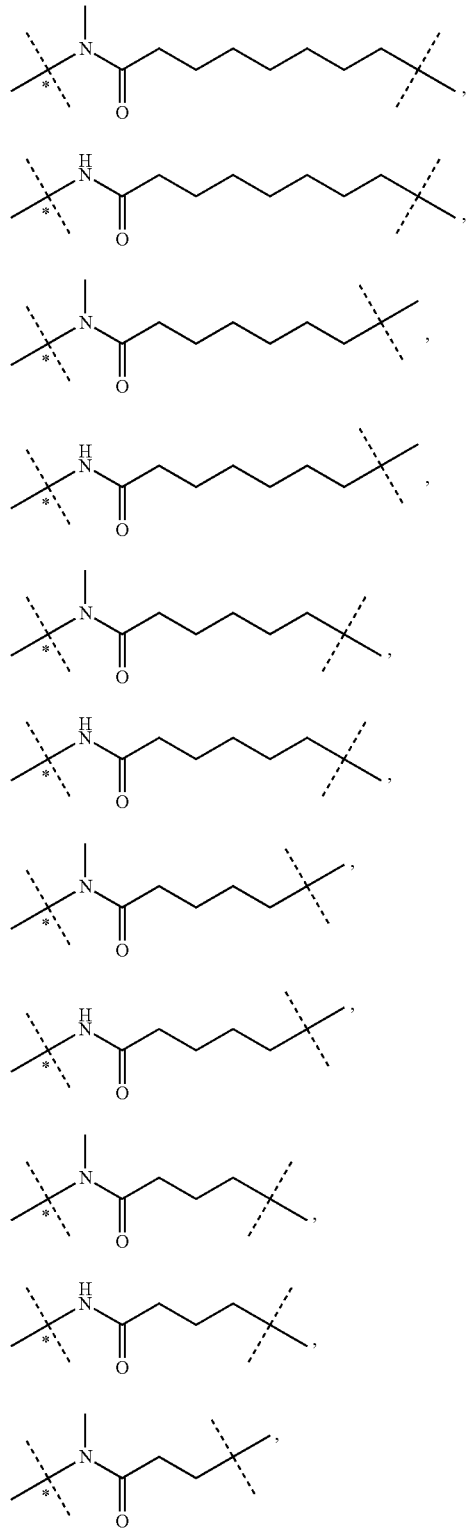

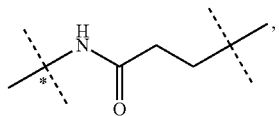

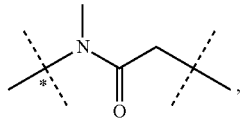

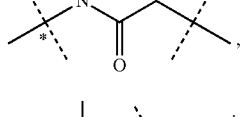

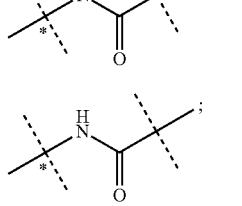

wherein
the dashed line marked with the asterisk indicates attachment to -L¹-;
the unmarked dashed line indicates attachment to —Z or —Z'; and
wherein the moieties (ii), (iii), (iv), (v), (vi), (vii), (viii), (ix), (x), (xi), (xii), (xiii), (xiv), (xv), (xvi) and (xvii) are optionally further substituted.

In a preferred embodiment -L²- is selected from the group consisting of

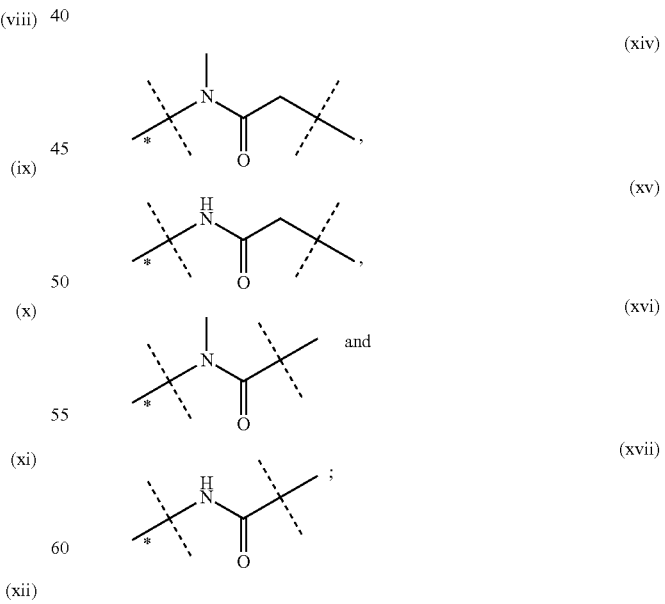

wherein
the dashed line marked with the asterisk indicates attachment to -L¹-; and
the unmarked dashed line indicates attachment to —Z or —Z'.

Even more preferred -L$^2$- is selected from the group consisting of

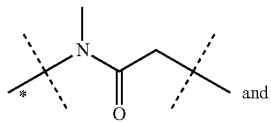
(xiv)

and

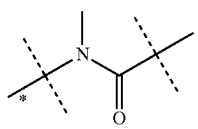
(xvi)

wherein the dashed line marked with the asterisk indicates attachment to -L$^1$-; and the unmarked dashed line indicates attachment to —Z or —Z'.

Even more preferably -L$^2$- is of formula (xvi)

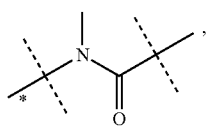
(xvi)

wherein the dashed line marked with the asterisk indicates attachment to -L$^1$-; and the unmarked dashed line indicates attachment to —Z or —Z'.

In one preferred embodiment the moiety -L$^1$-L$^2$- is selected from the group consisting of

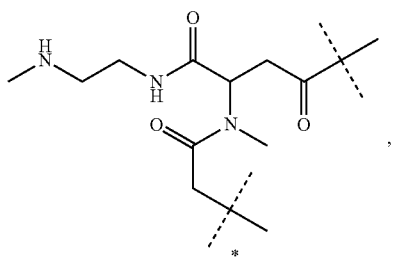
(IId-i)

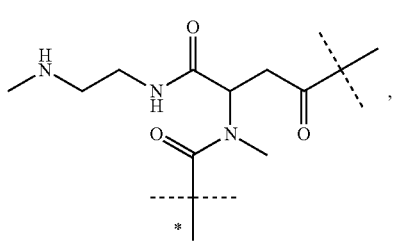
(IId-ii)

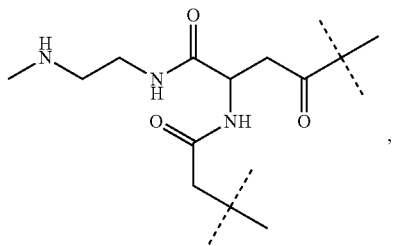
(IId-iii)

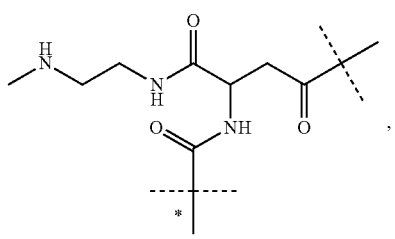
(IId-iv)

wherein the unmarked dashed line indicates the attachment to a nitrogen of -D which is a CNP agonist moiety by forming an amide bond; and the dashed line marked with the asterisk indicates attachment to —Z or —Z'.

In an even more preferred embodiment the moiety -L$^1$-L$^2$- is of formula (IId-ii)

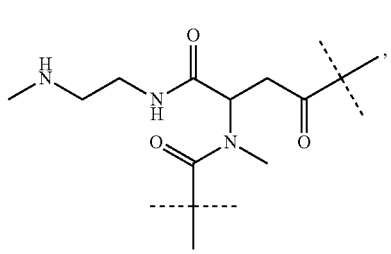
(IId-ii)

wherein the unmarked dashed line indicates the attachment to a nitrogen of -D which is a CNP agonist moiety by forming an amide bond; and the dashed line marked with the asterisk indicates attachment to —Z or —Z'.

In a most preferred embodiment the moiety -L$^1$-L$^2$- is of formula (IId-ii')

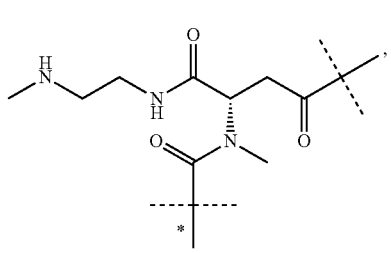
(IId-ii')

wherein
the unmarked dashed line indicates the attachment to a nitrogen of -D which is a CNP agonist moiety by forming an amide bond; and
the dashed line marked with the asterisk indicates attachment to —Z or —Z'.

In another preferred embodiment the moiety -L$^1$-L$^2$- is selected from the group consisting of

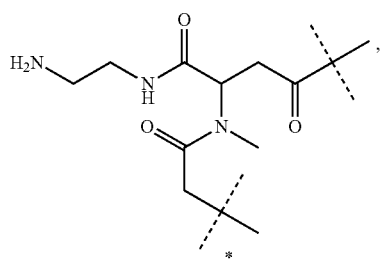
(IId-ia)

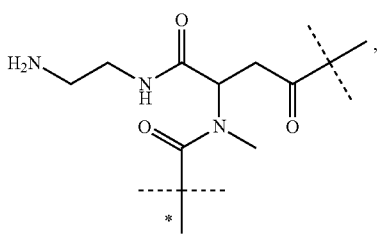
(IId-iia)

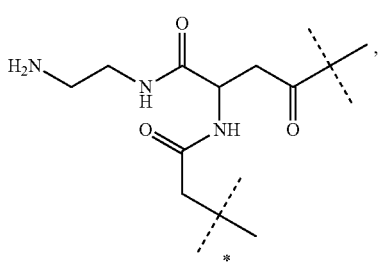
(IId-iiia)

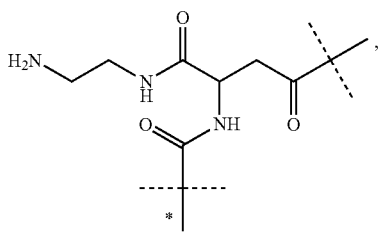
(IId-iva)

wherein
the unmarked dashed line indicates the attachment to a nitrogen of -D which is a CNP agonist moiety by forming an amide bond; and
the dashed line marked with the asterisk indicates attachment to —Z or —Z'.

In an even more preferred embodiment the moiety -L$^1$-L$^2$- is of formula (IId-iia)

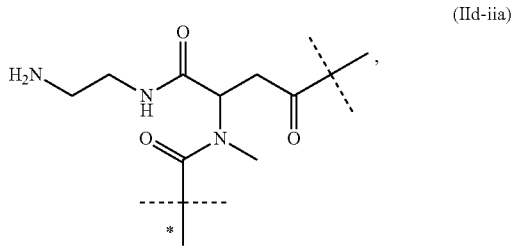
(IId-iia)

wherein
the unmarked dashed line indicates the attachment to a nitrogen of -D which is a CNP agonist moiety by forming an amide bond; and
the dashed line marked with the asterisk indicates attachment to —Z or —Z'.

In a most preferred embodiment the moiety -L$^1$-L$^2$- is of formula (IId-iia')

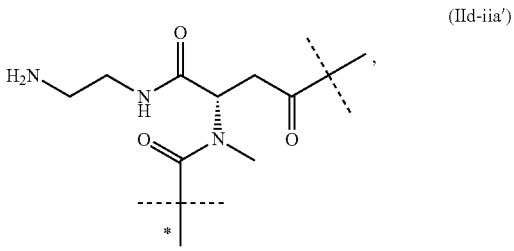
(IId-iia')

wherein
the unmarked dashed line indicates the attachment to a nitrogen of -D which is a CNP agonist moiety by forming an amide bond; and
the dashed line marked with the asterisk indicates attachment to —Z or —Z'.

In another preferred embodiment the moiety -L$^1$-L$^2$- is selected from the group consisting of

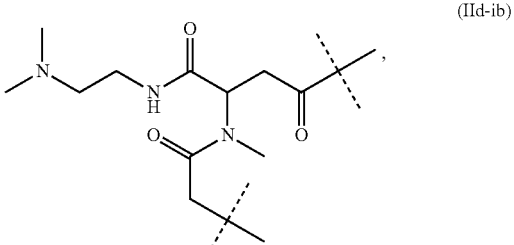
(IId-ib)

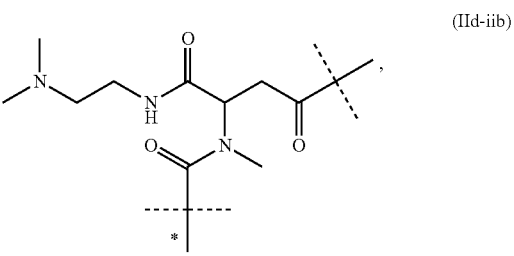
(IId-iib)

-continued

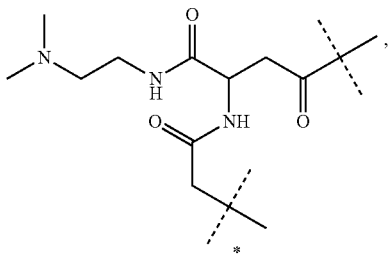
(IId-iiib)

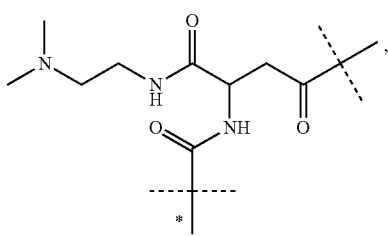
(IId-ivb)

wherein
the unmarked dashed line indicates the attachment to a nitrogen of -D which is a CNP agonist moiety by forming an amide bond; and
the dashed line marked with the asterisk indicates attachment to —Z or —Z'.

In an even more preferred embodiment the moiety -$L^1$-$L^2$- is of formula (IId-iib)

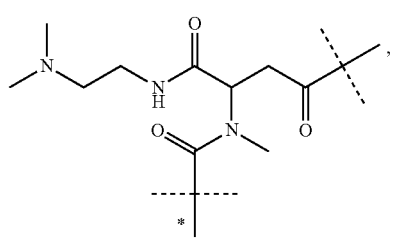
(IId-iib)

wherein
the unmarked dashed line indicates the attachment to a nitrogen of -D which is a CNP agonist moiety by forming an amide bond; and
the dashed line marked with the asterisk indicates attachment to —Z or —Z'.

In a most preferred embodiment the moiety -$L^1$-$L^2$- is of formula (IId-iib')

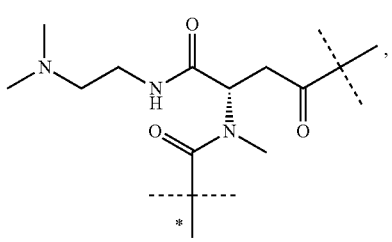
(IId-iib')

wherein
the unmarked dashed line indicates the attachment to a nitrogen of -D which is a CNP agonist moiety by forming an amide bond; and
the dashed line marked with the asterisk indicates attachment to —Z or —Z'.

Preferably, —Z of formula (Ia) or (Ib) has a molecular weight ranging from 5 to 200 kDa. Even more preferably, —Z of formula (Ia) or (Ib) has a molecular weight ranging from 8 to 100 kDa, even more preferably ranging from 10 to 80 kDa, even more preferably from 12 to 60, even more preferably from 15 to 40 and most preferably —Z of formula (Ia) or (Ib) has a molecular weight of about 20 kDa. In another equally preferred embodiment —Z of formula (Ia) or (Ib) has a molecular weight of about 40 kDa.

The carrier —Z of formula (Ia) or (Ib) comprises a $C_{8-24}$ alkyl or a polymer. Preferably, —Z of formula (Ia) or (Ib) comprises a polymer, preferably a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In another preferred embodiment, —Z of formula (Ia) or (Ib) comprises a fatty acid derivate. Preferred fatty acid derivatives are those disclosed in WO 2005/027978 A2 and WO 2014/060512 A1 which are herewith incorporated by reference.

In one embodiment —Z of formula (Ia) or (Ib) comprises a protein. Preferred proteins are selected from the group consisting of carboxyl-terminal peptide of the chorionic gonadotropin as described in US 2012/0035101 A1 which are herewith incorporated by reference; albumin; XTEN sequences as described in WO 2011123813 A2 which are herewith incorporated by reference; proline/alanine random coil sequences as described in WO 2011/144756 A1 which are herewith incorporated by reference; proline/alanine/serine random coil sequences as described in WO 2008/155134 A1 and WO 2013/024049 A1 which are herewith incorporated by reference; and Fc fusion proteins.

In one embodiment —Z of formula (Ia) or (Ib) is a polysarcosine.

In another preferred embodiment —Z of formula (Ia) or (Ib) comprises a poly(N-methylglycine).

In a particularly preferred embodiment —Z of formula (Ia) or (Ib) comprises a random coil protein moiety.

In one preferred embodiment —Z of formula (Ia) or (Ib) comprises one random coil protein moiety.

In another preferred embodiment —Z of formula (Ia) or (Ib) comprises two random coil protein moieties.

In another preferred embodiment —Z of formula (Ia) or (Ib) comprises three random coil protein moieties.

In another preferred embodiment —Z of formula (Ia) or (Ib) comprises four random coil protein moieties.

In another preferred embodiment —Z of formula (Ia) or (Ib) comprises five random coil protein moieties.

In another preferred embodiment —Z of formula (Ia) or (Ib) comprises six random coil protein moieties.

In another preferred embodiment —Z of formula (Ia) or (Ib) comprises seven random coil protein moieties.

In another preferred embodiment —Z of formula (Ia) or (Ib) comprises eight random coil proteins moieties.

Preferably such random coil protein moiety comprises at least 25 amino acid residues and at most 2000 amino acids. Even more preferably such random coil protein moiety comprises at least 30 amino acid residues and at most 1500 amino acid residues. Even more preferably such random coil protein moiety comprises at least 50 amino acid residues and at most 500 amino acid residues.

In a preferred embodiment, —Z of formula (Ia) or (Ib) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine and proline. Even more preferably, at least 10%, but less than 75%, preferably less than 65%, of the total number of amino acid residues of such random coil protein moiety are proline residues. Preferably, such random coil protein moiety is as described in WO 2011/144756 A1 which is hereby incorporated by reference in its entirety. Even more preferably —Z comprises at least one moiety selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:51 and SEQ ID NO:61 as disclosed in WO2011/144756 which are hereby incorporated by reference. A moiety comprising such random coil protein comprising alanine and proline will be referred to as "PA" or "PA moiety".

Accordingly, —Z of formula (Ia) or (Ib) comprises a PA moiety.

In an equally preferred embodiment, —Z of formula (Ia) or (Ib) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, serine and proline. Even more preferably, at least 4%, but less than 40% of the total number of amino acid residues of such random coil protein moiety are proline residues. Preferably, such random coil protein moiety is as described in WO 2008/155134 A1 which is hereby incorporated by reference in its entirety. Even more preferably —Z of formula (Ia) or (Ib) comprises at least one moiety selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:40, SEQ ID NO:42, SEQ ID NO:44, SEQ ID NO:46, SEQ ID NO:50, SEQ ID NO:52, SEQ ID NO:54 and SEQ ID NO:56 as disclosed in WO 2008/155134 A1, which are hereby incorporated by reference. A moiety comprising such random coil protein moiety comprising alanine, serine and proline will be referred to as "PAS" or "PAS moiety".

Accordingly, —Z of formula (Ia) or (Ib) comprises a PAS moiety.

In an equally preferred embodiment, —Z of formula (Ia) or (Ib) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine and proline. A moiety comprising such random coil protein moiety comprising alanine, glycine and proline will be referred to as "PAG" or "PAG moiety".

Accordingly, —Z of formula (Ia) or (Ib) comprises a PAG moiety.

In an equally preferred embodiment, —Z of formula (Ia) or (Ib) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from proline and glycine. A moiety comprising such random coil protein moiety comprising proline and glycine will be referred to as "PG" or "PG moiety".

Preferably, such PG moiety comprises a moiety of formula (a-0)

$$[(Gly)_p\text{-Pro-}(Gly)_q]_r \quad (a\text{-}0);$$

wherein p is selected from the group consisting of 0, 1, 2, 3, 4 and 5;

q is selected from the group consisting of 0, 1, 2, 3, 4 and 5;

r is an integer ranging from and including 10 to 1000;

provided that at least one of p and q is at least 1;

Preferably, p of formula (a-0) is selected from the group consisting of 1, 2 and 3.

Preferably, q of formula (a-0) is selected from 0, 1 and 2.

Even more preferably the PG moiety comprises the sequence of SEQ ID:NO 97: GGPGGPGPGGPGGPGPGGPG Even more preferably, the PG moiety comprises the sequence of formula (a-0-a)

$$(GGPGGPGPGGPGGPGPGGPG)_v \quad (a\text{-}0\text{-}a),$$

wherein v is an integer ranging from and including 1 to 50.

It is understood that the sequence of formula (a-0-a) comprises v replicates of the sequence of SEQ ID NO:97.

Accordingly, —Z of formula (Ia) or (Ib) comprises a PG moiety.

In an equally preferred embodiment, —Z of formula (Ia) or (Ib) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine, serine, threonine, glutamate and proline. Preferably, such random coil protein moiety is as described in WO 2010/091122 A1 which is hereby incorporated by reference. Even more preferably —Z of formula (Ia) or (Ib) comprises at least one moiety selected from the group consisting of SEQ ID NO:182, SEQ ID NO:183, SEQ ID NO:184; SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:1715, SEQ ID NO:1716, SEQ ID NO:1718, SEQ ID NO:1719, SEQ ID NO:1720, SEQ ID NO:1721 and SEQ ID NO:1722 as disclosed in WO2010/091122A1, which are hereby incorporated by reference. A moiety comprising such random coil protein moiety comprising alanine, glycine, serine, threonine, glutamate and proline will be referred to as "XTEN" or "XTEN moiety" in line with its designation in WO 2010/091122 A1.

Accordingly, —Z of formula (Ia) or (Ib) comprises an XTEN moiety.

In another preferred embodiment —Z of formula (Ia) or (Ib) is a hyaluronic acid-based polymer.

In one embodiment —Z of formula (Ia) or (Ib) is a carrier as disclosed in WO 2012/02047 A1 which is herewith incorporated by reference.

In another embodiment —Z of formula (Ia) or (Ib) is a carrier as disclosed in WO 2013/024048 A1 which is herewith incorporated by reference.

In another preferred embodiment —Z of formula (Ia) or (Ib) is a PEG-based polymer. Even more preferably —Z of formula (Ia) or (Ib) is a branched or multi-arm PEG-based polymer.

In a preferred embodiment —Z of formula (Ia) or (Ib) is a branched polymer. In one embodiment —Z of formula (Ia) or (Ib) is a branched polymer having one, two, three, four, five or six branching points. Preferably, —Z of formula (Ia) or (Ib) is a branched polymer having one, two or three branching points. In one embodiment —Z of formula (Ia) or (Ib) is a branched polymer having one branching point. In another embodiment —Z of formula (Ia) or (Ib) is a branched polymer having two branching points. In another embodiment —Z of formula (Ia) or (Ib) is a branched polymer having three branching points.

A branching point is preferably selected from the group consisting of —N<, —CH< and >C<. Preferably such branched moiety —Z of formula (Ia) or (Ib) is PEG-based.

In one embodiment such branched moiety —Z of formula (Ia) or (Ib) has a molecular weight ranging from and including 5 kDa to 500 kDa, more preferably ranging from and including 10 kDa to 250 Da, even more preferably ranging from and including 10 kDa to 150 kDa, even more preferably ranging from and including 12 kDa to 100 kDa and most preferably ranging from and including 15 kDa to 80 kDa.

Preferably, such branched moiety —Z of formula (Ia) or (Ib) has a molecular weight ranging from and including 10 kDa to 80 kDa. In one embodiment the molecular weight is about 10 kDa. In another embodiment the molecular weight of such branched moiety —Z of formula (Ia) or (Ib) is about 20 kDa. In another embodiment the molecular weight of such branched moiety —Z of formula (Ia) or (Ib) is about 30 kDa. In another embodiment the molecular weight of such a branched moiety —Z of formula (Ia) or (Ib) is about 40 kDa. In another embodiment the molecular weight of such a branched moiety —Z of formula (Ia) or (Ib) is about 50 kDa. In another embodiment the molecular weight of such a branched moiety —Z of formula (Ia) or (Ib) is about 60 kDa. In another embodiment the molecular weight of such a branched moiety —Z of formula (Ia) or (Ib) is about 70 kDa. In another embodiment the molecular weight of such a branched moiety —Z of formula (Ia) or (Ib) is about 80 kDa. Most preferably, such branched moiety —Z of formula (Ia) or (Ib) has a molecular weight of about 40 kDa.

Applicants found that an N-terminal attachment of a moiety $-L^1-L^2-Z$ is significantly more efficient with regard to NEP-stability than attachment at an internal site and that the least efficient attachment site with regard to NEP-stability is at the ring part of a CNP moiety. However, applicants surprisingly found that this disadvantage of attachment to the ring with regard to NEP-stability can be compensated by using a branched moiety —Z having a molecular weight of at least 10 kDa, such as at least 12 kDa, such as at least 15 kDa, such as at least 18 kDa, such as at least 20 kDa, such as at least 24 kDa, such as at least 25 kDa, such as at least 27 kDa, such as at least 30 kDa. Preferably, such branched moiety —Z has a molecular weight of no more than 500 kDa, preferably of no more than 250 kDa, preferably of no more than 200 Da, preferably of no more than 150 kDa and most preferably no more than 100 kDa. Most preferably such branched moiety —Z has a molecular weight of about 40 kDa. Consequently, the use of such branched moiety —Z at the ring part of the CNP moiety does not only lead to increased NEP-stability, but combines increased NEP-stability with reduced NPR-B binding associated with attachment to the ring.

It was surprisingly found that even though the ring moiety is involved in NPR-C binding, attachment of a 5 kDa carrier to the ring moiety did not have a significant effect on NPR-C affinity. Furthermore, it was surprisingly found that a 4×10 kDa carrier, i.e. a branched carrier having four 10 kDa arms, attached to the ring moiety is more efficient in reducing NPR-C affinity than a 2×20 kDa carrier, i.e. a branched carrier having two 20 kDa arms, even though the total molecular weight was the same. It is thus not only the total molecular weight of the carrier attached to the ring moiety, but the particular branching pattern of the carrier that influences NPR-C binding affinity.

This finding is also supported by the NPR-C affinity measured with a 4-arm 40 kDa carrier having a different branching pattern which still exhibited a high NPR-C affinity.

In summary, it was surprisingly found that NPR-C affinity can be efficiently reduced with a multi-branched carrier attached to the ring moiety having a first branching point close to the CNP moiety, such as less than 300 atoms from the CNP moiety, preferably 200 atoms from the CNP moiety, even more preferably 100 atoms from the CNP moiety, even more preferably less than 50 atoms from the CNP moiety, even more preferably less than 25 atoms from the CNP moiety and most preferably less than 10 atoms from the CNP moiety.

Even more preferably, one or more further branching point(s) is/are located within less than 500 atoms from the CNP moiety, even more preferably 300 atoms from the CNP moiety, even more preferably less than 200 atoms from the CNP moiety, even more preferably less than 100 atoms from the CNP moiety, even more preferably less than 75 atoms from the CNP moiety, even more preferably less than 50 atoms from the CNP moiety, even more preferably less than 40 atoms from the CNP moiety and most preferably less than 35 atoms from the CNP moiety.

It was in addition also found that such branching pattern is beneficial for in vivo stability of the CNP moiety, i.e. protection against proteolytic degradation. It was surprisingly found that N-terminal degradation was stronger when using a 2×20 kDa carrier compared to 4×10 kDa carrier. Likewise, using a 4-arm 40 kDa carrier having a different branching pattern exhibited even stronger N-terminal degradation.

Preferably, —Z or —Z' comprises a moiety

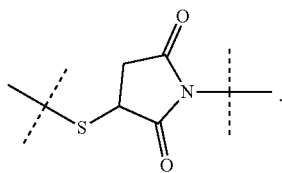

In an equally preferred embodiment —Z or —Z' comprises an amide bond.

In one embodiment —Z of formula (Ia) or (Ib) comprises a moiety of formula (a)

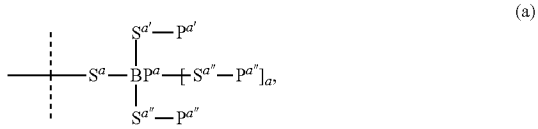

wherein
the dashed line indicates attachment to -L$^2$- or to the remainder of —Z;
BP$^a$ is a branching point selected from the group consisting of —N<, —CR< and >C<;
—R is selected from the group consisting of —H and C$_{1-6}$ alkyl;
a is 0 if BP$^a$ is —N< or —CR< and n is 1 if BP$^a$ is >C<;
—S$^a$—, —S$^{a'}$—, —S$^{a''}$— and —S$^{a'''}$— are independently of each other a chemical bond or are selected from the group consisting of C$_{1-50}$ alkyl, C$_{2-50}$ alkenyl, and C$_{2-50}$ alkynyl; wherein C$_{1-50}$ alkyl, C$_{2-50}$ alkenyl, and C$_{2-50}$ alkynyl are optionally substituted with one or more —R$^1$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^2$)—, —S(O)$_2$N(R$^2$)—, —S(O)N(R$^2$)—, —S(O)$_2$—, —S(O)—, —N(R$^2$)S(O)$_2$N(R$^{2a}$)—, —S—, —N(R$^2$)—, —OC(OR$^2$)(R$^{2a}$)—, —N(R$^2$)C(O)N(R$^{2a}$)—, and —OC(O)N(R$^2$)—;
each -T- is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —R$^1$, which are the same or different;
each —R$^1$ is independently selected from the group consisting of halogen, —CN, oxo (=O), —COOR$^3$, —OR$^3$, —C(O)R$^3$, —C(O)N(R$^3$R$^{3a}$), —S(O)$_2$N(R$^3$R$^{3a}$), —S(O)N(R$^3$R$^{3a}$), —S(O)$_2$R$^3$, —S(O)R$^3$, —N(R$^3$)S(O)$_2$N(R$^{3a}$R$^{3b}$), —SR$^3$, —N(R$^3$R$^{3a}$), —NO$_2$, —OC(O)R$^3$, —N(R$^3$)C(O)R$^{3a}$, —N(R$^3$)S(O)$_2$R$^{3a}$, —N(R$^3$)S(O)R$^{3a}$, —N(R$^3$)C(O)OR$^{3a}$, —N(R$^3$)C(O)N(R$^{3a}$R$^{3b}$), —OC(O)N(R$^3$R$^{3a}$), and C$_{1-6}$ alkyl; wherein C$_{1-6}$ alkyl is optionally substituted with one or more halogen, which are the same or different;
each —R$^2$, —R$^{2a}$, —R$^{3a}$ and R$^{3b}$ is independently selected from the group consisting of —H, and C$_{1-6}$ alkyl, wherein C$_{1-6}$ alkyl is optionally substituted with one or more halogen, which are the same or different; and
P$^{a'}$, —P$^{a''}$ and are —P$^{a'''}$ independently a polymeric moiety.

Optionally, the moiety of formula (a) is substituted with one or more substituents.

In one embodiment BP$^a$ of formula (a) is —N<.

In another embodiment BP$^a$ of formula (a) is —CR<. Preferably, —R is —H. Accordingly, a of formula (a) is preferably 0.

In another embodiment BP$^a$ of formula (a) is >C<.

In one embodiment —S$^a$— of formula (a) is a chemical bond.

In another embodiment —S$^a$— of formula (a) is selected from the group consisting of C$_{1-10}$ alkyl, C$_{2-10}$ alkenyl and C$_{2-10}$ alkynyl, which C$_{1-10}$ alkyl, C$_{2-10}$ alkenyl and C$_{2-10}$ alkynyl are optionally interrupted by one or more chemical groups selected from the group consisting of —C(O)O—, —O—, —C(O)—, —C(O)N(R$^4$)—, —S(O)$_2$N(R$^4$)—, —S(O)N(R$^4$)—, —S(O)$_2$—, —S(O)—, —N(R$^4$)S(O)$_2$N(R$^{4a}$)—, —S—, —N(R$^4$)—, —OC(OR$^4$)(R$^{4a}$)—, —N(R$^4$)C(O)N(R$^{4a}$)—, and —OC(O)N(R$^4$)—; wherein —R$^4$ and —R$^{4a}$ are independently selected from the group consisting of —H, methyl, ethyl, propyl and butyl. Preferably —S$^a$— of formula (a) is selected from the group consisting of methyl, ethyl, propyl, butyl, which are optionally interrupted by one or more chemical groups selected from the group consisting of —O—, —C(O)— and —C(O)N(R$^4$)—.

In one embodiment —S$^{a'}$— of formula (a) is a chemical bond.

In another embodiment —S$^{a'}$— of formula (a) is selected from the group consisting of C$_{1-10}$ alkyl, C$_{2-10}$ alkenyl and C$_{2-10}$ alkynyl, which C$_{1-10}$ alkyl, C$_{2-10}$ alkenyl and C$_{2-10}$ alkynyl are optionally interrupted by one or more chemical groups selected from the group consisting of —C(O)O—, —O—, —C(O)—, —C(O)N(R$^4$)—, —S(O)$_2$N(R$^4$)—, —S(O)N(R$^4$)—, —S(O)$_2$—, —S(O)—, —N(R$^4$)S(O)$_2$N(R$^{4a}$)—, —S—, —N(R$^4$)—, —OC(OR$^4$)(R$^{4a}$)N(R$^4$)C(O)N(R$^{4a}$)—, and —OC(O)N(R$^4$)—; wherein —R$^4$ and —R$^{4a}$ are independently selected from the group consisting of —H, methyl, ethyl, propyl and butyl. Preferably —S$^{a'}$— of formula (a) is selected from the group consisting of methyl, ethyl, propyl, butyl, which are optionally interrupted by one or more chemical groups selected from the group consisting of —O—, —C(O)— and —C(O)N(R$^4$)—.

In one embodiment —S$^{a''}$— of formula (a) is a chemical bond.

In another embodiment —S$^{a''}$— of formula (a) is selected from the group consisting of C$_{1-10}$ alkyl, C$_{2-10}$ alkenyl and C$_{2-10}$ alkynyl, which C$_{1-10}$ alkyl, C$_{2-10}$ alkenyl and C$_{2-10}$ alkynyl are optionally interrupted by one or more chemical groups selected from the group consisting of —C(O)O—, —O—, —C(O)—, —C(O)N(R$^4$)—, —S(O)$_2$N(R$^4$)—, —S(O)N(R$^4$)—, —S(O)$_2$—, —S(O)—, —N(R$^4$)S(O)$_2$N(R$^{4a}$)—, —S—, —N(R$^4$)—, —OC(OR$^4$)(R$^{4a}$)N(R$^4$)C(O)N(R$^{4a}$)—, and —OC(O)N(R$^4$)—; wherein —R$^4$ and —R$^{4a}$ are independently selected from the group consisting of —H, methyl, ethyl, propyl and butyl. Preferably —S$^{a''}$— of formula (a) is selected from the group consisting of methyl, ethyl, propyl, butyl, which are optionally interrupted by one or more chemical groups selected from the group consisting of —O—, —C(O)— and —C(O)N(R$^4$)—.

In one embodiment —S$^{a'''}$— of formula (a) is a chemical bond.

In another embodiment —S$^{a'''}$— of formula (a) is selected from the group consisting of C$_{1-10}$ alkyl, C$_{2-10}$ alkenyl and C$_{2-10}$ alkynyl, which C$_{1-10}$ alkyl, C$_{2-10}$ alkenyl and C$_{2-10}$ alkynyl are optionally interrupted by one or more chemical groups selected from the group consisting of —C(O)O—, —O—, —C(O)—, —C(O)N(R$^4$)—, —S(O)$_2$N(R$^4$)—, —S(O)N(R$^4$)—, —S(O)$_2$—, —S(O)—, —N(R$^4$)S(O)$_2$N(R$^{4a}$)—, —S—, —N(R$^4$)—, —OC(OR$^4$)(R$^{4a}$)N(R$^4$)C(O)N(R$^{4a}$)—, and —OC(O)N(R$^4$)—; wherein —R$^4$ and —R$^{4a}$ are independently selected from the group consisting of —H, methyl, ethyl, propyl and butyl. Preferably —S$^{a'''}$— of formula (a) is selected from the group consisting of methyl, ethyl, propyl, butyl, which are optionally interrupted by one or more chemical groups selected from the group consisting of —O—, —C(O)— and —C(O)N(R$^4$)—.

Preferably, —P$^{a'}$, —P$^{a''}$ and —P$^{a'''}$ of formula (a) independently comprise a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

Preferably, —P$^{a'}$, —P$^{a''}$ and —P$^{a'''}$ of formula (a) independently have a molecular weight ranging from and including 5 kDa to 50 kDa, more preferably have a molecular weight ranging from and including 5 kDa to 40 kDa, even more preferably ranging from and including 7.5 kDa to 35 kDa, even more preferably ranging from and 7.5 to 30 kDa, even more preferably ranging from and including 10 to 30 kDa.

In one embodiment —P$^{a'}$, P$^{a''}$ and —P$^{a'''}$ of formula (a) have a molecular weight of about 5 kDa.

In another embodiment —P$^{a'}$, P$^{a''}$ and —P$^{a'''}$ of formula (a) have a molecular weight of about 7.5 kDa.

In another embodiment —P$^{a'}$, P$^{a''}$ and —P$^{a'''}$ of formula (a) have a molecular weight of about 10 kDa.

In another embodiment —P$^{a'}$, —P$^{a''}$ and —P$^{a'''}$ of formula (a) have a molecular weight of about 12.5 kDa.

In another embodiment —P$^{a'}$, —P$^{a''}$ and —P$^{a'''}$ of formula (a) have a molecular weight of about 15 kDa.

In another embodiment —P$^{a'}$, —P$^{a''}$ and —P$^{a'''}$ of formula (a) have a molecular weight of about 20 kDa.

More preferably, —P$^{a'}$, —P$^{a''}$ and —P$^{a'''}$ of formula (a) independently comprise a PEG-based moiety. Even more preferably, —P$^{a'}$, —P$^{a''}$ and —P$^{a'''}$ of formula (a) independently comprise a PEG-based moiety comprising at least 20% PEG, even more preferably at least 30%, even more preferably at least 40% PEG, even more preferably at least 50% PEG, even more preferably at least 60% PEG, even more preferably at least 70% PEG, even more preferably at least 80% PEG and most preferably at least 90% PEG.

In an equally preferred embodiment —P$^{a'}$, —P$^{a''}$ and —P$^{a'''}$ of formula (a) independently comprise a protein moiety, more preferably a random coil protein moiety and most preferably a random coil protein moiety selected from the group consisting of PA, PAS, PAG, PG and XTEN moieties.

In one embodiment —P$^{a'}$, P$^{a''}$ and —P$^{a'''}$ of formula (a) are a PA moiety.

In another embodiment —P$^{a'}$, —P$^{a''}$ and —P$^{a'''}$ of formula (a) are a PAS moiety.

In another embodiment —P$^{a'}$, —P$^{a''}$ and —P$^{a'''}$ of formula (a) are a PAG moiety.

In another embodiment —P$^{a'}$, —P$^{a''}$ and —P$^{a'''}$ of formula (a) are a PG moiety.

In another embodiment —P$^{a'}$, P$^{a''}$ and —P$^{a'''}$ of formula (a) are an XTEN moiety.

In one embodiment —Z comprises one moiety of formula (a).

In another embodiment —Z comprises two moieties of formula (a).

In another embodiment —Z comprises three moieties of formula (a).

In another embodiment —Z comprises four moieties of formula (a).

In another embodiment —Z comprises five moieties of formula (a).

In another embodiment —Z comprises six moieties of formula (a).

In a preferred embodiment —Z comprises two moieties of formula (a).

In a preferred embodiment —Z comprises a moiety of formula (b)

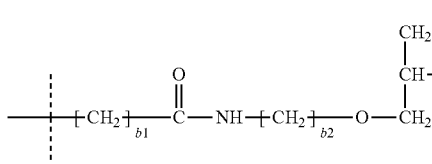 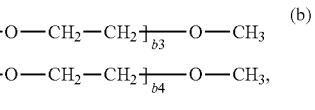 (b)

wherein the dashed line indicates attachment to -L$^2$- or to the remainder of —Z;

b1 is selected from the group consisting of 0, 1, 2, 3, 4, 5, 6, 7 and 8;

b2 is selected from the group consisting of 1, 2, 3, 4, 5, 6, 7 and 8;

b3 is an integer ranging from and including 150 to 1000; preferably ranging from and including 150 to 500; and most preferably ranging from and including 200 to 460; and b4 is an integer ranging from and including 150 to 1000; preferably ranging from and including 150 to 500; and most preferably ranging from and including 200 to 460.

Optionally, the moiety of formula (b) is substituted with one or more substituents.

Preferably, b3 and b4 of formula (b) are the same integer.

In one preferred embodiment b3 and b4 both an integer ranging from 200 to 250 and most preferably b3 and b4 of formula (b) are about 225.

In another preferred embodiment b3 and b4 are both an integer ranging from 400 to 500 and most preferably b3 and b4 of formula (b) are about 450.

Preferably, b1 of formula (b) is selected from the group consisting of 0, 1, 2, 3 and 4. More preferably b1 of formula (b) is selected from the group consisting of 1, 2 and 3. Most preferably b1 of formula (b) is 2.

Preferably, b2 of formula (b) is selected from the group consisting of 1, 2, 3, 4 and 5. More preferably b2 of formula (b) is selected from the group consisting of 2, 3 and 4. Most preferably b2 of formula (b) is 3.

In one particularly preferred embodiment b1 of formula (b) is 2, b2 of formula (b) is 3, and b3 and b4 are both about 450.

In another particularly preferred embodiment b1 of formula (b) is 2, b2 of formula (b) is 3, and b3 and b4 are both about 225.

In one embodiment —Z comprises one moiety of formula (b).

In another embodiment —Z comprises two moieties of formula (b).

In another embodiment —Z comprises three moieties of formula (b).

In another embodiment —Z comprises four moieties of formula (b).

In another embodiment —Z comprises five moieties of formula (b).

In another embodiment —Z comprises six moieties of formula (b).

In a preferred embodiment —Z comprises two moieties of formula (b).

In an even more preferred embodiment —Z comprises a moiety of formula (c)

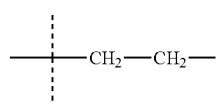 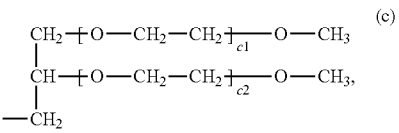 (c)

wherein the dashed line indicates attachment to -L$^2$- or to the remainder of —Z;

c1 and c2 are independently an integer ranging from and including 150 to 500;

preferably ranging from and including 200 to 460.

Optionally, the moiety of formula (c) is substituted with one or more substituents.

Preferably both c1 and c2 of formula (c) are the same integer.

In one preferred embodiment c1 and c2 of formula (c) range from and include 200 to 250 and most preferably are about 225. In another preferred embodiment c1 and c2 of formula (c) range from and include 400 to 500 and most preferably are about 450.

In a preferred embodiment the moiety —Z is a branched PEG-based polymer comprising at least 10% PEG, has one branching point and two PEG-based polymer arms and has a molecular weight of about 40 kDa. Accordingly, each of the two PEG-based polymer arms has a molecular weight of about 20 kDa. Preferably the branching point is —CH<.

In one embodiment —Z comprises one moiety of formula (c).

In another embodiment —Z comprises two moieties of formula (c).

In another embodiment —Z comprises three moieties of formula (c).

In another embodiment —Z comprises four moieties of formula (c).

In another embodiment —Z comprises five moieties of formula (c).

In another embodiment —Z comprises six moieties of formula (c).

In a preferred embodiment —Z comprises two moieties of formula (c).

In one preferred embodiment the moiety —Z is of formula (d)

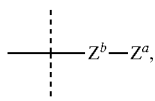

wherein
the dashed line indicates attachment to -L²-;
$Z^b$— is selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more —R¹, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N(R²)—, —S(O)₂N(R²)—, —S(O)N(R²)—, —S(O)₂—, —S(O)—, —N(R²)S(O)₂N(R²ᵃ)—, —S—, —N(R²)—, —OC(OR²)(R²ᵃ)—, —N(R²)C(O)N(R²ᵃ)—, and —OC(O)N(R²)—;
each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —R¹, which are the same or different;
each —R¹ is independently selected from the group consisting of halogen, —CN, oxo (=O), —COOR³, —OR³, —C(O)R³, —C(O)N(R³R³ᵃ), —S(O)₂N(R³R³ᵃ), —S(O)N(R³R³ᵃ), —S(O)₂R³, —S(O)R³, —N(R³)S(O)₂N(R³ᵃR³ᵇ), —SR³, —N(R³R³ᵃ), —NO₂, —OC(O)R³, —N(R³)C(O)R³ᵃ, —N(R³)S(O)₂R³ᵃ, —N(R³)S(O)R³ᵃ, —N(R³)C(O)OR³ᵃ, —N(R³)C(O)N(R³ᵃR³ᵇ), —OC(O)N(R³R³ᵃ), and $C_{1-6}$ alkyl;
wherein $C_{1-6}$ alkyl is optionally substituted with one or more halogen, which are the same or different;
each —R², —R²ᵃ, —R³, —R³ᵃ and R³ᵇ is independently selected from the group consisting of —H, and $C_{1-6}$ alkyl, wherein $C_{1-6}$ alkyl is optionally substituted with one or more halogen, which are the same or different;
and
—Zᵃ is

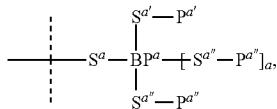

wherein
BPᵃ, —Sᵃ—, —Sᵃ'—, —Sᵃ"—, —Pᵃ—, —Pᵃ', —Pᵃ", —Pᵃ'" and a are used as defined for formula (a).

Optionally, the moiety of formula (d) is substituted with one or more substituents.
Preferred embodiments of BPᵃ, —Sᵃ—, —Sᵃ'—, —Sᵃ"—, —Sᵃ'"—, —Pᵃ', —Pᵃ", —Pᵃ'" of formula (d) are as defined above for formula (a).
Preferably, —Zᵃ of formula (d) is of formula (b). Preferred embodiments of b1, b2, b3 and b4 are as described for formula (b).
In an even more preferred embodiment the moiety —Z of formula (Ia) or (Ib) is of formula (e)

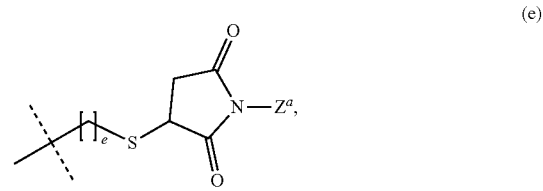

wherein
the dashed line indicates attachment to -L²-;
e is selected from the group consisting of 1, 2, 3, 4, 5, 6, 7, 8, 9, 10, 11, 12, 13, 14 and 15; and
—Zᵃ is

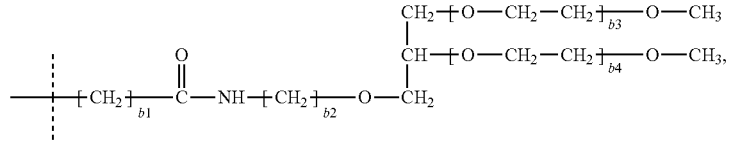

wherein
b1, b2, b3 and b4 are used as defined for formula (b).
Optionally, the moiety of formula (e) is substituted with one or more substituents.
Preferred embodiments for b1, b2, b3 and b4 of formula (e) are as defined above for formula (b).
In one embodiment e of formula (e) is 1. In another embodiment e of formula (e) is 2. In another embodiment e of formula (e) is 3. In another embodiment e of formula (e) is 4. In another embodiment e of formula (e) is 5. In another embodiment e of formula (e) is 6. In another embodiment e of formula (e) is 7. In another embodiment e of formula (e) is 8. In another embodiment e of formula (e) is 9. In another embodiment e of formula (e) is 10. In another embodiment e of formula (e) is 11. In another embodiment e of formula (e) is 12. In another embodiment e of formula (e) is 13. In another embodiment e of formula (e) is 14. In another embodiment e of formula (e) is 15.
Preferably e of formula (e) is selected from the group consisting of 2, 3, 4, 5, 6, 7, 8 and 9. Even more preferably, e of formula (e) is selected from 3, 4, 5 and 6. Most preferably e of formula (e) is 5.
Preferably e of formula (e) is 5, b1 of formula (e) is 2, b2 of formula (e) is 3 and b3 and b4 of formula (e) are both about 450.
In an equally preferred embodiment the moiety —Z of formula (Ia) or (Ib) is of formula (e-i) or (e-i'):

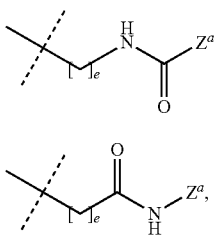
(e-i)

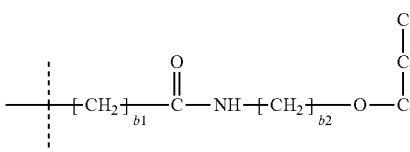
(e-i')

wherein
the dashed line indicates attachment to -L$^2$-,
e is selected from the group consisting of 1, 2, 3, 4, 5, 6, 7, 8, 9, 10, 11, 12, 13, 14 and 15;
—Z$^a$ is

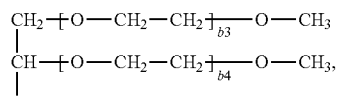

wherein
b1, b2, b3 and b4 are used as defined for formula (b).
Preferred embodiments for b1, b2, b3 and b4 of formula (e-i) and (e-i') are as defined above for formula (b).
Preferred embodiments for e of formula (e-i) and (e-i') are as described for formula (e).
Preferably, b1 of formula (e-i) and (e-i') is 2, b2 of formula (e-i) and (e-i') is 3 and b3 and b4 of formula (e-i) and (e-i') are both about 450.
In a preferred embodiment —Z of formula (Ia) or (Ib) is of formula (e-i).
In another preferred embodiment the moiety —Z is a branched PEG-based polymer comprising at least 10% PEG, has three branching points and four PEG-based polymer arms and has a molecular weight of about 40 kDa. Accordingly, each of the four PEG-based polymer arms has a molecular weight of about 10 kDa. Preferably each of the three branching points is —CH<.
In a preferred embodiment the moiety —Z is of formula (f)

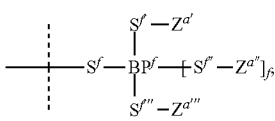
(F)

wherein
the dashed line indicates attachment to -L$^2$-;
BP$^f$ is a branching point selected from the group consisting of —N<, —CR< and >C<;
—R is selected from the group consisting of —H and C$_{1-6}$ alkyl;
f is 0 if BP$^f$ is —N< or —CR< and f is 1 if BP$^f$ is >C<;
—S$^f$—, —S$^{f'}$—, —S$^{f''}$— and —S$^{f'''}$— are independently either a chemical bond or are independently selected from the group consisting of C$_{1-50}$ alkyl, C$_{2-50}$ alkenyl, and C$_{2-50}$ alkynyl; wherein C$_{1-50}$ alkyl, C$_{2-50}$ alkenyl, and C$_{2-50}$ alkynyl are optionally substituted with one or more —R$^1$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^2$)—, —S(O)$_2$N(R$^2$)—, —S(O)N(R$^2$)—, —S(O)$_2$—, —S(O)—, —N(R$^2$)S(O)$_2$N(R$^{2a}$)—, —S—, —N(R$^2$)—, —OC(OR$^2$)(R$^{2a}$), —N(R$^2$)C(O)N(R$^{2a}$)—, and —OC(O)N(R$^2$)—;

each -T- is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —R$^1$, which are the same or different;

each R$^1$ is independently selected from the group consisting of halogen, —CN, oxo (=O), —COOR$^3$, —OR$^3$, —C(O)R$^3$, —C(O)N(R$^3$R$^{3a}$), —S(O)$_2$N(R$^3$R$^{3a}$), —S(O)N(R$^3$R$^{3a}$), —S(O)$_2$R$^3$, —S(O)R$^3$, —N(R$^3$)S(O)$_2$N(R$^{3a}$R$^{3b}$), —SR$^3$, —N(R$^3$R$^{3a}$), —NO$_2$, —OC(O)R$^3$, —N(R$^3$)C(O)R$^{3a}$, —N(R$^3$)S(O)$_2$R$^{3a}$, —N(R$^3$)S(O)R$^{3a}$, —N(R$^3$)C(O)OR$^{3a}$, —N(R$^3$)C(O)N(R$^{3a}$R$^{3b}$), —OC(O)N(R$^3$R$^{3a}$), and C$_{1-6}$ alkyl; wherein C$_{1-6}$ alkyl is optionally substituted with one or more halogen, which are the same or different;

each —R$^2$, —R$^{2a}$, —R$^3$, —R$^{3a}$ and R$^{3b}$ is independently selected from the group consisting of —H, and C$_{1-6}$ alkyl, wherein C$_{1-6}$ alkyl is optionally substituted with one or more halogen, which are the same or different;
and
—Z$^{a'}$, —Z$^{a''}$ and —Z$^{a'''}$ are independently

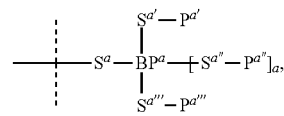

wherein
BP$^a$, —S$^a$—, —S$^{a'}$—, —S$^{a''}$, —S$^{a'''}$—, —P$^{a'}$, —P$^{a''}$, —P$^{a'''}$ and a are used as defined for formula (a).
Optionally, the moiety of formula (f) is substituted with one or more substituents.
Preferred embodiments of BP$^a$, —S$^a$—, —S$^{a'}$—, —S$^{a''}$, —P$^{a'}$, —P$^{a''}$ and —P$^{a'''}$ of formula (f) are as defined above for formula (a).
Preferably BP$^f$ of formula (f) is —CR< and r is 0. Preferably —R is —H.
Preferably —S$^f$— of formula (f) is a chemical bond.
Preferably, —Z$^{a'}$, —Z$^{a''}$ and —Z$^{a'''}$ of formula (f) have the same structure. Preferably, —Z$^{a'}$, —Z$^{a''}$ and —Z$^{a'''}$ of formula (f) are of formula (b).

Preferred embodiments of b1, b2, b3 and b4 are as described for formula (b).

Preferably —$S^f$— of formula (f) is a chemical bond, $BP^a$ of formula (f) is —CR< with —R being —H. Even more preferably —$S^f$— of formula (f) is a chemical bond, $BP^a$ of formula (f) is —CR< with —R being —H and —$Z^{a\prime}$, —$Z^{a\prime\prime}$ and —$Z^{a\prime\prime\prime}$ of formula (f) are of formula (b).

Even more preferably —Z is of formula (g)

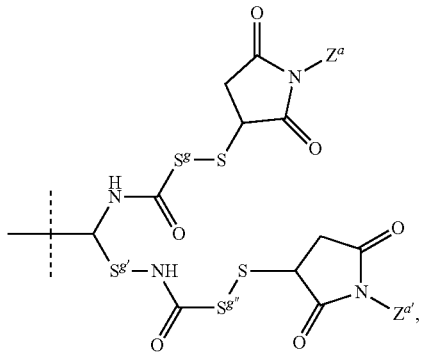

(g)

wherein the dashed line indicates attachment to -$L^2$-;

—$S^g$—, —$S^{g\prime}$— and —$S^{g\prime\prime}$— are independently selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more —$R^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^2$)—, —S(O)$_2$N($R^2$)—, —S(O)N($R^2$)—, —S(O)$_2$—, —S(O)—, —N($R^2$)S(O)$_2$N($R^{2a}$)—, —S—, —N($R^2$)—, —OC(O$R^2$)($R^{2a}$), —N($R^2$)C(O)N($R^{2a}$)—, and —OC(O)N($R^2$)—;

each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —$R^1$, which are the same or different;

each $R^1$ is independently selected from the group consisting of halogen, —CN, oxo (=O), —COO$R^3$, —O$R^3$, —C(O)$R^3$, —C(O)N($R^3R^{3a}$), —S(O)$_2$N($R^3R^{3a}$), —S(O)N($R^3R^{3a}$), —S(O)$_2R^3$, —S(O)$R^3$, —N($R^3$)S(O)$_2$N($R^{3a}R^{3b}$), —S$R^3$, —N($R^3R^{3a}$), —NO$_2$, —OC(O)$R^3$, —N($R^3$)C(O)$R^{3a}$, —N($R^3$)S(O)$_2R^{3a}$, —N($R^3$)S(O)$R^{3a}$, —N($R^3$)C(O)O$R^{3a}$, —N($R^3$)C(O)N($R^{3a}R^{3b}$), —OC(O)N($R^3R^{3a}$), and $C_{1-6}$ alkyl;

wherein $C_{1-6}$ alkyl is optionally substituted with one or more halogen, which are the same or different;

each —$R^2$, —$R^{2a}$, —$R^3$, —$R^{3a}$ and —$R^{3b}$ is independently selected from the group consisting of —H, and $C_{1-6}$ alkyl, wherein $C_{1-6}$ alkyl is optionally substituted with one or more halogen, which are the same or different;

and

—$Z^a$ and —$Z^{a\prime}$ are independently

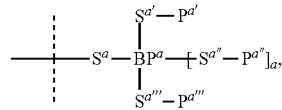

wherein $BP^a$, —$S^a$—, —$S^{a\prime}$—, —$S^{a\prime\prime}$—, —$S^{a\prime\prime\prime}$—, —$P^{a\prime}$, —$P^{a\prime\prime}$, —$P^{a\prime\prime\prime}$ and a are used as defined for formula (a).

Optionally, the moiety of formula (g) is substituted with one or more substituents.

Preferred embodiments of $BP^a$, —$S^a$—, —$S^{a\prime}$—, —$S^{a\prime\prime}$—, —$P^{a\prime}$, —$P^{a\prime\prime}$ and —$P^{a\prime\prime\prime}$ of formula (g) are as defined above for formula (a).

Preferably, —$S^g$— of formula (g) is selected from the group consisting of $C_{1-6}$ alkyl, $C_{2-6}$ alkenyl and $C_{2-6}$ alkynyl, which are optionally substituted with one or more —$R^1$, which is the same or different, wherein —$R^1$ is selected from the group consisting of halogen, oxo (=O), —COO$R^3$, —O$R^3$, —C(O)$R^3$, —C(O)N($R^3R^{3a}$), —S(O)$_2$N($R^3R^{3a}$), —S(O)N($R^3R^{3a}$), —S(O)$_2R^3$, —S(O)$R^3$, —N($R^3$)S(O)$_2$N($R^{3a}R^{3b}$), —S$R^3$, —N($R^3R^{3a}$), —NO$_2$, —OC(O)$R^3$, —N($R^3$)C(O)$R^{3a}$, —N($R^3$)S(O)$_2R^{3a}$, —N($R^3$)S(O)$R^{3a}$, —N($R^3$)C(O)O$R^{3a}$, —N($R^3$)C(O)N($R^{3a}R^{3b}$), —OC(O)N($R^3R^{3a}$), and $C_{1-6}$ alkyl; wherein $C_{1-6}$ alkyl is optionally substituted with one or more halogen, which are the same or different; and —$R^3$, —$R^{3a}$ and —$R^{3b}$ are independently selected from —H, methyl, ethyl, propyl and butyl.

Even more preferably —$S^g$— of formula (g) is selected from $C_{1-6}$ alkyl.

Preferably, —$S^{g\prime}$— of formula (g) is selected from the group consisting of $C_{1-6}$ alkyl, $C_{2-6}$ alkenyl and $C_{2-6}$ alkynyl, which are optionally substituted with one or more —$R^1$, which is the same or different, wherein —$R^1$ is selected from the group consisting of halogen, oxo (=O), —COO$R^3$, —O$R^3$, —C(O)$R^3$, —C(O)N($R^3R^{3a}$), —S(O)$_2$N($R^3R^{3a}$), —S(O)N($R^3R^{3a}$), —S(O)$_2R^3$, —S(O)$R^3$, —N($R^3$)S(O)$_2$N($R^{3a}R^{3b}$), —S$R^3$, —N($R^3R^{3a}$), —NO$_2$, —OC(O)$R^3$, —N($R^3$)C(O)$R^{3a}$, —N($R^3$)S(O)$_2R^{3a}$, —N($R^3$)S(O)$R^{3a}$, —N($R^3$)C(O)O$R^{3a}$, —N($R^3$)C(O)N($R^{3a}R^{3b}$), —OC(O)N($R^3R^{3a}$), and $C_{1-6}$ alkyl; wherein $C_{1-6}$ alkyl is optionally substituted with one or more halogen, which are the same or different; and —$R^3$, —$R^{3a}$ and —$R^{3b}$ are independently selected from —H, methyl, ethyl, propyl and butyl.

Even more preferably —$S^{g\prime}$— of formula (g) is selected from $C_{1-6}$ alkyl.

Preferably, —$S^{g\prime\prime}$— of formula (g) is selected from the group consisting of $C_{1-6}$ alkyl, $C_{2-6}$ alkenyl and $C_{2-6}$ alkynyl, which are optionally substituted with one or more —$R^1$, which is the same or different, wherein —$R^1$ is selected from the group consisting of halogen, oxo (=O), —COO$R^3$, —O$R^3$, —C(O)$R^3$, —C(O)N($R^3R^{3a}$), —S(O)$_2$N($R^3R^{3a}$), —S(O)N($R^3R^{3a}$), —S(O)$_2R^3$, —S(O)$R^3$, —N($R^3$)S(O)$_2$N($R^{3a}R^{3b}$), —S$R^3$, —N($R^3R^{3a}$), —NO$_2$, —OC(O)$R^3$, —N($R^3$)C(O)$R^{3a}$, —N($R^3$)S(O)$_2R^{3a}$, —N($R^3$)S(O)$R^{3a}$, —N($R^3$)

C(O)OR$^{3a}$, —N(R$^3$)C(O)N(R$^{3a}$R$^{3b}$), —OC(O)N(R$^3$R$^{3a}$), and C$_{1-6}$ alkyl; wherein C$_{1-6}$ alkyl is optionally substituted with one or more halogen, which are the same or different; and —R$^3$, —R$^{3a}$ and —R$^{3b}$ are independently selected from —H, methyl, ethyl, propyl and butyl.

Even more preferably —S$^{g''}$— of formula (g) is selected from C$_{1-6}$ alkyl.

Preferably, —Z$^a$ and —Z$^{a'}$ of formula (g) have the same structure. Preferably, —Z$^a$ and —Z$^{a'}$ of formula (g) are of formula (b).

In an alternative even more preferred embodiment —Z of formula (Ia) or (Ib) is of formula (g-i)

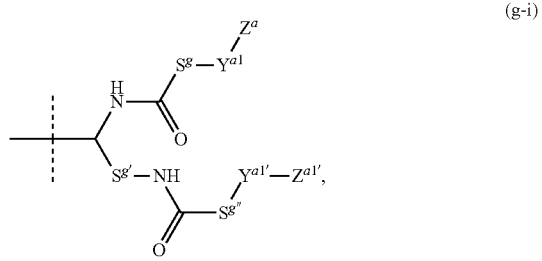

(g-i)

wherein
the dashed line indicates attachment to -L$^2$-;

—S$^g$—, —S$^{g'}$— and —S$^{g''}$— are independently selected from the group consisting of C$_{1-50}$ alkyl, C$_{2-50}$ alkenyl, and C$_{2-50}$ alkynyl; wherein C$_{1-50}$ alkyl, C$_{2-50}$ alkenyl, and C$_{2-50}$ alkynyl are optionally substituted with one or more —R$^1$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^2$)—, —S(O)$_2$N(R$^2$)—, —S(O)N(R$^2$)—, —S(O)$_2$—, —S(O)—, —N(R$^2$)S(O)$_2$N(R$^{2a}$)—, —S—, —N(R$^2$)—, —OC(OR$^2$)(R$^{2a}$)—, —N(R$^2$)C(O)N(R$^{2a}$)—, and —OC(O)N(R$^2$)—;

each -T- is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —R$^1$, which are the same or different;

each R$^1$ is independently selected from the group consisting of halogen, —CN, oxo (=O), —COOR$^3$, —OR$^3$, —C(O)R$^3$, —C(O)N(R$^3$R$^{3a}$), —S(O)$_2$N(R$^3$R$^{3a}$), —S(O)N(R$^3$R$^{3a}$), —S(O)$_2$R$^3$, —S(O)R$^3$, —N(R$^3$)S(O)$_2$N(R$^{3a}$R$^{3b}$), —SR$^3$, —N(R$^3$R$^{3a}$), —NO$_2$, —OC(O)R$^3$, —N(R$^3$)C(O)R$^{3a}$, —N(R$^3$)S(O)$_2$R$^{3a}$, —N(R$^3$)S(O)R$^{3a}$, —N(R$^3$)C(O)OR$^{3a}$, —N(R$^3$)C(O)N(R$^{3a}$R$^{3b}$), —OC(O)N(R$^3$R$^{3a}$), and C$_{1-6}$ alkyl; wherein C$_{1-6}$ alkyl is optionally substituted with one or more halogen, which are the same or different;

each —R$^2$, —R$^{2a}$, —R$^3$, —R$^{3a}$ and R$^{3b}$ is independently selected from the group consisting of —H, and C$_{1-6}$ alkyl, wherein C$_{1-6}$ alkyl is optionally substituted with one or more halogen, which are the same or different;

—Y$^{a1}$— and —Y$^{a1'}$— are

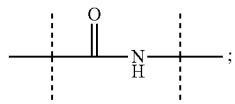

and
—Z$^a$ and —Z$^{a'}$ are independently

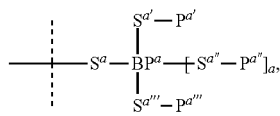

wherein
BP$^a$, —S$^a$—, —S$^{a'}$—, —S$^{a'''}$—, —P$^{a'}$, —P$^{a''}$, —P$^{a'''}$ and a are used as defined for formula (a).

Optionally, the moiety of formula (g-i) is substituted with one or more substituents.

Preferably, —Y$^{a1}$— and —Y$^{a1'}$— of formula (g-i) are both

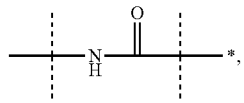

wherein the dashed line marked with the asterisk is attached to —Z$^a$ or —Z$^{a'}$, respectively.

Preferred embodiments of BP$^a$, —S$^a$—, —S$^{a'}$—, —S$^{a'''}$—, —P$^{a'}$, —P$^{a''}$ and —P$^{a'''}$ of formula (g-i) are as defined above for formula (a).

Preferred embodiments of —S$^g$—, —S$^{g'}$— and —S$^{g''}$— of formula (g-i) are as defined for formula (g).

Preferably, —Z$^a$ and —Z$^{a'}$ of formula (g-i) have the same structure. Preferably, —Z$^a$ and —Z$^{a'}$ of formula (g-i) are of formula (b). Preferred embodiments for b1, b2, b3 and b4 are as described for formula (b).

Even more preferably —Z is of formula (h)

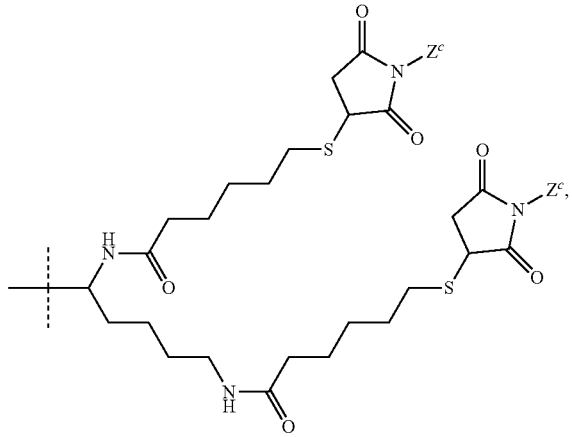

(h)

wherein
the dashed line indicates attachment to -L$^2$-; and
each —Z$^c$ is a moiety

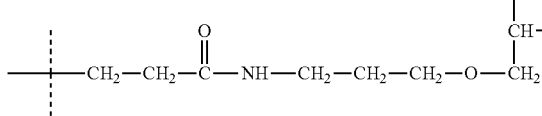
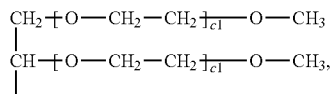

wherein
each c1 is an integer independently ranging from about 200 to 250.

Optionally, the moiety of formula (h) is substituted with one or more substituents.

Preferably both c1 of formula (h) are the same.

Preferably both c1 of formula (h) are about 225.

Even more preferably —Z of formula (Ia) or (Ib) is of formula (h-a)

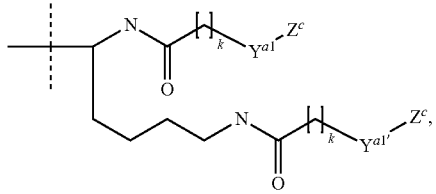

(h-a)

wherein
the dashed line indicates attachment to $-L^2-$;
each k is independently of each other selected from the group consisting of 1, 2, 3, 4, 5, 6, 7, 8, 9, 10, 11 and 12;
$—Y^{a1}—$ and $—Y^{a1'}—$ are

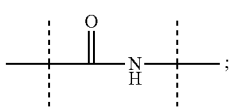

and
each $—Z^c$ is a moiety

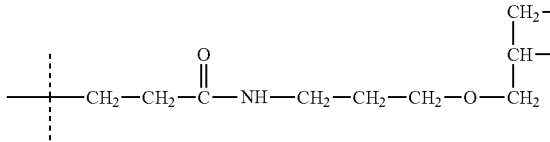
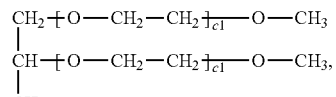

wherein
each c1 is an integer independently ranging from about 200 to 250.

Optionally, the moiety of formula (h-a) is substituted with one or more substituents.

Preferably, each k of formula (h-a) is independently selected from the group consisting of 2, 3, 4, 5, 6 and 7.

Preferably, both k of formula (h-a) are identical.

Preferably both c1 of formula (h-a) are the same.

Preferably both c1 of formula (h-a) are about 225.

Preferably, $—Y^{a1}—$ and $—Y^{a1'}—$ of formula (h-a) are both

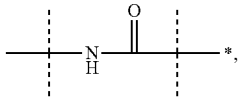

wherein the dashed line marked with the asterisk is attached to —$Z^c$.

In an even more preferred embodiment the moiety —Z is of formula (h-i)

(h-i)

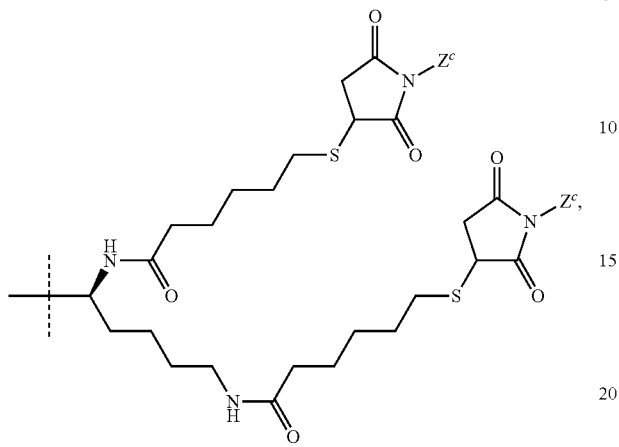

wherein
the dashed line indicates attachment to -$L^2$-; and
each —$Z^c$ is a moiety

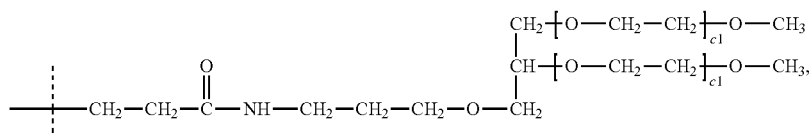

each c1 is an integer independently ranging from 200 to 250.

Optionally, the moiety of formula (h-i) is substituted with one or more substituents.

Preferably both c1 of formula (h-i) are the same.
Preferably both c1 of formula (h-i) are about 225.

In an alternative even more preferred embodiment the moiety —Z of formula (Ia) or (Ib) is of formula (h-ia)

(h-ia)

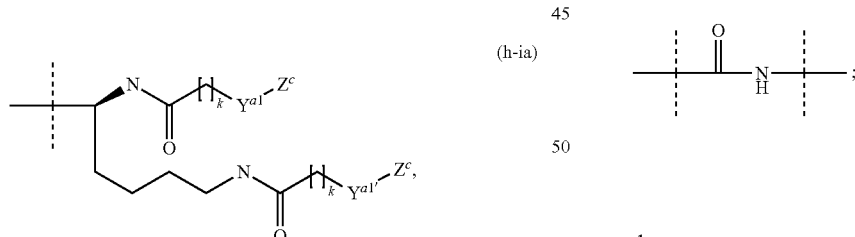

wherein
the dashed line indicates attachment to -$L^2$-;
each k is independently of each other selected from the group consisting of 1, 2, 3, 4, 5, 6, 7, 8, 9, 10, 11 and 12;
—$Y^{a1}$— and —$Y^{a1'}$— are

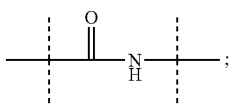

and
each —$Z^c$ is a moiety

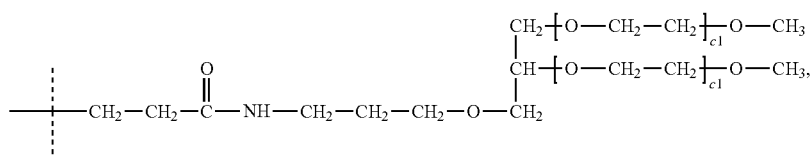

each c1 is an integer independently ranging from 200 to 250.

Preferably, each k of formula (h-ia) is independently selected from the group consisting of 2, 3, 4, 5, 6 and 7. Preferably, both k of formula (h-ia) are identical.

Preferably, —Y$^{a1}$— and —Y$^{a1'}$— of formula (h-ia) are both

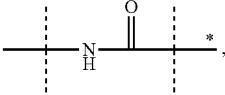

wherein the dashed line marked with the asterisk is attached to —Z$^c$.

In an equally preferred the embodiment —Z of formula (Ia) or (Ib) comprises a moiety selected from the group consisting of Preferably both c1 of formula (h-ia) are the same.
Preferably both c1 of formula (h-ia) are about 225.

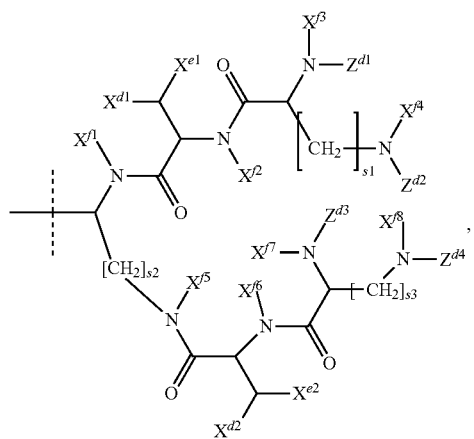

(j-i)

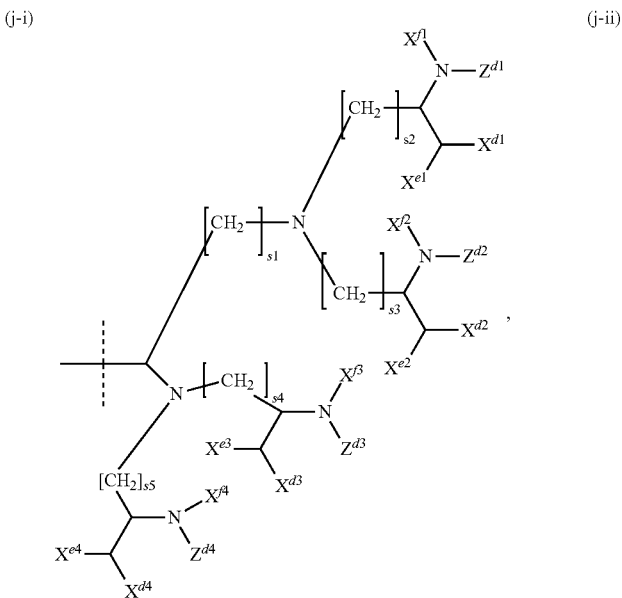

(j-ii)

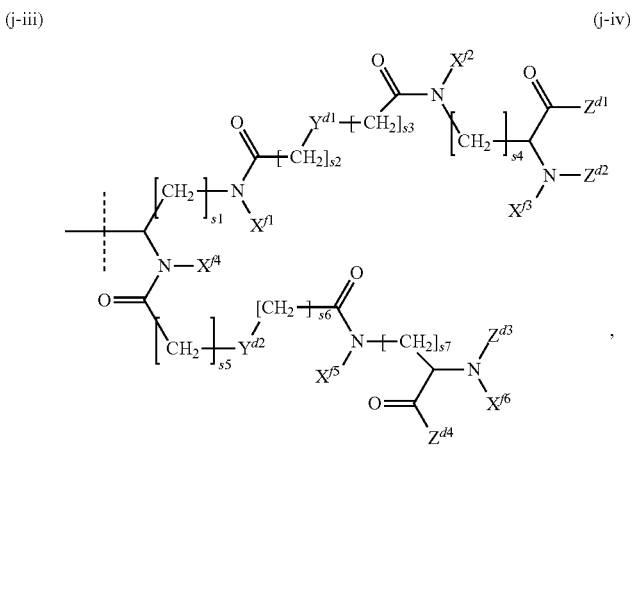

(j-iii)

, (j-iv)

,

-continued (j-v)

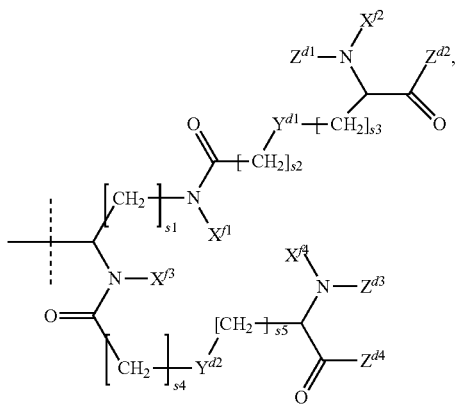

(j-vi)

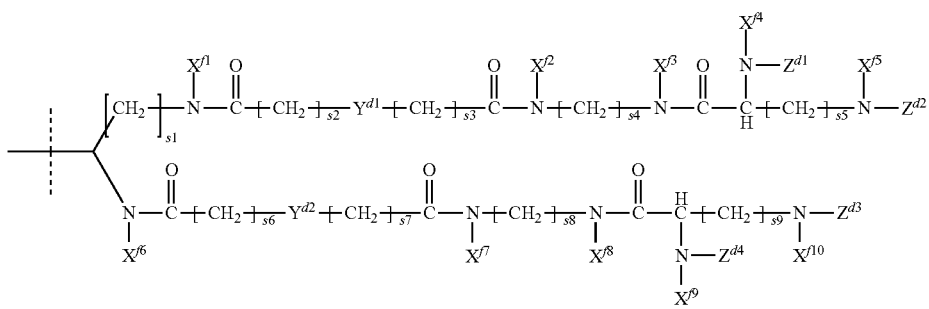

(j-vii)

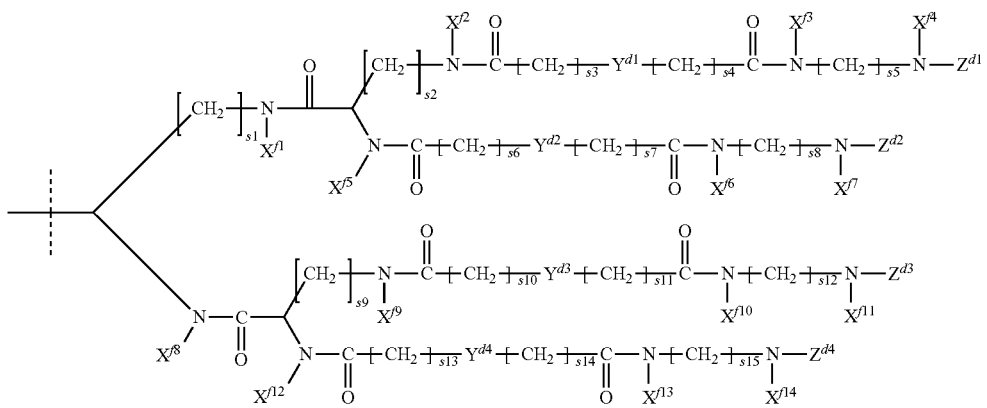

wherein
the dashed line indicates attachment to -$L^2$-;
s1, s2, s3, s4, s5, s6, s7, s8, s9, s10, s11, s12, s13, s14 and s15 are independently of each other selected from 1, 2, 3, 4, 5, 6, 7, 8, 9, 10;
—$X^{d1}$, —$X^{d2}$, —$X^{d3}$ and —$X^{d4}$ are independently of each other selected from the group consisting of —OH, —SH and —$NR^{g1}R^{g2}$; preferably —OH;
—$X^{e1}$, —$X^{e2}$, —$X^{e3}$ and —$X^{e4}$ are independently of each other selected from the group consisting of —H, $C_{1-6}$ alkyl, $C_{2-6}$ alkenyl and $C_{2-6}$ alkynyl;
—$R^{g1}$ and —$R^{g2}$ are independently of each other selected from the group consisting of —H, $C_{1-6}$ alkyl, $C_{2-6}$ alkenyl and $C_{2-6}$ alkynyl;
—$X^{f1}$, —$X^{f2}$, —$X^{f3}$, —$X^{f4}$, —$X^{f5}$, —$X^{f6}$, —$X^{f7}$, —$X^{f8}$, —$X^{f9}$, —$X^{f10}$, —$X^{f11}$, —$X^{f12}$, —$X^{f13}$ and —$X^{f14}$ are independently of each other selected from the group consisting of —H, $C_{1-6}$ alkyl, $C_{2-6}$ alkenyl and $C_{2-6}$ alkynyl; preferably —H;

—$Y^{d1}$—, —$Y^{d2}$—, —$Y^{d3}$— and —$Y^{d4}$— are independently of each other selected from the group consisting of

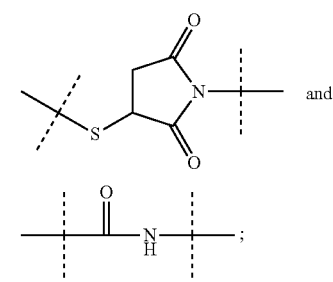

and

—$Z^{d1}$, —$Z^{d2}$, —$Z^{d3}$ and —$Z^{d4}$ are independently of each other a protein, more preferably a random coil protein and most preferably a random coil protein selected from the group consisting of PA, PAS, PAG, PG and XTEN.

In one preferred embodiment, —$Y^{d1}$— and —$Y^{d2}$— of formula (j-iv), (j-v) and (j-vi) and —$Y^{d1}$—, —$Y^{d2}$—, —$Y^{d3}$— and —$Y^{d4}$— of formula (j-vii) are

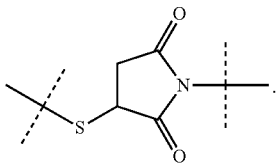

In another preferred embodiment, —$Y^{d1}$— and —$Y^{d2}$— of formula (j-iv), (j-v) and (j-vi) and —$Y^{d1}$—, —$Y^{d2}$—, —$Y^{d3}$— and —$Y^{d4}$— of formula (j-vii) are

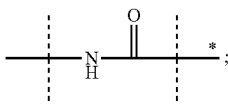

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

Preferably, —$X^{f1}$, —$X^{f2}$, —$X^{f3}$, —$X^{f4}$, —$X^{f5}$, —$X^{f6}$, —$X^{f7}$ and —$X^{f8}$ of formula (j-i) are —H; —$X^{d1}$ and —$X^{d2}$ of formula (j-i) are —OH; —$X^{e1}$ and —$X^{e2}$ of formula (j-i) are selected from the group consisting of —H and methyl; and s1, s2, s3 and s4 of formula (j-i) are selected from the group consisting of 2, 3, 4, 5 and 6. Even more preferably —$X^{f1}$, —$X^{f2}$, —$X^{f3}$, —$X^{f4}$, —$X^{f5}$, —$X^{f6}$, —$X^{f7}$ and —$X^{f8}$ of formula (j-i) are —H; —$X^{d1}$ and —$X^{d2}$ of formula (j-i) are —OH; —$X^{e1}$ and —$X^{e2}$ of formula (j-i) are —H; and s1, s2, s3 and s4 of formula (j-i) are 4.

Preferably, —$X^{f1}$, —$X^{f2}$, —$X^{f3}$ and —$X^{f4}$ of formula (j-ii) are —H; —$X^{d1}$, —$X^{d2}$, —$X^{d3}$ and —$X^{d2}$ of formula (j-ii) are —OH; —$X^{e1}$, —$X^{e2}$, —$X^{e3}$ and —$X^{e4}$ of formula (j-ii) are selected from the group consisting of —H and methyl; s1, s2, s3, s4 and s5 of formula (j-ii) are selected from the group consisting of 1, 2, 3, 4, 5 and 6. Even more preferably —$X^{f1}$, —$X^{f2}$, —$X^{f3}$ and —$X^{f4}$ of formula (j-ii) are —H; —$X^{d1}$, —$X^{d2}$, —$X^{d3}$ and —$X^{d2}$ of formula (j-ii) are —OH; —$X^{e1}$, —$X^{e2}$, —$X^{e3}$ and —$X^{e4}$ of formula (j-ii) are —H; s1 is 4 of formula (j-ii) and s2, s3, s4 and s5 of formula (j-ii) are 1.

Preferably, —$X^{f1}$, —$X^{f2}$, —$X^{f3}$, —$X^{f4}$, —$X^{f5}$, —$X^{f6}$, —$X^{f7}$, —$X^{f8}$, —$X^{f9}$ and —$X^{f10}$ of formula (j-iii) are —H; —$X^{d1}$, —$X^{d2}$, —$X^{d3}$ and —$X^{d4}$ of formula (j-iii) are —OH; —$X^{e1}$, —$X^{e2}$, —$X^{e3}$ and —$X^{e4}$ of formula (j-iii) are selected from the group consisting of —H and methyl; and s1, s2 and s3 of formula (j-iii) are selected from the group consisting of 2, 3, 4, 5 and 6. Even more preferably —$X^{f1}$, —$X^{f2}$, —$X^{f3}$, —$X^{f4}$, —$X^{f5}$, —$X^{f6}$, —$X^{f7}$, —$X^{f8}$, —$X^{f9}$ and —$X^{f10}$ of formula (j-iii) are —H; —$X^{d1}$, —$X^{d2}$, —$X^{d3}$ and —$X^{d4}$ of formula (j-iii) are —OH; —$X^{e1}$, —$X^{e2}$, —$X^{e3}$ and —$X^{e4}$ of formula (j-iii) are —H; and s1, s2 and s3 of formula (j-iii) are 4.

Preferably, —$X^{f1}$, —$X^{f2}$, —$X^{f3}$, —$X^{f4}$, —$X^{f5}$ and —$X^{f6}$ of formula (j-iv) are —H; s1, s2, s3, s4, s5, s6 and s7 of formula (j-iv) are selected from the group consisting of 1, 2, 3, 4, 5, 6 and 7; —$Y^{d1}$— and —$Y^{d2}$— are selected from the group consisting of

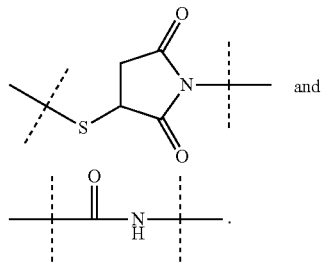

In an even more preferred embodiment —$X^{f1}$, —$X^{f2}$, —$X^{f3}$, —$X^{f4}$, —$X^{f5}$ and —$X^{f6}$ of formula (j-iv) are —H; s1 of formula (j-iv) is 3, s2 of formula (j-iv) is 5, s3 of formula (j-iv) is 2, s4 of formula (j-iv) is 4, s5 of formula (j-iv) is 5, s6 of formula (j-iv) is 2 and s7 of formula (j-iv) is 4; and —$Y^{d1}$— and —$Y^{d2}$— of formula (j-iv) are

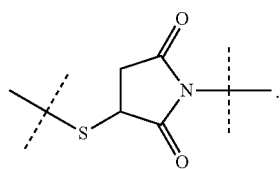

In an equally preferred embodiment —$X^{f1}$, —$X^{f2}$, —$X^{f3}$, —$X^{f4}$, —$X^{f5}$ and —$X^{f6}$ of formula (j-iv) are —H; s1 of formula (j-iv) is 3, s2 of formula (j-iv) is 5, s3 of formula (j-iv) is 2, s4 of formula (j-iv) is 4, s5 of formula (j-iv) is 5, s6 of formula (j-iv) is 2 and s7 of formula (j-iv) is 4; and —$Y^{d1}$— and —$Y^{d2}$— of formula (j-iv) are

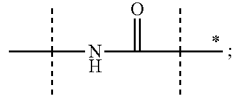

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

Preferably, —$X^{f1}$, —$X^{f2}$, —$X^{f3}$ and —$X^{f4}$ of formula (j-v) are —H; s1, s2, s3, s4 and s5 of formula (j-v) are selected from the group consisting of 1, 2, 3, 4, 5, 6 and 7; —$Y^{d1}$— and —$Y^{d2}$— of formula (j-v) are selected from the group consisting of

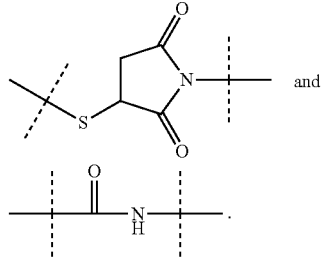

In an even more preferred embodiment —$X^{f1}$, —$X^{f2}$, —$X^{f3}$ and —$X^{f4}$ of formula (j-v) are —H; s1 of formula (j-v) is 3, s2 of formula (j-v) is 2, s3 of formula (j-v) is 1, s4 of formula (j-v) is 2 and s5 of formula (j-v) is 1; and —$Y^{d1}$— and —$Y^{d2}$— of formula (j-v) are

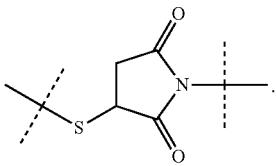

In an equally preferred embodiment —$X^{f1}$, —$X^{f2}$, —$X^{f3}$ and —$X^{f4}$ of formula (j-v) are —H; s1 of formula (j-v) is 3, s2 of formula (j-v) is 2, s3 of formula (j-v) is 1, s4 of formula (j-v) is 2 and s5 of formula (j-v) is 1; and —$Y^{d1}$— and —$Y^{d2}$— of formula (j-v) are

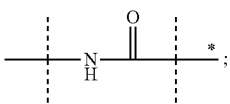

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

Preferably, —$X^{f1}$, —$X^{f2}$, —$X^{f3}$, —$X^{f4}$, —$X^{f5}$, —$X^{f6}$, —$X^{f7}$, —$X^{f9}$ and —$X^{f10}$ of formula (j-vi) are —H; s1, s2, s3, s4, s5, s6, s7, s8 and s9 of formula (j-vi) are selected from the group consisting of 1, 2, 3, 4, 5, 6 and 7; —$Y^{d1}$— and —$Y^{d2}$— of formula (j-vi) are selected from the group consisting of

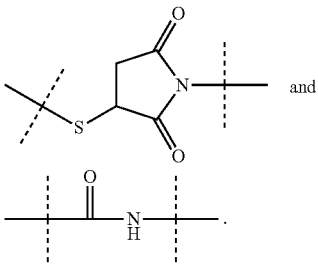

In an even more preferred embodiment —$X^{f1}$, —$X^{f2}$, —$X^{f3}$, —$X^{f4}$, —$X^{f5}$, —$X^{f6}$, —$X^{f7}$, —$X^{f8}$, —$X^{f9}$ and —$X^{f10}$ of formula (j-vi) are —H; s1 of formula (j-vi) is 4, s2 of formula (j-vi) is 5, s3 of formula (j-vi) is 2, s4 of formula (j-vi) is 4, s5 of formula (j-vi) is 4, s6 of formula (j-vi) is 5, s7 of formula (j-vi) is 2, s8 of formula (j-vi) is 4 and s9 of formula (j-vi) is 4; and —$Y^{d1}$— and —$Y^{d2}$— of formula (j-v) are

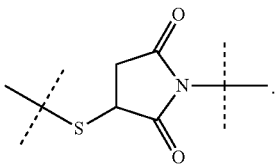

In an equally preferred embodiment —$X^{f1}$, —$X^{f2}$, —$X^{f3}$, —$X^{f4}$, —$X^{f5}$, —$X^{f6}$, —$X^{f7}$, —$X^{f8}$, —$X^{f9}$ and —$X^{f10}$ of formula (j-vi) are —H; s1 of formula (j-vi) is 4, s2 of formula (j-vi) is 5, s3 of formula (j-vi) is 2, s4 of formula (j-vi) is 4, s5 of formula (j-vi) is 4, s6 of formula (j-vi) is 5, s7 of formula (j-vi) is 2, s8 of formula (j-vi) is 4 and s9 of formula (j-vi) is 4; and —$Y^{d1}$— and —$Y^{d2}$— of formula (j-v) are

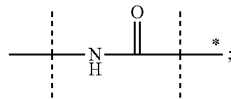

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

Preferably, —$X^{f1}$, —$X^{f2}$, —$X^{f3}$, —$X^{f4}$, —$X^{f5}$, —$X^{f6}$, —$X^{f7}$, —$X^{f8}$, —$X^{f9}$, —$X^{f10}$, —$X^{f11}$, —$X^{f12}$, —$X^{f13}$ and —$X^{f14}$ of formula (j-vii) are —H; s1, s2, s3, s4, s5, s6, s7, s8, s9, s10, s11, s12, s13, s14 and s15 of formula (j-vii) are selected from the group consisting of 1, 2, 3, 4, 5, 6 and 7; —$Y^{d1}$—, —$Y^{d2}$—, —$Y^{d3}$— and —$Y^{d4}$— of formula (j-vii) are selected from the group consisting of

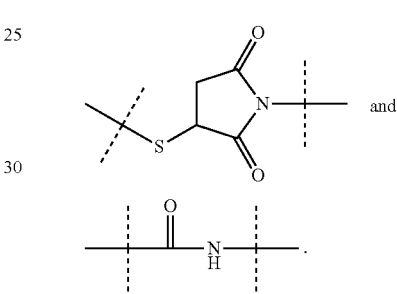

In an even more preferred embodiment —$X^{f1}$, —$X^{f2}$, —$X^{f3}$, —$X^{f4}$, —$X^{f5}$, —$X^{f6}$, —$X^{f7}$, —$X^{f8}$, —$X^{f9}$, —$X^{f10}$, —$X^{f11}$, —$X^{f12}$, —$X^{f13}$ and —$X^{f14}$ of formula (j-vii) are —H; are —H; s1 of formula (j-vii) is 4, s2 of formula (j-vii) is 4, s3 of formula (j-vii) is 5, s4 of formula (j-vii) is 2, s5 of formula (j-vii) is 4, s6 of formula (j-vii) is 5, s7 of formula (j-vii) is 2, s8 of formula (j-vii) is 4, s9 of formula (j-vii) is 4, s10 of formula (j-vii) is 5, s11 of formula (j-vii) is 2, s12 of formula (j-vii) is 4, s13 of formula (j-vii) is 5, s14 of formula (j-vii) is 2 and s15 of formula (j-vii) is 4; and —$Y^{d1}$—, —$Y^{d2}$—, —$Y^{d3}$— and —$Y^{d4}$— of formula (j-vii) are

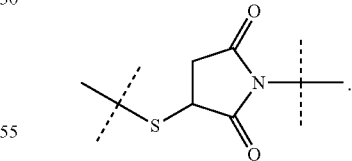

In an equally preferred embodiment —$X^{f1}$, —$X^{f2}$, —$X^{f3}$, —$X^{f4}$, —$X^{f5}$, —$X^{f6}$, —$X^{f7}$, —$X^{f8}$, —$X^{f9}$, —$X^{f10}$, —$X^{f11}$, —$X^{f12}$, —$X^{f13}$ and —$X^{f14}$ of formula (j-vii) are —H; are —H; s1 of formula (j-vii) is 4, s2 of formula (j-vii) is 4, s3 of formula (j-vii) is 5, s4 of formula (j-vii) is 2, s5 of formula (j-vii) is 4, s6 of formula (j-vii) is 5, s7 of formula (j-vii) is 2, s8 of formula (j-vii) is 4, s9 of formula (j-vii) is 4, s10 of formula (j-vii) is 5, s11 of formula (j-vii) is 2, s12 of formula (j-vii) is 4, s13 of formula (j-vii) is 5, s14 of formula (j-vii)

is 2 and s15 of formula (j-vii) is 4; and —$Y^{d1}$—, —$Y^{d2}$—, —$Y^{d3}$— and —$Y^{d4}$— of formula (j-vii) are

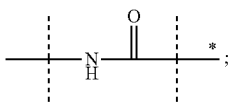

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

Preferably —$Z^{d1}$, —$Z^{d2}$, —$Z^{d3}$ and —$Z^{d4}$ of formula (j-i), (j-ii), (j-iii), (j-iv), (j-v), (j-vi) and (j-vii) have the same structure.

In one embodiment —$Z^{d1}$, —$Z^{d2}$, —$Z^{d3}$ and —$Z^{d4}$ of formula (j-i), (j-ii), (j-iii), (j-iv), (j-v), (j-vi) and (j-vii) are a PA moiety.

In another embodiment —$Z^{d1}$, —$Z^{d2}$, —$Z^{d3}$ and —$Z^{d4}$ of formula (j-i), (j-ii), (j-iii), (j-iv), (j-v), (j-vi) and (j-vii) are a PAS moiety.

In another embodiment —$Z^{d1}$, —$Z^{d2}$, —$Z^{d3}$ and —$Z^{d4}$ of formula (j-i), (j-ii), (j-iii), (j-iv), (j-v), (j-vi) and (j-vii) are a PAG moiety.

In another embodiment —$Z^{d1}$, —$Z^{d2}$, —$Z^{d3}$ and —$Z^{d4}$ of formula (j-i), (j-ii), (j-iii), (j-iv), (j-v), (j-vi) and (j-vii) are a PG moiety.

In another embodiment —$Z^{d1}$, —$Z^{d2}$, —$Z^{d3}$ and —$Z^{d4}$ of formula (j-i), (j-ii), (j-iii), (j-iv), (j-v), (j-vi) and (j-vii) are a XTEN moiety.

In a preferred embodiment the CNP agonist prodrug of the present invention is of formula (IIe)

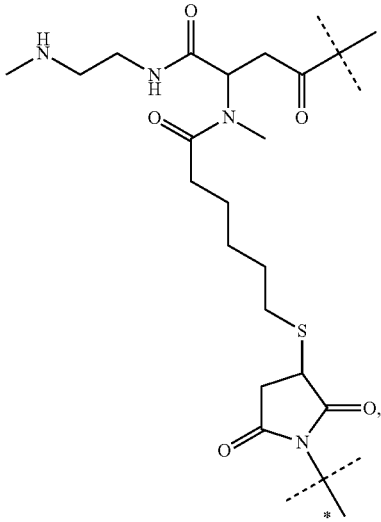

(IIe-)

wherein the unmarked dashed line indicates the attachment to a nitrogen of -D which is a CNP agonist moiety by forming an amide bond; and the dashed line marked with the asterisk indicates attachment to a moiety

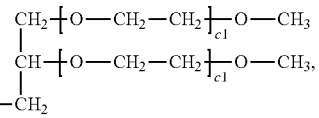

wherein each c1 is an integer independently ranging from 400 to 500.

Preferably, c1 of formula (IIe) is about 450.

In an equally preferred embodiment the CNP agonist prodrug of the present invention is of formula (IIe-i)

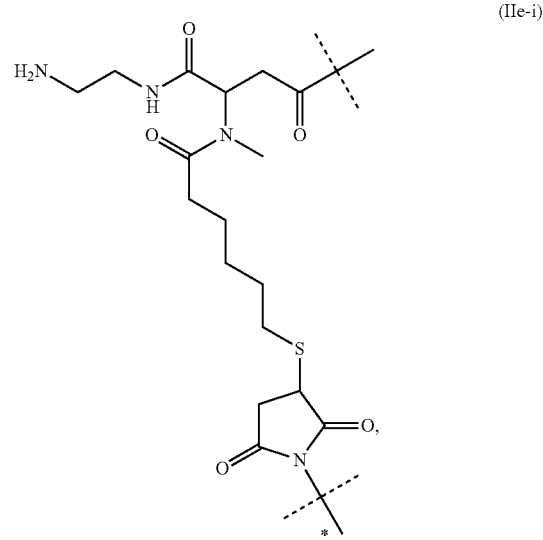

(IIe-i)

wherein the unmarked dashed line indicates the attachment to a nitrogen of -D which is a CNP agonist moiety by forming an amide bond; and the dashed line marked with the asterisk indicates attachment to a moiety

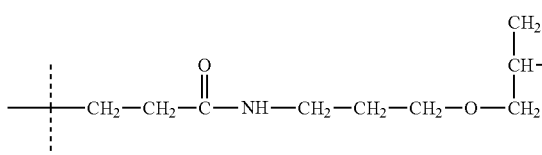
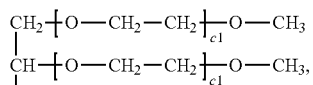

wherein
each c1 is an integer independently ranging from 400 to 500.

Preferably, c1 of formula (IIe-i) is about 450.

In another equally preferred embodiment the CNP agonist prodrug of the present invention is of formula (IIe-ii)

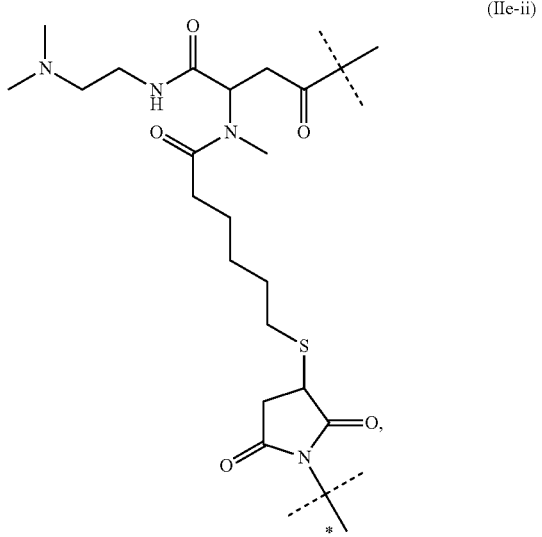

wherein
the unmarked dashed line indicates the attachment to a nitrogen of -D which is a CNP agonist moiety by forming an amide bond; and
the dashed line marked with the asterisk indicates attachment to a moiety

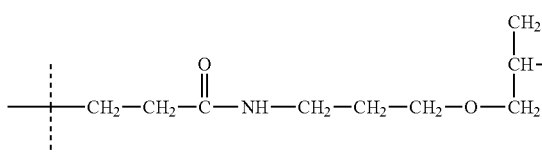

wherein
each c1 is an integer independently ranging from 400 to 500.

Preferably, c1 of formula (IIe-ii) is about 450.

Preferably -D of formula (IIe), (IIe-i) and (IIe-ii) is a CNP moiety, i.e. the prodrug of formula (IIe), (IIe-i) and (IIe-ii) is a CNP prodrug. Even more preferably -D of formula (IIe), (IIe-i) and (IIe-ii) is a CNP moiety having the sequence of SEQ ID NO:24, SEQ ID NO:25 or SEQ ID NO:30. Most preferably -D of formula (IIe), (IIe-i) and (IIe-ii) is a CNP moiety CNP having the sequence of SEQ ID NO:24. It is also preferred that D of formula ((IIe), (IIe-i) and (IIe-ii) is a CNP moiety CNP having the sequence of SEQ ID NO:20. D of formula ((IIe), (IIe-i) and (IIe-ii) is a CNP moiety CNP having the sequence of SEQ ID NO:21. D of formula ((IIe), (IIe-i) and (IIe-ii) is a CNP moiety CNP having the sequence of SEQ ID NO:22. D of formula ((IIe), (IIe-i) and (IIe-ii) is a CNP moiety CNP having the sequence of SEQ ID NO:23. D of formula ((IIe), (IIe-i) and (IIe-ii) is a CNP moiety CNP having the sequence of SEQ ID NO:30.

In one embodiment -D of formula (IIe), (IIe-i) and (IIe-ii) is a CNP moiety which is attached to -$L^1$- through the nitrogen of the N-terminal amine functional group of CNP.

In a preferred embodiment -D of formula (IIe), (IIe-i) and (IIe-ii) is a CNP moiety which is attached to -$L^1$- through a nitrogen provided by the amine functional group of a lysine side chain of the CNP moiety.

In one embodiment said lysine side chain is not part of the ring formed by the disulfide bridge between the cysteine residues at positions 22 and 38, if the CNP moiety is of SEQ ID NO:24.

Accordingly, in one embodiment the CNP moiety is connected to -$L^1$- in the CNP prodrug of formula (IIe), (IIe-i) and (IIe-ii) through the amine functional group provided by the side chain of the lysine at position 9, if the CNP has the sequence of SEQ ID NO:24.

In another embodiment the CNP moiety is connected to -$L^1$- in the CNP prodrug of formula (IIe), (IIe-i) and (IIe-ii) through the amine functional group provided by the side chain of the lysine at position 11, if the CNP has the sequence of SEQ ID NO:24.

In another embodiment the CNP moiety is connected to -$L^1$- in the CNP prodrug of formula (IIe), (IIe-i) and (IIe-ii) through the amine functional group provided by the side chain of the lysine at position 15, if the CNP has the sequence of SEQ ID NO:24.

In another embodiment the CNP moiety is connected to -$L^1$- in the CNP prodrug of formula (IIe), (IIe-i) and (IIe-ii) through the amine functional group provided by the side chain of the lysine at position 16, if the CNP has the sequence of SEQ ID NO:24.

In another embodiment the CNP moiety is connected to -$L^1$- in the CNP prodrug of formula (IIe), (IIe-i) and (IIe-ii) through the amine functional group provided by the side chain of the lysine at position 20, if the CNP has the sequence of SEQ ID NO:24.

In a preferred embodiment said lysine side chain is part of the ring formed by the disulfide bridge between the cysteine residues at positions 22 and 38, if the CNP moiety is of SEQ ID NO: 24.

Accordingly, in one embodiment the CNP moiety is connected to -$L^1$- in the CNP prodrug of formula (IIe), (IIe-i) and (IIe-ii) through the amine functional group provided by the side chain of the lysine at position 26, if the CNP has the sequence of SEQ ID NO:24.

It is understood that the positions of the cysteines and lysines mentioned above vary depending on the lengths of the CNP moiety and that the person skilled in the art will have no difficulty identifying the corresponding cysteines and lysines in longer or shorter versions of the CNP moiety and also understands that for example some lysines may not be present in shorter CNP moieties. It is further understood that as a result of for example site-directed mutagenesis there might be more lysine residues in the non-ring forming part and/or ring forming part of the CNP moiety.

In a preferred embodiment the CNP prodrug of the present invention is of formula (IIe), wherein c1 is about 450, -D is a CNP moiety having the sequence of SEQ ID NO:24 and is attached to -$L^1$- through the amine functional group provided by the side chain of the lysine at position 26.

In another preferred embodiment the CNP prodrug of the present invention is of formula (IIe-i), wherein c1 is about 450, the CNP moiety has the sequence of SEQ ID NO:24 and is attached to -$L^1$- through the amine functional group provided by the side chain of the lysine at position 26.

In another preferred embodiment the CNP prodrug of the present invention is of formula (IIe-ii), wherein c1 is about 450, the CNP moiety has the sequence of SEQ ID NO:24 and is attached to -$L^1$- through the amine functional group provided by the side chain of the lysine at position 26.

In another preferred embodiment the CNP agonist prodrug of the present invention is of formula (IIf)

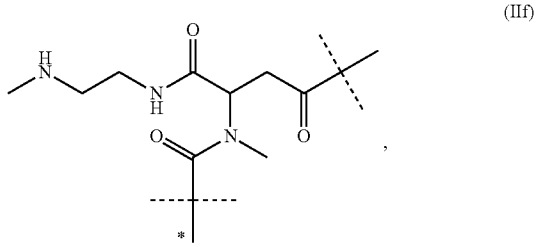

(IIf)

wherein
the unmarked dashed line indicates the attachment to a nitrogen of -D which is a CNP agonist moiety by forming an amide bond; and
the dashed line marked with the asterisk indicates attachment to —Z having the structure

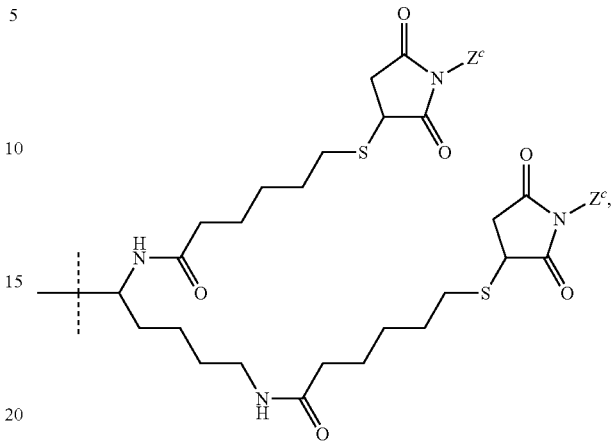

wherein
each —$Z^a$ is

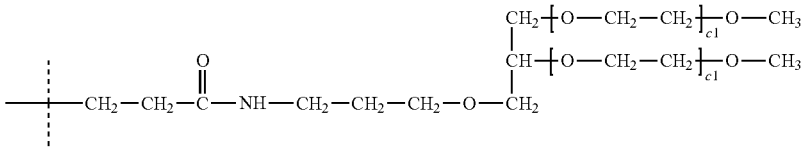

wherein
each c1 is an integer independently ranging from 200 to 250.
Preferably, each c1 of formula (IIf) is about 225.

In another preferred embodiment the CNP agonist prodrug of the present invention is of formula (IIf-i)

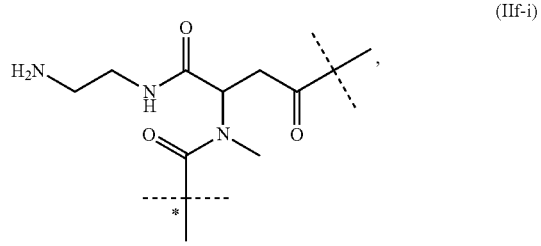

(IIf-i)

wherein
the unmarked dashed line indicates the attachment to a nitrogen of -D which is a CNP agonist moiety by forming an amide bond; and
the dashed line marked with the asterisk indicates attachment to —Z having the structure

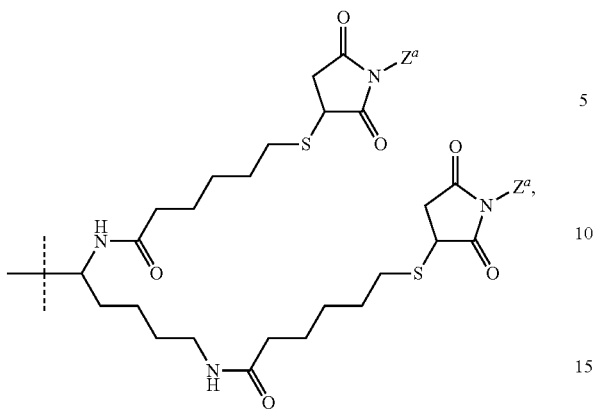

wherein
each —$Z^a$ is

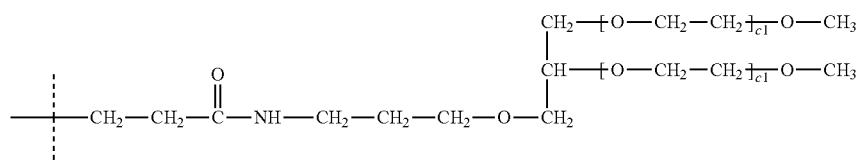

wherein
  each c1 is an integer independently ranging from 200 to 250.

Preferably, each c1 of formula (IIf-i) is about 225.

In another preferred embodiment the CNP agonist prodrug of the present invention is of formula (IIf-ii)

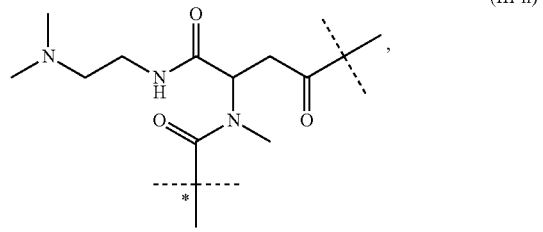

(IIf-ii)

wherein
  the unmarked dashed line indicates the attachment to a nitrogen of -D which is a CNP agonist moiety by forming an amide bond; and
  the dashed line marked with the asterisk indicates attachment to —Z having the structure

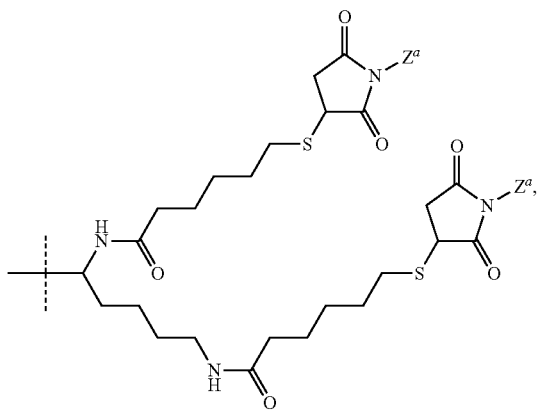

wherein
each —$Z^a$ is

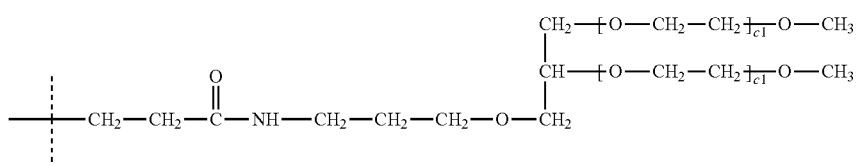

wherein
each c1 is an integer independently ranging from 200 to 250.

Preferably, each c1 of formula (IIf-ii) is about 225.

Preferably -D of formula MO, (IIf-i) and (IIf-ii) is a CNP moiety, i.e. the prodrug of formula (IIf-i) and (IIf-ii) is a CNP prodrug. Even more preferably -D of formula (IIf), (IIf-i) and (IIf-ii) is a CNP moiety having the sequence of SEQ ID NO:24, SEQ ID NO:25 or SEQ ID NO:30. Most preferably -D of formula MO, (IIf-i) and (IIf-ii) is a CNP moiety CNP having the sequence of SEQ ID NO:24. It is also preferred that -D of formula (IIf), (IIf-i) and (IIf-ii) is a CNP moiety CNP having the sequence of SEQ ID NO:20. -D of formula MO, (IIf-i) and (IIf-ii) is a CNP moiety CNP having the sequence of SEQ ID NO:21. -D of formula (IIf), (IIf-i) and (IIf-ii) is a CNP moiety CNP having the sequence of SEQ ID NO:22. -D of formula (IIf-i) and (IIf-ii) is a CNP moiety CNP having the sequence of SEQ ID NO:23. -D of formula (IIf), (IIf-i) and (IIf-ii) is a CNP moiety CNP having the sequence of SEQ ID NO:30.

In one embodiment -D of formula (IIf), (IIf-i) and (IIf-ii) is a CNP moiety which is attached to -$L^1$- through the nitrogen of the N-terminal amine functional group of CNP.

In a preferred embodiment -D of formula (IIf), (IIf-i) and (IIf-ii) is a CNP moiety which is attached to through a nitrogen provided by the amine functional group of a lysine side chain of the CNP moiety.

In one embodiment said lysine side chain is not part of the ring formed by the disulfide bridge between the cysteine residues at positions 22 and 38, if the CNP moiety is of SEQ ID NO:24.

Accordingly, in one embodiment the CNP moiety is connected to in the CNP prodrug of formula (IIf), (IIf-i) and (IIf-ii) through the amine functional group provided by the side chain of the lysine at position 9, if the CNP has the sequence of SEQ ID NO:24.

In another embodiment the CNP moiety is connected to -$L^1$- in the CNP prodrug of formula (IIf), (IIf-i) and (IIf-ii) through the amine functional group provided by the side chain of the lysine at position 11, if the CNP has the sequence of SEQ ID NO:24.

In another embodiment the CNP moiety is connected to -$L^1$- in the CNP prodrug of formula (IIf), (IIf-i) and (IIf-ii) through the amine functional group provided by the side chain of the lysine at position 15, if the CNP has the sequence of SEQ ID NO:24.

In another embodiment the CNP moiety is connected to -$L^1$- in the CNP prodrug of formula (IIf), (IIf-i) and (IIf-ii) through the amine functional group provided by the side chain of the lysine at position 16, if the CNP has the sequence of SEQ ID NO:24.

In another embodiment the CNP moiety is connected to -$L^1$- in the CNP prodrug of formula (IIf), (IIf-i) and (IIf-ii) through the amine functional group provided by the side chain of the lysine at position 20, if the CNP has the sequence of SEQ ID NO:24.

In a preferred embodiment said lysine side chain is part of the ring formed by the disulfide bridge between the cysteine residues at positions 22 and 38, if the CNP moiety is of SEQ ID NO:24.

Accordingly, in one embodiment the CNP moiety is connected to -$L^1$- in the CNP prodrug of formula (IIf) through the amine functional group provided by the side chain of the lysine at position 26, if the CNP has the sequence of SEQ ID NO:24.

In another preferred embodiment the CNP prodrug of the present invention is of formula (IIf-i), wherein c1 is about 225, the CNP moiety has the sequence of SEQ ID NO:24 and is attached to -$L^1$- through the amine functional group provided by the side chain of the lysine at position 26.

In a preferred embodiment the CNP prodrug of the present invention is of formula (IIf), wherein c1 is about 225, -D is a CNP moiety having the sequence of SEQ ID NO:20 and is attached to -$L^1$- through the amine functional group provided by the side chain of the lysine at position 30.

In another preferred embodiment the CNP prodrug of the present invention is of formula (IIf-i), wherein c1 is about 225, the CNP moiety has the sequence of SEQ ID NO:20 and is attached to -$L^1$- through the amine functional group provided by the side chain of the lysine at position 30.

In another preferred embodiment the CNP prodrug of the present invention is of formula (IIf-ii), wherein c1 is about 225, the CNP moiety has the sequence of SEQ ID NO:20 and is attached to -$L^1$- through the amine functional group provided by the side chain of the lysine at position 30.

In a preferred embodiment the CNP prodrug of the present invention is of formula (IIf), wherein c1 is about 225, -D is a CNP moiety having the sequence of SEQ ID NO:21 and is attached to -$L^1$- through the amine functional group provided by the side chain of the lysine at position 29.

In another preferred embodiment the CNP prodrug of the present invention is of formula (IIf-i), wherein c1 is about 225, the CNP moiety has the sequence of SEQ ID NO:21 and is attached to -$L^1$- through the amine functional group provided by the side chain of the lysine at position 29.

In another preferred embodiment the CNP prodrug of the present invention is of formula (IIf-ii), wherein c1 is about 225, the CNP moiety has the sequence of SEQ ID NO:21 and is attached to -$L^1$- through the amine functional group provided by the side chain of the lysine at position 29.

In a preferred embodiment the CNP prodrug of the present invention is of formula (IIf), wherein c1 is about 225, -D is a CNP moiety having the sequence of SEQ ID NO:22 and is attached to -$L^1$- through the amine functional group provided by the side chain of the lysine at position 28.

In another preferred embodiment the CNP prodrug of the present invention is of formula (IIf-i), wherein c1 is about 225, the CNP moiety has the sequence of SEQ ID NO:22 and is attached to -$L^1$- through the amine functional group provided by the side chain of the lysine at position 28.

In another preferred embodiment the CNP prodrug of the present invention is of formula (IIf-ii), wherein c1 is about 225, the CNP moiety has the sequence of SEQ ID NO:22 and is attached to -$L^1$- through the amine functional group provided by the side chain of the lysine at position 28.

In a preferred embodiment the CNP prodrug of the present invention is of formula (IIf), wherein c1 is about 225, -D is a CNP moiety having the sequence of SEQ ID NO:23 and is attached to -$L^1$- through the amine functional group provided by the side chain of the lysine at position 27.

In another preferred embodiment the CNP prodrug of the present invention is of formula (IIf-i), wherein c1 is about 225, the CNP moiety has the sequence of SEQ ID NO:23 and is attached to -$L^1$- through the amine functional group provided by the side chain of the lysine at position 27.

In another preferred embodiment the CNP prodrug of the present invention is of formula (IIf-ii), wherein c1 is about 225, the CNP moiety has the sequence of SEQ ID NO:23 and is attached to -$L^1$- through the amine functional group provided by the side chain of the lysine at position 27.

In a preferred embodiment the CNP prodrug of the present invention is of formula (IIf), wherein c1 is about 225, -D is a CNP moiety having the sequence of SEQ ID NO:30 and is attached to -L¹- through the amine functional group provided by the side chain of the lysine at position 27.

In another preferred embodiment the CNP prodrug of the present invention is of formula (IIf-i), wherein c1 is about 225, the CNP moiety has the sequence of SEQ ID NO:30 and is attached to -L¹- through the amine functional group provided by the side chain of the lysine at position 27.

In another preferred embodiment the CNP prodrug of the present invention is of formula (IIf-ii), wherein c1 is about 225, the CNP moiety has the sequence of SEQ ID NO:30 and is attached to -L¹- through the amine functional group provided by the side chain of the lysine at position 27.

In another preferred embodiment the CNP prodrug of the present invention is of formula (IIf-ii), wherein c1 is about 225, the CNP moiety has the sequence of SEQ ID NO:24 and is attached to -L¹- through the amine functional group provided by the side chain of the lysine at position 26.

It is understood that the positions of the cysteines and lysines mentioned above vary depending on the lengths of the CNP moiety and that the person skilled in the art will have no difficulty identifying the corresponding cysteines and lysines in longer or shorter versions of the CNP moiety and also understands that for example some lysines may not be present in shorter CNP moieties. It is further understood that as a result of for example site-directed mutagenesis there might be more lysine residues in the non-ring forming part and/or ring forming part of the CNP moiety.

In a preferred embodiment the CNP prodrug of the present invention is of formula (IIf), wherein c1 is about 225, -D is a CNP moiety having the sequence of SEQ ID NO:24 and is attached to through the amine functional group provided by the side chain of the lysine at position 26.

In another preferred embodiment the CNP prodrug of the present invention is of formula (IIf')

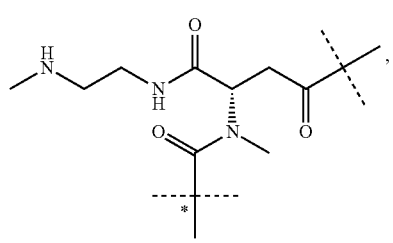
(IIf')

wherein
the unmarked dashed line indicates the attachment to a nitrogen provided by the side chain of the lysine at position 26 of the CNP moiety of SEQ ID NO:24 by forming an amide bond; and the dashed line marked with the asterisk indicates attachment to —Z having the structure

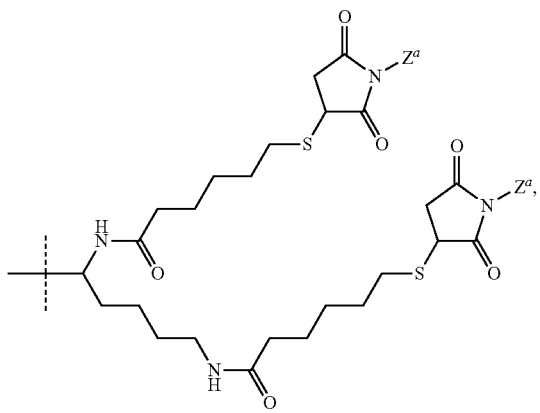

wherein
each $Z^a$ is

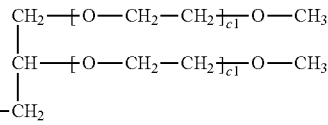

wherein
each c1 is an integer independently ranging from 200 to 250.

Preferably, each c1 of formula (IIf') is about 225.

In another preferred embodiment the CNP prodrug of the present invention is of formula (IIf-i')

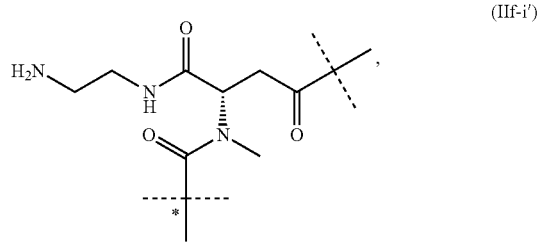
(IIf-i')

wherein
the unmarked dashed line indicates the attachment to a nitrogen provided by the side chain of the lysine at position 26 of the CNP moiety of SEQ ID NO:24 by forming an amide bond; and the dashed line marked with the asterisk indicates attachment to —Z having the structure

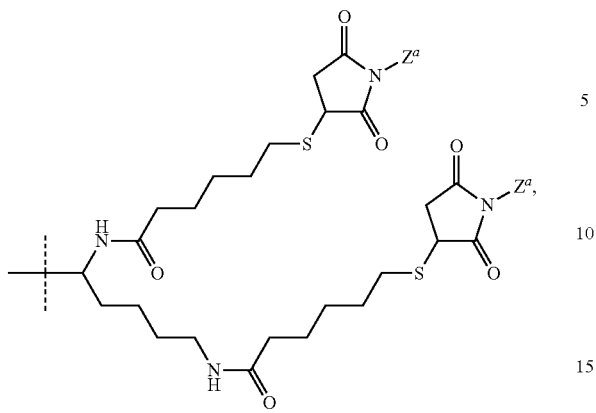

wherein
each $Z^a$ is

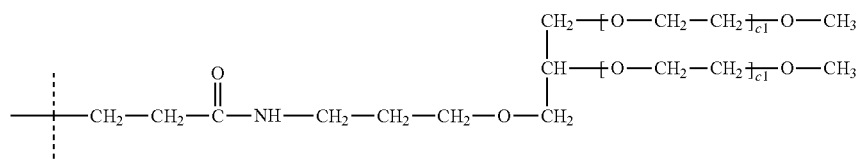

wherein
each c1 is an integer independently ranging from 200 to 250.

Preferably, each c1 of formula (IIf-i') is about 225.

In another preferred embodiment the CNP prodrug of the present invention is of formula (IIf-ii')

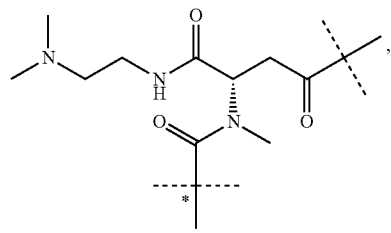

(IIf-ii')

wherein
the unmarked dashed line indicates the attachment to a nitrogen provided by the side chain of the lysine at position 26 of the CNP moiety of SEQ ID NO:24 by forming an amide bond; and the dashed line marked with the asterisk indicates attachment to —Z having the structure

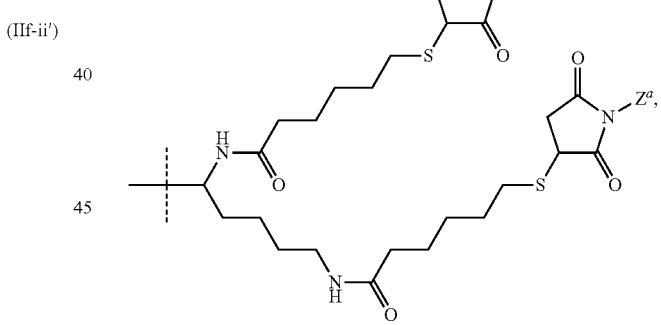

wherein
each $Z^a$ is

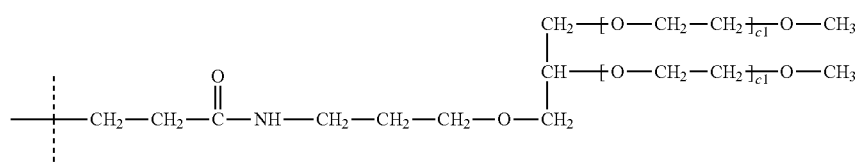

wherein
each c1 is an integer independently ranging from 200 to 250.

Preferably, each c1 of formula (IIf-ii') is about 225.

In an equally preferred embodiment the CNP agonist prodrug of the present invention is of formula (IIea)

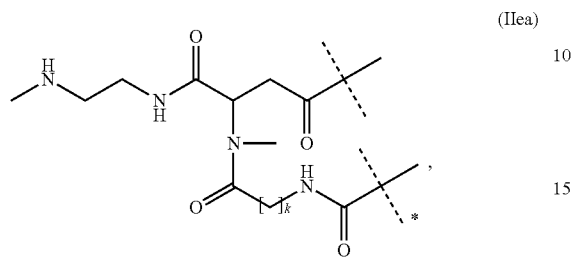

wherein
the unmarked dashed line indicates the attachment to a nitrogen of -D which is a CNP agonist moiety by forming an amide bond;
k is selected from the group consisting of 1, 2, 3, 4, 5, 6, 7, 8, 9, 10, 11 and 12; and the dashed line marked with the asterisk indicates attachment to a moiety

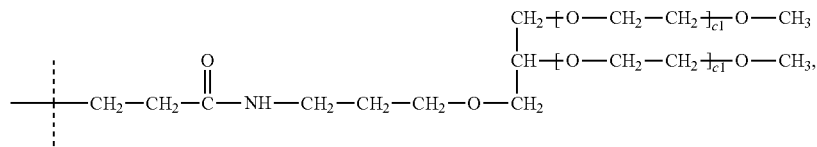

wherein
each c1 is an integer independently ranging from 400 to 500.

Preferably, c1 of formula (IIea) is about 450.

Preferably, k of formula (IIea) is selected from the group consisting of 2, 3, 4, 5, 6 and 7.

In an equally preferred embodiment the CNP agonist prodrug of the present invention is of formula (IIea-i)

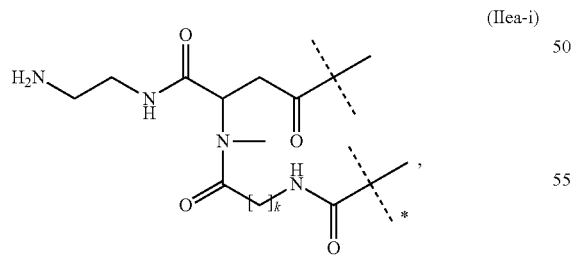

wherein
the unmarked dashed line indicates the attachment to a nitrogen of -D which is a CNP agonist moiety by forming an amide bond;
k is selected from the group consisting of 1, 2, 3, 4, 5, 6, 7, 8, 9, 10, 11 and 12; and
the dashed line marked with the asterisk indicates attachment to a moiety

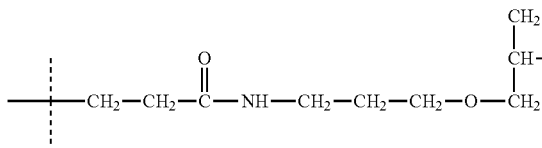

wherein
each c1 is an integer independently ranging from 400 to 500.

Preferably, k of formula (IIea-i) is selected from the group consisting of 2, 3, 4, 5, 6 and 7.

Preferably, c1 of formula (IIea-i) is about 450.

In another equally preferred embodiment the CNP agonist prodrug of the present invention is of formula (IIea-ii)

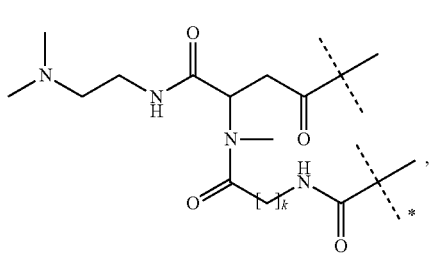

(IIea-ii)

wherein
the unmarked dashed line indicates the attachment to a nitrogen of -D which is a CNP agonist moiety by forming an amide bond;
k is selected from the group consisting of 1, 2, 3, 4, 5, 6, 7, 8, 9, 10, 11 and 12; and
the dashed line marked with the asterisk indicates attachment to a moiety

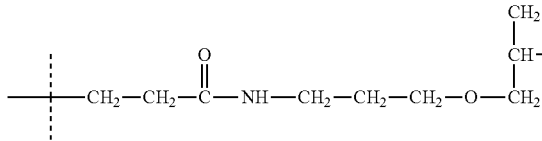

wherein
each c1 is an integer independently ranging from 400 to 500.

Preferably, k of formula (IIea-ii) is selected from the group consisting of 2, 3, 4, 5, 6 and 7.

Preferably, c1 of formula (IIea-ii) is about 450.

Preferably -D of formula (IIea), (IIea-i) and (IIea-ii) is a CNP moiety, i.e. the prodrug of formula (IIea), (IIea-i) and (IIea-ii) is a CNP prodrug. Even more preferably -D of formula (IIea), (IIea-i) and (IIea-ii) is a CNP moiety having the sequence of SEQ ID NO:24, SEQ ID NO:25 or SEQ ID NO:30. Most preferably -D of formula (IIea), (IIea-i) and (IIea-ii) is a CNP moiety CNP having the sequence of SEQ ID NO:24. It is also preferred that -D of formula (IIea), (IIea-i) and (IIea-ii) is a CNP moiety CNP having the sequence of SEQ ID NO:20. It is also preferred that -D of formula (IIea), (IIea-i) and (IIea-ii) is a CNP moiety CNP having the sequence of SEQ ID NO:21. It is also preferred that -D of formula (IIea), (IIea-i) and (IIea-ii) is a CNP moiety CNP having the sequence of SEQ ID NO:22. It is also preferred that -D of formula (IIea), (IIea-i) and (IIea-ii) is a CNP moiety CNP having the sequence of SEQ ID NO:23. It is also preferred that -D of formula (IIea), (IIea-i) and (IIea-ii) is a CNP moiety CNP having the sequence of SEQ ID NO:30.

In one embodiment -D of formula (IIea), (IIea-i) and (IIea-ii) is a CNP moiety which is attached to -$L^1$- through the nitrogen of the N-terminal amine functional group of CNP.

In a preferred embodiment -D of formula (IIea), (IIea-i) and (IIea-ii) is a CNP moiety which is attached to -$L^1$- through a nitrogen provided by the amine functional group of a lysine side chain of the CNP moiety.

In one embodiment said lysine side chain is not part of the ring formed by the disulfide bridge between the cysteine residues at positions 22 and 38, if the CNP moiety is of SEQ ID NO:24.

Accordingly, in one embodiment the CNP moiety is connected to -$L^1$- in the CNP prodrug of formula (IIea), (IIea-i) and (IIea-ii) through the amine functional group provided by the side chain of the lysine at position 9, if the CNP has the sequence of SEQ ID NO:24.

In another embodiment the CNP moiety is connected to -$L^1$- in the CNP prodrug of formula (IIea), (IIea-i) and (IIea-ii) through the amine functional group provided by the side chain of the lysine at position 11, if the CNP has the sequence of SEQ ID NO:24.

In another embodiment the CNP moiety is connected to -$L^1$- in the CNP prodrug of formula (IIea), (IIea-i) and (IIea-ii) through the amine functional group provided by the side chain of the lysine at position 15, if the CNP has the sequence of SEQ ID NO:24.

In another embodiment the CNP moiety is connected to -$L^1$- in the CNP prodrug of formula (IIea), (IIea-i) and (IIea-ii) through the amine functional group provided by the side chain of the lysine at position 16, if the CNP has the sequence of SEQ ID NO:24.

In another embodiment the CNP moiety is connected to -$L^1$- in the CNP prodrug of formula (IIea), (IIea-i) and (IIea-ii) through the amine functional group provided by the side chain of the lysine at position 20, if the CNP has the sequence of SEQ ID NO:24.

In a preferred embodiment said lysine side chain is part of the ring formed by the disulfide bridge between the cysteine residues at positions 22 and 38, if the CNP moiety is of SEQ ID NO: 24.

Accordingly, in one embodiment the CNP moiety is connected to -$L^1$- in the CNP prodrug of formula (IIea), (IIea-i) and (IIea-ii) through the amine functional group provided by the side chain of the lysine at position 26, if the CNP has the sequence of SEQ ID NO:24.

It is understood that the positions of the cysteines and lysines mentioned above vary depending on the lengths of the CNP moiety and that the person skilled in the art will have no difficulty identifying the corresponding cysteines and lysines in longer or shorter versions of the CNP moiety and also understands that for example some lysines may not be present in shorter CNP moieties. It is further understood that as a result of for example site-directed mutagenesis there might be more lysine residues in the non-ring forming part and/or ring forming part of the CNP moiety.

In a preferred embodiment the CNP prodrug of the present invention is of formula (IIea), wherein c1 is about 450, -D is a CNP moiety having the sequence of SEQ ID NO:24 and is attached to -$L^1$- through the amine functional group provided by the side chain of the lysine at position 26.

In another preferred embodiment the CNP prodrug of the present invention is of formula (IIea-i), wherein c1 is about 450, the CNP moiety has the sequence of SEQ ID NO:24 and is attached to -$L^1$- through the amine functional group provided by the side chain of the lysine at position 26.

In another preferred embodiment the CNP prodrug of the present invention is of formula (IIea-ii), wherein c1 is about 450, the CNP moiety has the sequence of SEQ ID NO:24 and is attached to -$L^1$- through the amine functional group provided by the side chain of the lysine at position 26.

In a preferred embodiment the CNP prodrug of the present invention is of formula (IIea), wherein c1 is about 450, -D is a CNP moiety having the sequence of SEQ ID NO:20 and is attached to -$L^1$- through the amine functional group provided by the side chain of the lysine at position 30.

In another preferred embodiment the CNP prodrug of the present invention is of formula (IIea-i), wherein c1 is about 450, the CNP moiety has the sequence of SEQ ID NO:20 and is attached to -$L^1$- through the amine functional group provided by the side chain of the lysine at position 30.

In another preferred embodiment the CNP prodrug of the present invention is of formula (IIea-ii), wherein c1 is about 450, the CNP moiety has the sequence of SEQ ID NO:20 and is attached to -$L^1$- through the amine functional group provided by the side chain of the lysine at position 30.

In a preferred embodiment the CNP prodrug of the present invention is of formula (IIea), wherein c1 is about 450, -D is a CNP moiety having the sequence of SEQ ID NO:21 and is attached to -$L^1$- through the amine functional group provided by the side chain of the lysine at position 29.

In another preferred embodiment the CNP prodrug of the present invention is of formula (IIea-i), wherein c1 is about 450, the CNP moiety has the sequence of SEQ ID NO:21 and is attached to -$L^1$- through the amine functional group provided by the side chain of the lysine at position 29.

In another preferred embodiment the CNP prodrug of the present invention is of formula (IIea-ii), wherein c1 is about 450, the CNP moiety has the sequence of SEQ ID NO:21 and is attached to -$L^1$- through the amine functional group provided by the side chain of the lysine at position 29.

In a preferred embodiment the CNP prodrug of the present invention is of formula (IIea), wherein c1 is about 450, -D is a CNP moiety having the sequence of SEQ ID NO:22 and is attached to -$L^1$- through the amine functional group provided by the side chain of the lysine at position 28.

In another preferred embodiment the CNP prodrug of the present invention is of formula (IIea-i), wherein c1 is about 450, the CNP moiety has the sequence of SEQ ID NO:22 and is attached to -$L^1$- through the amine functional group provided by the side chain of the lysine at position 28.

In another preferred embodiment the CNP prodrug of the present invention is of formula (IIea-ii), wherein c1 is about 450, the CNP moiety has the sequence of SEQ ID NO:22 and is attached to -$L^1$- through the amine functional group provided by the side chain of the lysine at position 28.

In a preferred embodiment the CNP prodrug of the present invention is of formula (IIea), wherein c1 is about 450, -D is a CNP moiety having the sequence of SEQ ID NO:23 and is attached to -$L^1$- through the amine functional group provided by the side chain of the lysine at position 27.

In another preferred embodiment the CNP prodrug of the present invention is of formula (IIea-i), wherein c1 is about 450, the CNP moiety has the sequence of SEQ ID NO:23 and is attached to -$L^1$- through the amine functional group provided by the side chain of the lysine at position 27.

In another preferred embodiment the CNP prodrug of the present invention is of formula (IIea-ii), wherein c1 is about 450, the CNP moiety has the sequence of SEQ ID NO:23 and is attached to -$L^1$- through the amine functional group provided by the side chain of the lysine at position 27.

In a preferred embodiment the CNP prodrug of the present invention is of formula (IIea), wherein c1 is about 450, -D is a CNP moiety having the sequence of SEQ ID NO:30 and is attached to -$L^1$- through the amine functional group provided by the side chain of the lysine at position 27.

In another preferred embodiment the CNP prodrug of the present invention is of formula (IIea-i), wherein c1 is about 450, the CNP moiety has the sequence of SEQ ID NO:30 and is attached to -$L^1$- through the amine functional group provided by the side chain of the lysine at position 27.

In another preferred embodiment the CNP prodrug of the present invention is of formula (IIea-ii), wherein c1 is about 450, the CNP moiety has the sequence of SEQ ID NO:30 and is attached to -$L^1$- through the amine functional group provided by the side chain of the lysine at position 27.

Accordingly, in a preferred embodiment the CNP prodrug of the present invention is of formula (IIea')

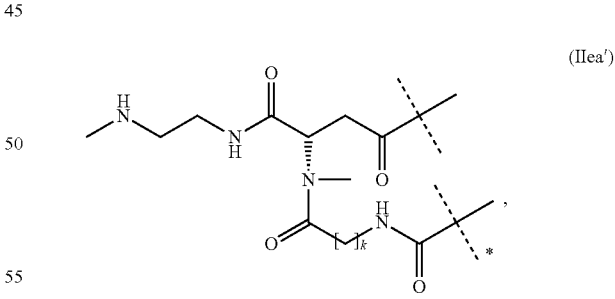

(IIea')

wherein the unmarked dashed line indicates the attachment to the nitrogen provided by the side chain of the lysine at position 26 of the CNP moiety of SEQ ID NO:24 by forming an amide bond;

k is selected from the group consisting of 1, 2, 3, 4, 5, 6, 7, 8, 9, 10, 11 and 12; and the dashed line marked with the asterisk indicates attachment to a moiety

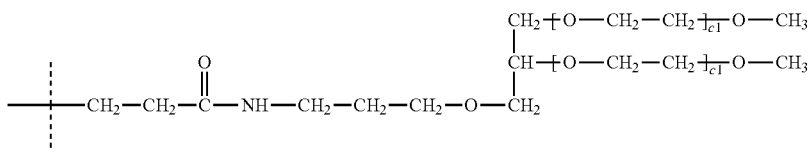

wherein
each c1 is an integer independently ranging from 400 to 500.

Preferably, k of formula (IIea') is selected from the group consisting of 2, 3, 4, 5, 6 and 7.

Preferably, each c1 of formula (IIea') is about 450.

In another preferred embodiment the CNP prodrug of the present invention is of formula (IIea-i')

(IIea-i')

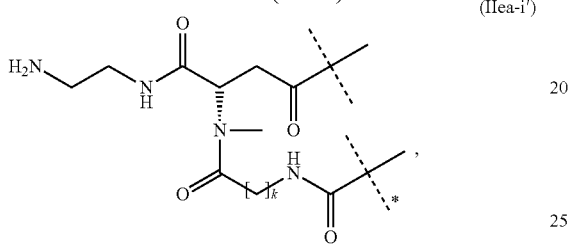

wherein
the unmarked dashed line indicates the attachment to a nitrogen provided by the side chain of the lysine at position 26 of the CNP moiety of SEQ ID NO:24 by forming an amide bond;
k is selected from the group consisting of 1, 2, 3, 4, 5, 6, 7, 8, 9, 10, 11 and 12; and
the dashed line marked with the asterisk indicates attachment to a moiety

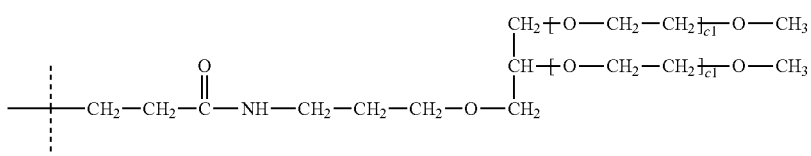

wherein
each c1 is an integer independently ranging from 400 to 500.

Preferably, k of formula (IIea-i') is selected from the group consisting of 2, 3, 4, 5, 6 and 7.

Preferably, each c1 of formula (IIea-i') is about 450.

In another preferred embodiment the CNP prodrug of the present invention is of formula (IIea-ii')

(IIea-ii')

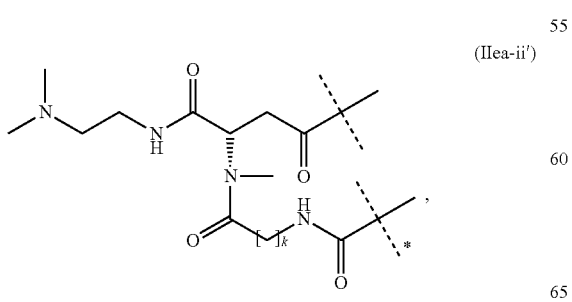

wherein
the unmarked dashed line indicates the attachment to a nitrogen provided by the side chain of the lysine at position 26 of the CNP moiety of SEQ ID NO:24 by forming an amide bond;
k is selected from the group consisting of 1, 2, 3, 4, 5, 6, 7, 8, 9, 10, 11 and 12; and
the dashed line marked with the asterisk indicates attachment to a moiety

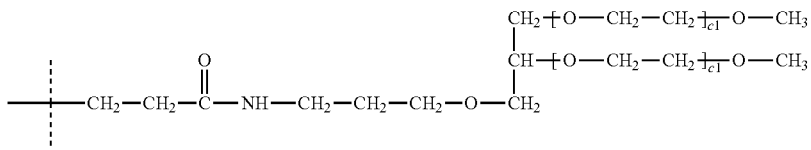

wherein
each c1 is an integer independently ranging from 400 to 500.
Preferably, k of formula (IIea-ii') is selected from the group consisting of 2, 3, 4, 5, 6 and 7.
Preferably, each c1 of formula (IIea-ii') is about 450.
In another preferred embodiment the CNP prodrug of the present invention is of formula (IIfa)

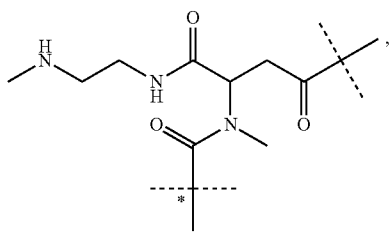
(IIfa)

wherein
the unmarked dashed line indicates the attachment to a nitrogen of -D which is a CNP moiety by forming an amide bond; and
the dashed line marked with the asterisk indicates attachment to —Z having the structure

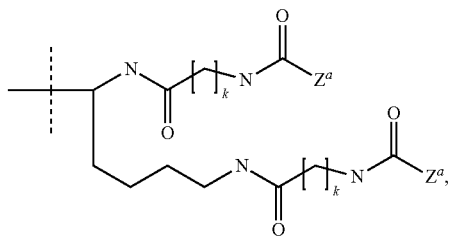

wherein
k is selected from the group consisting of 1, 2, 3, 4, 5, 6, 7, 8, 9, 10, 11 and 12;
each —$Z^a$ is

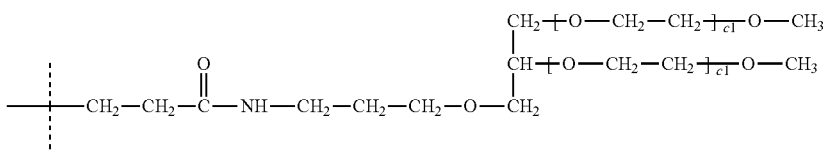

wherein
each c1 is an integer independently ranging from 200 to 250.

Preferably, k of formula (IIfa) is selected from the group consisting of 2, 3, 4, 5, 6 and 7.

Preferably, each c1 of formula (IIfa) is about 225.

In another preferred embodiment the CNP prodrug of the present invention is of formula (IIfa-i)

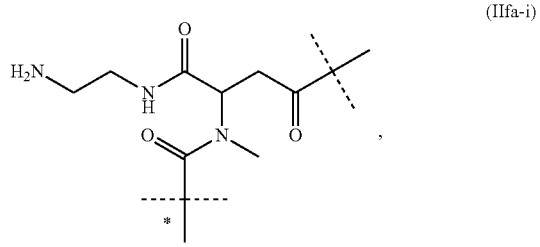

(IIfa-i)

wherein
the unmarked dashed line indicates the attachment to a nitrogen of -D which is a CNP moiety by forming an amide bond; and
the dashed line marked with the asterisk indicates attachment to —Z having the structure

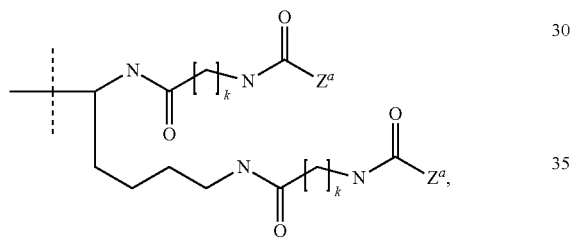

wherein
k is selected from the group consisting of 1, 2, 3, 4, 5, 6, 7, 8, 9, 10, 11 and 12;
each —$Z^a$ is

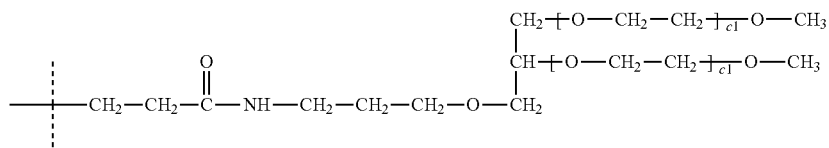

wherein
each c1 is an integer independently ranging from 200 to 250.

Preferably, k of formula (IIfa-i) is selected from the group consisting of 2, 3, 4, 5, 6 and 7.

Preferably, each c1 of formula (IIfa-i) is about 225.

In another preferred embodiment the CNP prodrug of the present invention is of formula (IIfa-ii)

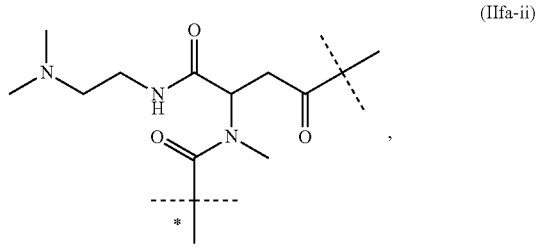

(IIfa-ii)

wherein
the unmarked dashed line indicates the attachment to a nitrogen of -D which is a CNP moiety by forming an amide bond; and
the dashed line marked with the asterisk indicates attachment to —Z having the structure

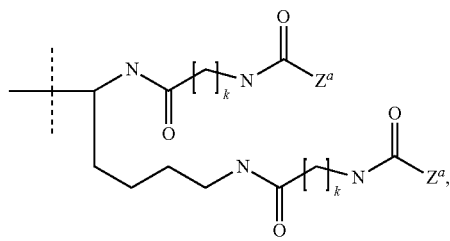

wherein
k is selected from the group consisting of 1, 2, 3, 4, 5, 6, 7, 8, 9, 10, 11 and 12;
each —$Z^a$ is

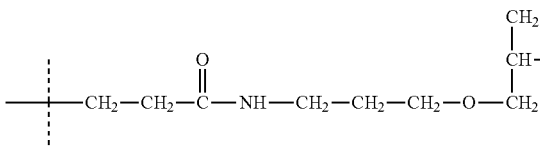
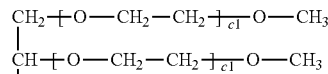

wherein each c1 is an integer independently ranging from 200 to 250.

Preferably, each c1 of formula (IIfa-ii) is about 225.

In one embodiment the CNP moiety of the CNP prodrug of formula (IIfa), (IIfa-i) and (IIfa-ii) has the sequence of SEQ ID NO:25.

In another embodiment the CNP moiety of the CNP prodrug of formula (IIfa), (IIfa-i) and (IIfa-ii) has the sequence of SEQ ID NO:20.

In another embodiment the CNP moiety of the CNP prodrug of formula (IIfa), (IIfa-i) and (IIfa-ii) has the sequence of SEQ ID NO:21.

In another embodiment the CNP moiety of the CNP prodrug of formula (IIfa), (IIfa-i) and (IIfa-ii) has the sequence of SEQ ID NO:22.

In another embodiment the CNP moiety of the CNP prodrug of formula (IIfa), (IIfa-i) and (IIfa-ii) has the sequence of SEQ ID NO:23.

In another embodiment the CNP moiety of the CNP prodrug of formula (IIfa), (IIfa-i) and (IIfa-ii) has the sequence of SEQ ID NO:30.

In a preferred embodiment the CNP moiety of the CNP prodrug of formula (IIfa), (IIfa-i) and (IIfa-ii) has the sequence of SEQ ID NO:24.

In one embodiment the CNP moiety is attached to in the CNP prodrug of formula (IIfa), (IIfa-i) and (IIfa-ii) through the nitrogen of the N-terminal amine functional group of CNP.

In another preferred embodiment the CNP prodrug of the present invention is of formula (IIf a')

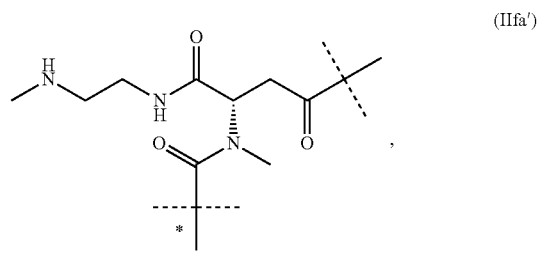

(IIfa')

wherein
the unmarked dashed line indicates the attachment to the nitrogen provided by the side chain of the lysine at position 26 of the CNP moiety of SEQ ID NO:24 by forming an amide bond; and
the dashed line marked with the asterisk indicates attachment to —Z having the structure

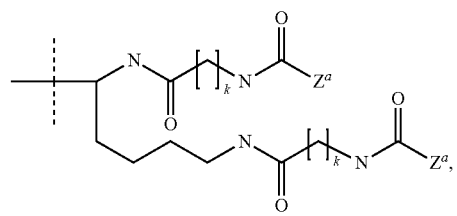

wherein
k is selected from the group consisting of 1, 2, 3, 4, 5, 6, 7, 8, 9, 10, 11 and 12;
each $Z^a$ is

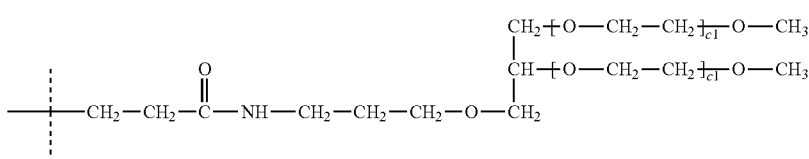

wherein
each c1 is an integer independently ranging from 200 to 250.

Preferably, k of formula (IIfa') is selected from the group consisting of 2, 3, 4, 5, 6 and 7.

Preferably, each c1 of formula (IIfa') is about 225.

In another preferred embodiment the CNP prodrug of the present invention is of formula (IIfa-i')

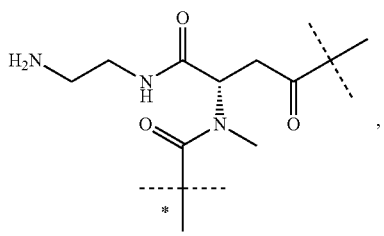

(IIfa-i')

wherein
the unmarked dashed line indicates the attachment to a nitrogen provided by the side chain of the lysine at position 26 of the CNP moiety of SEQ ID NO:24 by forming an amide bond; and
the dashed line marked with the asterisk indicates attachment to —Z having the structure

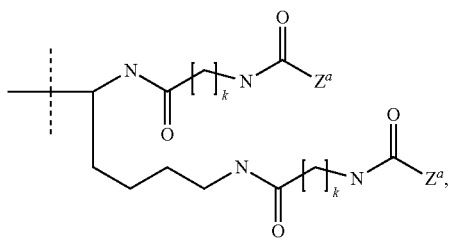

wherein
k is selected from the group consisting of 1, 2, 3, 4, 5, 6, 7, 8, 9, 10, 11 and 12;
each $Z^a$ is

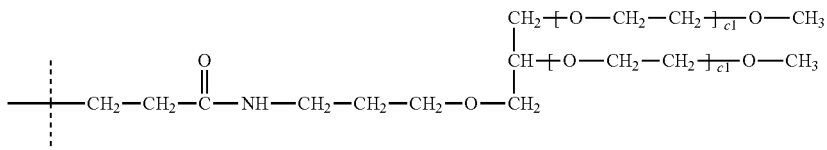

wherein
each c1 is an integer independently ranging from 200 to 250.

Preferably, k of formula (IIfa-i') is selected from the group consisting of 2, 3, 4, 5, 6 and 7. Preferably, each c1 of formula (IIfa-i') is about 225.

In another preferred embodiment the CNP prodrug of the present invention is of formula (IIfa-ii')

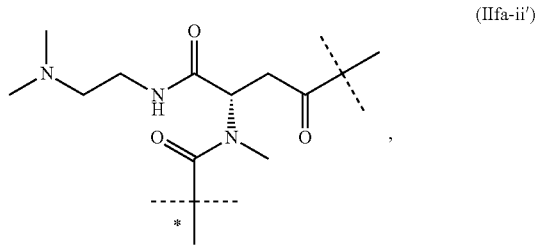

(IIfa-ii')

wherein
the unmarked dashed line indicates the attachment to a nitrogen provided by the side chain of the lysine at position 26 of the CNP moiety of SEQ ID NO:24 by forming an amide bond; and
the dashed line marked with the asterisk indicates attachment to —Z having the structure

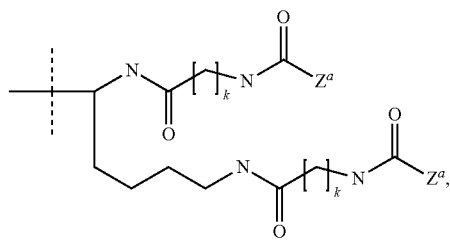

wherein
k is selected from the group consisting of 1, 2, 3, 4, 5, 6, 7, 8, 9, 10, 11 and 12;

each $Z^a$ is

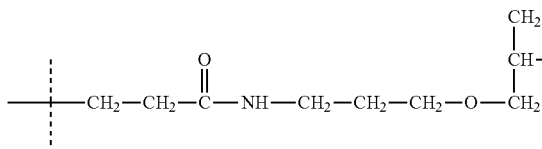
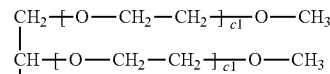

wherein
each c1 is an integer independently ranging from 200 to 250.

Preferably, k of formula (IIfa-ii') is selected from the group consisting of 2, 3, 4, 5, 6 and 7.

Preferably, each c1 of formula (IIfa-ii') is about 225.

Another aspect of the present invention is a pharmaceutical composition comprising at least one controlled-release CNP agonist of the present invention and at least one excipient.

In one embodiment the pharmaceutical composition comprising at least one controlled-release CNP agonist of the present invention and at least one excipient is a liquid or suspension formulation. It is understood that the pharmaceutical composition is a suspension formulation if the at least one controlled-release CNP agonist is water-insoluble.

In another embodiment the pharmaceutical composition comprising at least one controlled-release CNP agonist of the present invention and at least one excipient is a dry formulation.

Such liquid, suspension or dry pharmaceutical composition comprises at least one excipient. Excipients used in parenteral formulations may be categorized as, for example, buffering agents, isotonicity modifiers, preservatives, stabilizers, anti-adsorption agents, oxidation protection agents, viscosifiers/viscosity enhancing agents, or other auxiliary agents. However, in some cases, one excipient may have dual or triple functions. Preferably, the at least one excipient comprised in the pharmaceutical composition of the present invention is selected from the group consisting of (i) Buffering agents: physiologically tolerated buffers to maintain pH in a desired range, such as sodium phosphate, bicarbonate, succinate, histidine, citrate and acetate, sulphate, nitrate, chloride, pyruvate; antacids such as $Mg(OH)_2$ or $ZnCO_3$ may be also used;

(ii) Isotonicity modifiers: to minimize pain that can result from cell damage due to osmotic pressure differences at the injection depot; glycerin and sodium chloride are examples; effective concentrations can be determined by osmometry using an assumed osmolality of 285-315 mOsmol/kg for serum;

(iii) Preservatives and/or antimicrobials: multidose parenteral formulations require the addition of preservatives at a sufficient concentration to minimize risk of patients becoming infected upon injection and corresponding regulatory requirements have been established; typical preservatives include m-cresol, phenol, methylparaben, ethylparaben, propylparaben, butylparaben, chlorobutanol, benzyl alcohol, phenylmercuric nitrate, thimerosal, sorbic acid, potassium sorbate, benzoic acid, chlorocresol, and benzalkonium chloride;

(iv) Stabilizers: Stabilisation is achieved by strengthening of the protein-stabilising forces, by destabilisation of the denatured state, or by direct binding of excipients to the protein; stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives; in addition, oligomers or polymers such as cyclodextrins, dextran, dendrimers, PEG or PVP or protamine or HSA may be used;

(v) Anti-adsorption agents: Mainly ionic or non-ionic surfactants or other proteins or soluble polymers are used to coat or adsorb competitively to the inner surface of the formulation's container; e.g., poloxamer (Pluronic F-68), PEG dodecyl ether (Brij 35), polysorbate 20 and 80, dextran, polyethylene glycol, PEG-polyhistidine, BSA and HSA and gelatins; chosen concentration and type of excipient depends on the effect to be avoided but typically a monolayer of surfactant is formed at the interface just above the CMC value;

(vi) Oxidation protection agents: antioxidants such as ascorbic acid, ectoine, methionine, glutathione, monothioglycerol, morin, polyethylenimine (PEI), propyl gallate, and vitamin E; chelating agents such as citric acid, EDTA, hexaphosphate, and thioglycolic acid may also be used;

(vii) Viscosifiers or viscosity enhancers: retard settling of the particles in the vial and syringe and are used in order to facilitate mixing and resuspension of the particles and to make the suspension easier to inject (i.e., low force on the syringe plunger); suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly (hydroxy acids), such as poly(D,L- or L-lactic acid) (PLA) and poly(glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly(acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone; such block copolymers as well as the abovementioned poloxamers may exhibit reverse thermal gelation behavior (fluid state at room temperature to facilitate administration and gel state above sol-gel transition temperature at body temperature after injection);

(viii) Spreading or diffusing agent: modifies the permeability of connective tissue through the hydrolysis of components of the extracellular matrix in the interstitial space such as but not limited to hyaluronic acid, a polysaccharide found in the intercellular space of connective tissue; a spreading agent such as but not limited to hyaluronidase temporarily decreases the viscosity of the extracellular matrix and promotes diffusion of injected drugs; and (ix) Other auxiliary agents: such as wetting agents, viscosity modifiers, antibiotics, hyaluronidase; acids and bases such as hydrochloric acid and sodium hydroxide are auxiliary agents necessary for pH adjustment during manufacture.

Another aspect of the present invention is the controlled-release CNP agonist or a pharmaceutical composition comprising at least one controlled-release CNP agonist of the present invention for use as a medicament.

Preferably, said medicament is used in the treatment of a disease selected from the group consisting of achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, camptomelic dysplasia, congenital lethal hypophosphatasia, perinatal lethal type of osteogenesis imperfecta, short-rib polydactyly syndromes, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, spondyloepimetaphyseal dysplasia, neurofibromatosis, Legius syndrome, LEOPARD syndrome, Noonan syndrome, hereditary gingival fibromatosis, neurofibromatosis type 1, Legius syndrome, cardiofaciocutaneous syndrome, Costello syndrome, SHOX deficiency, idiopathic short stature, growth hormone deficiency, osteoarthritis, cleidocranial dysostosis, craniosynostosis (e.g., Muenke syndrome, Crouzon syndrome, Apert syndrome, Jackson-Weiss syndrome, Pfeiffer syndrome, or Crouzonodermoskeletal syndrome), dactyly, brachydactyly, camptodactyly, polydactyly, syndactyly, dyssegmental dysplasia, enchondromatosis, fibrous dysplasia, hereditary multiple exostoses, hypophosphatemic rickets, Jaffe-Lichtenstein syndrome, Marfan syndrome, McCune-Albright syndrome, osteopetrosis and osteopoikilosis.

In another embodiment said medicament is used in the treatment of an ophthalmic disorder, such as glaucoma and/or elevated intraocular pressure.

In another embodiment said medicament is used in the treatment of a cancer disease associated with overactivation of FGFR3, e.g., multiple myeloma, myeloproliferative syndrome, leukemia, plasma cell leukemia, lymphoma, glioblastoma, prostate cancer, bladder cancer, or mammary cancer.

In another embodiment said medicament is used in the treatment of a vascular smooth muscle disorder, preferably selected from the group consisting of hypertension, restenosis, arteriosclerosis, acute decompensated heart failure, congestive heart failure, cardiac edema, nephredema, hepatic edema, acute renal insufficiency, and chronic renal insufficiency.

In another embodiment said medicament is used in the treatment of hemorrhagic shock.

Preferably said medicament is used in the treatment of an achondroplasia phenotype selected from the group consisting of growth retardation, skull deformities, orthodontic defects, cervical cord compression, spinal stenosis, hydrocephalus, hearing loss due to chronic otitis, cardiovascular disease, neurological disease, and obesity.

Most preferably said medicament is used in the treatment of achondroplasia.

Another aspect of the present invention is the controlled-release CNP agonist or the pharmaceutical composition comprising at least one controlled-release CNP agonist of the present invention for use in a method of treatment of a disease which can be treated with a CNP agonist.

Preferably, said disease is selected from the group consisting of achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, camptomelic dysplasia, congenital lethal hypophosphatasia, perinatal lethal type of osteogenesis imperfecta, short-rib polydactyly syndromes, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, spondyloepimetaphyseal dysplasia, neurofibromatosis, Legius syndrome, LEOPARD syndrome, Noonan syndrome, hereditary gingival fibromatosis, neurofibromatosis type 1, Legius syndrome, cardiofaciocutaneous syndrome, Costello syndrome, SHOX deficiency, idiopathic short stature, growth hormone deficiency, osteoarthritis, cleidocranial dysostosis, craniosynostosis (e.g., Muenke syndrome, Crouzon syndrome, Apert syndrome, Jackson-Weiss syndrome, Pfeiffer syndrome, or Crouzonodermoskeletal syndrome), dactyly, brachydactyly, camptodactyly, polydactyly, syndactyly, dyssegmental dysplasia, enchondromatosis, fibrous dysplasia, hereditary multiple exostoses, hypophosphatemic rickets, Jaffe-Lichtenstein syndrome, Marfan syndrome, McCune-Albright syndrome, osteopetrosis and osteopoikilosis.

In another embodiment the disease is an ophthalmic disorder, such as glaucoma and/or elevated intraocular pressure.

In another embodiment said disease is associated with overactivation of FGFR3 in cancer, e.g., multiple myeloma, myeloproliferative syndrome, leukemia, plasma cell leukemia, lymphoma, glioblastoma, prostate cancer, bladder cancer, or mammary cancer.

In another embodiment said disease is a vascular smooth muscle disorder, preferably selected from the group consisting of hypertension, restenosis, arteriosclerosis, acute decompensated heart failure, congestive heart failure, cardiac edema, nephredema, hepatic edema, acute renal insufficiency, and chronic renal insufficiency.

In another embodiment said disease is hemorrhagic shock.

In another embodiment said disease is an achondroplasia phenotype selected from the group consisting of growth retardation, skull deformities, orthodontic defects, cervical cord compression, spinal stenosis, hydrocephalus, hearing loss due to chronic otitis, cardiovascular disease, neurological disease, and obesity.

Most preferably said disease is achondroplasia.

In one embodiment the patient undergoing the method of treatment of the present invention is a mammalian patient, preferably a human patient. In one embodiment this human patient is an adult. In a preferred embodiment the human patient is a pediatric patient.

Another aspect of the present invention is the use of the controlled-release CNP agonist or the pharmaceutical composition comprising at least one controlled-release CNP agonist of the present invention for the manufacture of a medicament for treating a disease which can be treated with CNP.

Preferably, said disease is selected from the group consisting of achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, camptomelic dysplasia, congenital lethal hypophosphatasia, perinatal lethal type of osteogenesis imperfecta, short-rib polydactyly syndromes, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, spondyloepimetaphyseal dysplasia, neurofibromatosis, Legius syndrome, LEOPARD syndrome, Noonan syndrome, hereditary gingival fibromatosis, neurofibromatosis type 1, Legius syndrome, cardiofaciocutaneous syndrome, Costello syndrome, SHOX deficiency, idiopathic short stature, growth hormone deficiency, osteoarthritis, cleidocranial dysostosis, craniosynostosis (e.g., Muenke syndrome, Crouzon syndrome, Apert syndrome, Jackson-Weiss syndrome, Pfeiffer syndrome, or Crouzonodermoskeletal syndrome), dactyly, brachydactyly, camptodactyly, polydactyly, syndactyly, dyssegmental dysplasia, enchondromatosis, fibrous dysplasia, hereditary multiple exostoses, hypophosphatemic rickets, Jaffe-Lichtenstein syndrome, Marfan syndrome, McCune-Albright syndrome, osteopetrosis and osteopoikilosis.

In another embodiment said disease is an ophthalmic disorder, such as glaucoma and/or elevated intraocular pressure.

In another embodiment said disease is associated with overactivation of FGFR3 in cancer, e.g., multiple myeloma, myeloproliferative syndrome, leukemia, plasma cell leukemia, lymphoma, glioblastoma, prostate cancer, bladder cancer, or mammary cancer.

In another embodiment said disease is a vascular smooth muscle disorder, preferably selected from the group consisting of hypertension, restenosis, arteriosclerosis, acute decompensated heart failure, congestive heart failure, cardiac edema, nephredema, hepatic edema, acute renal insufficiency, and chronic renal insufficiency.

In another embodiment said disease is hemorrhagic shock.

In another embodiment said disease is an achondroplasia phenotype selected from the group consisting of growth retardation, skull deformities, orthodontic defects, cervical cord compression, spinal stenosis, hydrocephalus, hearing loss due to chronic otitis, cardiovascular disease, neurological disease, and obesity.

Most preferably said disease is achondroplasia.

In one embodiment the disease to be treated with the controlled-release CNP agonist or the pharmaceutical composition comprising at least one controlled-release CNP agonist of the present invention occurs in a mammalian patient, preferably in a human patient. In one embodiment this human patient is an adult. In a preferred embodiment the human patient is a pediatric patient.

A further aspect of the present invention is a method of treating, controlling, delaying or preventing in a mammalian patient, preferably a human patient, in need of the treatment of one or more diseases which can be treated with a CNP agonist, comprising the step of administering to said patient in need thereof a therapeutically effective amount of the controlled-release CNP agonist or a pharmaceutical composition comprising at least one controlled-release CNP agonist of the present invention. In one embodiment the human patient is an adult. In a preferred embodiment the human patient is a pediatric patient.

Preferably, the one or more diseases which can be treated with CNP is selected from the group consisting of achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, camptomelic dysplasia, congenital lethal hypophosphatasia, perinatal lethal type of osteogenesis imperfecta, short-rib polydactyly syndromes, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, spondyloepimetaphyseal dysplasia, neurofibromatosis, Legius syndrome, LEOPARD syndrome, Noonan syndrome, hereditary gingival fibromatosis, neurofibromatosis type 1, Legius syndrome, cardiofaciocutaneous syndrome, Costello syndrome, SHOX deficiency, idiopathic short stature, growth hormone deficiency, osteoarthritis, cleidocranial dysostosis, craniosynostosis (e.g., Muenke syndrome, Crouzon syndrome, Apert syndrome, Jackson-Weiss syndrome, Pfeiffer syndrome, or Crouzonodermoskeletal syndrome), dactyly, brachydactyly, camptodactyly, polydactyly, syndactyly, dyssegmental dysplasia, enchondromatosis, fibrous dysplasia, hereditary multiple exostoses, hypophosphatemic rickets, Jaffe-Lichtenstein syndrome, Marfan syndrome, McCune-Albright syndrome, osteopetrosis and osteopoikilosis.

In another embodiment the one or more diseases which can be treated with CNP is an ophthalmic disorder, such as glaucoma and/or elevated intraocular pressure.

In another embodiment the one or more diseases which can be treated with CNP is associated with overactivation of FGFR3 in cancer, e.g., multiple myeloma, myeloproliferative syndrome, leukemia, plasma cell leukemia, lymphoma, glioblastoma, prostate cancer, bladder cancer, or mammary cancer.

In another embodiment the one or more diseases which can be treated with CNP is a vascular smooth muscle disorder, preferably selected from the group consisting of hypertension, restenosis, arteriosclerosis, acute decompensated heart failure, congestive heart failure, cardiac edema, nephredema, hepatic edema, acute renal insufficiency, and chronic renal insufficiency.

In another embodiment the one or more disease which can be treated with CNP is hemorrhagic shock.

In another embodiment the one or more diseases which can be treated with CNP is an achondroplasia phenotype selected from the group consisting of growth retardation, skull deformities, orthodontic defects, cervical cord compression, spinal stenosis, hydrocephalus, hearing loss due to chronic otitis, cardiovascular disease, neurological disease, and obesity.

Most preferably the one or more diseases which can be treated with CNP is achondroplasia.

An additional aspect of the present invention is a method of administering the controlled-release CNP agonist or the pharmaceutical composition comprising at least one controlled-release CNP agonist of the present invention, wherein the method comprises the step of administering the controlled-release CNP agonist or the pharmaceutical composition comprising at least one controlled-release CNP agonist of the present invention via topical, enteral or parenteral administration and by methods of external application, injection or infusion, including intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, intrasternal injection and infusion, direct delivery to the brain via implanted device allowing delivery of the invention or the like to brain tissue or brain fluids (e.g., Ommaya Reservoir), direct intracerebroventricular injection or infusion, injection or infusion into brain or brain associated regions, injection into the subchoroidal space, retro-orbital injection and ocular instillation, preferably via subcutaneous injection.

In a preferred embodiment, the present invention relates to a controlled-release CNP agonist or a pharmaceutical composition comprising at least one controlled-release CNP agonist of the present invention, for use in the treatment of achondroplasia via subcutaneous injection.

In a further aspect the present invention relates to a pharmaceutical composition comprising at least one controlled-release CNP agonist of the present invention or a pharmaceutically acceptable salt thereof, wherein the pharmaceutical composition comprises at least one further biologically active moiety or drug.

The at least one further biologically active moiety or drug may be in its free form (i.e in the form of a free drug), may be in the form of a stable conjugate or may be in the form of a controlled-release compound.

In one embodiment, the at least one further biologically active moiety or drug is a drug in its free form, i.e. the pharmaceutical composition of the present invention comprises at least one controlled-release CNP agonist and at least one further drug.

Preferably, the at least one further drug is selected from the group consisting of antihistamins; human anti-FGFR3 antibodies; soluble forms of human fibroblast growth factor receptor 3; tyrosine kinase inhibitors; statins; CNP agonists; growth hormone; IGF-1; ANP; BNP;

inhibitors of peptidases and proteases; and inhibitors of NPR-C.

A preferred antihistamin is meclozine.
A preferred tyrosine kinase inhibitor is NVP-BGJ398.
A preferred statin is rosuvastatin.

A preferred CNP agonist for the at least one further drug is vosoritide.

Preferred inhibitors of peptidases and proteases are NEP and furin inhibitors.

A preferred inhibitor for NEP are thiorphan and candoxatril.

Preferred inhibitors of NPR-C are the fragment of SEQ ID NO:98 (FGIPMDRIGRNPR) and antibody B701.

Preferred inhibitors of tyrosine kinases are as disclosed in U.S. Pat. Nos. 6,329,375 and 6,344,459, which are herewith incorporated by reference.

In one embodiment the at least one further drug is an antihistamin.

In another embodiment the at least one further drug is a human anti-FGFR3 antibody.

In another embodiment the at least one further drug is a soluble forms of human fibroblast growth factor receptor 3 (sFGFR3).

In another embodiment the at least one further drug is a tyrosine kinase inhibitor.

In another embodiment the at least one further drug is a statin.

In another embodiment the at least one further drug is a growth hormone.

In another embodiment the at least one further drug is a CNP agonist.

In another embodiment the at least one further drug is IGF-1.

In another embodiment the at least one further drug is ANP.

In another embodiment the at least one further is BNP.

In another embodiment the at least one further drug is an inhibitor of peptidases and proteases.

In another embodiment the at least one further drug is an inhibitor of NPR-C.

In another embodiment, the at least one further biologically active moiety or drug is in the form of a stable conjugate.

In one embodiment the at least one further biologically active moiety in the form of a stable conjugate comprises at least one biologically active moiety covalently conjugated through a stable linkage to a polymeric moiety, preferably to a water-soluble polymeric moiety, either directly or through a spacer moiety.

Preferably, such polymeric moiety, even more preferably water-soluble polymeric moiety, comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In another embodiment the at least one further biologically active moiety in the form of a stable conjugate is covalently conjugated through a stable linkage to an albumin-binding moiety. Preferably, said albumin-binding moiety is a $C_{8-24}$ alkyl moiety or fatty acid derivative. Preferred fatty acid derivatives are those disclosed in WO 2005/027978 A2 and WO 2014/060512 A1 which are herewith incorporated by reference.

Preferably, the at least one further biologically active moiety in the form of a stable conjugate comprises a biologically active moiety selected from the group consisting of antihistamins; human anti-FGFR3 antibodies; soluble forms of human fibroblast growth factor receptor 3 (sFGFR3); tyrosine kinase inhibitors; statins; CNP agonists; growth hormone; IGF-1; ANP; BNP; inhibitors of peptidases and proteases; and inhibitors of NPR-C.

A preferred antihistamin is meclozine.

A preferred tyrosine kinase inhibitor is NVP-BGJ398.

A preferred statin is rosuvastatin.

A preferred CNP agonist for the at least one further biologically active moiety is vosoritide.

Preferred inhibitors of peptidases and proteases are NEP and furin inhibitors.

A preferred inhibitor for NEP are thiorphan and candoxatril.

Preferred inhibitors of NPR-C are the fragment of SEQ ID NO:98 (FGIPMDRIGRNPR) and antibody B701.

Preferred inhibitors of tyrosine kinases are as disclosed in U.S. Pat. Nos. 6,329,375 and 6,344,459, which are herewith incorporated by reference.

In one embodiment the at least one further biologically active moiety in the form of a stable conjugate comprises an antihistamin moiety.

In another embodiment the at least one further biologically active moiety in the form of a stable conjugate comprises a human anti-FGFR3 antibody moiety.

In another embodiment the at least one further biologically active moiety in the form of a stable conjugate comprises a soluble forms of human fibroblast growth factor receptor 3 (sFGFR3) moiety.

In another embodiment the at least one further biologically active moiety in the form of a stable conjugate comprises a tyrosine kinase inhibitor moiety.

In another embodiment the at least one further biologically active moiety in the form of a stable conjugate comprises a statin moiety.

In another embodiment the at least one further biologically active moiety in the form of a stable conjugate comprises a growth hormone moiety.

In another embodiment the at least one further biologically active moiety in the form of a stable conjugate comprises a CNP agonist moiety.

In another embodiment the at least one further biologically active moiety in the form of a stable conjugate comprises an IGF-1 moiety.

In another embodiment the at least one further biologically active moiety in the form of a stable conjugate comprises an ANP moiety.

In another embodiment the at least one further biologically active moiety in the form of a stable conjugate comprises a BNP moiety.

In another embodiment the at least one further biologically active moiety in the form of a stable conjugate comprises an inhibitor of peptidases and proteases moiety.

In another embodiment the at least one further biologically active moiety in the form of a stable conjugate comprises an inhibitor of NPR-C moiety.

In another embodiment the at least one further biologically active moiety or drug is in the form of a controlled-release compound.

Preferably, the at least one further biologically active moiety or drug in the form of a controlled-release compound comprises at least one biologically active moiety or drug selected from the group consisting of antihistamine; human anti-FGFR3 antibodies; soluble forms of human fibroblast growth factor receptor 3; statins; CNP agonists; growth hormone; IGF-1; ANP; BNP; inhibitors of peptidases and proteases; inhibitors of tyrosine kinases; and inhibitors of NPR-C.

A preferred antihistamin is meclozine.

A preferred tyrosine kinase inhibitor is NVP-BGJ398.

A preferred statin is rosuvastatin.

A preferred CNP agonist for the at least one further drug is vosoritide.

Preferred inhibitors of peptidases and proteases are NEP and furin inhibitors.

A preferred inhibitor for NEP are thiorphan and candoxatril.

Preferred inhibitors of NPR-C are the fragment of SEQ ID NO:98 (FGIPMDRIGRNPR) and antibody B701.

Preferred inhibitors of tyrosine kinases are as disclosed in U.S. Pat. Nos. 6,329,375 and 6,344,459, which are herewith incorporated by reference.

In one embodiment the at least one further biologically active moiety or drug in the form of a controlled-release comprises an antihistamin moiety or drug.

In another embodiment the at least one further biologically active moiety or drug in the form of a controlled-release comprises a human anti-FGFR3 antibody moiety or drug.

In another embodiment the at least one further biologically active moiety or drug in the form of a controlled-release comprises a soluble forms of human fibroblast growth factor receptor 3 (sFGFR3) moiety or drug.

In another embodiment the at least one further biologically active moiety or drug in the form of a controlled-release comprises a tyrosine kinase inhibitor moiety or drug.

In another embodiment the at least one further biologically active moiety or drug in the form of a controlled-release comprises a statin moiety or drug.

In another embodiment the at least one further biologically active moiety or drug in the form of a controlled-release comprises a growth hormone moiety or drug.

In another embodiment the at least one further biologically active moiety or drug in the form of a controlled-release comprises a CNP agonist moiety or drug.

In another embodiment the at least one further biologically active moiety or drug in the form of a controlled-release comprises an IGF-1 moiety or drug.

In another embodiment the at least one further biologically active moiety or drug in the form of a controlled-release comprises an ANP moiety or drug.

In another embodiment the at least one further biologically active moiety or drug in the form of a controlled-release comprises a BNP moiety or drug.

In another embodiment the at least one further biologically active moiety or drug in the form of a controlled-release comprises an inhibitor of peptidases and proteases moiety or drug.

In another embodiment the at least one further biologically active moiety or drug in the form of a controlled-release comprises an inhibitor of NPR-C moiety or drug.

In one embodiment the at least one further biologically active moiety or drug in the form of a controlled-release compound is water-insoluble.

Preferably, such water-insoluble controlled-release compound is selected from the group consisting of crystals, nanoparticles, microparticles, nanospheres and microspheres.

In one embodiment the at least one further biologically active moiety or drug in the form of a water-insoluble controlled-release compound is a crystal comprising at least one drug or biologically active moiety.

In another embodiment the at least one further biologically active moiety or drug in the form of a water-insoluble controlled-release compound is a nanoparticle comprising at least one drug or biologically active moiety.

In another embodiment the at least one further biologically active moiety or drug in the form of a water-insoluble controlled-release compound is a microparticle comprising at least one drug or biologically active moiety.

In another embodiment the at least one further biologically active moiety or drug in the form of a water-insoluble controlled-release compound is a nanosphere comprising at least one drug or biologically active moiety.

In another embodiment the at least one further biologically active moiety or drug in the form of a water-insoluble controlled-release compound is a microsphere comprising at least one drug or biologically active moiety.

In one embodiment the at least one further biologically active moiety or drug in the form of a water-insoluble controlled-release compound is a vesicle comprising at least one drug or biologically active moiety. Preferably, such vesicle comprising at least one drug or biologically active moiety is a micelle, liposome or polymersome.

In one embodiment the at least one further biologically active moiety or drug in the form of a water-insoluble controlled-release compound is a micelle comprising at least one drug or biologically active moiety.

In another embodiment the at least one further biologically active moiety or drug in the form of a water-insoluble controlled-release compound is a liposome comprising at least one drug or biologically active moiety. Preferably, such liposome is selected from the group consisting of aquasomes; non-ionic surfactant vesicles, such as niosomes and proniosomes; cationic liposomes, such as LeciPlex; transfersomes; ethosomes; ufasomes; sphingosomes; and pharmacosomes.

In another embodiment the at least one further biologically active moiety or drug in the form of a water-insoluble controlled-release compound is a polymersome at least one drug or biologically active moiety.

In another embodiment the at least one further biologically active moiety or drug in the form of a water-insoluble controlled-release compound comprises at least one biologically active moiety or drug non-covalently embedded in a water-insoluble polymer. Preferably, such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In a preferred embodiment the at least one further biologically active moiety or drug in the form of a water-insoluble controlled-release compound comprises at least one drug or biologically active moiety non-covalently embedded in poly(lactic-co-glycolic acid) (PLGA).

In another embodiment the at least one further biologically active moiety or drug in the form of a water-insoluble controlled-release compound comprises at least one biologically active moiety covalently and reversibly conjugated to a water-insoluble polymer. Preferably such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

Preferably, the at least one further biologically active moiety or drug in the form of a water-insoluble controlled-release compound comprises at least one biologically active moiety or drug selected from the group consisting of anti-histamins; human anti-FGFR3 antibodies; soluble forms of human fibroblast growth factor receptor 3; tyrosine kinase inhibitors; statins; CNP agonists; growth hormone; IGF-1; ANP; BNP; inhibitors of peptidases and proteases; and inhibitors of NPR-C.

A preferred antihistamin is meclozine.

A preferred tyrosine kinase inhibitor is NVP-BGJ398.

A preferred statin is rosuvastatin.

A preferred CNP agonist for the at least one further drug is vosoritide.

Preferred inhibitors of peptidases and proteases are NEP and furin inhibitors.

A preferred inhibitor for NEP are thiorphan and candoxatril.

Preferred inhibitors of NPR-C are the fragment of SEQ ID NO:98 (FGIPMDRIGRNPR) and antibody B701.

Preferred inhibitors of tyrosine kinases are as disclosed in U.S. Pat. Nos. 6,329,375 and 6,344,459, which are herewith incorporated by reference.

In one embodiment the at least one further biologically active moiety or drug in the form of a water-insoluble controlled-release comprises an antihistamin moiety or drug.

In another embodiment the at least one further biologically active moiety or drug in the form of a water-insoluble controlled-release comprises a human anti-FGFR3 antibody moiety or drug.

In another embodiment the at least one further biologically active moiety or drug in the form of a water-insoluble controlled-release comprises a soluble forms of human fibroblast growth factor receptor 3 (sFGFR3) moiety or drug.

In another embodiment the at least one further biologically active moiety or drug in the form of a water-insoluble controlled-release comprises a tyrosine kinase inhibitor moiety or drug.

In another embodiment the at least one further biologically active moiety or drug in the form of a water-insoluble controlled-release comprises a statin moiety or drug.

In another embodiment the at least one further biologically active moiety or drug in the form of a water-insoluble controlled-release comprises a growth hormone moiety or drug.

In another embodiment the at least one further biologically active moiety or drug in the form of a water-insoluble controlled-release comprises a CNP agonist moiety or drug.

In another embodiment the at least one further biologically active moiety or drug in the form of a water-insoluble controlled-release comprises an IGF-1 moiety or drug.

In another embodiment the at least one further biologically active moiety or drug in the form of a water-insoluble controlled-release comprises an ANP moiety or drug.

In another embodiment the at least one further biologically active moiety or drug in the form of a water-insoluble controlled-release comprises a BNP moiety or drug.

In another embodiment the at least one further biologically active moiety or drug in the form of a water-insoluble controlled-release comprises an inhibitor of peptidases and proteases moiety or drug.

In another embodiment the at least one further biologically active moiety or drug in the form of a water-insoluble controlled-release comprises an inhibitor of NPR-C moiety or drug.

In another embodiment the at least one further biologically active moiety or drug in the form of a controlled-release compound is water-soluble.

In one embodiment the at least one further biologically active moiety or drug in the form of a water-soluble controlled-release compound comprises at least one biologically active moiety covalently conjugated through a reversible linkage to a water-soluble polymeric moiety, either directly or through a spacer moiety.

Preferably, such water-soluble polymeric moiety comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In another embodiment the at least one further biologically active moiety in the form of a water-soluble controlled-release compound is covalently conjugated through a stable linkage to an albumin-binding moiety. Preferably, said albumin-binding moiety is a $C_{8-24}$ alkyl moiety or fatty acid derivative. Preferred fatty acid derivatives are those disclosed in WO 2005/027978 A2 and WO 2014/060512 A1 which are herewith incorporated by reference.

Preferably, the at least one further biologically active moiety in the form of a water-soluble controlled-release comprises a biologically active moiety selected from the group consisting of antihistamins; human anti-FGFR3 antibodies; soluble forms of human fibroblast growth factor receptor 3; tyrosine kinase inhibitors; statins; CNP agonists; growth hormone; IGF-1; ANP; BNP; inhibitors of peptidases and proteases; and inhibitors of NPR-C.

A preferred antihistamin is meclozine.

A preferred tyrosine kinase inhibitor is NVP-BGJ398.

A preferred statin is rosuvastatin.

A preferred CNP agonist for the at least one further drug is vosoritide.

Preferred inhibitors of peptidases and proteases are NEP and furin inhibitors.

A preferred inhibitor for NEP are thiorphan and candoxatril.

Preferred inhibitors of NPR-C are the fragment of SEQ ID NO:98 (FGIPMDRIGRNPR) and antibody B701.

Preferred inhibitors of tyrosine kinases are as disclosed in U.S. Pat. Nos. 6,329,375 and 6,344,459, which are herewith incorporated by reference.

In one embodiment the at least one further biologically active moiety or drug in the form of a water-soluble controlled-release comprises an antihistamin moiety or drug.

In another embodiment the at least one further biologically active moiety or drug in the form of a water-soluble controlled-release comprises a human anti-FGFR3 antibody moiety or drug.

In another embodiment the at least one further biologically active moiety or drug in the form of a water-soluble controlled-release comprises a soluble forms of human fibroblast growth factor receptor 3 (sFGFR3) moiety or drug.

In another embodiment the at least one further biologically active moiety or drug in the form of a water-soluble controlled-release comprises a tyrosine kinase inhibitor moiety or drug.

In another embodiment the at least one further biologically active moiety or drug in the form of a water-soluble controlled-release comprises a statin moiety or drug.

In another embodiment the at least one further biologically active moiety or drug in the form of a water-soluble controlled-release comprises a growth hormone moiety or drug. A preferred water-soluble controlled-release growth hormone compound is compound 2 of example 2 of WO2016/079114A1. Accordingly, a preferred water-soluble controlled-release growth hormone compound has the following structure:

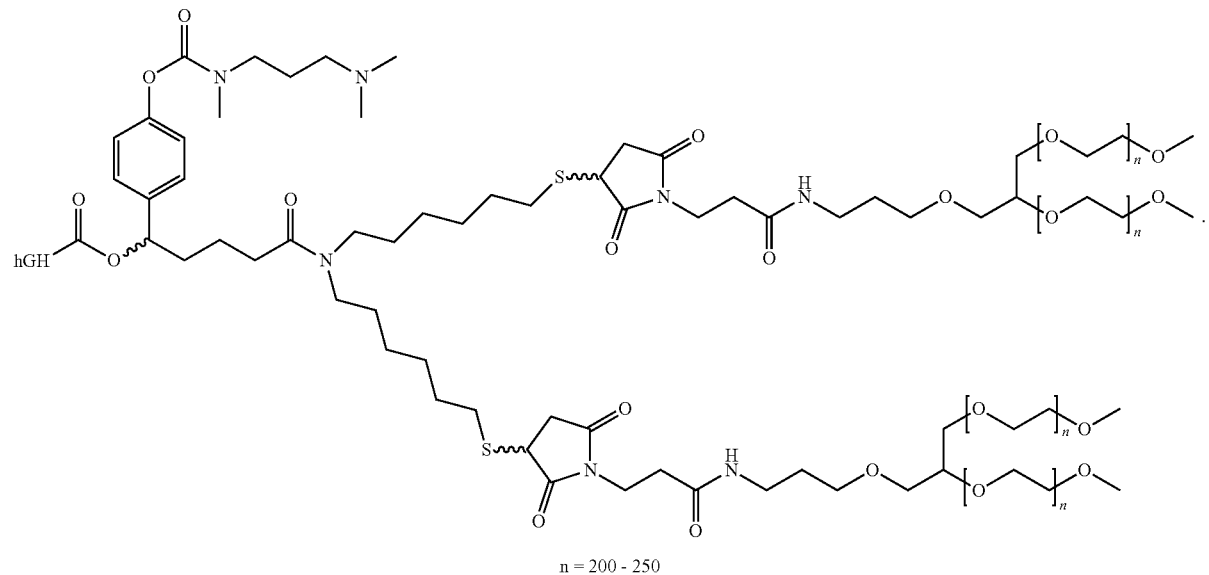

n = 200 - 250

In another embodiment the at least one further biologically active moiety or drug in the form of a water-soluble controlled-release comprises a CNP agonist moiety or drug.

In another embodiment the at least one further biologically active moiety or drug in the form of a water-soluble controlled-release comprises an IGF-1 moiety or drug.

In another embodiment the at least one further biologically active moiety or drug in the form of a water-soluble controlled-release comprises an ANP moiety or drug.

In another embodiment the at least one further biologically active moiety or drug in the form of a water-soluble controlled-release comprises a BNP moiety or drug.

In another embodiment the at least one further biologically active moiety or drug in the form of a water-soluble controlled-release comprises an inhibitor of peptidases and proteases moiety or drug.

In another embodiment the at least one further biologically active moiety or drug in the form of a water-soluble controlled-release comprises an inhibitor of NPR-C moiety or drug.

Another aspect of the present invention is the pharmaceutical composition of the present invention for use as a medicament.

Another aspect of the present invention is the pharmaceutical composition of the present invention for use in the treatment of a patient suffering from a disorder that benefits from stimulating growth.

Preferably, the patient is a mammalian patient, more preferably a human patient.

Preferably, such disorders that benefit from stimulating growth are selected from the group comprising achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, camptomelic dysplasia, congenital lethal hypophosphatasia, perinatal lethal type of osteogenesis imperfecta, short-rib polydactyly syndromes, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia. Most preferably, the disorder that benefits from stimulating growth is achondroplasia.

Another aspect of the present invention is a method of treating a patient suffering from a disorder that benefits from stimulating growth by administering the pharmaceutical composition of the present invention.

Preferably, the patient is a mammalian patient, more preferably a human patient.

Preferably, such disorders that benefit from stimulating growth are selected from the group comprising achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, camptomelic dysplasia, congenital lethal hypophosphatasia, perinatal lethal type of osteogenesis imperfecta, short-rib polydactyly syndromes, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia. Most preferably, the disorder that benefits from stimulating growth is achondroplasia.

If the CNP agonist is a polypeptide, such polypeptide may be prepared by standard solid-phase peptide synthesis methods, e.g. by Boc chemistry (R. B. Merrifield, J. Am. Chem. Soc., 85(14): 2149-2154 (1963)). Alternatively, Fmoc (fluorenylmethoxycarbonyl) chemistry may be employed.

Methods known in the art can be employed to improve purity and/or yield, including the use of pseudoproline or other dipeptide building blocks, fragment coupling and others (J. Wade et al., Lett. Pept. Sci., 7(2):107-112 (2000); Y. Fujiwara et al., Chem. Pharm. Bull., 44(7):1326-1331 (1996); P. Cherkupally et al., Eur. J. Org. Chem., 6372-6378 (2013)).

Alternatively, if the CNP agonist is a polypeptide, such polypeptide may be produced by recombinant synthesis processes.

FIG. 1: Structure of CNP according to SEQ ID NO:1.

EXAMPLES

Materials and Methods

CNP SEQ ID No:1 was obtained from Bachem AG, Bubendorf, Switzerland (CNP-22, human, catalogue no. H-1296). CNP-34 SEQ ID No:40 and CNP-38 SEQ ID No:24 were obtained from CASLO ApS, Kongens Lyngby, Denmark.

Side chain protected CNP-38 on CTC resin having Boc protected N-terminus and ivDde protected side chain of Lys26 (synthesized by Fmoc-strategy) was obtained from CASLO ApS, Kongens Lyngby, Denmark.

Side chain protected CNP-34 on TCP Tentagel resin having Boc protected N-terminus and ivDde protected side chain of either Lys12, Lys16 or Lys22 (synthesized by Fmoc-strategy) was obtained from Peptide Specialty Laboratories GmbH, Heidelberg, Germany. Side chain protected CNP-38 on TCP tentagel resin having free N-terminus (synthesized by Fmoc-strategy) was obtained from Peptide Specialty Laboratories GmbH, Heidelberg, Germany.

Methoxy PEG amine 5 kDa was obtained from Rapp Polymere GmbH, Tuebingen, Germany. All other PEGs used in this work were acquired from NOF Europe N.V., Grobbendonk, Belgium.

Fmoc-N-Me-Asp(OtBu)-OH was obtained from Bachem AG, Bubendorf, Switzerland. 5-Trityl-6-mercaptohexanoic acid was purchased from Polypeptide, Strasbourg, France. HATU was obtained from Merck Biosciences GmbH, Schwalbach/Ts, Germany.

2,4-Dimethylbenzyl alcohol was obtained from abcr GmbH, Karlsruhe, Germany.

Fmoc-N-Me-Asp(OBn)-OH was obtained from Peptide International Inc., Louisville, Ky., USA.

Neutral Endopeptidase (NEP) was obtained from Enzo Life Sciences GmbH, Lörrach, Germany.

All other chemicals and reagents were purchased from Sigma Aldrich GmbH, Taufkirchen, Germany.

Syringes equipped with polyethylene fits (MultiSynTech GmbH, Witten, Germany) were used as reaction vessels or for washing steps for peptide resins.

General Procedure for the Removal of ivDde Protecting Group from Side Chain Protected CNPs on Resin.

The resin was pre-swollen in DMF for 30 min and the solvent was discarded. The ivDde group was removed by incubating the resin with DMF/hydrazine hydrate 4/1 (v/v, 2.5 mL/g resin) for 8×15 min. For each step fresh DMF/hydrazine hydrate solution was used. Finally, the resin was washed with DMF (10×), DCM (10×) and dried in vacuo.

RP-HPLC Purification

For preparative RP-HPLC a Waters 600 controller and a 2487 Dual Absorbance Detector was used, equipped with the following columns: Waters XBridge™ BEH300 Prep C18 5 µm, 150×10 mm, flow rate 6 mL/min, or Waters XBridge™ BEH300 Prep C18 10 µm, 150×30 mm, flow rate 40 mL/min. Linear gradients of solvent system A (water containing 0.1% TFA v/v or 0.01% conc. HCl v/v) and solvent system B (acetonitrile containing 0.1% TFA v/v or 0.01% conc. HCl v/v) were used.

HPLC fractions containing product were pooled and lyophilized if not stated otherwise.

Flash Chromatography

Flash chromatography purifications were performed on an Isolera One system from Biotage AB, Sweden, using Biotage KP-Sil silica cartridges and n-heptane and ethyl acetate as eluents. Products were detected at 254 nm.

Analytical Methods

Analytical ultra-performance LC (UPLC)-MS was performed on a Waters Acquity system equipped with a Waters BEH300 C18 column (2.1×50 mm, 1.7 µm particle size, flow: 0.25 mL/min; solvent A: water containing 0.04% TFA (v/v), solvent B: acetonitrile containing 0.05% TFA (v/v)) coupled to a LTQ Orbitrap Discovery mass spectrometer from Thermo Scientific or coupled to a Waters Micromass ZQ.

Size exclusion chromatography (SEC) was performed using an Amersham Bioscience AEKTAbasic system equipped with a Superdex 200 5/150 GL column (Amersham Bioscience/GE Healthcare) equipped with a 0.45 µm inlet filter, if not stated otherwise. 20 mM sodium phosphate, 140 mM NaCl, pH 7.4, was used as mobile phase.

Due to the reversible nature of the attachment of -L$^1$- to -D measurements for NEP-stability and receptor affinity were made using stable analogs of the CNP prodrugs of the present invention, i.e. they were made using similar structures to those of the CNP prodrugs of the present invention which instead of a reversible attachment of —Z to -D have a stable attachment.

This was necessary, because the CNP prodrugs of the present invention would release CNP in the course of the experiment and said released CNP would have influenced the result.

Quantification of Plasma Total CNP-38 Concentrations

Plasma total CNP-38 concentrations (conjugated and released CNP-38) were determined by quantification of the N-terminal signature peptide (sequence: LQEHPNAR; residues 1-8 of SEQ ID NO:24) and C-terminal signature peptide (sequence: IGSMSGLGC; residues 30-38 of SEQ ID NO:24) after tryptic digestion.

LC-MS analysis was carried out by using an Agilent 1290 UPLC coupled to an Agilent 6550 iFunnel Q-TOF mass spectrometer via an ESI probe. Chromatography was performed on a Waters Acquity BEH300 C18 analytical column (50×2.1 mm I.D., 1.7 µm particle size) with pre-filter at a flow rate of 0.25 mL/min (T=25° C.). Water (UPLC grade)

containing 0.2% formic acid (v/v) was used as mobile phase A and acetonitrile (UPLC grade) with 0.2% formic acid as mobile phase B. The gradient system comprised a short isocratic step at the initial parameters of 0.1% B for 3.0 min followed by a linear increase from 0.1% B to 16% B in 17 min. Mass analysis was performed in the single ion monitoring (SIM) mode, monitoring the ions m/z 482.75 $[M+2H]^{2+}$ (N-terminal) and m/z 824.36 $[M+H]^{1+}$ (C-terminal). As internal standard deuterated CNP-38 peptide was used.

Calibration standards of CNP-38 conjugate in blank plasma were prepared as follows: The thawed Li-heparin cynomolgous plasma was first homogenized, then centrifuged for 5 minutes. The CNP-38 conjugate formulation was diluted to a working solution of 10 µg/mL (conjugate CNP-38 eq.) in DMSO and spiked into blank plasma at concentrations between 9.3 ng/100 µL (conjugate CNP-38 eq.) and 139.5 ng/100 µL (conjugate CNP-38 eq.). These solutions were used for the generation of a calibration curve. Calibration curves were weighted $1/x^2$ for both signature peptides (N- and C-Terminal). For quality control, three quality control samples were prepared accordingly with contents of 116.2 ng/100 µL (high QC, conjugate CNP-38 eq.), 69.75 ng/100 µL (mid QC, conjugate CNP-38 eq.) and 23.25 ng/100 µL (low QC, conjugate CNP-38 eq.).

For sample preparation, protein precipitation was carried out by addition of 300 µL of pre-cooled (0° C.) methanol to 100 µL of the plasma sample. 200 µL of the supernatant were transferred into a new well-plate and evaporated to dryness (under a gentle nitrogen stream at 35° C.). 100 µL of reconstitution solvent (Thermo digestion buffer, order number 60109-101, Thermo Fisher Scientific GmbH, Dreieich, Germany) were used to dissolve the residue. 20 µg of trypsin (order number V5111, Promega GmbH, Mannheim, Germany) were dissolved in 20 µL of 10 mM acetic acid. 2 µL of the trypsin solution were added to each cavity.

After 4 hours incubation at 37° C. (water bath), 5 µL of a 0.5 M TCEP solution were added to each cavity and incubated again for 5 min at 96° C. After the samples had cooled to room temperature, 3 µL acetonitrile were added. The eluates were transferred into vials. 10 µL were injected into the UPLC-MS system.

Example 1

Synthesis of Linker Reagent 1f

Linker reagent 1f was synthesized according to the following scheme:

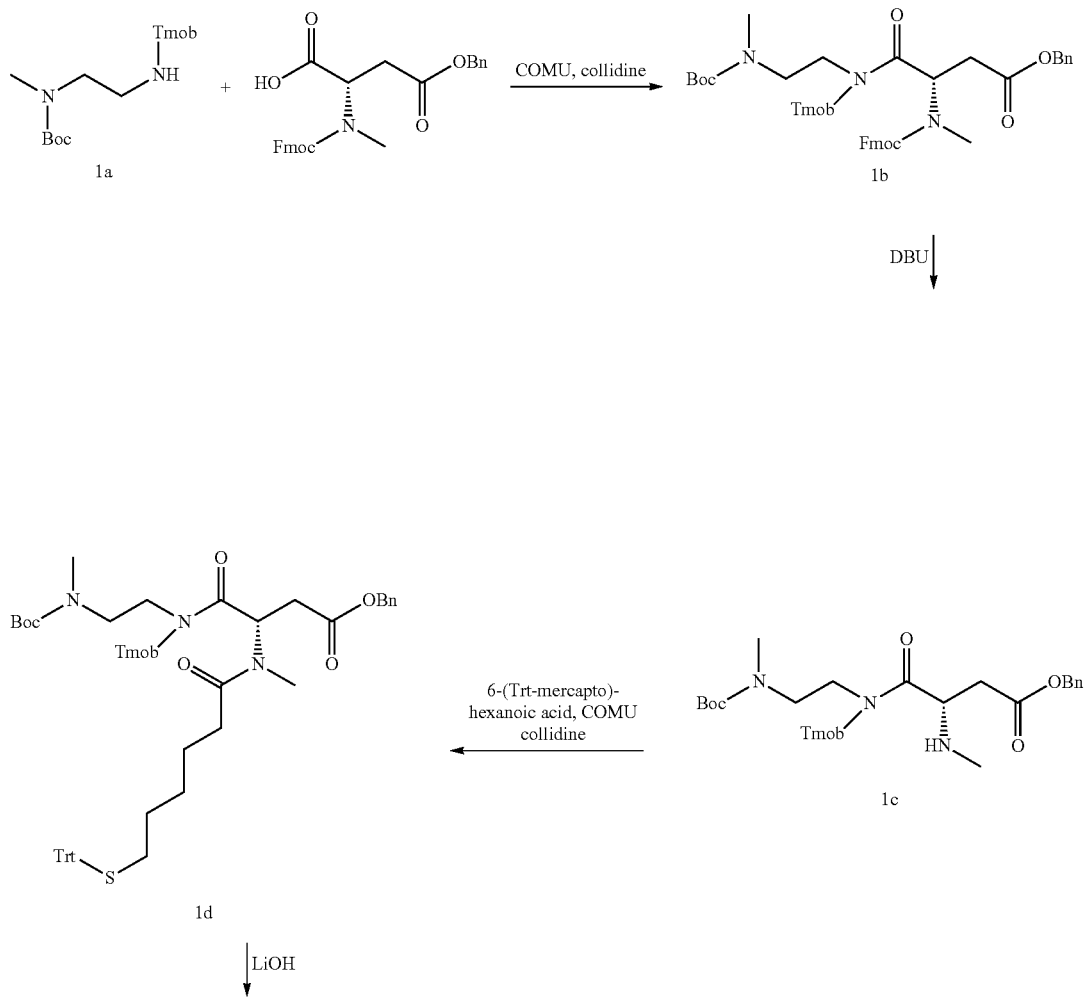

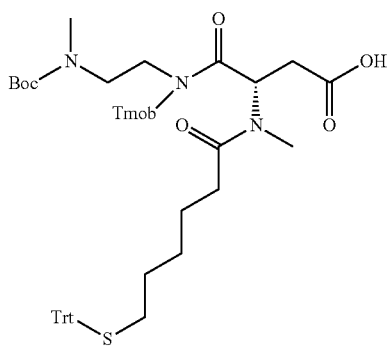

1e

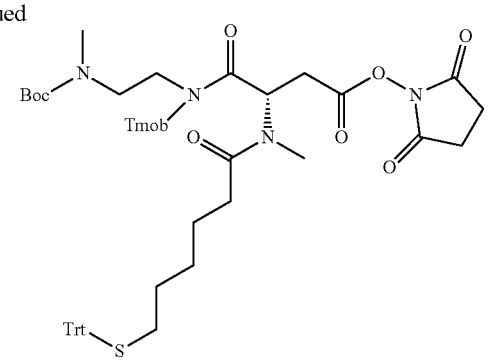

1f

To a solution of N-methyl-N-Boc-ethylenediamine (2 g, 11.48 mmol) and NaCNBH$_3$ (819 mg, 12.63 mmol) in MeOH (20 mL) was added 2,4,6-trimethoxybenzaldehyde (2.08 g, 10.61 mmol) portion wise. The mixture was stirred at rt for 90 min, acidified with 3 M HCl (4 mL) and stirred further 15 min. The reaction mixture was added to saturated NaHCO$_3$ solution (200 mL) and extracted 5× with CH$_2$Cl$_2$. The combined organic phases were dried over Na$_2$SO$_4$ and the solvents were evaporated under reduced pressure. The resulting N-methyl-N-Boc-N'-Tmob-ethylenediamine 1a was dried in vacuo and used in the next reaction step without further purification.

Yield: 3.76 g (11.48 mmol, 89% purity, 1a: double Tmob protected product=8:1)

MS: m/z 355.22=[M+H]$^+$, (calculated monoisotopic mass=354.21).

To a solution of 1a (2 g, 5.65 mmol) in CH$_2$Cl$_2$ (24 mL) COMU (4.84 g, 11.3 mmol), N-Fmoc-N-Me-Asp(OBn)-OH (2.08 g, 4.52 mmol) and 2,4,6-collidine (2.65 mL, 20.34 mmol) were added. The reaction mixture was stirred for 3 h at rt, diluted with CH$_2$Cl$_2$ (250 mL) and washed 3× with 0.1 M H$_2$SO$_4$ (100 mL) and 3× with brine (100 mL). The aqueous phases were re-extracted with CH$_2$Cl$_2$ (100 mL). The combined organic phases were dried over Na$_2$SO$_4$, filtrated and the residue concentrated to a volume of 24 mL. 1b was purified using flash chromatography.

Yield: 5.31 g (148%, 6.66 mmol)

MS: m/z 796.38=[M+H]$^+$, (calculated monoisotopic mass=795.37).

To a solution of 1b (5.31 g, max. 4.52 mmol) in THF (60 mL) DBU (1.8 mL, 3% v/v) was added. The solution was stirred for 12 min at rt, diluted with CH$_2$Cl$_2$ (400 mL) and washed 3× with 0.1 M H$_2$SO$_4$ (150 mL) and 3× with brine (150 mL). The aqueous phases were re-extracted with CH$_2$Cl$_2$ (100 mL). The combined organic phases were dried over Na$_2$SO$_4$ and filtrated. 1c was isolated upon evaporation of the solvent and used in the next reaction without further purification.

MS: m/z 574.31=[M+H]$^+$, (calculated monoisotopic mass=573.30).

1c (5.31 g, 4.52 mmol, crude) was dissolved in acetonitrile (26 mL) and COMU (3.87 g, 9.04 mmol), 6-tritylmercaptohexanoic acid (2.12 g, 5.42 mmol) and 2,4,6-collidine (2.35 mL, 18.08 mmol) were added. The reaction mixture was stirred for 4 h at rt, diluted with CH$_2$Cl$_2$ (400 mL) and washed 3× with 0.1 M H$_2$SO$_4$ (100 mL) and 3× with brine (100 mL). The aqueous phases were re-extracted with CH$_2$Cl$_2$ (100 mL). The combined organic phases were dried over Na$_2$SO$_4$, filtrated and 1d was isolated upon evaporation of the solvent. Product 1d was purified using flash chromatography.

Yield: 2.63 g (62%, 94% purity)

MS: m/z 856.41=[M+H]$^+$, (calculated monoisotopic mass=855.41).

To a solution of 1d (2.63 g, 2.78 mmol) in i-PrOH (33 mL) and H$_2$O (11 mL) was added LiOH (267 mg, 11.12 mmol) and the reaction mixture was stirred for 70 min at rt. The mixture was diluted with CH$_2$Cl$_2$ (200 mL) and washed 3× with 0.1 M H$_2$SO$_4$ (50 mL) and 3× with brine (50 mL). The aqueous phases were re-extracted with CH$_2$Cl$_2$ (100 mL). The combined organic phases were dried over Na$_2$SO$_4$, filtrated and 1e was isolated upon evaporation of the solvent. 1e was purified using flash chromatography.

Yield: 2.1 g (88%)

MS: m/z 878.4=[M+Na]$^+$, (calculated monoisotopic mass=855.40).

To a solution of 1e (170 mg, 0.198 mmol) in anhydrous DCM (4 mL) were added DCC (123 mg, 0.59 mmol), and a catalytic amount of DMAP. After 5 min N-hydroxysuccinimide (114 mg, 0.99 mmol) was added and the reaction mixture was stirred at rt for 1 h. The reaction mixture was filtered, the solvent was removed in vacuo and the residue was taken up in 90% acetonitrile plus 0.1% TFA (3.4 mL). The crude mixture was purified by RP-HPLC. Product fractions were neutralized with 0.5 M pH 7.4 phosphate buffer and concentrated. The remaining aqueous phase was extracted with DCM and 1f was isolated upon evaporation of the solvent.

Yield: 154 mg (81%)

MS: m/z 953.4=[M+H]$^+$, (calculated monoisotopic mass=952.43).

Example 2

Synthesis of N$^{\varepsilon K4/\varepsilon K10}$-CNP Mono-Linker Thiol 2, N$^{\varepsilon K4}$-CNP Mono-Linker Thiol 2c and N$^{\varepsilon K10}$-CNP Mono-Linker Thiol 2d

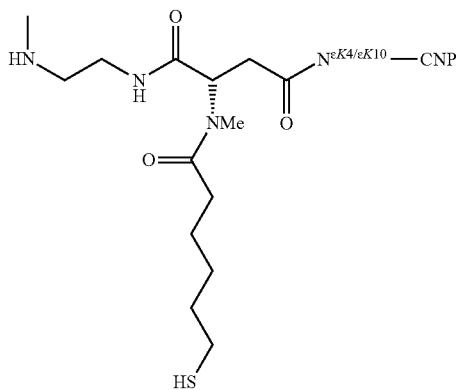

$N^{\epsilon K4/\epsilon K10}$-CNP mono-linker thiol (mixture of regioisomers with linker conjugated at side chain amino group of Lys4 or Lys10) 2 is prepared by dissolving CNP-22 (5.2 µmol) in 0.6 mL DMSO. 0.15 mL 0.375 M borate buffer, adjusted to pH 8.5 with tetrabutyl-ammonium hydroxide hydrate, 60 µL DIPEA and if (6.1 mg, 7.1 µmol) in 0.34 mL of DMSO are added and the mixture is stirred for 30 min at rt. Reaction mixture is diluted with 2 mL acetonitrile/water 1/1 (v/v) and 200 µL AcOH and the protected $N^{\epsilon K4/\epsilon K10}$-CNP mono-linker conjugate is isolated from the reaction mixture by RP-HPLC.

Optimized RP-HPLC gradients can be used for isolation of $N^{\epsilon K4}$-CNP mono-linker thiol 2a and $N^{\epsilon K10}$—CNP mono-linker thiol 2b.

Removal of protecting groups is affected by treatment of lyophilized product fractions with 0.6 mL of 90/10/2/2 (v/v/v/v) HFIP/TFA/TES/water for 1 h at rt. The deprotected $N^{\epsilon K4/\epsilon K10}$-CNP mono-linker thiol 2 is purified by RP-HPLC. Identity and purity of the product is determined by ESI-LCMS.

Deprotected $N^{\epsilon K4}$-CNP mono-linker thiol 2c and $N^{\epsilon K10}$-CNP mono-linker thiol 2d can be obtained likewise from 2a and 2b, respectively.

Example 3

Synthesis of $N^{\alpha G1}$-CNP Mono-Linker Thiol 3

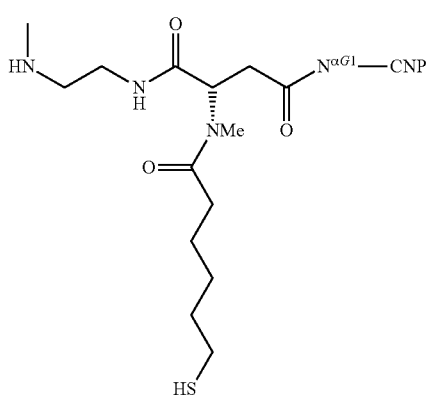

$N^{\alpha G1}$-CNP mono-linker thiol 3 is prepared by dissolving CNP-22 (5.2 µmol) in 0.6 mL DMSO. 0.25 mL 0.5 M phosphate buffer pH 7.4 and if (6.1 mg, 7.1 µmol) in 0.34 mL of DMSO are added and the mixture is stirred for several hours at rt. Reaction mixture is diluted with 2 mL acetonitrile/water 1/1 (v/v) and 200 µL AcOH and the protected $N^{\alpha G1}$-CNP mono-linker thiol is isolated from the reaction mixture by RP-HPLC.

Removal of protecting groups is affected by treatment of lyophilized product fractions with 0.6 mL of 90/10/2/2 (v/v/v/v) HFIP/TFA/TES/water for 1 h at rt. The deprotected $N^{\alpha G1}$-CNP mono-linker thiol 3 is purified by RP-HPLC. Identity and purity of the product is determined by ESI-LCMS.

Example 4

PEGylation of CNP Mono-Linker Thiols 2c, 2d and 3

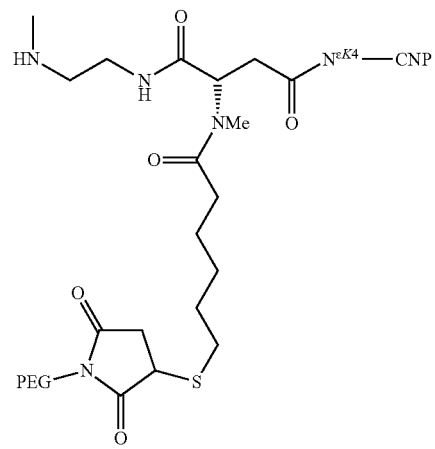

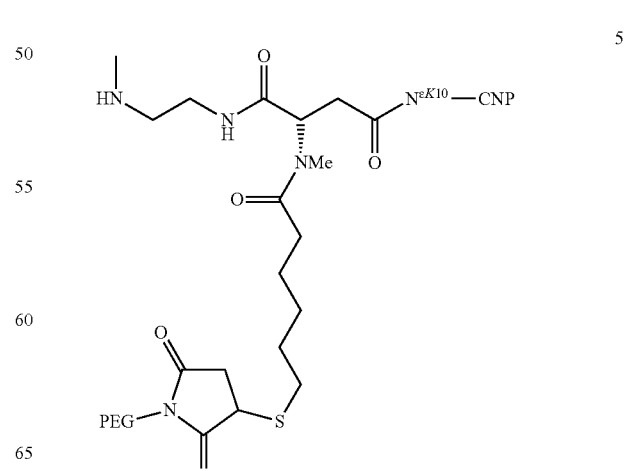

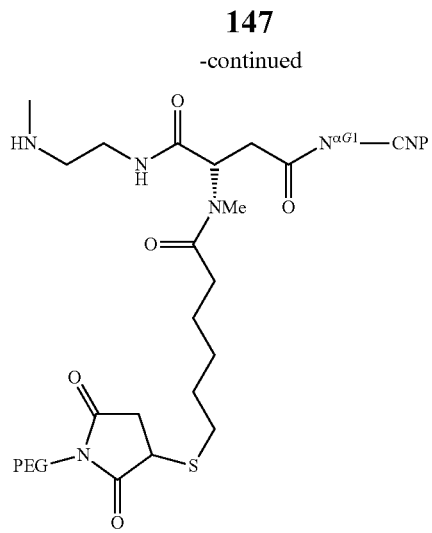

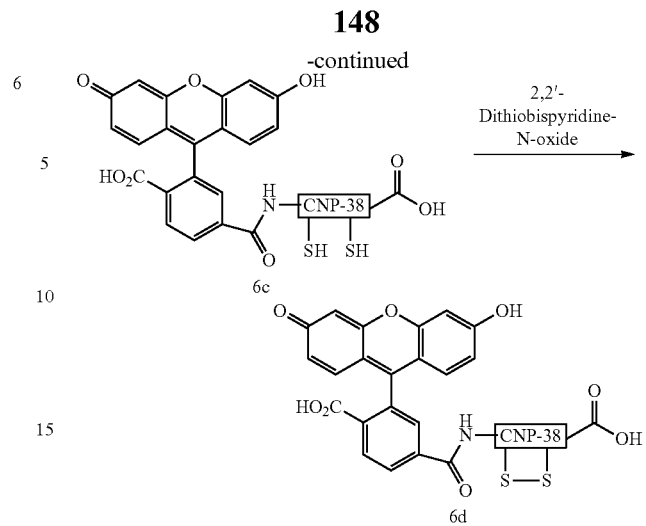

1 μmol CNP mono-linker thiol 2c is dissolved in 0.5 mL acetonitrile/0.2 M succinate buffer pH 3.8 1/1 (v/v) 1.2 μmol of linear 40 kDa PEG-maleimide is added and the mixture is stirred at rt. The reaction is quenched by addition of 20 μL AcOH and CNP conjugate 4 is purified by preparative RP-HPLC.

CNP conjugates 5 and 6 are prepared likewise from 1 μmol CNP mono-linker thiols 2d and 3.

CNP content is determined by quantitative amino acid analysis after total hydrolysis under acidic conditions.

Example 5

Release Kinetics In Vitro

CNP conjugates 4, 5 and 6 are dissolved in 60 mM sodium phosphate, 3 mM EDTA, 0.01% Tween-20, pH 7.4 at a concentration of approximately 2 mg/mL and filtered sterile. Mixtures are incubated at 37° C. At time points aliquots are withdrawn and analysed by RP-HPLC and ESI-MS. UV-signals correlating to liberated CNP are integrated and plotted against incubation time.

Curve-fitting software is applied to estimate the corresponding halftime of release.

Example 6

Synthesis of Fluorescein Labelled CNP-38 6d

Compound 6d was synthesized according to the following scheme:

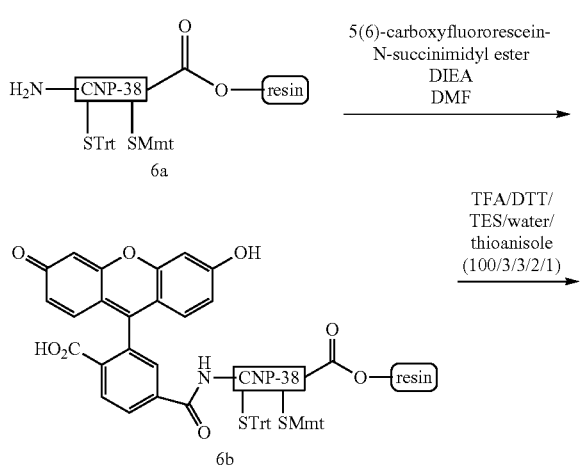

Side chain protected CNP-38 on TCP tentagel resin having free N-terminus 6a (0.50 g, 35.4 μmol) was pre-swollen in DMF for 30 min. A solution of 5(6)-carboxyfluorescein-N-succinimidyl ester (41.9 mg, 88.5 μmol) and DIEA (30.9 μL, 177 μmol) in DMF (1.6 mL) was drawn onto the resin and the mixture was shaken over night at rt. The resin was washed 10× each with DMF and $CH_2Cl_2$ and dried in vacuo affording 6b.

Cleavage of the peptide from resin and removal of protecting groups was achieved by treatment of the resin with 7 mL cleavage cocktail 100/3/3/2/1 (v/w/v/v/v) TFA/DTT/TES/water/thioanisole for 1 h at rt. Crude 6c was precipitated in pre-cooled (−18° C.) diethyl ether and purified by RP-HPLC affording 6c. The combined HPLC fractions were used directly in the next step.

MS: m/z 1105.80=[M+4H]$^{4+}$, (calculated monoisotopic mass for [M+4H]$^{4+}$=1105.81).

To the combined HPLC product fractions of 6c (115 mL) 30 mL of 0.5 M citric acid buffer (pH=5.00) and 8 mL of a 10 mM 2,2'-dithiobis(pyridine-N-oxide) solution in 1/1 (v/v) acetonitrile/water were added. The mixture was stirred for 60 min at rt then diluted with 350 mL of water containing 0.1% TFA (v/v). 6d was purified by RP-HPLC.

Yield: 16.1 mg (2.90 μmol, 8.2% over 3 steps) labelled CNP-38*10 TFA

MS: m/z 1105.30=[M+4H]$^{4+}$, (calculated monoisotopic mass for [M+4H]$^{4+}$=1105.30).

Example 7

Synthesis of Dmb Protected 6-Mercaptohexanoic Acid 7

Compound 7 was synthesized according to the following scheme:

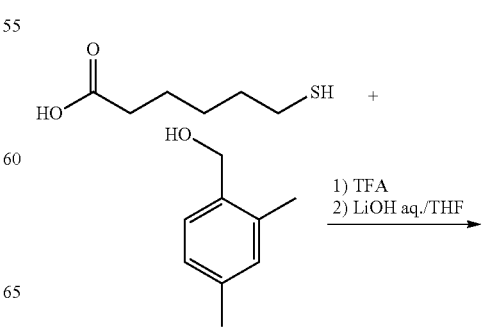

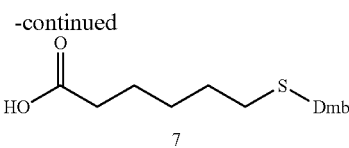

To a solution of 6-mercaptohexanoic acid (7.10 g, 47.90 mmol) in trifluoroacetic acid (20 mL), 2,4-dimethylbenzyl alcohol (13.5 g, 95.80 mmol) was added. The mixture was stirred at rt for 60 min and then the trifluoroacetic acid was removed in vacuo. The residue was dissolved in a mixture of 95.8 mL LiOH (3 M) and THF (81 mL) and stirred at rt for 60 min. The solvent was removed in vacuo and the aqueous residue was extracted 3× with EtOAc (200 mL). The combined organic phases were dried over MgSO$_4$, and the solvent was removed in vacuo. 7 was purified by RP-HPLC.

Yield: 2.27 g (8.52 mmol, 18%)

MS: m/z 267.01=[M+H]$^+$, (calculated monoisotopic mass=266.13).

Example 8

Synthesis of Linker Reagent 8c

Linker reagent 8c was synthesized according to the following scheme:

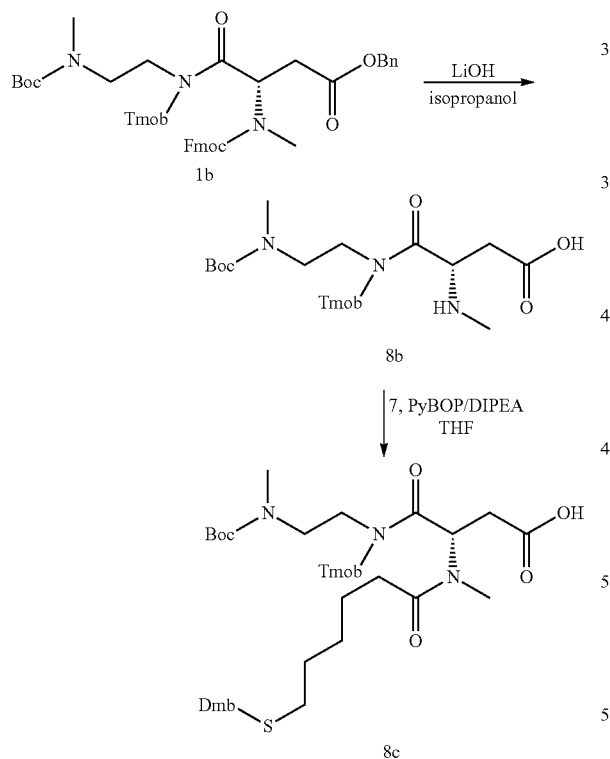

To a solution of 1b (21.6 g, 27.18 mmol) in isopropanol (401 mL) were added water (130 mL) and LiOH (3.90 g, 163.06 mmol). The reaction mixture was stirred for 3 h at rt, then it was diluted with toluene (300 mL) and washed 3× with 0.1 M HCl (200 mL). The combined aqueous phases were washed 3× with toluene (100 mL). The aqueous phase was basified with 4 M NaOH (4 mL) to a pH of 8.5 and extracted 8× with CH$_2$Cl$_2$ (200 mL). The combined CH$_2$Cl$_2$ phases were washed with brine (50 mL), dried over Na$_2$SO$_4$.

8b was isolated upon evaporation of the solvent and used in the next reaction without further purification.

Yield: 11.89 g (24.59 mmol, 90%)

MS: m/z 484.16=[M+H]$^+$, (calculated monoisotopic mass=483.26).

To a solution of 7 (293 mg, 1.10 mmol) and PyBOP (572 mg, 1.10 mmol) in THF (10 mL) was added DIEA (0.52 mL, 3.00 mmol) under a N2-atmosphere. The reaction mixture was stirred for 60 min at rt. A solution of 8b (484 mg, 1.00 mmol) in THF (2 mL) was added and the reaction was stirred for a further 60 min. The reaction was quenched with 2 M citric acid solution (10 mL) and the THF was removed in vacuo. The resulting aqueous phase was then extracted 2× with EtOAc (15 mL) and the combined organic layers were washed with water (10 mL) and brine (10 mL), and dried over MgSO$_4$. The solvent was removed in vacuo and 8c was purified by RP HPLC.

Yield: 330 mg (0.451 mmol, 45%)

MS: m/z 732.34=[M+H]$^+$, (calculated monoisotopic mass=731.38).

Example 9

Synthesis of Linker Reagent 9

Linker reagent 9 was synthesized according to the following scheme:

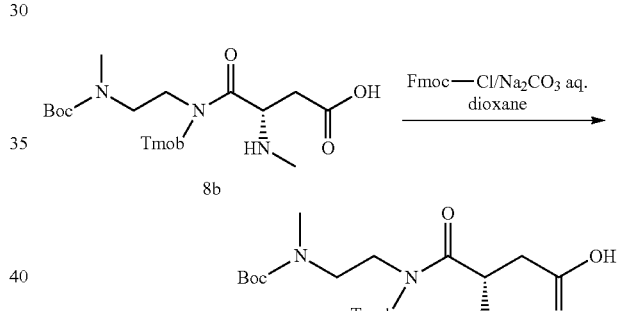

To a solution of 8b (2.00 g, 4.14 mmol) and Fmoc-Cl (1.07 g, 4.14 mmol) in dioxane (20 mL) was added 1 M Na$_2$CO$_3$ solution (20 mL). The reaction mixture was stirred for 40 min at rt. Water (100 mL) and diethyl ether (100 mL) were added and the aqueous phase was extracted 2× with diethyl ether (100 mL). The aqueous phase was acidified with conc. HCl until pH 1 and again extracted 3× with diethyl ether. The combined organic phases were dried over Na$_2$SO$_4$ and the solvent was removed in vacuo. 9 was used in the next step without further purification.

Yield: 2.63 g (3.73 mmol, 90%)

MS: m/z 728.32=[M+Na]$^+$, (calculated monoisotopic mass=705.33).

Example 10

Synthesis of Reversible Lys26 CNP-38 PEG2×20 kDa Conjugate 10f

Conjugate 10f was synthesized according to the following scheme:

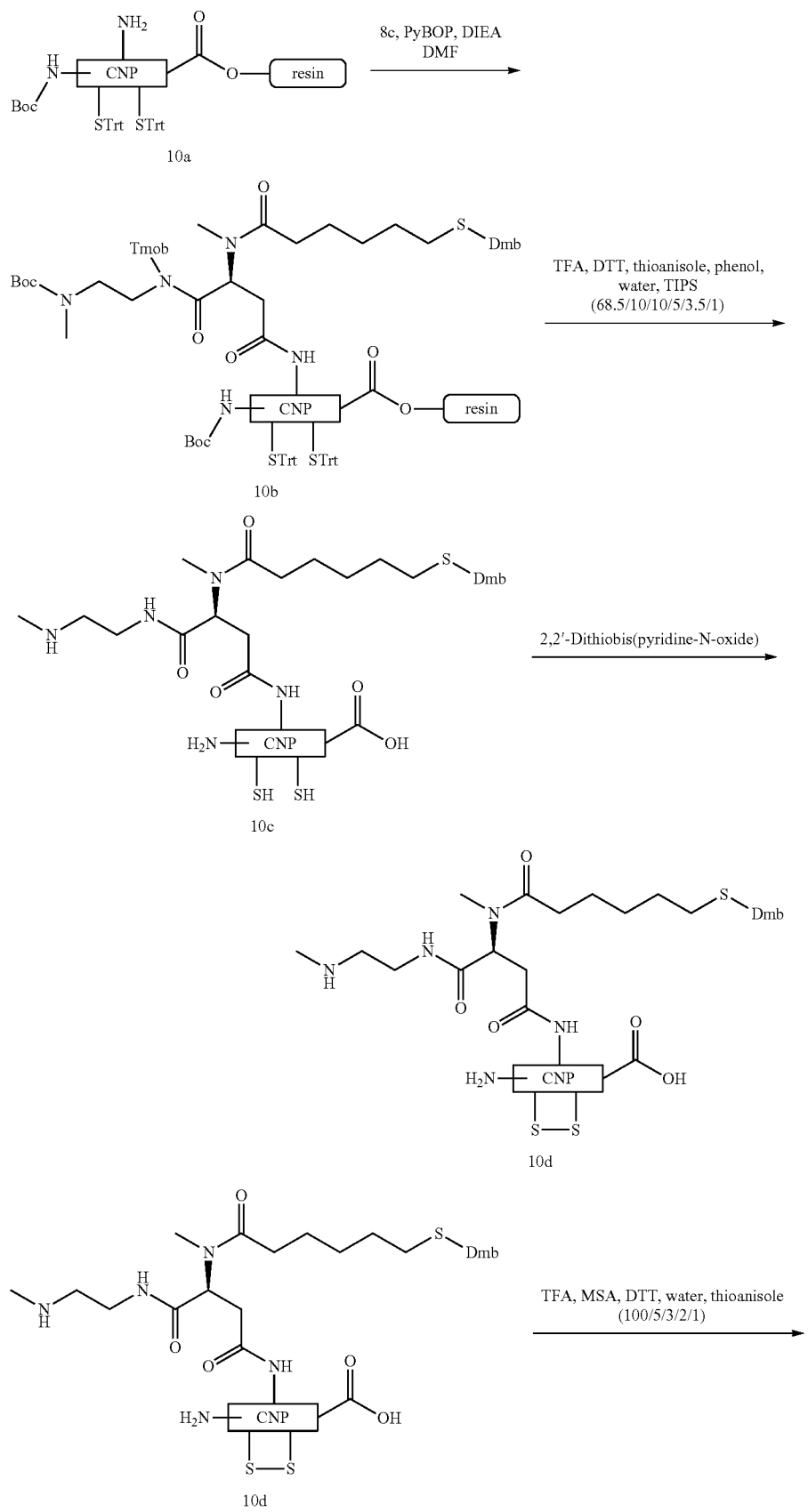

-continued

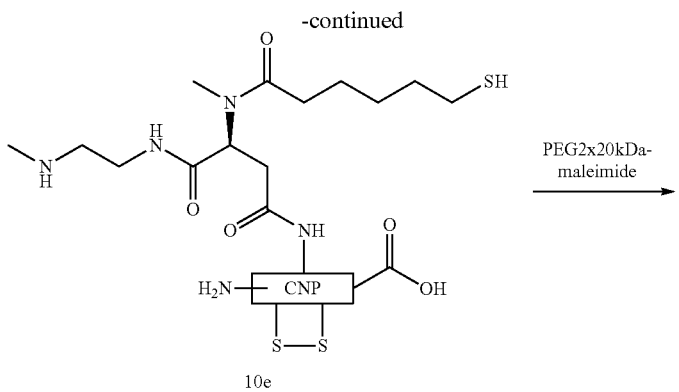

10e

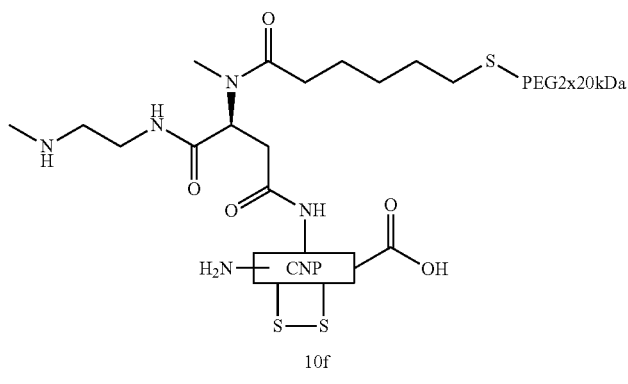

10f 2.00 g (0.21 mmol) of side chain protected CNP-38 on CTC resin having Boc protected N-terminus and ivDde protected side chain of Lys26 was ivDde deprotected according to the procedure given in Materials and Methods to obtain 10a. A solution of linker reagent 8c (336 mg, 0.46 mmol), PyBOP (239 mg, 0.46 mmol) and DIEA (182 µL, 1.04 mmol) in DMF (5 mL) was incubated for 10 min at rt, then added to the resin 10a. The suspension was shaken for 2 h at rt. The resin was washed 10× with DMF (10 mL) and 10× with DCM (10 mL) and dried in vacuo for 15 min. Cleavage of the peptide from resin and removal of protecting groups was achieved by treatment of the resin with 15 mL pre-cooled (−18° C.) cleavage cocktail 68.5/10/10/5/3.5/1 (v/w/v/v/v/v) TFA/DTT/thioanisole/phenol/water/TIPS. The mixture was allowed to warm to rt and was agitated for 60 min. The resin was filtered off and crude 10c was precipitated in pre-cooled diethyl ether (−18° C.). The precipitate was dissolved in ACN/water and purified by RP-HPLC. The combined HPLC fractions were used directly in the next step.

MS: m/z 1124.60=$[M+4H]^{4+}$, (calculated monoisotopic mass for $[M+4H]^{4+}$=1124.59).

To the combined HPLC fractions of 10c (250 mL) 40 mL of 0.5 M citric acid buffer (pH=5.00) and 7 mL of a 0.01 M solution of 2,2'-dithiobis(pyridine-N-oxide) solution in 1/1 (v/v) acetonitrile/water were added. After incubation for 5 min at rt the reaction was complete. The mixture was diluted with 500 mL water containing 0.1% TFA (v/v) and acidified with AcOH (20 mL) to a pH of approx. 2. 10d was purified by RP-HPLC.

Yield: 101 mg (17.3 µma 9%) CNP-38-linker-Dmb*10 TFA

MS: m/z 1124.10=$[M+4H]^{4+}$, (calculated monoisotopic mass for $[M+4H]^{4+}$=1124.09).

Cleavage of the Dmb protecting group was achieved by adding 30 mL pre-cooled (−18° C.) cleavage cocktail 100/5/3/2/1 (v/v/w/v/v) TFA/MSA/DTT/water/thioanisole to 10d (101 mg, 17.3 µmol) and stirring for 3 h at 0° C. Crude 10e was precipitated in pre-cooled (−18° C.) diethyl ether. The precipitate was dissolved in water containing 0.1% TFA (v/v) and incubated for 10 min in order to hydrolyze any TFA esters. 10e was purified by RP-HPLC. Product fractions were combined and freeze dried.

Yield: 46 mg (8.34 µmol, 48%) CNP-38-linker-thiol*10 TFA

MS: m/z 1094.58=$[M+4H]^{4+}$, (calculated monoisotopic mass for $[M+4H]^{4+}$=1094.57).

To a solution of 10e (46 mg, 8.43 µmol) in 1.15 mL water containing 0.1% TFA (v/v) was added a solution of PEG 2×20 kDa maleimide (Sunbright GL2-400MA, 870 mg, 21.75 µmol) in 4.35 mL water containing 0.1% TFA (v/v), followed by 0.5 M lactic acid buffer (1.07 mL, pH=4.20). The mixture was stirred at rt for 4 h. Conjugate 10f was purified by RP-HPLC.

Yield: 233 mg (5.21 µma 62%) conjugate 10f*10 HCl

Example 11

Synthesis of Reversible Lys26 CNP-38 PEG4×10 kDa Conjugate 11i

Conjugate 11i was synthesized according to the following scheme:

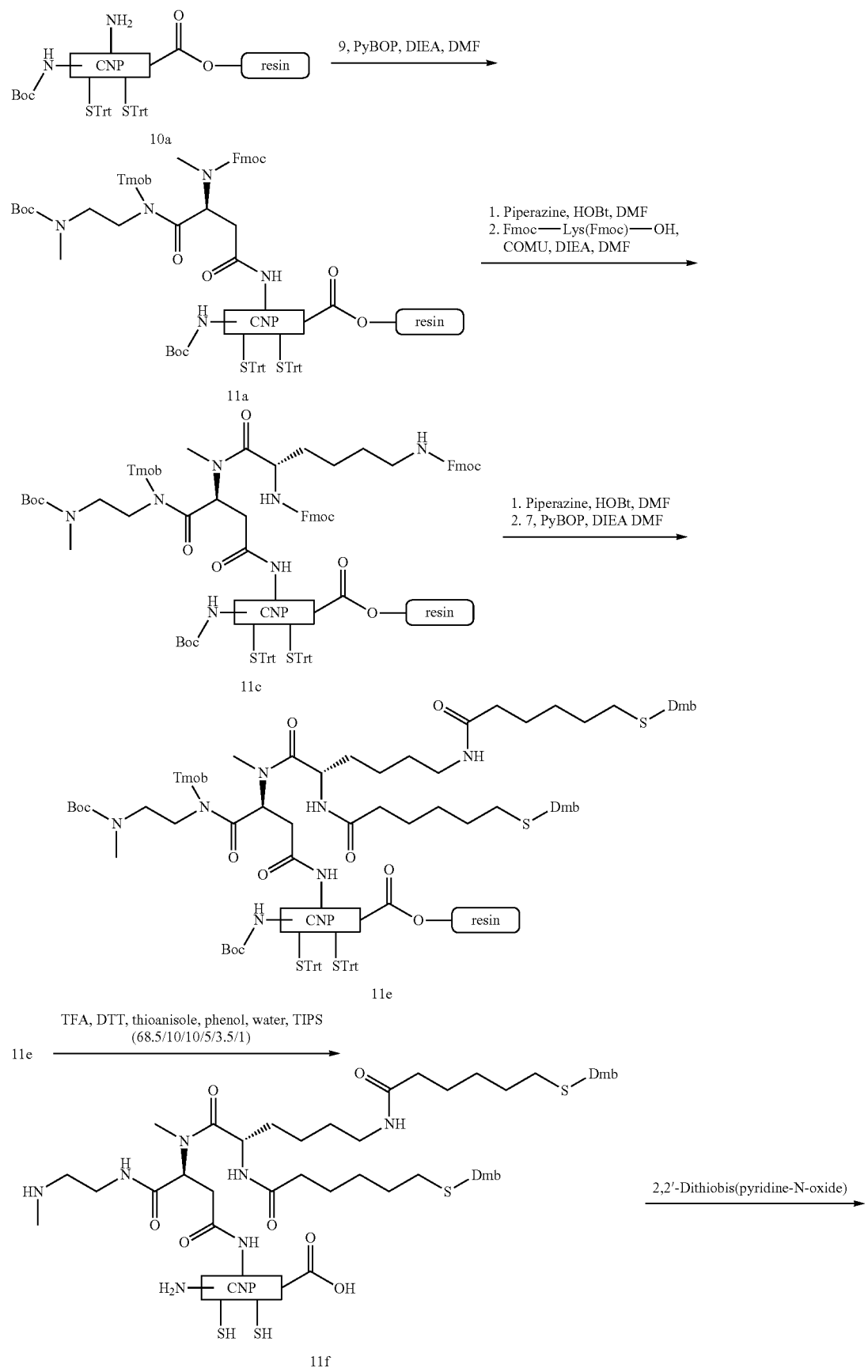

-continued

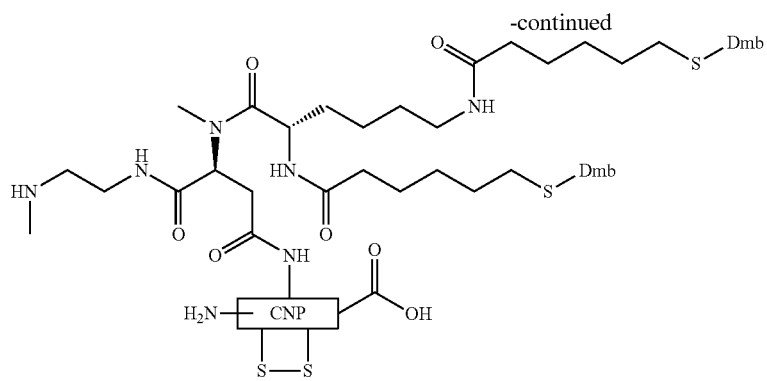

11g

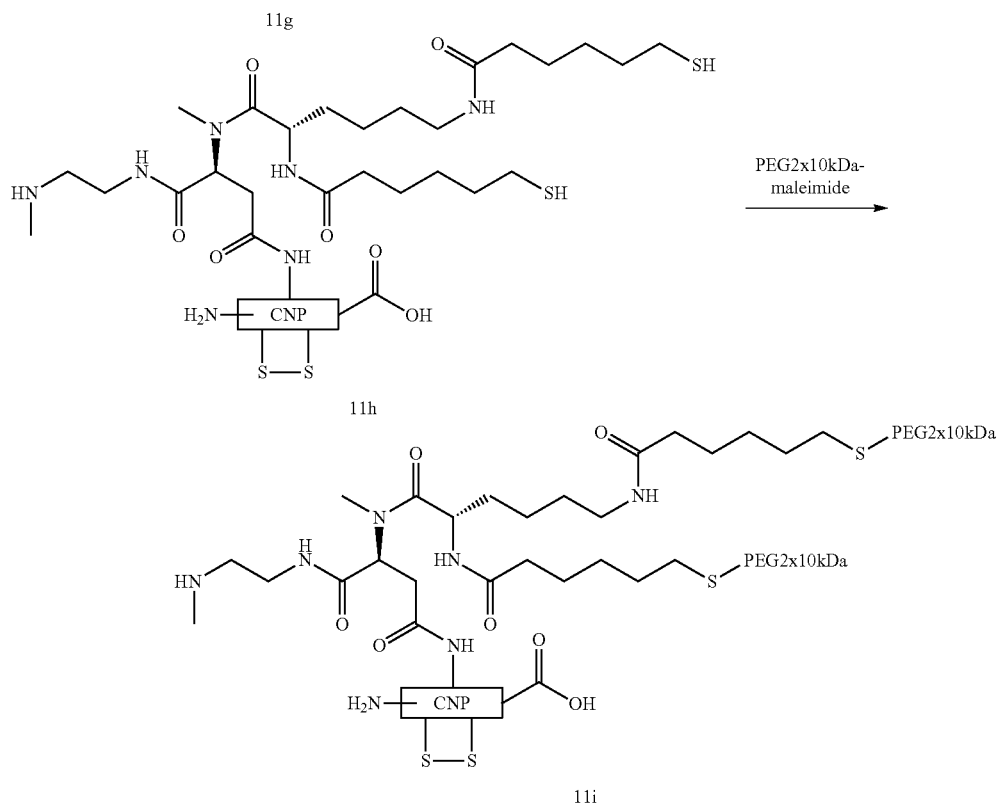

To a solution of 9 (353 mg, 0.50 mmol) and PyBOP (260 mg, 0.50 mmol) in DMF (9 mL) was added DIEA (105 µL, 0.60 mmol). This mixture was drawn onto Lys26-side-chain deprotected CNP-38 resin 10a (2.00 g, 0.21 mmol) and the suspension was shaken for 2 h at rt in order to afford resin 11a. The resin was washed 10× with DMF (7 mL). Cleavage of the Fmoc protecting group in 11a was carried out with a solution of HOBt (0.68 g, 5.03 mmol) and piperazine (3.00 g, 34.83 mmol) in DMF (47 mL). Therefore, the resin was incubated 5× with 10 mL of the cleavage mixture for 15 min at rt each time. Then, the resin was washed 7× with DMF (7 mL).

A solution of Fmoc-Lys(Fmoc)-OH (449 mg, 0.76 mmol), COMU (325 mg, 0.76 mmol) and DIEA (165 µL, 0.95 mmol) in DMF (9 mL) was prepared and drawn onto the resin. The mixture was shaken for 2 h at rt. The procedure was repeated twice, each for 1 h with freshly prepared coupling mixture. The resin was washed 10× with DMF (7 mL) and the remaining free amino groups were capped with 8 mL 1/1/2 (v/v/v) Ac$_2$O/pyridine/DMF.

Cleavage of the Fmoc protecting groups in 11e was carried out with a solution of HOBt (0.68 g, 5.03 mmol), piperazine (3.00 g, 34.83 mmol) in DMF (47 mL). Therefore, the resin was incubated 5× with 10 mL of the cleavage mixture for 15 min at rt each time. The resin was washed 7× with DMF (7 mL).

To a solution of 7 (266 mg, 1.00 mmol) and PyBOP (520 mg, 1.00 mmol) in DMF (9 mL) was added DIEA (209 µL, 1.20 mmol). This mixture was drawn onto the resin and was shaken for 2 h at rt. The resin was washed 7× with DMF (7 mL) affording resin 11e. Cleavage of the peptide from resin and removal of protecting groups was achieved by treatment of the resin with 15 mL pre-cooled (−18° C.) cleavage cocktail 68.5/10/10/5/3.5/1 (v/w/v/v/v/v) TFA/DTT/thioanisole/phenol/water/TIPS. The mixture was allowed to warm to rt and was agitated for 3 h at rt. The resin was filtered off and crude 11f was precipitated in pre-cooled (−18° C.) diethyl ether and purified by RP-HPLC. The combined HPLC fractions were used directly in the next step.

MS: m/z 1218.66=[M+4H]$^{4+}$, (calculated monoisotopic mass for [M+4H]$^{4+}$=1218.65).

To the combined HPLC product fractions of 11f (1 L) 160 mL of 0.5 M citric acid buffer (pH=5.00) and 100 mL of a 50 mM 2,2'-dithiobis(pyridine-N-oxide) solution in 9/1 (v/v) acetonitrile/water were added. The mixture was stirred for 4 h at rt and then diluted with 1 L of water containing 0.1% TFA (v/v). 11g was purified by RP-HPLC. The product fractions were combined and lyophilized.

Yield: 64.3 mg (10.7 μmol, 6%) CNP-38-linker-DMB*10 TFA

MS: m/z 1218.15=[M+4H]$^{4+}$, (calculated monoisotopic mass for [M+4H]$^{4+}$=1218.14).

Cleavage of the Dmb protecting group was achieved by adding 45 mL of pre-cooled (−18° C.) cleavage cocktail 100/5/3/2/1 (v/v/w/v/v) TFA/MSA/DTT/water/thioanisole to 11g (61.8 mg, 10.3 μmol), and then stirring for 4 h at 0° C. Crude 11h was precipitated in pre-cooled (−18° C.) ether. The precipitate was dissolved in a solution of 1/1 (v/v) acetonitrile/water containing 0.1% TFA (v/v) and incubated for 4 h at rt in order to hydrolyze any TFA esters. 11h was purified by RP-HPLC.

Yield: 38.4 mg (6.65 μmol, 65%) CNP-38-linker-thiol*10 TFA

MS: m/z 1159.11=[M+4H]$^{4+}$, (calculated monoisotopic mass for [M+4H]$^{4+}$=1159.10).

To a solution of 11h (34.6 mg, 5.99 μmol) in 1 mL water containing 0.1% TFA (v/v) was added a solution of PEG 2×10 kDa maleimide (Sunbright GL2-200MA, 1.12 g, 56.03 μmol) in 6.1 mL water containing 0.1% TFA (v/v), followed by 0.5 M lactic acid buffer (1.46 mL, pH=4.00). The mixture was stirred at rt for 4 h. Conjugate 11i was purified by RP-HPLC.

Yield: 227 mg (4.96 μmol, 83%) conjugate 11i*10 HCl

Example 12

Synthesis of Permanent Lys26 CNP-38 PEG4×10 kDa Conjugate 12g

Conjugate 12g was synthesized according to the following scheme:

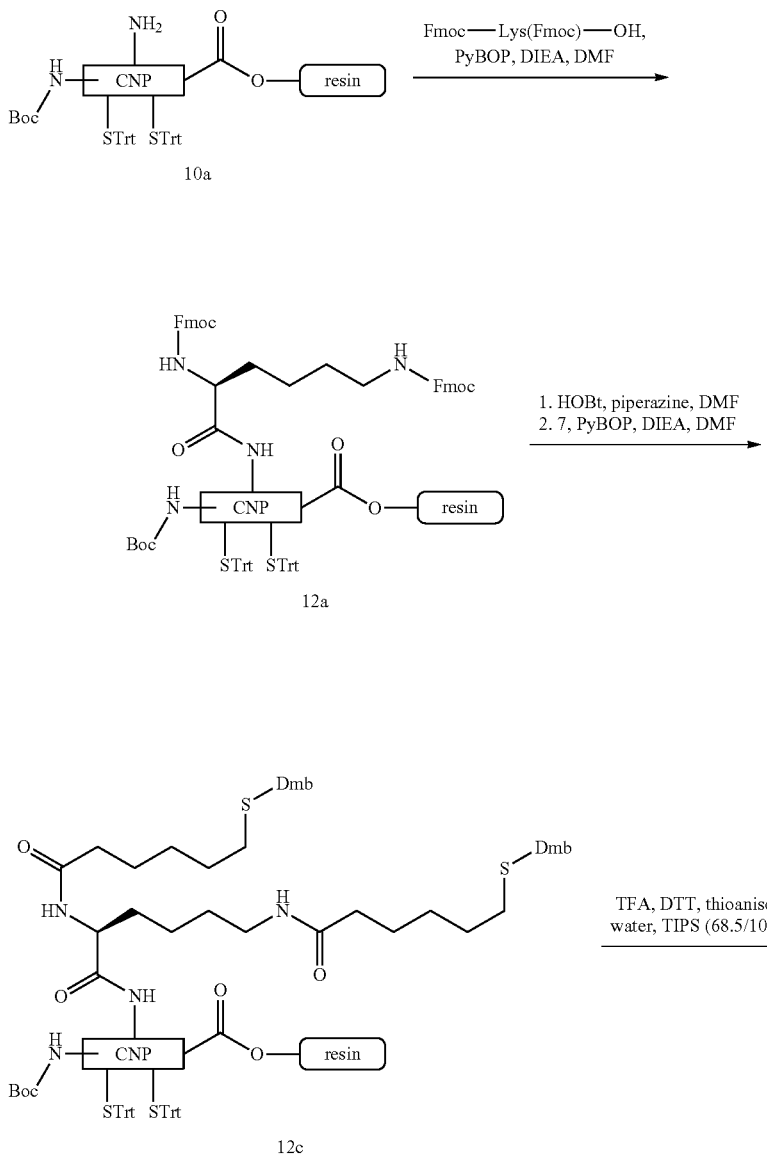

-continued
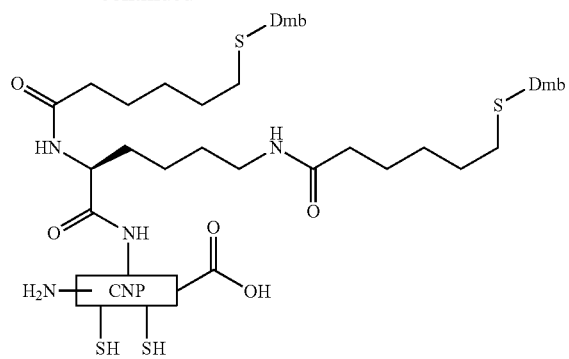
12d
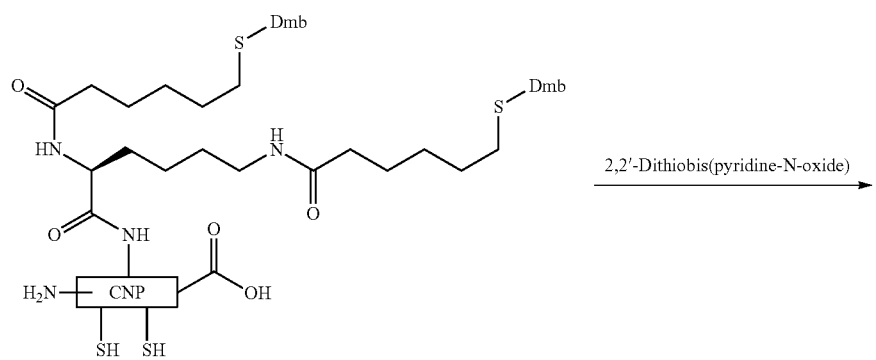
2,2′-Dithiobis(pyridine-N-oxide) →
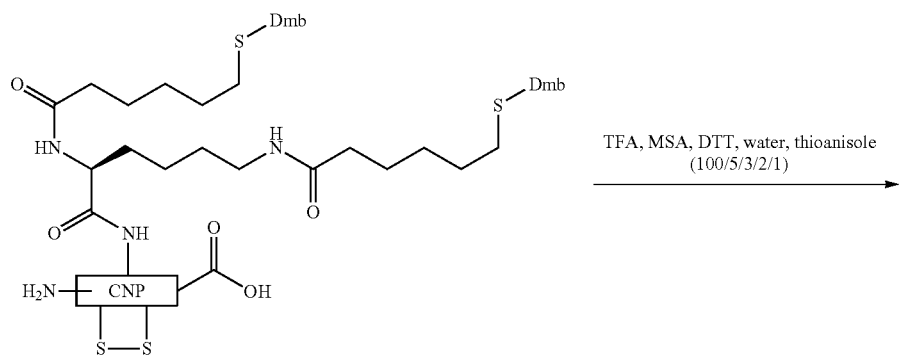
12e
TFA, MSA, DTT, water, thioanisole
(100/5/3/2/1) →
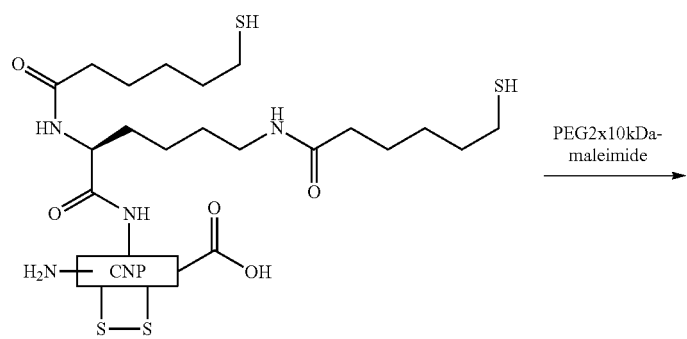
12f
PEG2x10kDa-
maleimide →

-continued

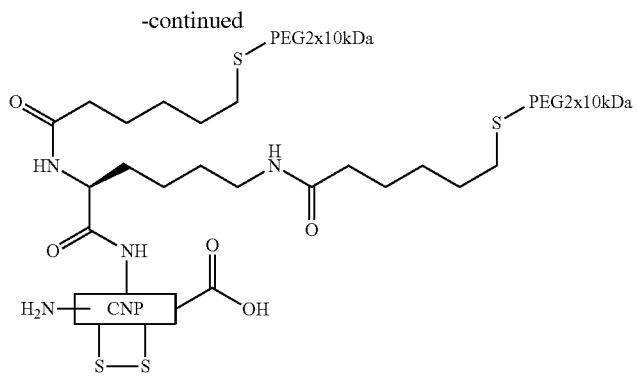

12g

To a solution of Fmoc-Lys(Fmoc)-OH (365 mg, 0.62 mmol) and PyBOP (322 mg, 0.62 mmol) in DMF (4.6 mL) was added DIEA (0.11 mL, 0.62 mmol). The mixture was drawn onto resin 10a (2.0 g, 0.21 mmol). The suspension was shaken for 2 h at rt. The resin was washed 10× with DMF (7 mL). Cleavage of the Fmoc protecting groups in 12a was carried out with a solution of HOBt (1.35 g, 9.99 mmol), piperazine (6.00 g, 69.66 mmol) in DMF (94 mL). Therefore, the resin was incubated 5× with the cleavage mixture for 15 min at rt each time, affording resin 12b. Then the resin was washed 7× with DMF (7 mL).

To a solution of 7 (283 mg, 1.06 mmol) and PyBOP (552 mg, 1.06 mmol) in DMF (6.5 mL), DIEA (185 µL, 1.06 mmol) was added and the mixture was drawn onto resin 12b (2.07 g, 0.10 mmol/g, 0.21 mmol). The mixture was shaken for 2 h at rt. Then, the resin was washed 10× each with DMF (7 mL) and CH$_2$Cl$_2$ (7 mL) and dried in vacuo.

Cleavage of the peptide from resin and removal of protecting groups was achieved by treatment of the resin with 15 mL pre-cooled (−18° C.) cleavage cocktail 68.5/10/10/5/3.5/1 (v/w/v/v/v/v) TFA/DTT/thioanisole/phenol/water/TIPS. The mixture was allowed to warm to rt and was agitated for 2.5 h. The resin was filtered off and crude 12d was precipitated in pre-cooled diethyl ether (−18° C.) and purified by RP-HPLC. The combined HPLC fractions were used directly in the next step.

MS: m/z 1172.37=[M+4H]$^{4+}$, (calculated monoisotopic mass for [M+4H]$^{4+}$=1172.37).

To the combined HPLC product fractions of 12d (390 mL) 58.5 mL of 0.5 M citric acid buffer (pH=5.00) and 8.9 mL of a 10 mM 2,2'-dithiobis(pyridine-N-oxide) solution in 1/1 (v/v) acetonitrile/water were added. The mixture was stirred for 10 min at rt then diluted with 400 mL of water containing 0.1% TFA (v/v). 12e was purified by RP-HPLC.

Yield: 100 mg (17.5 µmol, 8% over 6 steps) CNP-38-linker-Dmb*9 TFA

MS: m/z 1171.87=[M+4H]$^{4+}$, (calculated monoisotopic mass for [M+4H]$^{4+}$=1171.84

Cleavage of the Dmb protecting group was achieved by adding 65 mL pre-cooled (−18° C.) cleavage cocktail 100/5/3/2/1 (v/v/w/v/v) TFA/MSA/DTT/water/thioanisole to 12e (100 mg, 17.5 µmol) and stirring for 3.5 h at 0° C. Crude 12f was precipitated in pre-cooled (−18° C.) diethyl ether. The precipitate was dissolved in water containing 0.1% TFA (v/v) and incubated for 2 h at rt in order to hydrolyze any TFA esters. 12f was purified by RP-HPLC.

Yield: 43.4 mg (7.92 µmol, 45%) CNP-38-linker-thiol*9TFA

MS: m/z 1112.83=[M+4H]$^{4+}$, (calculated monoisotopic mass for [M+4H]$^{4+}$=1112.82).

To a solution of 12f (39.6 mg, 7.22 µmol) in 1 mL water containing 0.1% TFA (v/v) was added a solution of PEG 2×10 kDa maleimide (Sunbright GL2-200MA, 1.22 g, 59.94 µmol) in 6.16 mL water containing 0.1% TFA (v/v), followed by 0.5 M lactic acid buffer (1.41 mL, pH=4.20). The mixture was stirred at rt for 4 h. Conjugate 12g was purified by RP-HPLC.

Yield: 204 mg (4.48 µmol, 57%) conjugate 12g*9 HCl

Example 13

Synthesis of PEG5 kDa Thiol 13c

PEG5 kDa thiol 13c was synthesized according to the following scheme:

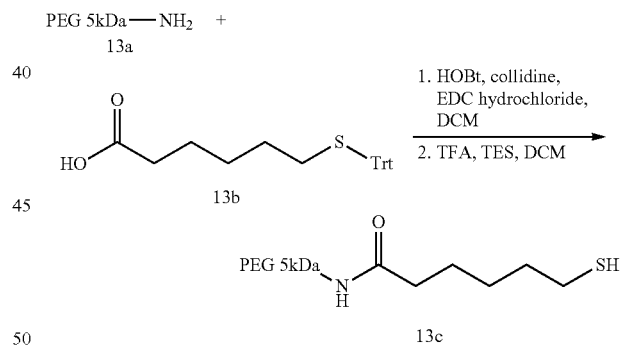

To a solution of 13b (58.6 mg, 0.15 mmol), HOBt (22.9 mg, 0.15 mmol) and EDC hydrochloride (28.8 mg, 0.15 mmol) in DCM (1.00 mL) 2,4,6-collidine (121 mg, 1.00 mmol) was added. Then, a solution of methoxy PEG amine 5 kDa 13a (500 mg, 0.10 mmol) in DCM (4.00 mL) was added and the mixture was stirred for 16 h at rt. The solvent was evaporated and the mixture was dissolved in ACN/water and purified by RP-HPLC. The amount of solvent was reduced in vacuo and the aqueous residue was extracted with DCM (1×100 mL, 2×50 mL). The combined organic layers were reduced in vacuo to 20 mL. TFA (1.6 mL) and TES (3.5 mL) were added and the mixture was stirred at rt for 4.5 h. 13c was precipitated in diethyl ether, stored over night at −20° C., filtered and dried in vacuo.

Yield: 372 mg (72 µmol, 72%)

Example 14

Synthesis of Permanent N-Terminal CNP-34 PEG 5 kDa Conjugate 14e

Conjugate 14e was synthesized according to the following scheme:

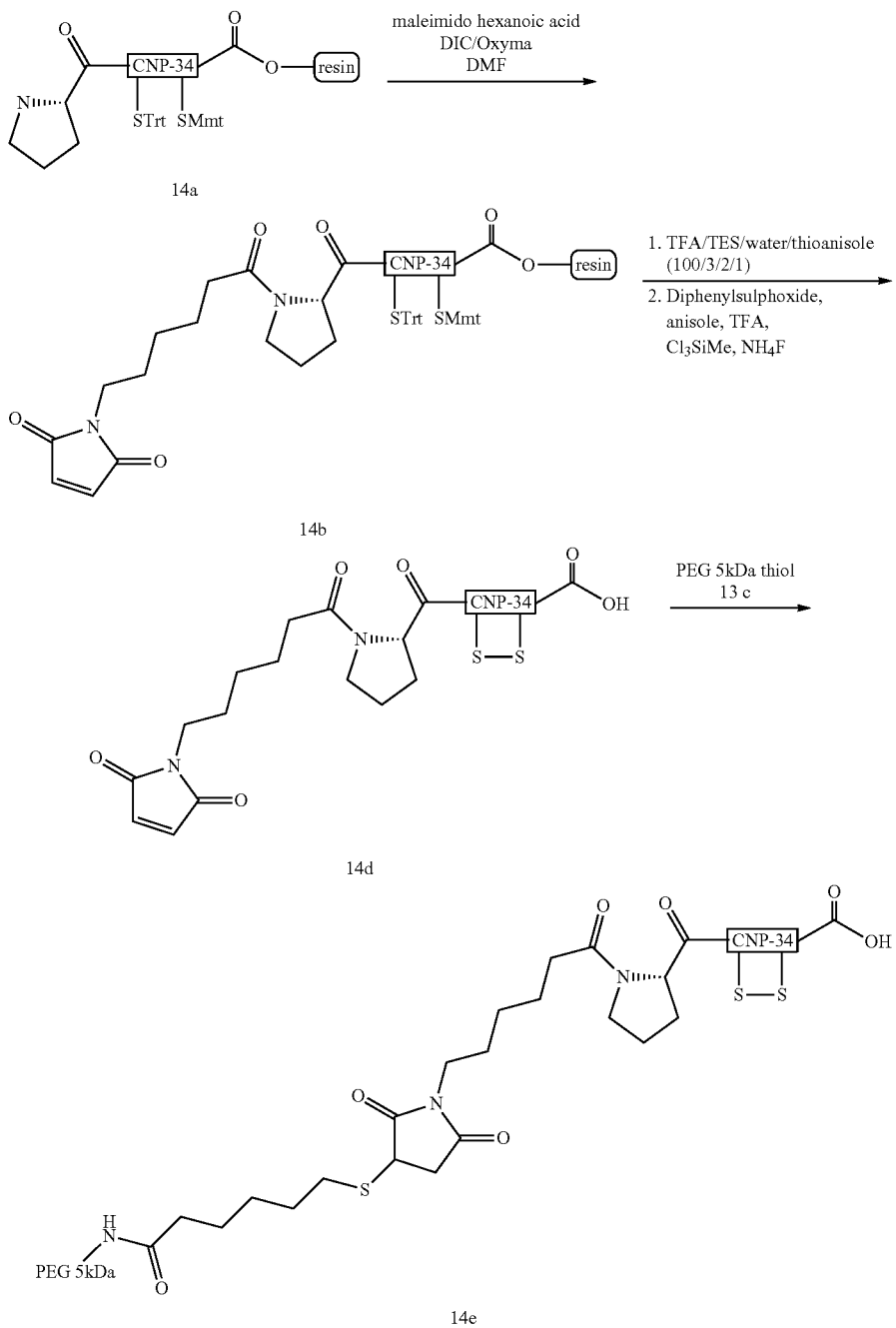

Side chain protected CNP-34 on TCP tentagel resin having free N-terminus 14a (0.78 g, 70 µmol) was pre-swollen in DMF for 30 min. A solution of maleimido hexanoic acid (85.3 mg, 0.40 mmol), DIC (50.9 mg, 0.40 mmol) and Oxyma (57.4 mL, 0.40 mmol) in DMF (6 mL) was drawn onto the resin and the mixture was shaken for 30 min at rt. The coupling then was repeated once with freshly prepared coupling solution. The resin was washed 10× each with DMF and $CH_2Cl_2$ and dried in vacuo affording 14b.

Cleavage of the peptide from resin and removal of protecting groups was achieved by treatment of the resin with 6 mL cleavage cocktail 100/3/2/1 (v/v/v/v) TFA/TES/water/thioanisole for 1.5 h at rt. The crude peptide was precipitated in pre-cooled (−18° C.) diethyl ether.

MS: m/z 937.77=$[M+4H]^{4+}$, (calculated monoisotopic mass for $[M+4H]^{4+}$=937.74).

The precipitate was dissolved in 15 mL TFA. A solution of diphenylsulfoxide (68.06 mg, 0.34 mmol) and anisole (0.18 mL, 1.68 mmol) in 5 mL TFA was added. Trichloromethylsilane (0.47 mL, 4.17 mmol) was added and the mixture was stirred for 15 min at rt. Ammonium fluoride (0.38 g, 10.3 mmol) was added and the solution was agitated for a further 2 min. The crude material was precipitated in pre-cooled (−18° C.) diethyl ether and purified by RP-HPLC affording 14d.

Yield: 8.30 mg (1.78 µmol, 82% purity, 1.4% over 3 steps) CNP-34-Malhx*8 TFA

MS: m/z 937.26=[M+4H]$^{4+}$, (calculated monoisotopic mass for [M+4H]$^{4+}$=937.23).

To a solution of 14d (7.34 mg, 1.57 µmol) in 200 µL 1/1 (v/v) acetonitrile/water containing 0.1% TFA (v/v) was added a solution of 13c (20 mg, 3.90 µmol) in 200 µL water containing 0.1% TFA (v/v), followed by 200 µL 0.5 M acetate buffer (pH=5.00). The mixture was incubated at rt for 30 min. Conjugate 14e was purified by RP-HPLC.

Yield: 9.92 mg (1.01 µmol, 57%) conjugate 14e*8 TFA

Example 15

Synthesis of Permanent N-Terminal CNP-38 PEG 5 kDa Conjugate 15e

Conjugate 15e was synthesized according to the following scheme:

Compound 15d was synthesized as described for 14d, except that side chain protected CNP-38 on TCP tentagel resin having free N-terminus 15a (1.34 g, 0.12 mmol) was used as starting material.

Yield: 15.6 mg (2.94 µma 6.6%) CNP-38-Malhx*9 TFA

MS: m/z 1064.05=[M+4H]$^{4+}$, (calculated monoisotopic mass for [M+4H]$^{4+}$=1064.04).

Conjugate 15e was synthesized as described for 14e, except that 15d (8.34 g, 1.58 mmol) was used as starting material.

Yield: 9.47 mg (0.91 µma 31%) conjugate 15e*9 TFA

Example 16

Synthesis of Permanent Lys12 CNP-34 PEG 5 kDa Conjugate 16e

Conjugate 16e was synthesized according to the following scheme:

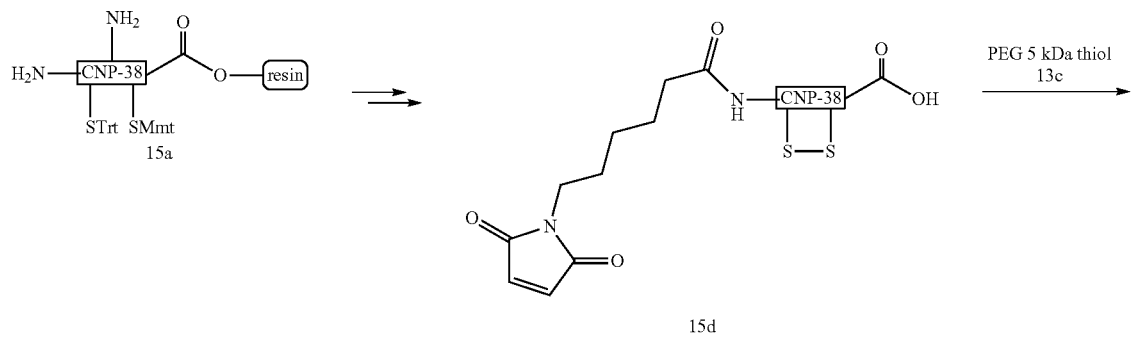

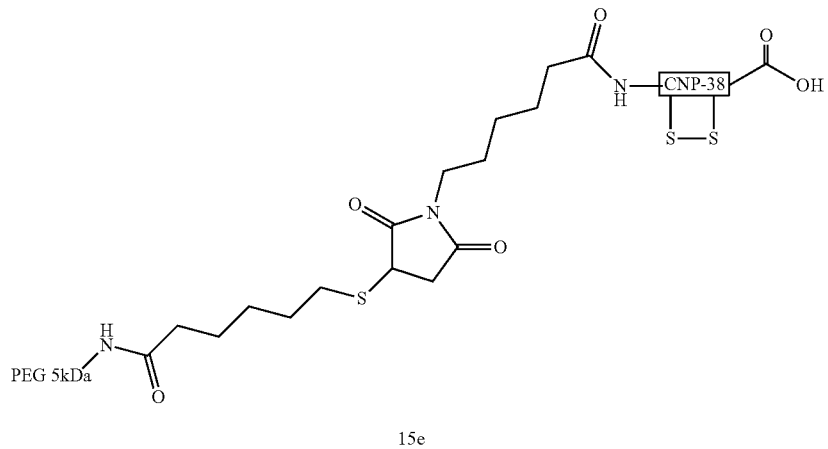

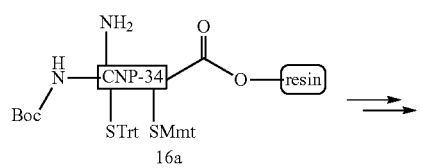

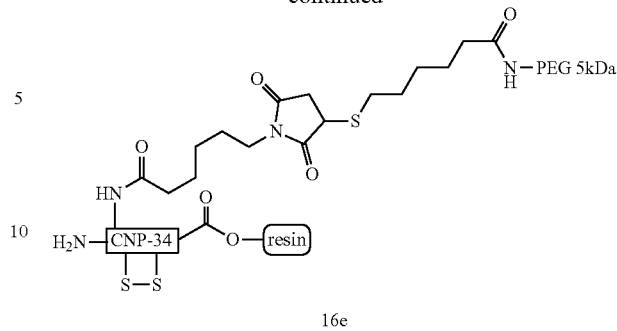

1.00 g (0.10 mmol) of side chain protected CNP-34 on TCP tentagel resin having Boc protected N-terminus and ivDde protected side chain of Lys12 was ivDde deprotected according to the procedure given in Materials and Methods to obtain 16a.

Compound 16d was synthesized as described for 14d, except that resin 16a (1.00 g, 0.10 mmol) was used as starting material.

Yield: 17.0 mg (3.65 µmol, 3.7%) CNP-34-Lys12-Malhx*8 TFA

MS: m/z 937.25=$[M+4H]^{4+}$, (calculated monoisotopic mass for $[M+4H]^{4+}$=937.23).

Conjugate 16e was synthesized as described for 14e, except that 16d (17 mg, 3.65 µmol) was used as starting material.

Yield: 12.2 mg (1.25 µmol, 34%) conjugate 16e*8 TFA

Example 17

Synthesis of Permanent Lys16 CNP-34 PEG 5 kDa Conjugate 17e

Conjugate 17e was synthesized according to the following scheme:

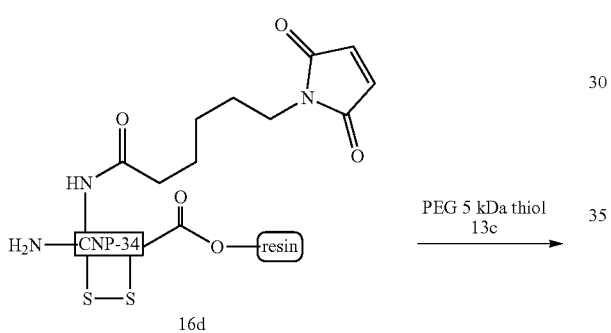

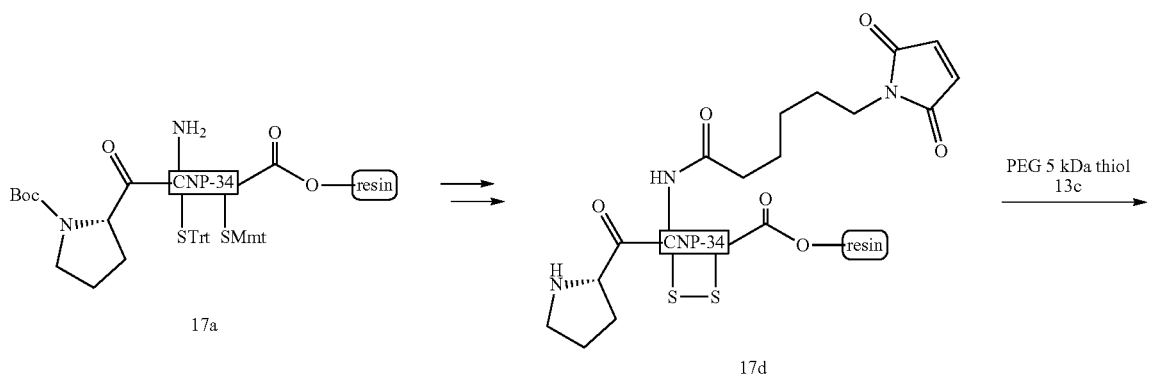

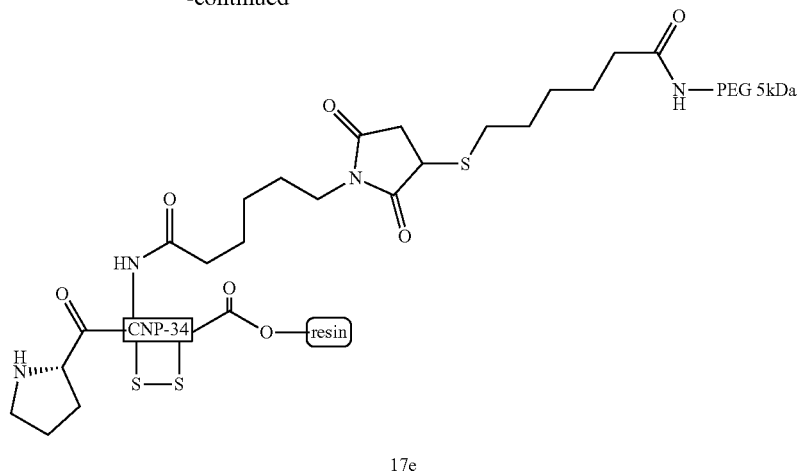

17e 0.78 g (0.07 mmol) of side chain protected CNP-34 on TCP tentagel resin having Boc protected N-terminus and ivDde protected side chain of Lys16 was ivDde deprotected according to the procedure given in Materials and Methods to obtain 17a.

Compound 17d was synthesized as described for 14d, except that resin 17a (0.78 g, 0.13 mmol) was used as starting material.

Yield: 5.39 mg (1.16 μmol, 1.7%) CNP-34-Lys16-Malhx*8 TFA

MS: m/z 937.26=[M+4H]$^{4+}$, (calculated monoisotopic mass for [M+4H]$^{4+}$=937.23).

Conjugate 17e was synthesized as described for 14e, except that 17d (5.39 mg, 1.16 μmol) was used as starting material.

Yield: 10.7 mg (1.09 μmol, 94%) conjugate 17e*8 TFA

Example 18

Synthesis of Permanent Lys22 CNP-34 PEG 5 kDa Conjugate 18e

Conjugate 18e was synthesized according to the following scheme:

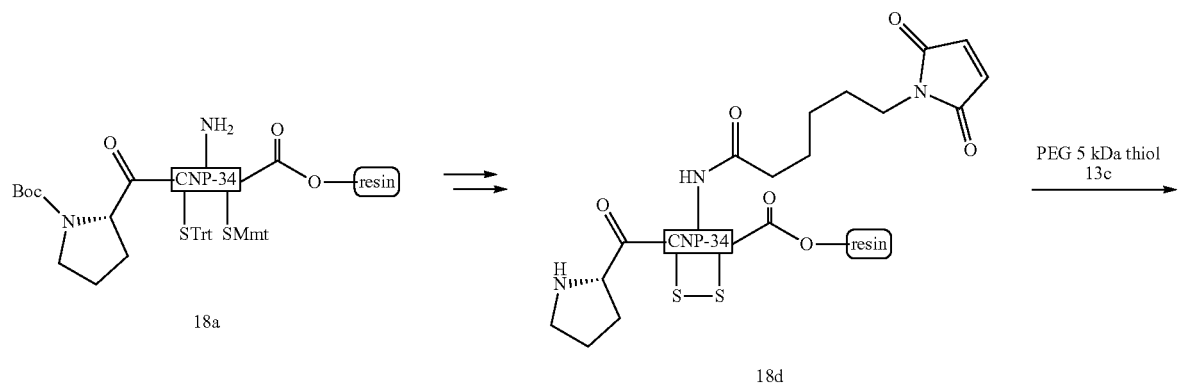

18a         18d

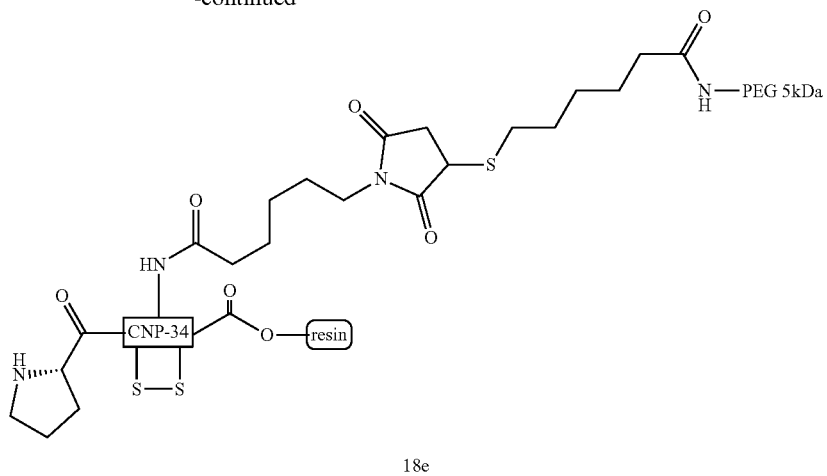

18e 1.07 g (0.11 mmol) of side chain protected CNP-34 on TCP tentagel resin having Boc protected N-terminus and ivDde protected side chain of Lys22 was ivDde deprotected according to the procedure given in Materials and Methods to obtain 18a.

Compound 18d was synthesized as described for 14d, except that resin 18a (1.07 g, 0.11 mmol) was used as starting material.

Yield: 5.20 mg (1.12 µmol, 1.0%) CNP-34-Lys22-Malhx*8 TFA

MS: m/z 937.26=[M+4H]$^{4+}$, (calculated monoisotopic mass for [M+4H]$^{4+}$=937.23).

Conjugate 18e was synthesized as described for 14e, except that 18d (5.2 mg, 1.12 µmol) was used as starting material.

Yield: 4.20 mg (0.43 µmol, 38%) conjugate 18e*8 TFA

Example 19

Synthesis of Permanent Lys26 CNP-38 PEG 5 kDa Conjugate 19e

Conjugate 19e was synthesized according to the following scheme:

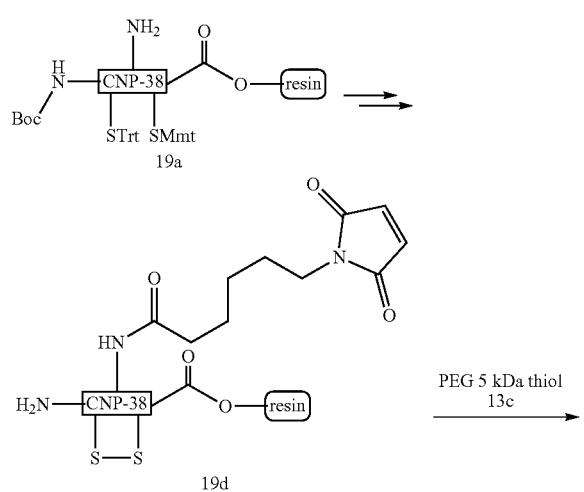

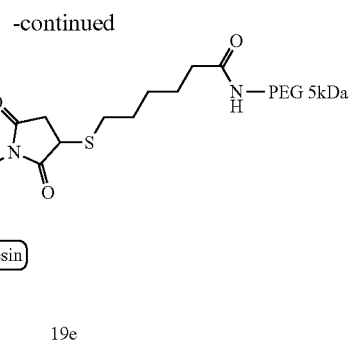

19e (0.865 g, 0.10 mmol) of side chain protected CNP-38 on TCP tentagel resin having Boc protected N-terminus and ivDde protected side chain of Lys26 was ivDde deprotected according to the procedure given in Materials and Methods to obtain 19a.

Compound 19d was synthesized as described for 14d, except that resin 19a (0.865 g, 0.10 mmol) was used as starting material.

Yield: 10.3 mg (1.95 µmol, 2.0%) CNP-38-Lys26-Malhx*9 TFA

MS: m/z 1064.05=[M+4H]$^{4+}$, (calculated monoisotopic mass for [M+4H]$^{4+}$=1064.04).

Conjugate 19e was synthesized as described for 14e, except that 19d (4.70 mg, 1.10 µmol) was used as starting material.

Yield: 3.20 mg (0.31 µmol, 28%) conjugate 19e*9 TFA

Example 20

Release Kinetics In Vitro

CNP conjugates 10f and 11i were dissolved in a PBS buffer containing 3 mM EDTA and 10 mM methionine, pH 7.4 at a concentration of approximately 1 mg conjugate/mL. The solutions was filtered sterile and were incubated at 37° C. At time points aliquots were withdrawn and analysed by RP-HPLC and ESI-MS. UV-signals correlating to liberated CNP were integrated and plotted against incubation time.

Curve-fitting software was applied to estimate the corresponding halftime of release.

Results:

For conjugate 10f a release half life time of 8.5 d (±1 d) was obtained.

For conjugate 11i a release half life time of 9.5 d (±1.5 d) was obtained.

Example 21

Functional cGMP Stimulation in NIH-3T3 Cells with CNP Variants

Functional activity of CNP variants were determined in a cell-based assay with NIH-3T3 cells (Murine Embryo Fibroblast cell line). These cells express endogenously the NPR-B receptor on the cell surface. Stimulation of the NPR-B receptor with CNP leads to intracellular production of the second messenger cGMP which is detected with a commercially available cGMP assay. NIH-3T3 cells were routinely cultured in DMEM F-12 medium with 5% FBS and 5 mM glutamine at 37° C. and 5% $CO_2$. For each assay, 50,000 cells were resuspended in stimulation buffer (Dulbecco's PBS with IBMX) and incubated with the CNP variants in different concentrations. CNP (dilutions were made in PBS with 0.2% BSA). After incubation of 30 min at 37° C. and 5% $CO_2$, the cells were lyzed and cGMP levels were determined with a commercially available cGMP TR-FRET assay (Cisbio, cGMP kit, Cat. No. 62GM2PEB). PEGylated CNP variants were always characterized in comparison with the non-PEGylated version in the same experiment batch. If possible, evaluation of the residual activity was done via the relative $EC_{50}$- parameter of the resulting dose-response curve (restricted model with common slope).

TABLE 1

Residual NPR-B activity of PEGylated CNP variants in a cell-based assay as determined against the non-PEGylated CNP variant

| Compound | CNP Variant PEGylation | $EC_{50}$ compound/$EC_{50}$ CNP-38 |
| --- | --- | --- |
| 15e | CNP-38 5 kDa PEG, N-Terminus | >5 |
| 19e | CNP-38 5 kDa PEG, Lys26 | >100 |
| 12g | CNP-38 4 × 10 kDa PEG, Lys26 | >>100 |
| 11i | CNP-38 4 × 10 kDa PEG, Lys26 | >>100 |
| 10f | CNP-38 2 × 20 kDa PEG, Lys26 | >>100 |

Comparing the tested PEG attachment sites, the attachment at the Lys26 (ring-lysine) showed the highest functional activity reduction, whereas the N-terminal attachment showed relatively high residual functional activity values. Increasing the PEG size resulted in a better shielding of the CNP molecule and a lower residual functional activity.

Example 22

NPR-C Affinity Assay

For the NPR-C affinity assay, an NPR-C expressing Hek293 cell line was developed. The coding region of the NPR-C reference sequence (BC131540) was cloned into a lentiviral vector under a CMV promoter for constitutive receptor expression. A bicistronic element located on the vector for puromycin resistance was used as eukaryotic selection marker. After transduction, stably growing cell pools were subjected to qRT-PCR for confirmation of receptor mRNA-expression compared to parental Hek293 cells. A NPR-C-expressing cell pool was expanded and frozen as master cell bank for CNP sample testing.

For the assay, growing cells are trypsinized from the cell flask bottom, counted, and seeded in a 96-well plate (1.5× $10^5$/well) and centrifuged. Supernatants are discarded. CNP standard and sample are serially diluted over 9 steps in PBS 0.2% BSA and transferred to the micro plate in duplicates and mixed with cells. After 30 min incubation at room temperature, Fluorescein-labelled CNP 6d was added to each well with a constant concentration and cells were incubated for additional 45 min at room temperature. Subsequently, cells were analyzed by flow cytometry using mean fluorescence intensity of the FITC channel (FL1, Beckman Coulter FC500MPL) as read out.

Standard curve and sample curve were generated in an analysis software (PLA 2.0) using a 4PL fit for potency and/or $IC_{50}$ calculation.

TABLE 2

Residual NPR-C affinity of PEGylated CNP-38 variants in a cell-based assay versus CNP-38

| Compound | PEGylation | $IC_{50}$ of PEGylated CNP-38/$IC_{50}$ CNP-38 |
| --- | --- | --- |
| 15e | 5 kDa PEG, N-Terminus | 0.53 |
| 19e | 5 kDa PEG, Lys26 | 1.1 |
| 10f | 2 × 20 kDa PEG, Lys26 (reversible conjugate, first carrier branching point close to CNP moiety) | 12 |
| 12g | 4 × 10 kDa PEG, Lys26 (permanent conjugate, first carrier branching point close to the CNP moiety) | 143 |
| 11i | 4 × 10 kDa PEG, Lys26 (reversible conjugate, first carrier branching point close to the CNP moiety) | 91 |
| 31d | 4 × 10 kDa PEG, Lys26 (reversible conjugate, first carrier branching point not close to the CNP moiety | 1.7 |

Example 23

Growth Study in FVB Mice after 5 Weeks Treatment with CNP-38 by Daily Subcutaneous Bolus Injection or by Continuous Subcutaneous Infusion This study was performed in order to test the effect of daily subcutaneous bolus injection vs. continuous subcutaneous infusion of CNP-38 on animal growth. 21- to 22-days-old wild-type FVB male mice (n=9/group) were given 50 nmol/kg/d CNP-38 or vehicle (30 mM acetate pH 4 containing 5% sucrose and 1% benzylic alcohol) either by daily subcutaneous bolus injection or by continuous subcutaneous infusion in the scapular region over 35 days. Continuous infusion was applied by Alzet osmotic pumps model 1002 for week 1-2, followed by model 1004 for week 3-5. CNP-38 concentrations in the pumps were adjusted for the mean animal weight at study day 7 (pump model 1002) or study day 25 (pump model 1004). Growth was determined at d 35 by total body length measurement and X-ray measurements of the right femur and tibia.

Results of animals treated by daily subcutaneous bolus injection: At d 35, total body length of CNP-38 treated animals was 110.2%, right femur length was 105.6% and right tibia length was 104.0% compared to vehicle treated animals.

Results of animals treated by continuous subcutaneous infusion: At d 35, total body length of CNP-38 treated animals was 121.7%, right femur length was 107.5% and right tibia length was 112.2% compared to vehicle treated animals.

It was concluded that continuous subcutaneous infusion or related slow release formulations of CNP-38 (e.g. a slow releasing CNP-38 prodrug) are at least as effective as daily subcutaneous bolus injection in eliciting growth in the appendicular and axial skeleton.

Example 24

Pharmacokinetic Study of Permanent Lys26 CNP-38 PEG4×10 kDa Conjugate 12g in Cynomolgus Monkeys This study was performed in order to show the suitability of 12g as a model compound for a slow release CNP-38 prodrug in cynomolgus monkeys. Male cynomolgus monkeys (2-4 years old, 3.5-4.1 kg) received either a single intravenous (n=3 animals) or a single subcutaneous (n=2 animals) administration of 12g at a dose of 0.146 mg CNP-38 eq/kg. Blood samples were collected up to 168 h post dose, and plasma was generated. Plasma total CNP-38 concentrations were determined by quantification of the N-terminal signature peptide (sequence: LQEHPNAR; residues 1-8 of SEQ ID NO:24) and C-terminal signature peptide (sequence: IGSMSGLGC; residues 30-38 of SEQ ID NO:24) after tryptic digestion as described in Materials and Methods.

Results: Dose administrations were well tolerated with no visible signs of discomfort during administration and following administration. No dose site reactions were observed any time throughout the study. After intravenous injection the CNP-38 $t_{max}$ was observed at 15 min (earliest time point analyzed), followed by a slow decay in CNP-38 content with a half life time of approx. 24 h. After subcutaneous injection the CNP-38 concentration peaked at a $t_{max}$ of 48 h. At 168 h the CNP-38 concentration was still as high as ca. 50% of $c_{max}$. The bioavailability was ca. 50%.

Similar PK curves were obtained for the N- and the C-terminal signature peptide up to 168 h post dose, indicating the presence of intact CNP-38 in the conjugate.

The favourable long lasting PK over several days and the stability of CNP-38 in the conjugate indicates the suitability of the permanent model compound Lys26 CNP-38 PEG 4×10 kDa conjugate 12g as a slow releasing CNP-38 prodrug after subcutaneous injection. It can be concluded that similar conjugates having a transiently Lys26 linked CNP-38 (like e.g. 11i) are suitable CNP-38 prodrugs providing long lasting levels of released bioactive CNP-38 over several days.

Example 25

Pharmacokinetic Study of Transient Conjugates 10f and 11i in Cynomolgus Monkeys

This study was performed in order to show the suitability of 10f and 11i as slow release CNP-38 prodrugs in cynomolgus monkeys. Male cynomolgus monkeys (2-4 years old, 3-5 kg) received either a single subcutaneous administration (n=3 animals) of compound 10f or a single subcutaneous (n=3 animals) administration of 11i at a dose of 0.146 mg CNP-38 eq/kg. Blood samples were collected up to 168 h post dose, and plasma was generated. Plasma levels of total CNP-38 content were analyzed as described in example 24. In order to analyze the plasma content of free CNP-38, the blood samples were acidified after withdrawal by adding 20 vol % of 0.5 M sodium citrate buffer pH 4 to stop further CNP-38 release from the conjugate. Free CNP-38 levels in plasma can e.g. be determined by ELISA using a CNP antibody that binds to the ring region of CNP, as described in the literature (U.S. Pat. No. 8,377,884 B2), or by LC-MS/MS.

Results: Dose administrations were well tolerated with no visible signs of discomfort during administration and following administration. No dose site reactions were observed any time throughout the study. After dose administration the total CNP-38 $t_{max}$ was observed at 12 h for compound 10f and 24 h for compound 11i. Total CNP-38 plasma levels were below LOQ (100 ng/mL, C-terminal peptide) after 120 h for compound 10f, while the plasma level was still as high as ca. 30% of $c_{max}$ for compound 11i after 168 h (C-terminal peptide). For compound 11i similar terminal half life of 3-4 d was found for the C-terminal and the N-terminal peptide, indicating the presence of intact CNP-38 in the conjugate.

Conclusion: The favourable long lasting PK over several days and the stability of CNP-38 in the conjugate 11i indicates its suitability as CNP-38 prodrug for providing long lasting levels of released bioactive CNP-38 over several days.

Example 26

Digest of CNP Variants by Neutral Endopeptidase In Vitro

In order to determine the in vitro stability of various CNP variants including different peptide chain lengths and PEGylations using different PEGylation sites and PEG molecules in the presence of Neutral Endopeptidase (NEP), a NEP digest assay was established. This assay monitored the decrease of the non-digested CNP variant (normalized with the internal standard PFP) over time in reference to the $t_0$-time point.

In detail, recombinant human NEP (2.5 μg/mL final concentration) and the standard pentafluorophenol (PFP; 40 μg/mL final concentration) were added to the CNP variant (100 CNP equivalents/mL) in digest buffer (50 mM Tris-HCl, pH 7.4, 10 mM NaCl). The solution was incubated at 37° C. and 500 rpm for up to 4 days. Samples were taken at different time intervals. The reaction was stopped by a combined reduction and heat denaturation adding TCEP (tris(2-carboxyethyl)phosphine; 25 mM final concentration) and incubating the mixture at 95° C., 500 rpm for 5 minutes. The resulting reaction products were assigned using HPLC-MS. The half life of each CNP variant was calculated via the ratio change in the HPLC-UV peak areas of CNP and PFP over time. To compensate for variations in the protease activity, a CNP-38 or CNP-34 digest was carried out in every batch measurement as reference.

Table 3 lists the half-lives, based on the in vitro NEP cleavage assay, of various CNP variants of different lengths and having various PEG molecules attached to different side chains.

| Compound | CNP-variant | PEGylation | half life norm. [h] |
|---|---|---|---|
| CNP-22[1] | CNP-22 | — | 0.32 |
| CNP-34[1] | CNP-34 | — | 4.15 |
| 14e[1] | CNP-34 | 5 kDa PEG, N-Terminus | Almost no proteolysis after 4 days. |
| 17e[1] | CNP 34 | 5 kDa PEG, Lys16 | 54.23 |
| 18e[1] | CNP-34 | 5 kDa PEG, Lys22 | 38.87 |
| 16e[1] | CNP-34 | 5 kDa PEG, Lys12 | No evaluation possible. |

-continued

| Compound | CNP-variant | PEGylation | half life norm. [h] |
|---|---|---|---|
| CNP-38[2] | CNP-38 | — | 12.10 |
| 19e[2] | CNP-38 | 5 kDa PEG, Lys26 | 62.76 |
| 15e[2] | CNP-38 | 5 kDa PEG, N-Terminus | Almost no proteolysis after 4 days. |
| 12g[2] | CNP-38 | 4 × 10 kDa PEG, -Lys26 | Almost no proteolysis after 4 days. |

[1]Due to variations in NEP catalytic activity between experiments, a mean was formed of all CNP-34 half life measurements (4.15 h) and the CNP-34 conjugates' half life measurements were normalized to this mean using a coefficient to calculate the adjusted $t_{1/2}$.

[2]Due to variations in NEP catalytic activity between experiments, a mean was formed of all CNP-38 half life measurements (12.10 h) and the CNP-38 conjugates' half life measurements were normalized to this mean using a coefficient to calculate the adjusted $t_{1/2}$.

The rank order of resistance towards NEP is as follows: The longer CNP-variant (CNP-38) is more stable than the shorter CNP variant (CNP-34), which in turn is more stable than the shorter CNP-22. The order of the PEG-attachment sites is as follows: N-terminal>next-to-ring>ring. Therefore, an N-terminal PEG attachment confers the highest stability towards the proteolytic digest with NEP for the tested conjugates. The stability of CNP-38 PEGylated at Lys26 can be increased with increasing PEG size.

Example 27

Synthesis of Asn-Linker Reagent 29b

Asn-linker reagent 29b was synthesized according to the following scheme:

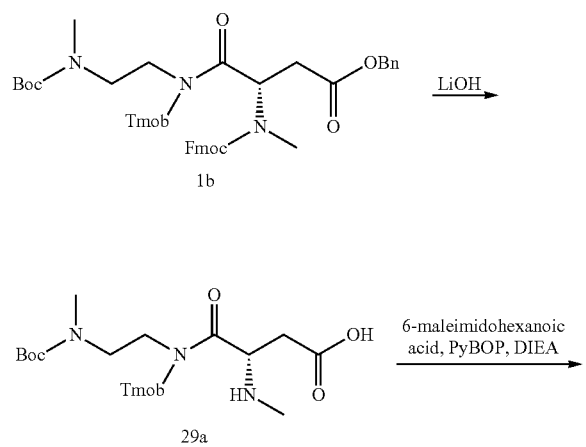

29a

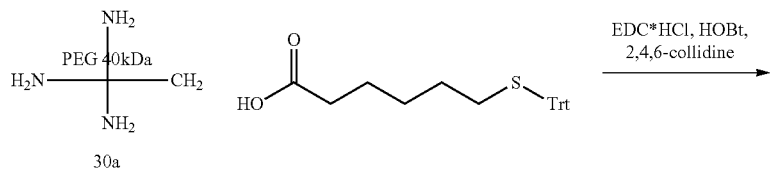

29b

To a solution of 1b (12.85 g, 16.14 mmol) in isopropanol (238 mL), H$_2$O (77.5 mL) and LiOH (2.32 g, 96.87 mmol) were added. The reaction mixture was stirred for 4 h at rt. Afterwards, the reaction mixture was diluted with toluene (300 mL). The phases were separated and the organic phase was washed 3× with 0.1 M HCl (200 mL). The phases were separated again. The aqueous phase was extracted 3× with toluene (100 mL). The product was found in the acidic aqueous phase and the pH value of this phase was adjusted to pH 8.5 by the addition of 4 N NaOH. Then, the aqueous phase was extracted 3× with CH$_2$Cl$_2$ (200 mL). The organic phase was washed with brine (50 mL), dried over Na$_2$SO$_4$ and filtrated. 29a was isolated upon evaporation of the solvent and used in the next reaction without further purification.

Yield: 6.46 g (13.36 mmol, 83%)

MS: m/z 484.06=[M+H]$^+$, (calculated monoisotopic mass=483.26).

To a solution of 6-maleimidohexanoic acid (1.73 g, 8.19 mmol) in THF (70 mL), PyBOP (4.26 g, 8.19 mmol) and DIEA (3.89 mL, 22.33 mmol) were added. Then, the reaction mixture was stirred for 2 h at rt. Afterwards, 29a (3.60 g, 7.44 mmol) was dissolved in THF (10 mL) and added to the reaction mixture. The reaction was stirred at rt overnight. Then, methyl-tert-butylether (300 mL) was added. The organic phase was washed 2× with 0.1 M HCl solution (200 mL). The combined aqueous phases were extracted 2× with methyl-tert-butylether (200 mL). The combined organic phases were washed with brine (150 mL), dried over Na$_2$SO$_4$ and filtrated. The solvent was evaporated in vacuo. 29b was purified using flash chromatography.

Yield: 3.34 g (4.94 mmol, 66%)

MS: m/z 677.34=[M+H]$^+$, (calculated monoisotopic mass=676.33).

Example 28

Synthesis of 4-Arm-Thiol-PEG 40 kDa 30c 4-arm-thiol PEG 30c was synthesized according to the following scheme:

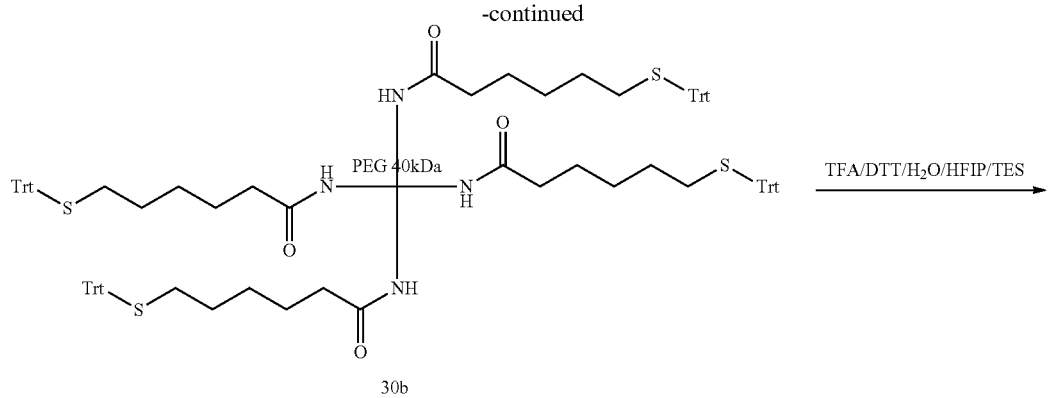

30b

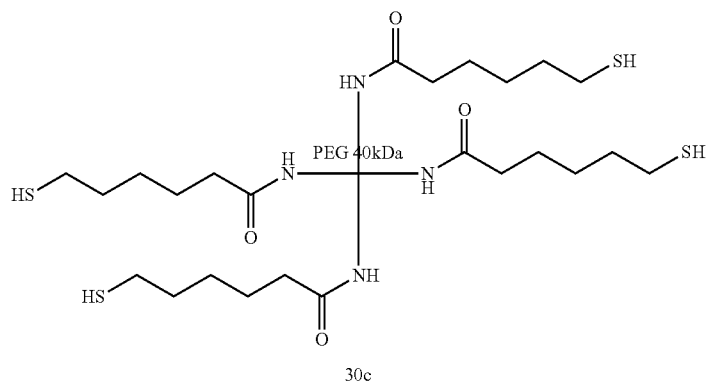

30c

To a solution of 6-tritylmercapto-hexanoic acid (111.72 mg, 286.02 µmol), HOBt (43.81 mg, 286.06 µmol) and EDC*HCl (54.84 mg, 286.06 µmol) in CH$_2$Cl$_2$ (5 mL) was added 2,4,6-collidine (251 µL, 1.91 mmol). Then, this solution was added to a solution of 4-arm amino PEG 40 kDa (NOF, Sunbright PTE-400PA, 1.30 g, 31.78 µmol) in CH$_2$Cl$_2$ (10 mL). The reaction mixture was stirred over night at rt. Afterwards, the solvent was evaporated (water bath 30° C.). 30b was purified by RP-HPLC.

Yield: 650.5 mg (48%).

Cleavage of the Trt protecting group was achieved by adding the cleavage cocktail (DTT 500 mg/TFA 500 µL/water 500 µL, TES 2.5 mL/HFIP 5.0 mL/CH$_2$Cl$_2$ 25.0 mL) to 30b (500 mg, 11.79 µmol) and incubating for 30 min at rt. 30c was obtained after precipitation in pre-cooled (−18° C.) diethyl ether.

Yield: 401.3 mg (82%; 93.3% purity).

Example 29

Synthesis of Conjugate 31d

Conjugate 31d was synthesized according to the following scheme:

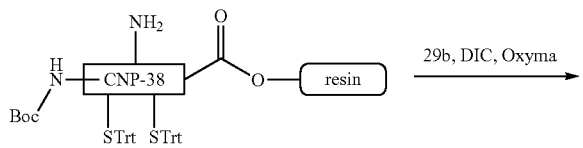

10a

-continued
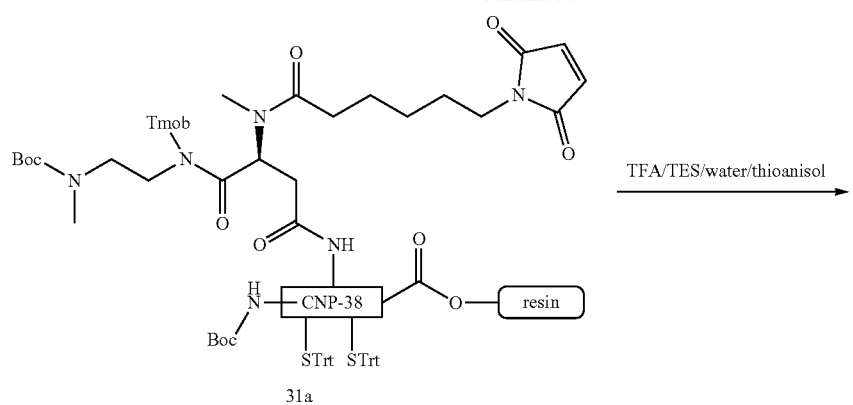
31a
TFA/TES/water/thioanisol →
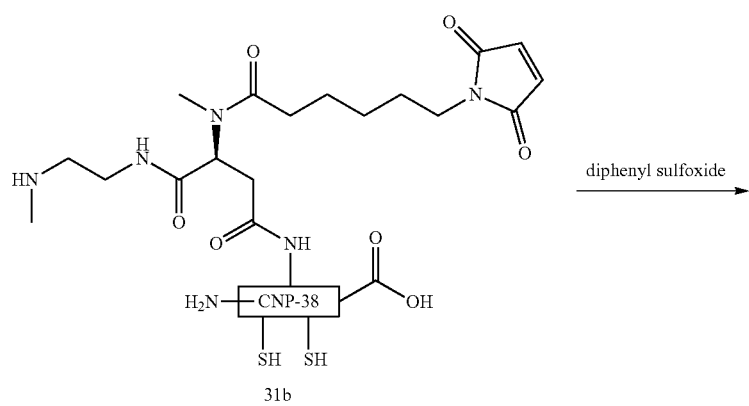
31b
diphenyl sulfoxide →
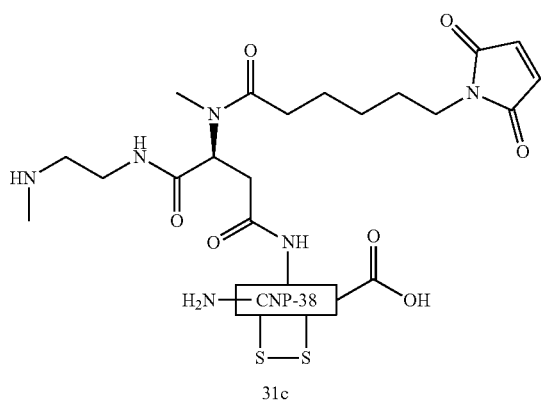
31c

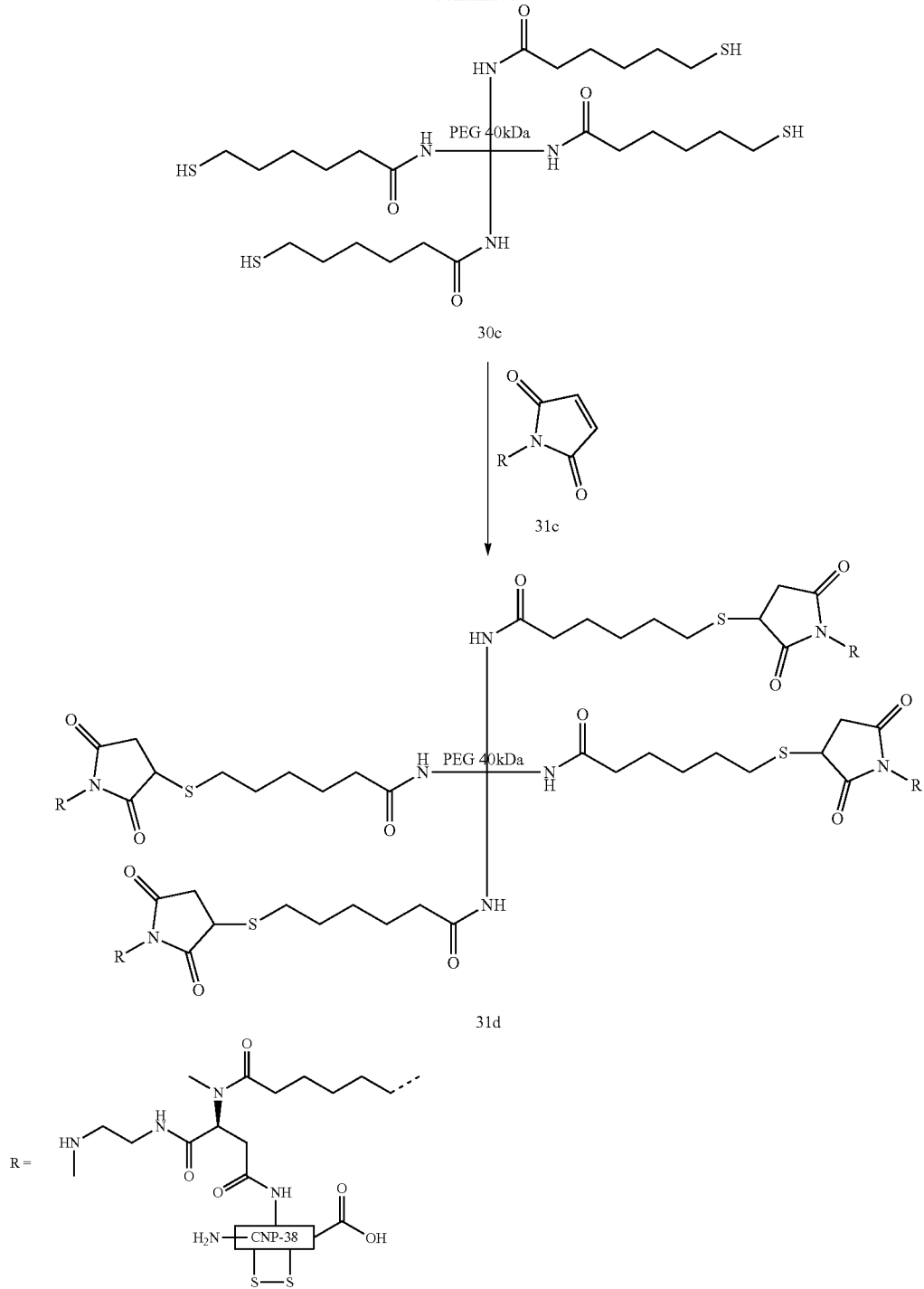

A solution of linker reagent 29b (3.82 g, 5.64 mmol), OxymaPure (802 mg, 5.64 mmol) and DIC (868 µL, 5.64 mmol) in DMF (42.5 mL) was added to the resin 10a (18 g, 1.85 mmol). The suspension was shaken for 100 min at rt to afford resin 31a. The resin was washed 10× with DMF (10 mL) and 10× with DCM (10 mL) and dried in vacuo for 15 min. Cleavage of the peptide from resin and removal of protecting groups was achieved by treatment of the resin with 135 mL cleavage cocktail 100/3/2/1 (v/v/v/v) TFA/ TES/water/thioanisole. The mixture was agitated for 60 min at rt. Crude 31b was precipitated in pre-cooled diethyl ether (−18° C.).

The precipitate was dissolved in TFA (423 mL). To this solution, a solution of diphenyl sulfoxide (1.87 g, 9.25 mmol) and anisole (5.05 mL, 46.25 mmol) in TFA (40 mL) was added. Afterwards, trichloromethylsilane (13.3 mL, 114.7 mmol) was added and the reaction mixture was stirred for 15 min at rt. Then, ammonium fluoride (10.96 g, 296 mmol) was added and the solution was stirred for 2 min in a water bath at rt. Crude 31c was precipitated in pre-cooled diethyl ether (−18° C.) and purified by RP-HPLC.

Yield: 187 mg (34.2 μmol, 16%) CNP-38-linker*9 TFA

MS: m/z 1110.33=[M+4H]$^{4+}$, (calculated monoisotopic mass for [M+4H]$^{4+}$=1110.33).

To a solution of 31c (88.0 mg, 16.1 μmol) in 4.40 mL MeCN/H$_2$O (1:1) containing 0.1% TFA (v/v) was added a solution of 4-arm-thiol-PEG 40 kDa 30c (107.35 mg, 2.59 μmol) in 1.45 mL water containing 0.1% TFA and 1 mM EDTA, followed by 0.5 M phosphate buffer containing 3 mM EDTA (1.46 mL, pH 6.0). The mixture was incubated for 2 h at rt. Conjugate 31d was purified by RP-HPLC.

Yield: 129 mg (2.09 μmol, 80%) conjugate 16d*36 TFA

Example 30

Alternative Synthesis of Dmb Protected 6-Mercapto-hexanoic Acid 7

Dmb-protected mercapto hexanoic acid 7 was synthesized according to the following scheme:

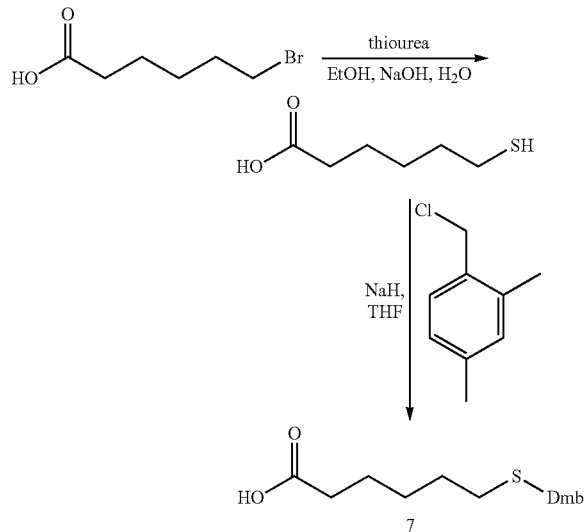

To a solution of 6-bromohexanoic acid (100 g, 0.513 mmol) in EtOH (1.0 L) was added thiourea (47 g, 0.615 mmol) in one portion at 20° C. Then, the suspension was heated up to 78° C. (a clear solution was formed) and stirred for 12 h. A solution of NaOH (62 g, 1.54 mol) in H$_2$O (1.0 L) was added dropwise with a constant pressure funnel. Afterwards, refluxing was continued for additional 2 h. The reaction mixture was poured into H$_2$O (1 L) and extracted with EtOAc (1 L). The aqueous phase was acidified with con. HCl towards pH=2 and then extracted 3× with EtOAc (500 mL). The combined organic phases were washed with brine (400 mL). Afterwards, the combined organic phases were dried over Na$_2$SO$_4$, filtrated and the solvent was evaporated under reduced pressure at 45° C. The 6-mercaptohexanoic acid was used in the next reaction without further purification.

Yield: 62 g (crude)

$^1$H-NMR (400 MHz, CDCl$_3$): δ=2.50-2.55 (q, J=7.2 Hz, 2H), 2.36 (t, J=7.6 Hz, 2H), 1.66-1.61 (m, 4H), 1.41-1.49 (m, 2H), 1.34 (t, J=7.6 Hz, 1H) ppm.

6-mercaptohexanoic acid (27.0 g, 0.182 mmol) was charged in a 1 L three-necked bottom flask with anhydrous THF (540 mL). The solution was degassed by freeze-pump-thaw technique and the cooled to 0° C. with an external ice bath. NaH (18.2, 455.4 mmol, 4.16 mL, 60% purity) was added with spoon horns over 30 min at 0° C. Then, 2,6-dimethylbenzylchloride (28.2 g, 0.182 mol) was added in one portion. The reaction mixture was warmed up to 20° C. and stirred for 12 h. The reaction mixture was poured into H$_2$O (540 mL) and extracted 2× with MTBE (540 mL). Afterwards, the aqueous phase was acidified with conc. HCl towards pH=2 and then extracted 3× with MTBE (500 mL). The combined organic phases were washed with brine (500 mL), dried over Na$_2$SO$_4$ and filtrated. 7 was isolated upon evaporation of the solvent under reduced pressure at 45° C. as a yellow oil.

Yield: 41.5 g (0.16 mol, 85%)

$^1$H-NMR (400 MHz, DMSO-d$_6$): δ=11.99 (s, 1H), 7.05-7.07 (d, J=6.8 Hz, 1H), 6.97 (s, 1H), 6.91-6.92 (d, J=6.8 Hz, 1H), 3.66 (s, 2H), 2.38-2.39 (m, 2H), 2.29 (s, 3H), 2.23 (s, 3H), 2.16-2.19 (m, 2H), 1.40-1.55 (m, 4H), 1.22-1.38 (m, 2H) ppm MS (neg. mode): m/z 265.0=[M−H]$^−$, (calculated monoisotopic mass=265.13).

Example 31

Synthesis of Linker Reagent 33c

Linker reagent 33c was synthesized according to the following scheme:

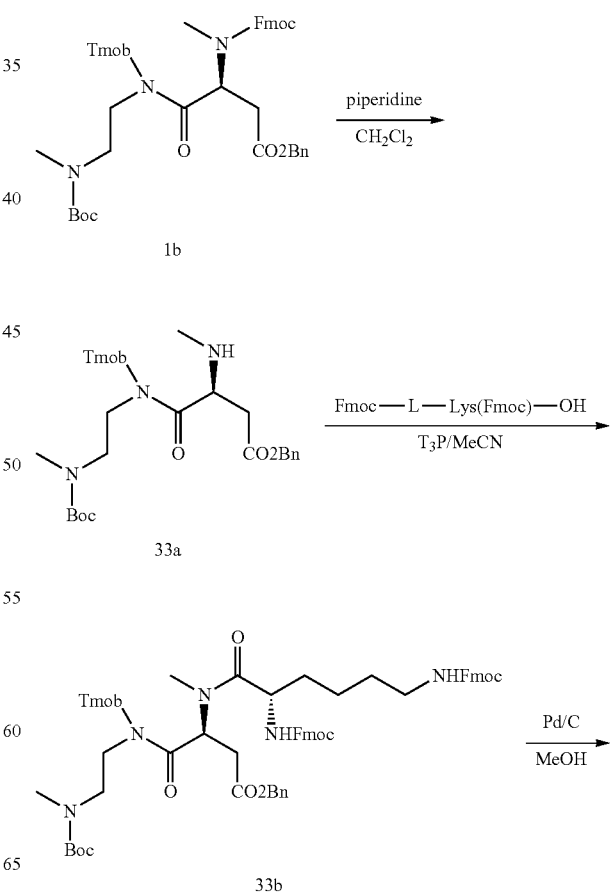

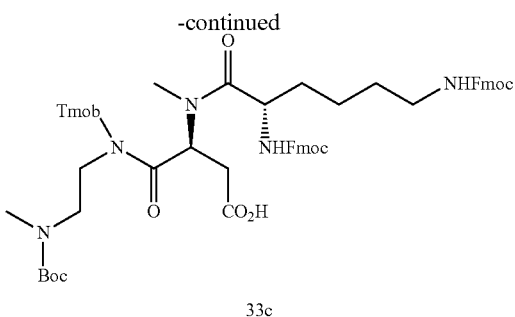

33c

Four reactions were carried out in parallel. To a solution of compound 1b (60 g, 75 mmol) in CH$_2$Cl$_2$ (300 mL) was added piperidine (58 g, 0.68 mol, 67 mL). The reaction mixture was stirred at rt for 4 h. The four reactions which were performed in parallel were combined for work-up. The reaction mixture was diluted with H$_2$O (500 mL) and adjusted with a 0.5 N HCl solution towards pH=3~4. The organic phase was separated and the aqueous phase was extracted with CH$_2$Cl$_2$ (800 mL). The combined organic phases were washed with brine (400 mL) and 5% saturated NaHCO$_3$ solution (400 mL) in turn. Then, the combined organic phases were dried over Na$_2$SO$_4$, filtered and the solvent was evaporated in vacuo. 33a was purified by chromatography on silica (100-200 mesh) with DCM/MeOH (20/1 to 4/1).

Yield: 150 g (87%)

$^1$H-NMR (400 MHz, DMSO-d$_6$): δ=7.34-7.38 (m, 4H), 6.25-7.29 (m, 2H), 5.08-5.19 (m, 2H), 4.60-4.68 (m, 1H), 4.32-4.40 (m, 2H), 3.73-3.79 (m, 9H), 3.10-3.27 (m, 3H), 2.65-3.05 (m, 8H), 1.36 (s, 9H) ppm.

Two reactions were carried out in parallel. To a solution of Fmoc-L-Lys(Fmoc)-OH (79 g, 0.13 mol), 33a (70 g, 0.12 mol), 4-ethyl-morpholine (70 g, 0.61 mol, 77 mL) in MeCN (850 mL) was added dropwise T3P (50% in EtOAc; 140 g, 0.22 mol) over a period of 30 min. After addition, the reaction mixture was stirred at rt for 18 h. The two reactions which were performed in parallel were combined for work-up. The reaction mixture was diluted with H$_2$O/CH$_2$Cl$_2$ (1:1, 2 L) and then adjusted with 0.5 N HCl solution towards pH=3~4. The organic phase was separated and the aqueous phase was extracted with CH$_2$Cl$_2$ (1 L). The combined organic phases were washed with brine (800 mL) and 5% NaHCO$_3$ solution (800 mL) in turn. Then, the combined organic phases were dried over Na$_2$SO$_4$, filtered and the solvent was evaporated in vacuo. 33b was purified by chromatography on silica (100-200 mesh) with petroleum ether/ethyl acetate (5/1 to 1/1).

Yield: 160 g (57%)

$^1$H-NMR (400 MHz, DMSO-d$_6$): δ=7.80-7.90 (m, 4H), 7.61-7.68 (m, 5H), 7.20-7.40 (m, 14H), 6.14-6.28 (m, 3H), 5.01-5.07 (m, 2H), 4.15-4.36 (m, 8H), 3.71-3.77 (m, 9H), 2.80-3.53 (m, 9H), 2.66-2.75 (m, 4H), 2.36-2.39 (m, 1H), 1.52-1.55 (m, 2H), 0.88-1.19 (m, 13H) ppm.

Two reactions were carried out in parallel. To a solution of 33b (60 g, 52 mmol) in MeOH (1.2 L) was added 10% Pd/C (18 g) in a 2 L hydrogenated bottle. The reaction mixture was degassed and purged 3× with H$_2$ and then stirred at 25° C. under H2-atmosphere (45 psi) for 2.5 h. The two reactions which were performed in parallel were combined for work-up. The reaction mixture was filtered by diatomite and the filtrate was concentrated in vacuo to give crude 33c. 33c was purified by chromatography on silica (100-200 mesh) with DCM/MeOH (200/1 to 100/3).

Yield: 70 g (63%)

$^1$H-NMR (400 MHz, DMSO-d$_6$): δ=12.15 (s, 1H), 7.87-7.89 (m, 4H), 7.50-7.70 (m, 5H), 7.31-7.40 (m, 9H), 6.20-6.23 (m, 2H), 4.13-4.36 (m, 10H), 3.70-3.77 (m, 9H), 2.62-3.10 (m, 12H), 2.30-2.34 (m, 1H), 2.14-2.18 (m, 1H), 1.50-1.58 (m, 2H), 1.25-1.34 (m, 13H) ppm MS: m/z 1056.4=[M+H]$^+$, (calculated monoisotopic mass=1056.50).

Example 32

Alternative Synthesis of 11c

Compound 11c was synthesized according to the following scheme:

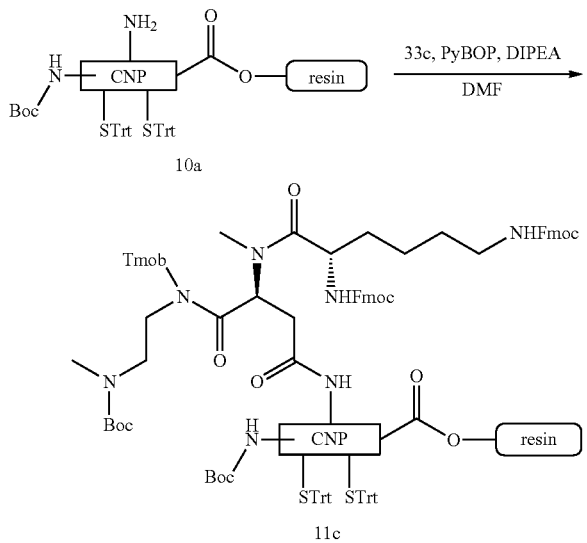

A solution of linker reagent 33c (3.21 g, 3.04 mmol), PyBOP (1.58 g, 3.04 mmol) and DIPEA (848 mL, 4.86 mmol) in DMF (24.0 mL) was incubated for 5 min at rt, then added to the resin 10a (12 g, 1.21 mmol). The suspension was shaken for 2.5 h at rt. The resin was washed 10× with DMF (10 mL) and 10× with DCM (10 mL) and dried in vacuo for 60 min.

Example 33

CNP-38 and Conjugate 11i: Evaluation of Cardiovascular Effects in the Conscious Mouse (Subcutaneous Administration)

The purpose of this study was to evaluate the haemodynamic side effects of 11i at dose level equivalent to a CNP-38 dose level eliciting haemodynamic side effects (decrease in blood pressure) in the telemetered mouse.

Male Crl:CD1(ICR) mice (age range 8-13 weeks and body weight range 27.3-35.6 g at start of dosing) were surgically implanted with a TA11PA-C10 telemetry transmitter (Data Sciences International (DSI)) in the carotid artery. The body of the transmitter was placed subcutaneously in the lateral flank of the mouse. The mice were dosed subcutaneously in a latin square crossover design with at least 72 hours between dosing occasions. Mice were dosed with 1) vehicle (10 mM succinate, 46.0 g/L mannitol, pH 4.00), 2) CNP-38 (800 µg CNP-38/kg, 10 mM succinate, 46.0 g/L mannitol, pH 4.00) or 3) 11i (800 µg CNP-38 eq/kg, 10 mM succinate, 46.0 g/L mannitol, pH 4.00). At least four mice were included at each dose level. Blood pressure (systolic (SAP), diastolic (DAP) and mean (MAP) and heart rate (HR, derived from blood pressure), were recorded using a digital data capture system linked with a DSI™ Ponemah data acquisition and analysis system. The capture system allowed recording of the cardiovascular parameters whilst the mice were in individual cages. On the day of each test session the animals were weighed and a predose recording was performed for at least 60 min prior to dosing. Each mouse was returned to the home cage and the cardiovascular parameters were recorded for approximately 48 hours post-dose. Blood pressure and HR were reported at the following time points: −30, −20, −10, 5, 15 and 30 min postdose and 1, 2, 6, 12, 18, 24, 30, 36, 42 and 48 hours postdose. Each time point was presented as the average value of five minute's recording prior to the time point. The monitoring period was selected to cover exposure to the test items both prior to and after $T_{max}$.

Results: Compared to predose values, vehicle dosed animals had increased MAP at the 5, 15, and 30 min post dose sampling time point. This was considered a normal physiological response due to handling and dosing. The same physiological increase in MAP was seen for animals dosed with 11i at the 5, 15, and 30 min post dose sampling time point predose. In 3 of 4 animals dosed with CNP-38 the physiological increase in MAP was not evident. On the contrary, 3 of 4 CNP-38 dosed animals showed a significant decrease in MAP at the 5, 15, and 30 min post dose sampling time point. During the remaining ten time points there were no difference in MAP between animals dosed with vehicle, CNP-38 and 11i.

MAP (mmHg) Predose to 30 Min Cost Dose (Mean±SD)

|  | Vehicle (n = 10) | 11i (n = 4) | CNP-38 (n = 4) |
| --- | --- | --- | --- |
| predose | 101.9 ± 10.0 | 106.4 ± 10.7 | 106.8 ± 13.4 |
| 5 min post dose | 125.9 ± 7.3 | 122.8 ± 5.9 | 102.0 ± 7.5 |
| 15 min post dose | 126.3 ± 6.9 | 121.5 ± 7.5 | 89.5 ± 29.4 |
| 30 min post dose | 114.4 ± 15.3 | 111.5 ± 13.7 | 99.5 ± 25.2 |

Similar trends were seen for SAP and DAP for all dose levels. HR was not impacted by treatment with CNP-38 or 11i.

In conclusion, subcutaneous administration of 11i did not decrease blood pressure as seen for an equivalent dosage CNP-38.

Example 34

Pharmacokinetic Profile of CNP-38 after Subcutaneous Single-Dose Administration to Cynomolgus Monkeys This study was performed in order to test the pharmacokinetics of CNP-38 after subcutaneous (s.c.) administration in cynomolgus monkeys. Three male monkeys (2-4 years old, 3-5 kg) received a single s.c. injection at a dose of 40 µg/kg of CNP-38. Blood samples were collected at 5, 10, 15, 30, 45 min and 1, 2, 4, 8 hours upon dose.

Method: Plasma levels of CNP were analysed using a commercially available competitive radioimmuno-assay (RK-012-03, Phoenix Pharmaceuticals, CA). The assay was applied essentially as described by the manufacturer. The assay is based on competitive binding between 125I-labelled CNP (supplied in the kit) and unlabeled CNP (from study sample or calibrants) to an anti-CNP antibody. When the concentration of CNP in the sample increases, the amount of 125I-labelled CNP that is able to bind to the antibody decreases. By measuring the amount of 125I-labelled CNP bound as a function of the concentration of peptide, it is possible to construct a calibration curve from which the concentration of peptide in the sample can be determined.

A few changes to the supplied assay protocol were made. These changes included using in-house CNP calibrant and QC samples to secure consistency between assay runs. In order to shorten the duration of the assay, the initial incubation of samples with antibodies was performed at room temperature for 5 hours (instead of 16-24 hours at 4° C.). Due to matrix effects in monkey plasma, the minimal required dilution was set at 1:10, yielding an assay range of 150-1080 pg/mL CNP.

Results: Administration of CNP-38 to cynomolgus monkeys was well tolerated. After s.c. injection, the CNP-38 median $T_{max}$ was observed at 10 min, with a mean half-life time of approximately 7 min.

| PK Parameter | Result |
| --- | --- |
| $T_{max}$ (median) | 10 min |
| $C_{max}$ (mean) | 7.9 ng/mL |
| $AUC_{tlast}$ (mean) | 2.5 h * ng/mL |
| Half-life (mean) | 6.6 min |

Example 35

Pharmacokinetic Profile of Conjugate 11i after Subcutaneous Single-Dose Administration to Cynomolgus Monkeys This study was performed in order to investigate pharmacokinetics of 11i after s.c. administration in cynomolgus monkeys. Four male animals (2-4 years old, 3-5 kg) received a single s.c. injection of 11i at a dose of 40 µg CNP-38 eq/kg. Blood samples were collected up to 168 h post dose and plasma was generated (LiHeparin). Total CNP-38 concentrations were determined by LC-MS/MS Method: The term "total CNP-38" refers to a combination of both free CNP-38 and CNP-38 bound in the CNP-38 conjugate. Plasma total CNP-38 concentrations were determined by quantification of the C-terminal signature peptide (sequence: IGSMSGLGC; residues 30-38 of SEQ ID NO:24) after tryptic digestion and disulfide bridge reduction.

LC-MS analysis was carried out by using an Agilent 1290 UPLC coupled to an Agilent 6460 Triple Quad mass spectrometer via an ESI probe. Chromatography was performed on a Waters Acquity BEH C18 analytical column (50×1.0 mm I.D., 1.7 µm particle size, 130 Å) with pre-filter at a flow rate of 0.5 mL/min (T=45° C.). Water (Ultrapure ≤500 ppt sodium grade) containing 0.1% formic acid (v/v) was used as mobile phase A and acetonitrile (ULC/MS grade) with 0.1% formic acid as mobile phase B. The gradient system comprised a short isocratic step at the initial parameters of 0.1% B for 0.5 min followed by a linear increase from 0.1% B to 30% B in 1.5 min. Mass analysis was performed in the multiple reaction monitoring (MRM) mode, monitoring the reactions of the ionisation m/z 824.5 $[M+H]^{1+}$ to 515.2. As internal standard deuterated CNP-38 conjugate was used.

Calibration standards of CNP-38 conjugate in blank plasma were prepared as follows: The thawed Li-heparin cynomolgus plasma was first homogenized, then centrifuged for 5 minutes. The CNP-38 conjugate formulation was diluted to eight different calibration working solutions containing between 0.103 and 51.28 µg/mL (CNP-38 eq.) in 50% methanol/50% water/0.1% formic acid (v/v/v). The working solutions were spiked into blank plasma at concentrations between 10.3 ng/mL (CNP-38 eq.) and 5128 ng/mL (CNP-38 eq.). The standards were used for the generation of a calibration curve. A calibration curve was generated based on analyte to internal standard peak area ratios using weighted ($1/x^2$) linear regression and the sample concentrations were determined by back-calculation against the calibration curve.

For sample preparation, protein precipitation was carried out by addition of 200 µL of precooled (0° C.) acetonitrile to 50 µL of the plasma sample and 10 µL of internal standard solution (2.8 µg/mL CNP-38 eq. in 50% methanol/50% water/0.1% formic acid (v/v/v)). 200 µL of the supernatant were transferred into a new well-plate and evaporated to dryness (under a gentle nitrogen stream at 35° C.). For reconstitution solvent 100 µg Trypsin (order number V5111, Promega GmbH, Mannheim, Germany) were dissolved in 100 µL 10 mM acetic acid. 2.5 mL Tris buffer and 500 µL methanol were added. 50 µL of the resulting reconstitution solvent were added to each cavity of the-well plate. After 3 hours incubation at 37° C. (Eppendorf ThermoMixer with ThermoTop), 5 µL of a 0.5 M TCEP solution were added to each cavity and incubated again for 30 min at 37° C. After the samples had cooled to room temperature, 2 µL 60% formic acid in water were added. 10 µL were injected into the UHPLC-MS system. Results: Administration of 11i to cynomolgus monkeys was well tolerated. After s.c. injection the 11i median $T_{max}$ was 36 h, and with a mean half-life time of 107 h.

| PK Parameter | Result |
|---|---|
| $T_{max}$ (median) | 36 hours |
| $C_{max}$ (mean) | 316 ng/mL |
| $AUC_{tlast}$ (mean) | 38,051 h * ng/mL |
| Half-life (mean) | 107 hours |

Example 36

Functional cGMP Stimulation in NIH-3T3 Cells with Released CNP 11i was incubated under physiological conditions (1 mg CNP-38 eq/mL), as described in Example 20. After 7 d, released CNP-38 was isolated by RP-HPLC and analyzed for bioactivity as described in Example 21.

| Compound | CNP Variant | PEGylation | $EC_{50}$ compound/$EC_{50}$ CNP-38 |
|---|---|---|---|
| Released CNP-38 | CNP-38 | — | 1 |

Example 37

Alternative Synthesis of 11h

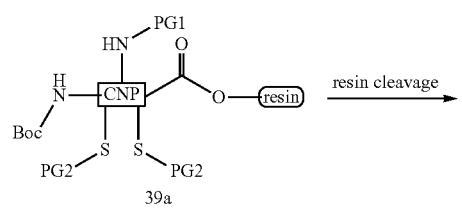

39a

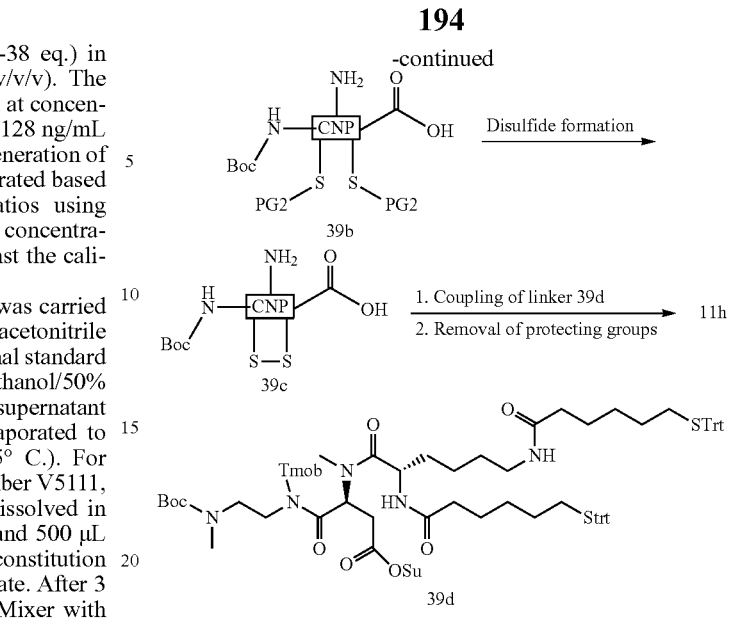

Alternative synthesis of compound 11h: 39a is synthesized by solid phase synthesis as described in Material and Methods. Protecting group PG1 for the ring lysin side chain and protecting groups PG2 for the cysteine side chains is Mmt. Mild resin cleavage and disulfide formation by iodine treatment affords compound 39c. After coupling of linker molecule 39d and global deprotection, 11h is purified by RP-HPLC.

ABBREVIATIONS

ACH achondroplasia
ACN acetonitrile
AcOH acetic acid
$AUC_{tlast}$ Area Under the Curve to the last quantifiable time point
Bn benzyl
Boc tert-butyloxycarbonyl
BSA bovine serum albumin
cGMP cyclic guanosine monophosphate
$C_{max}$ Maximum concentration
CMV cytomegalovirus
CNP C-type natriuretic peptide
COMU (1-cyano-2-ethoxy-2-oxoethylidenaminooxy)dimethylamino-morpholino-carbenium hexafluorophosphate
conc. Concentrated
d day
CTC Chlorotritylchloride polystyrol
DAP Diastolic arterial pressure
DBU 1,3-diazabicyclo[5.4.0]undecene
DCC N,N'-dicyclohexylcarbodiimide
DCM dichloromethane
DIC N,N'-diisopropylcarbodiimide
DIEA N,N-diisopropylethylamine
DIPEA N,N-diisopropylethylamine
DMAP dimethylamino-pyridine
DMEM Dulbecco's modified Eagle's medium
Dmb 2,4-dimethylbenzyl
DMEM Dulbecco's modified eagle medium
DMF N,N-dimethylformamide
DMSO dimethylsulfoxide
DTT dithiothreitol
EC50 half maximal effective concentration
EDC 1-ethyl-3-(3-dimethylaminopropyl)carbodiimide EDTA ethylenediaminetetraacetic acid
ELISA enzyme-linked immunosorbent assay
eq stoichiometric equivalent
ESI-MS electrospray ionization mass spectrometry
Et ethyl
EtOAc ethyl acetate
EtOH ethanol
FBS fetal bovine serum
FGFR3 fibroblast-growth-factor-receptor 3
FITC fluorescein isothiocyanate
Fmoc 9-fluorenylmethyloxycarbonyl
h hour
HATU O-(7-azabenzotriazole-1-yl)-N,N,N',N'-tetramethyl-uronium hexafluorophosphate
HCH hypochondroplasia
HFIP hexafluoroisopropanol
HPLC high performance liquid chromatography
HOBt N-hydroxybenzotriazole
HR Heart rate
IBMX 3-isobutyl-1-methylxanthine
iPrOH 2-propanol
iv intravenous
ivDde 4,4-dimethyl-2,6-dioxocyclohex-1-ylidene)-3-methylbutyl
LC liquid chromatography
LTQ linear trap quadrupole
Mal 3-maleimido propyl
MAP Mean arterial pressure
Me methyl
MeOH methanol
min minutes
Mmt monomethoxytrityl
MS mass spectrum/mass spectrometry
MSA methanesulfonic acid
MTBE methyl-tert-butylether
Mtt methyltrityl
MW molecular weight
m/z mass-to-charge ratio
NEP neutral endopeptidase
NHS N-hydroxy succinimide
NPR natriuretic peptide receptor
OtBu tert-butyloxy
PBS phosphate buffered saline
PEG poly(ethylene glycol)
PFP pentafluorophenol
pH potentia Hydrogenii
Pr propyl
PyBOP benzotriazol-1-yl-oxytripyrrolidinophosphonium hexafluorophosphate
Q-TOF quadrupole time-of-flight
qRT-PCR quantitative real-time polymerase chain reaction
RP-HPLC reversed-phase high performance liquid chromatography
rpm rounds per minute
rt room temperature
SIM single ion monitoring
SAP Systolic arterial pressure
SEC size exclusion chromatography
sc subcutaneous
Su succinimidyl
$T_3P$ 2,4,6-tripropyl-1,3,5,2,4,6-trioxatriphosphorinane-2,4,6-trioxide
TCEP tris(2-carboxyethyl)phosphine
TCP tritylchloride polystyro
TD thanatophoric dysplasia
TES triethylsilane
TFA trifluoroacetic acid
THF tetrahydrofuran
TIPS triisoproylsilane
$T_{max}$ Time of maximum concentration
TMEDA N,N,N'N'-tetramethylethylene diamine
Tmob 2,4,6-trimethoxybenzyl
TR-FRET time-resolved fluorescence energy transfer
Trt triphenylmethyl, trityl
UPLC ultra performance liquid chromatography
UV ultraviolet
vs. versus
ZQ single quadrupole

---

SEQUENCE LISTING

```
<160> NUMBER OF SEQ ID NOS: 98

<210> SEQ ID NO 1
<211> LENGTH: 22
<212> TYPE: PRT
<213> ORGANISM: Homo sapiens
<220> FEATURE:
<221> NAME/KEY: DISULFID
<222> LOCATION: (6)..(22)

<400> SEQUENCE: 1

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 2
<211> LENGTH: 53
<212> TYPE: PRT
<213> ORGANISM: Homo sapiens
<220> FEATURE:
<221> NAME/KEY: DISULFID
<222> LOCATION: (37)..(53)

<400> SEQUENCE: 2
```

```
Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 3
<211> LENGTH: 54
<212> TYPE: PRT
<213> ORGANISM: Artificial Sequence
<220> FEATURE:
<223> OTHER INFORMATION: G-CNP-53
<220> FEATURE:
<221> NAME/KEY: DISULFID
<222> LOCATION: (38)..(54)

<400> SEQUENCE: 3

Gly Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50

<210> SEQ ID NO 4
<211> LENGTH: 54
<212> TYPE: PRT
<213> ORGANISM: Artificial Sequence
<220> FEATURE:
<223> OTHER INFORMATION: M-CNP-53
<220> FEATURE:
<221> NAME/KEY: DISULFID
<222> LOCATION: (38)..(54)

<400> SEQUENCE: 4

Met Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50

<210> SEQ ID NO 5
<211> LENGTH: 54
<212> TYPE: PRT
<213> ORGANISM: Artificial Sequence
<220> FEATURE:
<223> OTHER INFORMATION: P-CNP-53
<220> FEATURE:
<221> NAME/KEY: DISULFID
<222> LOCATION: (38)..(54)

<400> SEQUENCE: 5

Pro Asp Leu Arg Val Asp Thr Lys Ser Arg Ala Ala Trp Ala Arg Leu
1               5                   10                  15
```

```
Leu Gln Glu His Pro Asn Ala Arg Lys Tyr Lys Gly Ala Asn Lys Lys
                20                  25                  30

Gly Leu Ser Lys Gly Cys Phe Gly Leu Lys Leu Asp Arg Ile Gly Ser
            35                  40                  45

Met Ser Gly Leu Gly Cys
        50

<210> SEQ ID NO 6
<211> LENGTH: 53
<212> TYPE: PRT
<213> ORGANISM: Artificial Sequence
<220> FEATURE:
<223> OTHER INFORMATION: CNP-53 M48N
<220> FEATURE:
<221> NAME/KEY: DISULFID
<222> LOCATION: (37)..(53)

<400> SEQUENCE: 6

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
                20                  25                  30

Leu Ser Lys Gly Cys Phe Gly Leu Lys Leu Asp Arg Ile Gly Ser Asn
            35                  40                  45

Ser Gly Leu Gly Cys
        50

<210> SEQ ID NO 7
<211> LENGTH: 36
<212> TYPE: PRT
<213> ORGANISM: Artificial Sequence
<220> FEATURE:
<223> OTHER INFORMATION: CNP-53 with deletion of amino acids 15-31
<220> FEATURE:
<221> NAME/KEY: DISULFID
<222> LOCATION: (20)..(36)

<400> SEQUENCE: 7

Asp Leu Arg Val Asp Thr Lys Ser Arg Ala Ala Trp Ala Arg Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 8
<211> LENGTH: 52
<212> TYPE: PRT
<213> ORGANISM: Artificial Sequence
<220> FEATURE:
<223> OTHER INFORMATION: CNP-52
<220> FEATURE:
<221> NAME/KEY: DISULFID
<222> LOCATION: (36)..(52)

<400> SEQUENCE: 8

Leu Arg Val Asp Thr Lys Ser Arg Ala Ala Trp Ala Arg Leu Leu Gln
1               5                   10                  15

Glu His Pro Asn Ala Arg Lys Tyr Lys Gly Ala Asn Lys Lys Gly Leu
                20                  25                  30

Ser Lys Gly Cys Phe Gly Leu Lys Leu Asp Arg Ile Gly Ser Met Ser
            35                  40                  45

Gly Leu Gly Cys
```

<210> SEQ ID NO 9
<211> LENGTH: 51
<212> TYPE: PRT
<213> ORGANISM: Artificial Sequence
<220> FEATURE:
<223> OTHER INFORMATION: CNP-51
<220> FEATURE:
<221> NAME/KEY: DISULFID
<222> LOCATION: (35)..(51)

<400> SEQUENCE: 9

```
Arg Val Asp Thr Lys Ser Arg Ala Ala Trp Ala Arg Leu Leu Gln Glu
1               5                   10                  15

His Pro Asn Ala Arg Lys Tyr Lys Gly Ala Asn Lys Lys Gly Leu Ser
            20                  25                  30

Lys Gly Cys Phe Gly Leu Lys Leu Asp Arg Ile Gly Ser Met Ser Gly
        35                  40                  45

Leu Gly Cys
        50
```

<210> SEQ ID NO 10
<211> LENGTH: 50
<212> TYPE: PRT
<213> ORGANISM: Artificial Sequence
<220> FEATURE:
<223> OTHER INFORMATION: CNP-50
<220> FEATURE:
<221> NAME/KEY: DISULFID
<222> LOCATION: (34)..(50)

<400> SEQUENCE: 10

```
Val Asp Thr Lys Ser Arg Ala Ala Trp Ala Arg Leu Leu Gln Glu His
1               5                   10                  15

Pro Asn Ala Arg Lys Tyr Lys Gly Ala Asn Lys Lys Gly Leu Ser Lys
            20                  25                  30

Gly Cys Phe Gly Leu Lys Leu Asp Arg Ile Gly Ser Met Ser Gly Leu
        35                  40                  45

Gly Cys
    50
```

<210> SEQ ID NO 11
<211> LENGTH: 49
<212> TYPE: PRT
<213> ORGANISM: Artificial Sequence
<220> FEATURE:
<223> OTHER INFORMATION: CNP-49
<220> FEATURE:
<221> NAME/KEY: DISULFID
<222> LOCATION: (33)..(49)

<400> SEQUENCE: 11

```
Asp Thr Lys Ser Arg Ala Ala Trp Ala Arg Leu Leu Gln Glu His Pro
1               5                   10                  15

Asn Ala Arg Lys Tyr Lys Gly Ala Asn Lys Lys Gly Leu Ser Lys Gly
            20                  25                  30

Cys Phe Gly Leu Lys Leu Asp Arg Ile Gly Ser Met Ser Gly Leu Gly
        35                  40                  45

Cys
```

<210> SEQ ID NO 12
<211> LENGTH: 48

```
<212> TYPE: PRT
<213> ORGANISM: Artificial Sequence
<220> FEATURE:
<223> OTHER INFORMATION: CNP-48
<220> FEATURE:
<221> NAME/KEY: DISULFID
<222> LOCATION: (32)..(48)

<400> SEQUENCE: 12

Thr Lys Ser Arg Ala Ala Trp Ala Arg Leu Leu Gln Glu His Pro Asn
1               5                   10                  15

Ala Arg Lys Tyr Lys Gly Ala Asn Lys Lys Gly Leu Ser Lys Gly Cys
            20                  25                  30

Phe Gly Leu Lys Leu Asp Arg Ile Gly Ser Met Ser Gly Leu Gly Cys
        35                  40                  45

<210> SEQ ID NO 13
<211> LENGTH: 47
<212> TYPE: PRT
<213> ORGANISM: Artificial Sequence
<220> FEATURE:
<223> OTHER INFORMATION: CNP-47
<220> FEATURE:
<221> NAME/KEY: DISULFID
<222> LOCATION: (31)..(47)

<400> SEQUENCE: 13

Lys Ser Arg Ala Ala Trp Ala Arg Leu Leu Gln Glu His Pro Asn Ala
1               5                   10                  15

Arg Lys Tyr Lys Gly Ala Asn Lys Lys Gly Leu Ser Lys Gly Cys Phe
            20                  25                  30

Gly Leu Lys Leu Asp Arg Ile Gly Ser Met Ser Gly Leu Gly Cys
        35                  40                  45

<210> SEQ ID NO 14
<211> LENGTH: 46
<212> TYPE: PRT
<213> ORGANISM: Artificial Sequence
<220> FEATURE:
<223> OTHER INFORMATION: CNP-46
<220> FEATURE:
<221> NAME/KEY: DISULFID
<222> LOCATION: (30)..(46)

<400> SEQUENCE: 14

Ser Arg Ala Ala Trp Ala Arg Leu Leu Gln Glu His Pro Asn Ala Arg
1               5                   10                  15

Lys Tyr Lys Gly Ala Asn Lys Lys Gly Leu Ser Lys Gly Cys Phe Gly
            20                  25                  30

Leu Lys Leu Asp Arg Ile Gly Ser Met Ser Gly Leu Gly Cys
        35                  40                  45

<210> SEQ ID NO 15
<211> LENGTH: 45
<212> TYPE: PRT
<213> ORGANISM: Artificial Sequence
<220> FEATURE:
<223> OTHER INFORMATION: CNP-45
<220> FEATURE:
<221> NAME/KEY: DISULFID
<222> LOCATION: (29)..(45)

<400> SEQUENCE: 15

Arg Ala Ala Trp Ala Arg Leu Leu Gln Glu His Pro Asn Ala Arg Lys
1               5                   10                  15
```

Tyr Lys Gly Ala Asn Lys Lys Gly Leu Ser Lys Gly Cys Phe Gly Leu
                20                  25                  30

Lys Leu Asp Arg Ile Gly Ser Met Ser Gly Leu Gly Cys
        35                  40                  45

<210> SEQ ID NO 16
<211> LENGTH: 44
<212> TYPE: PRT
<213> ORGANISM: Artificial Sequence
<220> FEATURE:
<223> OTHER INFORMATION: CNP-44
<220> FEATURE:
<221> NAME/KEY: DISULFID
<222> LOCATION: (28)..(44)

<400> SEQUENCE: 16

Ala Ala Trp Ala Arg Leu Leu Gln Glu His Pro Asn Ala Arg Lys Tyr
1               5                   10                  15

Lys Gly Ala Asn Lys Lys Gly Leu Ser Lys Gly Cys Phe Gly Leu Lys
                20                  25                  30

Leu Asp Arg Ile Gly Ser Met Ser Gly Leu Gly Cys
        35                  40

<210> SEQ ID NO 17
<211> LENGTH: 35
<212> TYPE: PRT
<213> ORGANISM: Artificial Sequence
<220> FEATURE:
<223> OTHER INFORMATION: CNP-44 with a deletion of amino acids 14-22
<220> FEATURE:
<221> NAME/KEY: DISULFID
<222> LOCATION: (19)..(35)

<400> SEQUENCE: 17

Ala Ala Trp Ala Arg Leu Leu Gln Glu His Pro Asn Ala Gly Leu Ser
1               5                   10                  15

Lys Gly Cys Phe Gly Leu Lys Leu Asp Arg Ile Gly Ser Met Ser Gly
                20                  25                  30

Leu Gly Cys
        35

<210> SEQ ID NO 18
<211> LENGTH: 36
<212> TYPE: PRT
<213> ORGANISM: Artificial Sequence
<220> FEATURE:
<223> OTHER INFORMATION: CNP-44 with a deletion of amino acids 15-22
<220> FEATURE:
<221> NAME/KEY: DISULFID
<222> LOCATION: (20)..(36)

<400> SEQUENCE: 18

Ala Ala Trp Ala Arg Leu Leu Gln Glu His Pro Asn Ala Arg Gly Leu
1               5                   10                  15

Ser Lys Gly Cys Phe Gly Leu Lys Leu Asp Arg Ile Gly Ser Met Ser
                20                  25                  30

Gly Leu Gly Cys
        35

<210> SEQ ID NO 19
<211> LENGTH: 43
<212> TYPE: PRT
<213> ORGANISM: Artificial Sequence
<220> FEATURE:
<223> OTHER INFORMATION: CNP-43

```
<220> FEATURE:
<221> NAME/KEY: DISULFID
<222> LOCATION: (27)..(43)

<400> SEQUENCE: 19

Ala Trp Ala Arg Leu Leu Gln Glu His Pro Asn Ala Arg Lys Tyr Lys
1               5                   10                  15

Gly Ala Asn Lys Lys Gly Leu Ser Lys Gly Cys Phe Gly Leu Lys Leu
                20                  25                  30

Asp Arg Ile Gly Ser Met Ser Gly Leu Gly Cys
            35                  40

<210> SEQ ID NO 20
<211> LENGTH: 42
<212> TYPE: PRT
<213> ORGANISM: Artificial Sequence
<220> FEATURE:
<223> OTHER INFORMATION: CNP-42
<220> FEATURE:
<221> NAME/KEY: DISULFID
<222> LOCATION: (26)..(42)

<400> SEQUENCE: 20

Trp Ala Arg Leu Leu Gln Glu His Pro Asn Ala Arg Lys Tyr Lys Gly
1               5                   10                  15

Ala Asn Lys Lys Gly Leu Ser Lys Gly Cys Phe Gly Leu Lys Leu Asp
                20                  25                  30

Arg Ile Gly Ser Met Ser Gly Leu Gly Cys
            35                  40

<210> SEQ ID NO 21
<211> LENGTH: 41
<212> TYPE: PRT
<213> ORGANISM: Artificial Sequence
<220> FEATURE:
<223> OTHER INFORMATION: CNP-41
<220> FEATURE:
<221> NAME/KEY: DISULFID
<222> LOCATION: (25)..(41)

<400> SEQUENCE: 21

Ala Arg Leu Leu Gln Glu His Pro Asn Ala Arg Lys Tyr Lys Gly Ala
1               5                   10                  15

Asn Lys Lys Gly Leu Ser Lys Gly Cys Phe Gly Leu Lys Leu Asp Arg
                20                  25                  30

Ile Gly Ser Met Ser Gly Leu Gly Cys
            35                  40

<210> SEQ ID NO 22
<211> LENGTH: 40
<212> TYPE: PRT
<213> ORGANISM: Artificial Sequence
<220> FEATURE:
<223> OTHER INFORMATION: CNP-40
<220> FEATURE:
<221> NAME/KEY: DISULFID
<222> LOCATION: (24)..(40)

<400> SEQUENCE: 22

Arg Leu Leu Gln Glu His Pro Asn Ala Arg Lys Tyr Lys Gly Ala Asn
1               5                   10                  15

Lys Lys Gly Leu Ser Lys Gly Cys Phe Gly Leu Lys Leu Asp Arg Ile
                20                  25                  30

Gly Ser Met Ser Gly Leu Gly Cys
```

<210> SEQ ID NO 23
<211> LENGTH: 39
<212> TYPE: PRT
<213> ORGANISM: Artificial Sequence
<220> FEATURE:
<223> OTHER INFORMATION: CNP-39
<220> FEATURE:
<221> NAME/KEY: DISULFID
<222> LOCATION: (23)..(39)

<400> SEQUENCE: 23

Leu Leu Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 24
<211> LENGTH: 38
<212> TYPE: PRT
<213> ORGANISM: Artificial Sequence
<220> FEATURE:
<223> OTHER INFORMATION: CNP-38
<220> FEATURE:
<221> NAME/KEY: DISULFID
<222> LOCATION: (22)..(38)

<400> SEQUENCE: 24

Leu Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 25
<211> LENGTH: 37
<212> TYPE: PRT
<213> ORGANISM: Artificial Sequence
<220> FEATURE:
<223> OTHER INFORMATION: CNP-37
<220> FEATURE:
<221> NAME/KEY: DISULFID
<222> LOCATION: (21)..(37)

<400> SEQUENCE: 25

Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 26
<211> LENGTH: 37
<212> TYPE: PRT
<213> ORGANISM: Artificial Sequence
<220> FEATURE:
<223> OTHER INFORMATION: CNP-37 mit Q1pQ (pQ = pyroglutamate)
<220> FEATURE:
<221> NAME/KEY: MISC_FEATURE
<222> LOCATION: (1)..(1)
<223> OTHER INFORMATION: X = pyroglutamate

```
<220> FEATURE:
<221> NAME/KEY: DISULFID
<222> LOCATION: (21)..(37)

<400> SEQUENCE: 26

Xaa Glu His Pro Asn Ala Arg Lys Tyr Lys Gly Ala Asn Lys Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 27
<211> LENGTH: 38
<212> TYPE: PRT
<213> ORGANISM: Artificial Sequence
<220> FEATURE:
<223> OTHER INFORMATION: G-CNP-37
<220> FEATURE:
<221> NAME/KEY: DISULFID
<222> LOCATION: (22)..(38)

<400> SEQUENCE: 27

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 28
<211> LENGTH: 38
<212> TYPE: PRT
<213> ORGANISM: Artificial Sequence
<220> FEATURE:
<223> OTHER INFORMATION: P-CNP-37
<220> FEATURE:
<221> NAME/KEY: DISULFID
<222> LOCATION: (22)..(38)

<400> SEQUENCE: 28

Pro Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 29
<211> LENGTH: 38
<212> TYPE: PRT
<213> ORGANISM: Artificial Sequence
<220> FEATURE:
<223> OTHER INFORMATION: M-CNP-37
<220> FEATURE:
<221> NAME/KEY: DISULFID
<222> LOCATION: (22)..(38)

<400> SEQUENCE: 29

Met Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
```

<210> SEQ ID NO 30
<211> LENGTH: 39
<212> TYPE: PRT
<213> ORGANISM: Artificial Sequence
<220> FEATURE:
<223> OTHER INFORMATION: PG-CNP-37
<220> FEATURE:
<221> NAME/KEY: DISULFID
<222> LOCATION: (23)..(39)

<400> SEQUENCE: 30

```
Pro Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
                20                  25                  30

Ser Met Ser Gly Leu Gly Cys
            35
```

<210> SEQ ID NO 31
<211> LENGTH: 39
<212> TYPE: PRT
<213> ORGANISM: Artificial Sequence
<220> FEATURE:
<223> OTHER INFORMATION: MG-CNP-37
<220> FEATURE:
<221> NAME/KEY: DISULFID
<222> LOCATION: (23)..(39)

<400> SEQUENCE: 31

```
Met Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
                20                  25                  30

Ser Met Ser Gly Leu Gly Cys
            35
```

<210> SEQ ID NO 32
<211> LENGTH: 37
<212> TYPE: PRT
<213> ORGANISM: Artificial Sequence
<220> FEATURE:
<223> OTHER INFORMATION: CNP-37 M32N
<220> FEATURE:
<221> NAME/KEY: DISULFID
<222> LOCATION: (21)..(37)

<400> SEQUENCE: 32

```
Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Asn
                20                  25                  30

Ser Gly Leu Gly Cys
            35
```

<210> SEQ ID NO 33
<211> LENGTH: 38
<212> TYPE: PRT
<213> ORGANISM: Artificial Sequence
<220> FEATURE:
<223> OTHER INFORMATION: G-CNP-37 M32N
<220> FEATURE:
<221> NAME/KEY: DISULFID
<222> LOCATION: (22)..(38)

-continued

```
<400> SEQUENCE: 33

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Asn Ser Gly Leu Gly Cys
            35

<210> SEQ ID NO 34
<211> LENGTH: 38
<212> TYPE: PRT
<213> ORGANISM: Artificial Sequence
<220> FEATURE:
<223> OTHER INFORMATION: G-CNP-37 K14Q
<220> FEATURE:
<221> NAME/KEY: DISULFID
<222> LOCATION: (22)..(38)

<400> SEQUENCE: 34

Gly Gln Glu His Pro Asn Ala Arg Lys Tyr Lys Gly Ala Asn Gln Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
            35

<210> SEQ ID NO 35
<211> LENGTH: 38
<212> TYPE: PRT
<213> ORGANISM: Artificial Sequence
<220> FEATURE:
<223> OTHER INFORMATION: G-CNP-37 K14P
<220> FEATURE:
<221> NAME/KEY: DISULFID
<222> LOCATION: (22)..(38)

<400> SEQUENCE: 35

Gly Gln Glu His Pro Asn Ala Arg Lys Tyr Lys Gly Ala Asn Pro Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
            35

<210> SEQ ID NO 36
<211> LENGTH: 37
<212> TYPE: PRT
<213> ORGANISM: Artificial Sequence
<220> FEATURE:
<223> OTHER INFORMATION: G-CNP-37 K14Q, deletion of amino acid 15
<220> FEATURE:
<221> NAME/KEY: DISULFID
<222> LOCATION: (21)..(37)

<400> SEQUENCE: 36

Gly Gln Glu His Pro Asn Ala Arg Lys Tyr Lys Gly Ala Asn Gln Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 37
```

```
<211> LENGTH: 38
<212> TYPE: PRT
<213> ORGANISM: Artificial Sequence
<220> FEATURE:
<223> OTHER INFORMATION: G-CNP-37 K14Q, K15Q
<220> FEATURE:
<221> NAME/KEY: DISULFID
<222> LOCATION: (22)..(38)

<400> SEQUENCE: 37

Gly Gln Glu His Pro Asn Ala Arg Lys Tyr Lys Gly Ala Asn Gln Gln
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 38
<211> LENGTH: 36
<212> TYPE: PRT
<213> ORGANISM: Artificial Sequence
<220> FEATURE:
<223> OTHER INFORMATION: CNP-36
<220> FEATURE:
<221> NAME/KEY: DISULFID
<222> LOCATION: (20)..(36)

<400> SEQUENCE: 38

Glu His Pro Asn Ala Arg Lys Tyr Lys Gly Ala Asn Lys Lys Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 39
<211> LENGTH: 35
<212> TYPE: PRT
<213> ORGANISM: Artificial Sequence
<220> FEATURE:
<223> OTHER INFORMATION: CNP-35
<220> FEATURE:
<221> NAME/KEY: DISULFID
<222> LOCATION: (19)..(35)

<400> SEQUENCE: 39

His Pro Asn Ala Arg Lys Tyr Lys Gly Ala Asn Lys Lys Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 40
<211> LENGTH: 34
<212> TYPE: PRT
<213> ORGANISM: Artificial Sequence
<220> FEATURE:
<223> OTHER INFORMATION: CNP-34
<220> FEATURE:
<221> NAME/KEY: DISULFID
<222> LOCATION: (18)..(34)

<400> SEQUENCE: 40

Pro Asn Ala Arg Lys Tyr Lys Gly Ala Asn Lys Lys Gly Leu Ser Lys
1               5                   10                  15
```

```
Gly Cys Phe Gly Leu Lys Leu Asp Arg Ile Gly Ser Met Ser Gly Leu
            20                  25                  30

Gly Cys
```

<210> SEQ ID NO 41
<211> LENGTH: 33
<212> TYPE: PRT
<213> ORGANISM: Artificial Sequence
<220> FEATURE:
<223> OTHER INFORMATION: CNP-33
<220> FEATURE:
<221> NAME/KEY: DISULFID
<222> LOCATION: (17)..(33)

<400> SEQUENCE: 41

```
Asn Ala Arg Lys Tyr Lys Gly Ala Asn Lys Lys Gly Leu Ser Lys Gly
1               5                   10                  15

Cys Phe Gly Leu Lys Leu Asp Arg Ile Gly Ser Met Ser Gly Leu Gly
            20                  25                  30

Cys
```

<210> SEQ ID NO 42
<211> LENGTH: 32
<212> TYPE: PRT
<213> ORGANISM: Artificial Sequence
<220> FEATURE:
<223> OTHER INFORMATION: CNP-32
<220> FEATURE:
<221> NAME/KEY: DISULFID
<222> LOCATION: (16)..(32)

<400> SEQUENCE: 42

```
Ala Arg Lys Tyr Lys Gly Ala Asn Lys Lys Gly Leu Ser Lys Gly Cys
1               5                   10                  15

Phe Gly Leu Lys Leu Asp Arg Ile Gly Ser Met Ser Gly Leu Gly Cys
            20                  25                  30
```

<210> SEQ ID NO 43
<211> LENGTH: 31
<212> TYPE: PRT
<213> ORGANISM: Artificial Sequence
<220> FEATURE:
<223> OTHER INFORMATION: CNP-31
<220> FEATURE:
<221> NAME/KEY: DISULFID
<222> LOCATION: (15)..(31)

<400> SEQUENCE: 43

```
Arg Lys Tyr Lys Gly Ala Asn Lys Lys Gly Leu Ser Lys Gly Cys Phe
1               5                   10                  15

Gly Leu Lys Leu Asp Arg Ile Gly Ser Met Ser Gly Leu Gly Cys
            20                  25                  30
```

<210> SEQ ID NO 44
<211> LENGTH: 30
<212> TYPE: PRT
<213> ORGANISM: Artificial Sequence
<220> FEATURE:
<223> OTHER INFORMATION: CNP-30
<220> FEATURE:
<221> NAME/KEY: DISULFID
<222> LOCATION: (14)..(30)

<400> SEQUENCE: 44

```
Lys Tyr Lys Gly Ala Asn Lys Lys Gly Leu Ser Lys Gly Cys Phe Gly
```

```
1               5                   10                  15
Leu Lys Leu Asp Arg Ile Gly Ser Met Ser Gly Leu Gly Cys
            20                  25                  30

<210> SEQ ID NO 45
<211> LENGTH: 29
<212> TYPE: PRT
<213> ORGANISM: Artificial Sequence
<220> FEATURE:
<223> OTHER INFORMATION: CNP-29
<220> FEATURE:
<221> NAME/KEY: DISULFID
<222> LOCATION: (13)..(29)

<400> SEQUENCE: 45

Tyr Lys Gly Ala Asn Lys Lys Gly Leu Ser Lys Gly Cys Phe Gly Leu
1               5                   10                  15
Lys Leu Asp Arg Ile Gly Ser Met Ser Gly Leu Gly Cys
            20                  25

<210> SEQ ID NO 46
<211> LENGTH: 28
<212> TYPE: PRT
<213> ORGANISM: Artificial Sequence
<220> FEATURE:
<223> OTHER INFORMATION: CNP-28
<220> FEATURE:
<221> NAME/KEY: DISULFID
<222> LOCATION: (12)..(28)

<400> SEQUENCE: 46

Lys Gly Ala Asn Lys Lys Gly Leu Ser Lys Gly Cys Phe Gly Leu Lys
1               5                   10                  15
Leu Asp Arg Ile Gly Ser Met Ser Gly Leu Gly Cys
            20                  25

<210> SEQ ID NO 47
<211> LENGTH: 38
<212> TYPE: PRT
<213> ORGANISM: Artificial Sequence
<220> FEATURE:
<223> OTHER INFORMATION: GHKSEVAHRF-CNP-28
<220> FEATURE:
<221> NAME/KEY: DISULFID
<222> LOCATION: (22)..(38)

<400> SEQUENCE: 47

Gly His Lys Ser Glu Val Ala His Arg Phe Lys Gly Ala Asn Lys Lys
1               5                   10                  15
Gly Leu Ser Lys Gly Cys Phe Gly Leu Lys Leu Asp Arg Ile Gly Ser
            20                  25                  30
Met Ser Gly Leu Gly Cys
        35

<210> SEQ ID NO 48
<211> LENGTH: 27
<212> TYPE: PRT
<213> ORGANISM: Artificial Sequence
<220> FEATURE:
<223> OTHER INFORMATION: CNP-27
<220> FEATURE:
<221> NAME/KEY: DISULFID
<222> LOCATION: (11)..(27)

<400> SEQUENCE: 48

Gly Ala Asn Lys Lys Gly Leu Ser Lys Gly Cys Phe Gly Leu Lys Leu
```

```
                1               5                  10                  15
Asp Arg Ile Gly Ser Met Ser Gly Leu Gly Cys
            20                  25

<210> SEQ ID NO 49
<211> LENGTH: 27
<212> TYPE: PRT
<213> ORGANISM: Artificial Sequence
<220> FEATURE:
<223> OTHER INFORMATION: CNP-27 K4Q, K5Q
<220> FEATURE:
<221> NAME/KEY: DISULFID
<222> LOCATION: (11)..(27)

<400> SEQUENCE: 49

Gly Ala Asn Gln Gln Gly Leu Ser Lys Gly Cys Phe Gly Leu Lys Leu
1               5                  10                  15

Asp Arg Ile Gly Ser Met Ser Gly Leu Gly Cys
            20                  25

<210> SEQ ID NO 50
<211> LENGTH: 27
<212> TYPE: PRT
<213> ORGANISM: Artificial Sequence
<220> FEATURE:
<223> OTHER INFORMATION: CNP-27 K4R, K5R
<220> FEATURE:
<221> NAME/KEY: DISULFID
<222> LOCATION: (11)..(27)

<400> SEQUENCE: 50

Gly Ala Asn Arg Arg Gly Leu Ser Lys Gly Cys Phe Gly Leu Lys Leu
1               5                  10                  15

Asp Arg Ile Gly Ser Met Ser Gly Leu Gly Cys
            20                  25

<210> SEQ ID NO 51
<211> LENGTH: 27
<212> TYPE: PRT
<213> ORGANISM: Artificial Sequence
<220> FEATURE:
<223> OTHER INFORMATION: CNP-27 K4P, K5R
<220> FEATURE:
<221> NAME/KEY: DISULFID
<222> LOCATION: (11)..(27)

<400> SEQUENCE: 51

Gly Ala Asn Pro Arg Gly Leu Ser Lys Gly Cys Phe Gly Leu Lys Leu
1               5                  10                  15

Asp Arg Ile Gly Ser Met Ser Gly Leu Gly Cys
            20                  25

<210> SEQ ID NO 52
<211> LENGTH: 27
<212> TYPE: PRT
<213> ORGANISM: Artificial Sequence
<220> FEATURE:
<223> OTHER INFORMATION: CNP-27 K4S, K5S
<220> FEATURE:
<221> NAME/KEY: DISULFID
<222> LOCATION: (11)..(27)

<400> SEQUENCE: 52

Gly Ala Asn Ser Ser Gly Leu Ser Lys Gly Cys Phe Gly Leu Lys Leu
1               5                  10                  15

Asp Arg Ile Gly Ser Met Ser Gly Leu Gly Cys
```

<210> SEQ ID NO 53
<211> LENGTH: 30
<212> TYPE: PRT
<213> ORGANISM: Artificial Sequence
<220> FEATURE:
<223> OTHER INFORMATION: GAN-CNP-27 K4P, K5R
<220> FEATURE:
<221> NAME/KEY: DISULFID
<222> LOCATION: (14)..(30)

<400> SEQUENCE: 53

Gly Ala Asn Gly Ala Asn Pro Arg Gly Leu Ser Arg Gly Cys Phe Gly
1               5                   10                  15

Leu Lys Leu Asp Arg Ile Gly Ser Met Ser Gly Leu Gly Cys
            20                  25                  30

<210> SEQ ID NO 54
<211> LENGTH: 27
<212> TYPE: PRT
<213> ORGANISM: Artificial Sequence
<220> FEATURE:
<223> OTHER INFORMATION: CNP-27 K4R, K5R, K9R
<220> FEATURE:
<221> NAME/KEY: DISULFID
<222> LOCATION: (11)..(27)

<400> SEQUENCE: 54

Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 55
<211> LENGTH: 27
<212> TYPE: PRT
<213> ORGANISM: Artificial Sequence
<220> FEATURE:
<223> OTHER INFORMATION: CNP-27 K4R, K5R, K9R, M22N
<220> FEATURE:
<221> NAME/KEY: DISULFID
<222> LOCATION: (11)..(27)

<400> SEQUENCE: 55

Gly Ala Asn Arg Arg Gly Leu Ser Arg Gly Cys Phe Gly Leu Lys Leu
1               5                   10                  15

Asp Arg Ile Gly Ser Asn Ser Gly Leu Gly Cys
            20                  25

<210> SEQ ID NO 56
<211> LENGTH: 28
<212> TYPE: PRT
<213> ORGANISM: Artificial Sequence
<220> FEATURE:
<223> OTHER INFORMATION: P-CNP-27 K4R, K5R, K9R
<220> FEATURE:
<221> NAME/KEY: DISULFID
<222> LOCATION: (12)..(28)

<400> SEQUENCE: 56

Pro Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
            20                  25

-continued

```
<210> SEQ ID NO 57
<211> LENGTH: 28
<212> TYPE: PRT
<213> ORGANISM: Artificial Sequence
<220> FEATURE:
<223> OTHER INFORMATION: M-CNP-27 K4R, K5R, K9R
<220> FEATURE:
<221> NAME/KEY: DISULFID
<222> LOCATION: (12)..(28)

<400> SEQUENCE: 57

Met Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
            20                  25

<210> SEQ ID NO 58
<211> LENGTH: 38
<212> TYPE: PRT
<213> ORGANISM: Artificial Sequence
<220> FEATURE:
<223> OTHER INFORMATION: Human Serum Albumine Fragment - CNP-27
<220> FEATURE:
<221> NAME/KEY: DISULFID
<222> LOCATION: (22)..(38)

<400> SEQUENCE: 58

Gly His Lys Ser Glu Val Ala His Arg Phe Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 59
<211> LENGTH: 38
<212> TYPE: PRT
<213> ORGANISM: Artificial Sequence
<220> FEATURE:
<223> OTHER INFORMATION: Human Serum Albumine Fragment - CNP-27 M22N
<220> FEATURE:
<221> NAME/KEY: DISULFID
<222> LOCATION: (22)..(38)

<400> SEQUENCE: 59

Gly His Lys Ser Glu Val Ala His Arg Phe Lys Gly Ala Asn Lys Lys
1               5                   10                  15

Gly Leu Ser Lys Gly Cys Phe Gly Leu Lys Leu Asp Arg Ile Gly Ser
            20                  25                  30

Asn Ser Gly Leu Gly Cys
        35

<210> SEQ ID NO 60
<211> LENGTH: 39
<212> TYPE: PRT
<213> ORGANISM: Artificial Sequence
<220> FEATURE:
<223> OTHER INFORMATION: methionine - Human Serum Albumine Fragment -
      CNP-27
<220> FEATURE:
<221> NAME/KEY: DISULFID
<222> LOCATION: (23)..(39)

<400> SEQUENCE: 60

Met Gly His Lys Ser Glu Val Ala His Arg Phe Lys Gly Ala Asn Lys
1               5                   10                  15
```

```
Lys Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 61
<211> LENGTH: 39
<212> TYPE: PRT
<213> ORGANISM: Artificial Sequence
<220> FEATURE:
<223> OTHER INFORMATION: proline - Human Serum Albumine Fragment -
      CNP-27
<220> FEATURE:
<221> NAME/KEY: DISULFID
<222> LOCATION: (23)..(39)

<400> SEQUENCE: 61

Pro Gly His Lys Ser Glu Val Ala His Arg Phe Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 62
<211> LENGTH: 26
<212> TYPE: PRT
<213> ORGANISM: Artificial Sequence
<220> FEATURE:
<223> OTHER INFORMATION: CNP-26
<220> FEATURE:
<221> NAME/KEY: DISULFID
<222> LOCATION: (10)..(26)

<400> SEQUENCE: 62

Ala Asn Lys Lys Gly Leu Ser Lys Gly Cys Phe Gly Leu Lys Leu Asp
1               5                   10                  15

Arg Ile Gly Ser Met Ser Gly Leu Gly Cys
            20                  25

<210> SEQ ID NO 63
<211> LENGTH: 25
<212> TYPE: PRT
<213> ORGANISM: Artificial Sequence
<220> FEATURE:
<223> OTHER INFORMATION: CNP-25
<220> FEATURE:
<221> NAME/KEY: DISULFID
<222> LOCATION: (9)..(25)

<400> SEQUENCE: 63

Asn Lys Lys Gly Leu Ser Lys Gly Cys Phe Gly Leu Lys Leu Asp Arg
1               5                   10                  15

Ile Gly Ser Met Ser Gly Leu Gly Cys
            20                  25

<210> SEQ ID NO 64
<211> LENGTH: 24
<212> TYPE: PRT
<213> ORGANISM: Artificial Sequence
<220> FEATURE:
<223> OTHER INFORMATION: CNP-24
<220> FEATURE:
<221> NAME/KEY: DISULFID
<222> LOCATION: (8)..(24)

<400> SEQUENCE: 64
```

```
Lys Lys Gly Leu Ser Lys Gly Cys Phe Gly Leu Lys Leu Asp Arg Ile
1               5                   10                  15

Gly Ser Met Ser Gly Leu Gly Cys
            20

<210> SEQ ID NO 65
<211> LENGTH: 23
<212> TYPE: PRT
<213> ORGANISM: Artificial Sequence
<220> FEATURE:
<223> OTHER INFORMATION: CNP-23
<220> FEATURE:
<221> NAME/KEY: DISULFID
<222> LOCATION: (7)..(23)

<400> SEQUENCE: 65

Lys Gly Leu Ser Lys Gly Cys Phe Gly Leu Lys Leu Asp Arg Ile Gly
1               5                   10                  15

Ser Met Ser Gly Leu Gly Cys
            20

<210> SEQ ID NO 66
<211> LENGTH: 23
<212> TYPE: PRT
<213> ORGANISM: Artificial Sequence
<220> FEATURE:
<223> OTHER INFORMATION: R-CNP-22
<220> FEATURE:
<221> NAME/KEY: DISULFID
<222> LOCATION: (7)..(23)

<400> SEQUENCE: 66

Arg Gly Leu Ser Lys Gly Cys Phe Gly Leu Lys Leu Asp Arg Ile Gly
1               5                   10                  15

Ser Met Ser Gly Leu Gly Cys
            20

<210> SEQ ID NO 67
<211> LENGTH: 24
<212> TYPE: PRT
<213> ORGANISM: Artificial Sequence
<220> FEATURE:
<223> OTHER INFORMATION: ER-CNP-22
<220> FEATURE:
<221> NAME/KEY: DISULFID
<222> LOCATION: (8)..(24)

<400> SEQUENCE: 67

Glu Arg Gly Leu Ser Lys Gly Cys Phe Gly Leu Lys Leu Asp Arg Ile
1               5                   10                  15

Gly Ser Met Ser Gly Leu Gly Cys
            20

<210> SEQ ID NO 68
<211> LENGTH: 23
<212> TYPE: PRT
<213> ORGANISM: Artificial Sequence
<220> FEATURE:
<223> OTHER INFORMATION: R-CNP-22 K4R
<220> FEATURE:
<221> NAME/KEY: DISULFID
<222> LOCATION: (7)..(23)

<400> SEQUENCE: 68

Arg Gly Leu Ser Arg Gly Cys Phe Gly Leu Lys Leu Asp Arg Ile Gly
1               5                   10                  15
```

```
Ser Met Ser Gly Leu Gly Cys
            20

<210> SEQ ID NO 69
<211> LENGTH: 24
<212> TYPE: PRT
<213> ORGANISM: Artificial Sequence
<220> FEATURE:
<223> OTHER INFORMATION: ER-CNP-22 4KR
<220> FEATURE:
<221> NAME/KEY: DISULFID
<222> LOCATION: (8)..(24)

<400> SEQUENCE: 69

Glu Arg Gly Leu Ser Arg Gly Cys Phe Gly Leu Lys Leu Asp Arg Ile
1               5                   10                  15

Gly Ser Met Ser Gly Leu Gly Cys
            20

<210> SEQ ID NO 70
<211> LENGTH: 24
<212> TYPE: PRT
<213> ORGANISM: Artificial Sequence
<220> FEATURE:
<223> OTHER INFORMATION: RR-CNP-22
<220> FEATURE:
<221> NAME/KEY: DISULFID
<222> LOCATION: (8)..(24)

<400> SEQUENCE: 70

Arg Arg Gly Leu Ser Arg Gly Cys Phe Gly Leu Lys Leu Asp Arg Ile
1               5                   10                  15

Gly Ser Met Ser Gly Leu Gly Cys
            20

<210> SEQ ID NO 71
<211> LENGTH: 37
<212> TYPE: PRT
<213> ORGANISM: Artificial Sequence
<220> FEATURE:
<223> OTHER INFORMATION: HRGP fragment - CNP-22
<220> FEATURE:
<221> NAME/KEY: DISULFID
<222> LOCATION: (21)..(37)

<400> SEQUENCE: 71

Gly His His Ser His Glu Gln His Pro His Gly Ala Asn Gln Gln Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 72
<211> LENGTH: 38
<212> TYPE: PRT
<213> ORGANISM: Artificial Sequence
<220> FEATURE:
<223> OTHER INFORMATION: HRGP fragment - CNP-22
<220> FEATURE:
<221> NAME/KEY: DISULFID
<222> LOCATION: (22)..(38)

<400> SEQUENCE: 72

Gly Ala His His Pro His Glu His Asp Thr His Gly Ala Asn Gln Gln
1               5                   10                  15
```

```
Gly Leu Ser Lys Gly Cys Phe Gly Leu Lys Leu Asp Arg Ile Gly Ser
            20                  25                  30

Met Ser Gly Leu Gly Cys
        35
```

<210> SEQ ID NO 73
<211> LENGTH: 37
<212> TYPE: PRT
<213> ORGANISM: Artificial Sequence
<220> FEATURE:
<223> OTHER INFORMATION: HRGP fragment - CNP-22
<220> FEATURE:
<221> NAME/KEY: DISULFID
<222> LOCATION: (21)..(37)

<400> SEQUENCE: 73

```
Gly His His Ser His Glu Gln His Pro His Gly Ala Asn Pro Arg Gly
1               5                   10                  15

Leu Ser Lys Gly Cys Phe Gly Leu Lys Leu Asp Arg Ile Gly Ser Met
            20                  25                  30

Ser Gly Leu Gly Cys
        35
```

<210> SEQ ID NO 74
<211> LENGTH: 36
<212> TYPE: PRT
<213> ORGANISM: Artificial Sequence
<220> FEATURE:
<223> OTHER INFORMATION: IgG1(FC) fragment - CNP-22
<220> FEATURE:
<221> NAME/KEY: DISULFID
<222> LOCATION: (20)..(36)

<400> SEQUENCE: 74

```
Gly Gln Pro Arg Glu Pro Gln Val Tyr Thr Leu Pro Pro Ser Gly Leu
1               5                   10                  15

Ser Lys Gly Cys Phe Gly Leu Lys Leu Asp Arg Ile Gly Ser Met Ser
            20                  25                  30

Gly Leu Gly Cys
        35
```

<210> SEQ ID NO 75
<211> LENGTH: 39
<212> TYPE: PRT
<213> ORGANISM: Artificial Sequence
<220> FEATURE:
<223> OTHER INFORMATION: Human Serum Albumine - CNP-22
<220> FEATURE:
<221> NAME/KEY: DISULFID
<222> LOCATION: (23)..(39)

<400> SEQUENCE: 75

```
Gly Gln His Lys Asp Asp Asn Pro Asn Leu Pro Arg Gly Ala Asn Pro
1               5                   10                  15

Arg Gly Leu Ser Lys Gly Cys Phe Gly Leu Lys Leu Asp Arg Ile Gly
            20                  25                  30

Ser Met Ser Gly Leu Gly Cys
        35
```

<210> SEQ ID NO 76
<211> LENGTH: 37
<212> TYPE: PRT
<213> ORGANISM: Artificial Sequence
<220> FEATURE:

<223> OTHER INFORMATION: Human Serum Albumine - CNP-22
<220> FEATURE:
<221> NAME/KEY: DISULFID
<222> LOCATION: (21)..(37)

<400> SEQUENCE: 76

Gly Glu Arg Ala Phe Lys Ala Trp Ala Val Ala Arg Leu Ser Gln Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 77
<211> LENGTH: 35
<212> TYPE: PRT
<213> ORGANISM: Artificial Sequence
<220> FEATURE:
<223> OTHER INFORMATION: osteocrin NPR C inhibitor fragment - CNP-22
<220> FEATURE:
<221> NAME/KEY: DISULFID
<222> LOCATION: (19)..(35)

<400> SEQUENCE: 77

Phe Gly Ile Pro Met Asp Arg Ile Gly Arg Asn Pro Arg Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 78
<211> LENGTH: 40
<212> TYPE: PRT
<213> ORGANISM: Artificial Sequence
<220> FEATURE:
<223> OTHER INFORMATION: FGF2 heparin-binding domain fragment - CNP-22
<220> FEATURE:
<221> NAME/KEY: DISULFID
<222> LOCATION: (24)..(40)

<400> SEQUENCE: 78

Gly Lys Arg Thr Gly Gln Tyr Lys Leu Gly Ser Lys Thr Gly Pro Gly
1               5                   10                  15

Pro Lys Gly Leu Ser Lys Gly Cys Phe Gly Leu Lys Leu Asp Arg Ile
            20                  25                  30

Gly Ser Met Ser Gly Leu Gly Cys
        35                  40

<210> SEQ ID NO 79
<211> LENGTH: 37
<212> TYPE: PRT
<213> ORGANISM: Artificial Sequence
<220> FEATURE:
<223> OTHER INFORMATION: IgG1(FC) fragment - CNP-22 K4R
<220> FEATURE:
<221> NAME/KEY: DISULFID
<222> LOCATION: (21)..(37)

<400> SEQUENCE: 79

Gly Gln Pro Arg Glu Pro Gln Val Tyr Thr Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 80
<211> LENGTH: 36
<212> TYPE: PRT
<213> ORGANISM: Artificial Sequence
<220> FEATURE:
<223> OTHER INFORMATION: Human Serum Albumine fragment - CNP-22 K4R
<220> FEATURE:
<221> NAME/KEY: DISULFID
<222> LOCATION: (20)..(36)

<400> SEQUENCE: 80

Gly Val Pro Gln Val Ser Thr Ser Thr Gly Ala Asn Gln Gln Gly Leu
1               5                   10                  15

Ser Arg Gly Cys Phe Gly Leu Lys Leu Asp Arg Ile Gly Ser Met Ser
            20                  25                  30

Gly Leu Gly Cys
        35

<210> SEQ ID NO 81
<211> LENGTH: 37
<212> TYPE: PRT
<213> ORGANISM: Artificial Sequence
<220> FEATURE:
<223> OTHER INFORMATION: fibronectin fragment - CNP-22
<220> FEATURE:
<221> NAME/KEY: DISULFID
<222> LOCATION: (21)..(37)

<400> SEQUENCE: 81

Gly Gln Pro Ser Ser Ser Ser Gln Ser Thr Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 82
<211> LENGTH: 37
<212> TYPE: PRT
<213> ORGANISM: Artificial Sequence
<220> FEATURE:
<223> OTHER INFORMATION: fibronectin fragment - CNP-22 K4R
<220> FEATURE:
<221> NAME/KEY: DISULFID
<222> LOCATION: (21)..(37)

<400> SEQUENCE: 82

Gly Gln Thr His Ser Ser Gly Thr Gln Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 83
<211> LENGTH: 37
<212> TYPE: PRT
<213> ORGANISM: Artificial Sequence
<220> FEATURE:
<223> OTHER INFORMATION: fibronectin fragment - CNP-22 K4R
<220> FEATURE:
<221> NAME/KEY: DISULFID
<222> LOCATION: (21)..(37)

<400> SEQUENCE: 83

Gly Ser Thr Gly Gln Trp His Ser Glu Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 84
<211> LENGTH: 37
<212> TYPE: PRT
<213> ORGANISM: Artificial Sequence
<220> FEATURE:
<223> OTHER INFORMATION: zinc finger fragment - CNP-22 K4R
<220> FEATURE:
<221> NAME/KEY: DISULFID
<222> LOCATION: (21)..(37)

<400> SEQUENCE: 84

Gly Ser Ser Ser Ser Ser Ser Ser Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 85
<211> LENGTH: 21
<212> TYPE: PRT
<213> ORGANISM: Artificial Sequence
<220> FEATURE:
<223> OTHER INFORMATION: CNP-21
<220> FEATURE:
<221> NAME/KEY: DISULFID
<222> LOCATION: (5)..(21)

<400> SEQUENCE: 85

Leu Ser Lys Gly Cys Phe Gly Leu Lys Leu Asp Arg Ile Gly Ser Met
1               5                   10                  15

Ser Gly Leu Gly Cys
            20

<210> SEQ ID NO 86
<211> LENGTH: 20
<212> TYPE: PRT
<213> ORGANISM: Artificial Sequence
<220> FEATURE:
<223> OTHER INFORMATION: CNP-20
<220> FEATURE:
<221> NAME/KEY: DISULFID
<222> LOCATION: (4)..(20)

<400> SEQUENCE: 86

Ser Lys Gly Cys Phe Gly Leu Lys Leu Asp Arg Ile Gly Ser Met Ser
1               5                   10                  15

Gly Leu Gly Cys
            20

<210> SEQ ID NO 87
<211> LENGTH: 19
<212> TYPE: PRT
<213> ORGANISM: Artificial Sequence
<220> FEATURE:
<223> OTHER INFORMATION: CNP-19

```
<220> FEATURE:
<221> NAME/KEY: DISULFID
<222> LOCATION: (3)..(19)

<400> SEQUENCE: 87

Lys Gly Cys Phe Gly Leu Lys Leu Asp Arg Ile Gly Ser Met Ser Gly
1               5                   10                  15

Leu Gly Cys

<210> SEQ ID NO 88
<211> LENGTH: 18
<212> TYPE: PRT
<213> ORGANISM: Artificial Sequence
<220> FEATURE:
<223> OTHER INFORMATION: CNP-18
<220> FEATURE:
<221> NAME/KEY: DISULFID
<222> LOCATION: (2)..(18)

<400> SEQUENCE: 88

Gly Cys Phe Gly Leu Lys Leu Asp Arg Ile Gly Ser Met Ser Gly Leu
1               5                   10                  15

Gly Cys

<210> SEQ ID NO 89
<211> LENGTH: 17
<212> TYPE: PRT
<213> ORGANISM: Artificial Sequence
<220> FEATURE:
<223> OTHER INFORMATION: CNP-17
<220> FEATURE:
<221> NAME/KEY: DISULFID
<222> LOCATION: (1)..(17)

<400> SEQUENCE: 89

Cys Phe Gly Leu Lys Leu Asp Arg Ile Gly Ser Met Ser Gly Leu Gly
1               5                   10                  15

Cys

<210> SEQ ID NO 90
<211> LENGTH: 32
<212> TYPE: PRT
<213> ORGANISM: Artificial Sequence
<220> FEATURE:
<223> OTHER INFORMATION: BNP fragment - CNP-17 - BNP- fragment
<220> FEATURE:
<221> NAME/KEY: DISULFID
<222> LOCATION: (10)..(26)

<400> SEQUENCE: 90

Ser Pro Lys Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
                20                  25                  30

<210> SEQ ID NO 91
<211> LENGTH: 38
<212> TYPE: PRT
<213> ORGANISM: Artificial Sequence
<220> FEATURE:
<223> OTHER INFORMATION: CNP-38 L1G
<220> FEATURE:
<221> NAME/KEY: DISULFID
<222> LOCATION: (22)..(38)

<400> SEQUENCE: 91
```

-continued

```
Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 92
<211> LENGTH: 37
<212> TYPE: PRT
<213> ORGANISM: Artificial Sequence
<220> FEATURE:
<223> OTHER INFORMATION: Ac-CNP-37
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (21)..(37)

<400> SEQUENCE: 92

Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 93
<211> LENGTH: 37
<212> TYPE: PRT
<213> ORGANISM: Artificial Sequence
<220> FEATURE:
<223> OTHER INFORMATION: CNP-37, Xaa = K or R, with the provision that
      at least one Xaa is R
<220> FEATURE:
<221> NAME/KEY: MISC_FEATURE
<222> LOCATION: (8)..(8)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln
<220> FEATURE:
<221> NAME/KEY: MISC_FEATURE
<222> LOCATION: (10)..(10)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln
<220> FEATURE:
<221> NAME/KEY: MISC_FEATURE
<222> LOCATION: (14)..(14)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln
<220> FEATURE:
<221> NAME/KEY: MISC_FEATURE
<222> LOCATION: (15)..(15)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln
<220> FEATURE:
<221> NAME/KEY: MISC_FEATURE
<222> LOCATION: (19)..(19)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln
<220> FEATURE:
<221> NAME/KEY: DISULFID
<222> LOCATION: (21)..(37)
<220> FEATURE:
<221> NAME/KEY: MISC_FEATURE
<222> LOCATION: (25)..(25)
```

```
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln

<400> SEQUENCE: 93

Gln Glu His Pro Asn Ala Arg Xaa Tyr Xaa Gly Ala Asn Xaa Xaa Gly
1               5                   10                  15

Leu Ser Xaa Gly Cys Phe Gly Leu Xaa Leu Asp Arg Ile Gly Ser Met
            20                  25                  30

Ser Gly Leu Gly Cys
        35

<210> SEQ ID NO 94
<211> LENGTH: 37
<212> TYPE: PRT
<213> ORGANISM: Artificial Sequence
<220> FEATURE:
<223> OTHER INFORMATION: mutated CNP-37
<220> FEATURE:
<221> NAME/KEY: MISC_FEATURE
<222> LOCATION: (14)..(14)
<223> OTHER INFORMATION: X is selected from the group consising of Lys,
      Arg, Pro, Ser and Gln, with the provision that at least one of the
      amino acids at position 14, 15, 19 and 25 is selected from the
      group consisting of  Arg, Pro, Ser and Gln
<220> FEATURE:
<221> NAME/KEY: MISC_FEATURE
<222> LOCATION: (15)..(15)
<223> OTHER INFORMATION: X is selected from the group consising of Lys,
      Arg, Pro, Ser and Gln, with the provision that at least one of the
      amino acids at position 14, 15, 19 and 25 is selected from the
      group consisting of  Arg, Pro, Ser and Gln
<220> FEATURE:
<221> NAME/KEY: MISC_FEATURE
<222> LOCATION: (19)..(19)
<223> OTHER INFORMATION: X is selected from the group consising of Lys,
      Arg, Pro, Ser and Gln, with the provision that at least one of the
      amino acids at position 14, 15, 19 and 25 is selected from the
      group consisting of  Arg, Pro, Ser and Gln
<220> FEATURE:
<221> NAME/KEY: DISULFID
<222> LOCATION: (21)..(37)
<220> FEATURE:
<221> NAME/KEY: MISC_FEATURE
<222> LOCATION: (25)..(25)
<223> OTHER INFORMATION: X is selected from the group consising of Lys,
      Arg, Pro, Ser and Gln, with the provision that at least one of the
      amino acids at position 14, 15, 19 and 25 is selected from the
      group consisting of  Arg, Pro, Ser and Gln

<400> SEQUENCE: 94

Gln Glu His Pro Asn Ala Arg Lys Tyr Lys Gly Ala Asn Xaa Xaa Gly
1               5                   10                  15

Leu Ser Xaa Gly Cys Phe Gly Leu Xaa Leu Asp Arg Ile Gly Ser Met
            20                  25                  30

Ser Gly Leu Gly Cys
        35

<210> SEQ ID NO 95
<211> LENGTH: 37
<212> TYPE: PRT
<213> ORGANISM: Artificial Sequence
<220> FEATURE:
<223> OTHER INFORMATION: mutated CNP-37
<220> FEATURE:
<221> NAME/KEY: MISC_FEATURE
<222> LOCATION: (14)..(15)
<223> OTHER INFORMATION: Xaa Xaa is selected from the group consisting
      of Lys Arg, Arg Lys, Lys Pro, Pro Lys, Ser Ser, Arg Ser, Ser Arg,
      Gln Lys, Gln Arg, Lys Gln, Arg Gln, Arg Arg and Gln Gln
<220> FEATURE:
```

```
<221> NAME/KEY: DISULFID
<222> LOCATION: (21)..(37)

<400> SEQUENCE: 95

Gln Glu His Pro Asn Ala Arg Lys Tyr Lys Gly Ala Asn Xaa Xaa Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 96
<211> LENGTH: 15
<212> TYPE: PRT
<213> ORGANISM: Homo sapiens

<400> SEQUENCE: 96

Phe Gly Leu Lys Leu Asp Arg Ile Gly Ser Met Ser Gly Leu Gly
1               5                   10                  15

<210> SEQ ID NO 97
<211> LENGTH: 20
<212> TYPE: PRT
<213> ORGANISM: Artificial Sequence
<220> FEATURE:
<223> OTHER INFORMATION: Artificial random coil

<400> SEQUENCE: 97

Gly Gly Pro Gly Gly Pro Gly Pro Gly Gly Pro Gly Gly Pro Gly Pro
1               5                   10                  15

Gly Gly Pro Gly
            20

<210> SEQ ID NO 98
<211> LENGTH: 13
<212> TYPE: PRT
<213> ORGANISM: Artificial Sequence
<220> FEATURE:
<223> OTHER INFORMATION: NPR-C inhibitor

<400> SEQUENCE: 98

Phe Gly Ile Pro Met Asp Arg Ile Gly Arg Asn Pro Arg
1               5                   10
```

The invention claimed is:

1. A controlled-release CNP agonist, wherein the controlled-release CNP agonist releases a CNP agonist in its free form with a release half-life of at least 6 hours under physiological conditions and which controlled-release CNP agonist has an $IC_{50}$ to the NPR-C receptor that is at least 5-fold higher than the $IC_{50}$ of the corresponding free CNP agonist-, wherein the controlled-release CNP agonist is of formula (Ia) or (Ib):

$$Z\text{-}(\text{-}L^2\text{-}L^1\text{-}D)_x \quad (Ia),$$

$$D\text{-}(\text{-}L^1\text{-}L^2\text{-}Z)_y \quad (Ib),$$

or comprises a conjugate D-L, wherein -L comprises a moiety -L$^1$-, which moiety -L$^1$- is substituted with -L$^2$-Z' and is optionally further substituted;
wherein
-D is the CNP agonist moiety, which is a CNP moiety having a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94 and SEQ ID NO:95;

-$L^1$- is a reversible prodrug linker moiety which is covalently and reversibly conjugated to the side chain of an amino acid residue of the ring moiety of -D or to the backbone of the ring moiety of -D;

-$L^2$- is a chemical bond or a spacer moiety;

—Z is a water-soluble branched polymer moiety having a first branching point less than 50 atoms from the CNP moiety;

—Z' is a hydrogel;

x is an integer selected from the group consisting of 1, 2, 3, 4, 5, 6, 7, 8, 9, 10, 11, 12, 13, 14, 15 and 16; and y is an integer selected from the group consisting of 1, 2, 3, 4 and 5.

2. A pharmaceutical composition comprising the controlled-release CNP agonist of claim 1 and at least one excipient.

3. A method of treating, controlling, delaying or preventing in a mammalian patient in need of the treatment of one or more diseases which can be treated with a CNP agonist, comprising the step of administering to said patient in need thereof a therapeutically effective amount of the controlled-release CNP agonist of claim 1 or a pharmaceutical composition comprising the controlled-release CNP agonist.

4. The method of claim 3, wherein the one or more diseases which can be treated with CNP is selected from the group consisting of achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, camptomelic dysplasia, congenital lethal hypophosphatasia, perinatal lethal type of osteogenesis imperfecta, short-rib polydactyly syndromes, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, spondyloepimetaphyseal dysplasia, neurofibromatosis, Legius syndrome, LEOPARD syndrome, Noonan syndrome, hereditary gingival fibromatosis, neurofibromatosis type 1, Legius syndrome, cardiofaciocutaneous syndrome, Costello syndrome, SHOX deficiency, idiopathic short stature, growth hormone deficiency, osteoarthritis, cleidocranial dysostosis, craniosynostosis, dactyly, brachydactyly, camptodactyly, polydactyly, syndactyly, dyssegmental dysplasia, enchondromatosis, fibrous dysplasia, hereditary multiple exostoses, hypophosphatemic rickets, Jaffe-Lichtenstein syndrome, Marfan syndrome, McCune-Albright syndrome, osteopetrosis and osteopoikilosis.

5. The method of claim 3, wherein the disease is achondroplasia.

6. The controlled-release CNP agonist of claim 1, wherein the $IC_{50}$ to the NPR-C receptor is at least 20-fold higher than the $IC_{50}$ of the corresponding free CNP agonist.

7. The controlled-release CNP agonist of claim 1, wherein the $IC_{50}$ to the NPR-C receptor is at least 50-fold higher than the $IC_{50}$ of the corresponding free CNP agonist.

8. The controlled-release CNP agonist of claim 1, wherein the CNP agonist is released with a release half-life of at least 24 hours under physiological conditions.

9. The controlled-release CNP agonist of claim 1, wherein the CNP agonist is released with a release half-life of at least 168 hours under physiological conditions.

10. The method of claim 3, wherein the disease is selected from the group consisting of Muenke syndrome, Crouzon syndrome, Apert syndrome, Jackson-Weiss syndrome, Pfeiffer syndrome and Crouzondermoskeletal syndrome.

\* \* \* \* \*

UNITED STATES PATENT AND TRADEMARK OFFICE
CERTIFICATE OF CORRECTION

PATENT NO. : 11,311,604 B2
APPLICATION NO. : 16/066980
DATED : April 26, 2022
INVENTOR(S) : Harald Rau et al.

It is certified that error appears in the above-identified patent and that said Letters Patent is hereby corrected as shown below:

In the Claims

In Column 249, Lines 54-55, Claim 1, delete "CNP agonist-," and insert -- CNP agonist, --, therefor.

In Column 249, Line 60, Claim 1, delete "$D\!-\!\!\left(\!-L^1\!-\!L^2\!-\!Z\right)^y$" and insert -- $D\!-\!\!\left(L^1\!-\!L^2\!-\!Z\right)_y$ --, therefor.

In Column 252, Line 40, Claim 10, delete "Crouzondermoskeletal syndrome." and insert -- Crouzonodermoskeletal syndrome. --, therefor.

Signed and Sealed this
First Day of August, 2023

Katherine Kelly Vidal
*Director of the United States Patent and Trademark Office*